US012590963B2

(12) United States Patent　　Androutsellis-Theotokis et al.

(10) Patent No.: US 12,590,963 B2
(45) Date of Patent: Mar. 31, 2026

(54) ANTI-CANCER TREATMENT OF PRESELECTED SUBJECTS AND SCREENING METHODS TO IDENTIFY SUSCEPTIBLE SUBJECTS

(71) Applicant: TUDAG TU Dresden Aktiengesellschaft, Dresden (DE)

(72) Inventors: Andreas Androutsellis-Theotokis, Dresden (DE); Steven Walter Poser, Seattle, WA (US)

(73) Assignee: TUDAG TU Dresden Aktiengesellschaft, Dresden (DE)

( * ) Notice: Subject to any disclaimer, the term of this patent is extended or adjusted under 35 U.S.C. 154(b) by 1383 days.

(21) Appl. No.: 16/972,015

(22) PCT Filed: May 23, 2019

(86) PCT No.: PCT/EP2019/063340
§ 371 (c)(1),
(2) Date: Dec. 4, 2020

(87) PCT Pub. No.: WO2019/233779
PCT Pub. Date: Dec. 12, 2019

(65) Prior Publication Data
US 2021/0231661 A1　　Jul. 29, 2021

(30) Foreign Application Priority Data
Jun. 6, 2018　(EP) ..................................... 18176272

(51) Int. Cl.
*G01N 33/574* (2006.01)
*G01N 33/50* (2006.01)

(52) U.S. Cl.
CPC ....... *G01N 33/574* (2013.01); *G01N 33/5008* (2013.01)

(58) Field of Classification Search
CPC ............. G01N 33/574; G01N 33/5008; G01N 2500/10; G01N 2800/52
See application file for complete search history.

(56) References Cited

U.S. PATENT DOCUMENTS

2015/0376710 A1　12/2015　Hatzis et al.

FOREIGN PATENT DOCUMENTS

WO　2014162008　10/2014
WO　2015181556　12/2015

OTHER PUBLICATIONS

Goodman et al., Critical Reviews in Toxicology, vol. 48, No. 1: 1-51 (Year: 2018).*
Miller et al., Biochemical Pharmacology, 79: 1272-80, (Year: 2010).*
Poser et al., Frontiers in Bioscience, 19: 718-726, (Year: 2014).*
Yang et al., Biomedicine and Pharmacotherapy, 101:1-7, May (Year: 2018).*
Mendes-Pereira et al "Genome-wide functional screen identifies a compendium of genes affecting sensitivity to tamoxifen", PNAS Feb. 21, 2012 109 (8) 2730-2735; seen on line at https://doi.org/10.1073/pnas.1018872108.
Park et al "PNAS Feb. 21, 2012 109 (8) 2730-2735; https://doi.org/10.1073/pnas.1018872108", Sci Rep 3, 1095 (2013). seen online at https://doi.org/10.1038/srep01095.
Mihaly et al "A meta analysis of gene expression-based biomarkers predicting outcome after tamoxifen treatment in breast cancer", Breast Cancer Res Treat, Jul. 2013; 140(2):219-32. seen online at doi: 10.1007/s10549-013-2622-y.

* cited by examiner

*Primary Examiner* — Kimberly Ballard
*Assistant Examiner* — Stacey N Macfarlane
(74) *Attorney, Agent, or Firm* — JMB Davis Ben-David

(57) ABSTRACT

The invention provides methods of screening a subject for a proliferative disease risk factor which comprises detecting the presence or absence of target cells. The presence of target cells in the subject indicates the subject is at increased risk of developing a proliferative disease or recurrence of a previously treated proliferative disease and defines a new patient subgroup susceptible for treatment with selected anti-proliferative compounds. Methods of screening compounds for the treatment of proliferative diseases based on the presence of target cells and the expression of certain biomarkers by said target cells are also disclosed, along with appropriate compounds and their use in methods of treating such diseases.

6 Claims, 13 Drawing Sheets

Specification includes a Sequence Listing.

A. All regulated genes:

X01
(290)

154   102   319

25

9   3

19

X04
(449)

X08
(56)

B. Down-regulated genes:

X08
(77)

53

X04
(60)

16  6   2

38   6

X08
(14)

C. Up-regulated genes:

X01
(213)

101   86   281

19

7   3

13

X04
(389)

X08
(42)

X01

X04

X08

A

B

Groups name
1 dichlorophenylethyl-imidazole
2 chlorobenzylphenole
3 quinolinole
4 16-membered macrocyclic lactones Chemical similarity Low similarity     High similarity 0.0    0.2    0.4    0.6    0.8    1.0

ANTI-CANCER TREATMENT OF PRESELECTED SUBJECTS AND SCREENING METHODS TO IDENTIFY SUSCEPTIBLE SUBJECTS

CROSS-REFERENCE TO RELATED APPLICATIONS

This is the U.S. National Stage of International Patent Application No. PCT/EP2019/063340 filed on May 23, 2019, which in turn claims the benefit of European Patent Application No. 18176272.5 filed on Jun. 6, 2018.

FIELD OF THE INVENTION

The invention provides methods of screening a subject for a proliferative disease risk factor which comprises detecting the presence or absence of target cells. The presence of target cells in the subject indicates the subject is at increased risk of developing a proliferative disease or recurrence of a previously treated proliferative disease. Methods of screening compounds for the treatment of proliferative diseases based on the presence of target cells and the expression of certain biomarkers by said target cells are also disclosed, along with appropriate compounds and their use in methods of treating such diseases.

BACKGROUND OF THE INVENTION

The World Health organization states: "Cancer causes 20% of deaths in the European Region. With more than 3 million new cases and 1.7 million deaths each year, cancer is the most important cause of death and morbidity in Europe after cardiovascular diseases". Current therapies for cancer are highly inadequate. Despite valiant efforts to shrink tumor size, patients are vulnerable to disease progression, recurrence, and metastasis, the manifestations of the regenerative properties of cancer.

A great difficulty in combating cancer lies in the fact that cancer cells are plastic, meaning that a cell can assume different states. Each state operates different signal transduction pathways and is susceptible to different treatments. These differences can be so great that a treatment that kills the cell in one state may actually help the cell in another state to grow better. For example, cancer cells in a state characterized by high Hes3 expression can be killed by Hes3 RNA interference whereas the same cells in a low Hes3 expression state are mostly unaffected. Also, whereas treatment with a JAK inhibitor improves the growth of cells in the Hes3 high state, it kills cells in the Hes3 low state.

This fundamental problem is hindering drug discovery programs. Most drug screening platforms use established media formulations that maintain the cells in a Hes3 low state. Consequently, the drugs that are identified are effective against this state and not necessarily against the Hes3 high state. Therefore, when these drugs are used therapeutically, they are able to kill many cells (the Hes3 low cells), thus shrinking the tumor but they are not able to kill the Hes3 high cells and the tumor comes back. It almost always comes back in a more aggressive form and it is speculated that this is because the Hes3 high cells are more primitive and more capable of regenerating the tumor. In other words, Hes3 high cells behave as cancer stem cells (CSC).

More specifically, cell culture systems used in basic research and drug screening programs are not sufficiently able to model the plastic properties of cancer cells. For example, under commonly-used serum-containing systems, brain tumor cells have a homogeneously large morphology, express low levels of Hes3, and their growth is not opposed by Hes3 RNA interference; in contrast, in serum-free containing systems supplemented with mitogens they have a homogeneously small morphology similar to that of non-cancerous neural stem cells, express high levels of Hes3 and Hes3 RNA interference induces cell death (Park et al., 2013). It is therefore likely that each different culture condition is only able to interrogate a specific state of these cells. This is an important limitation because it is likely that in the changing microenvironment of a tumor, a cell may be able to adopt different states during its lifespan, each of which may be susceptible to different anti-cancer treatments (Kodack et al., 2017).

It is important to try and define the different states that a tumor cell can assume under different culture conditions, to understand their significance to the in vivo situation, and to use these different states to identify drugs that target them. Drugs that target one state may be very different from drugs that target another. In fact, drugs that kill a cancer cell in one state may actually promote its growth in another. For example, Janus kinase (JAK) inhibition is considered as a therapeutic in oncology (Buchert et al., 2016, Mukthavaram et al., 2015), but we have also demonstrated that it powerfully promotes the growth of cultured primary human brain tumor cells with cancer stem cell characteristics in serum-free media (Park et al., 2013). JAK activity opposes the expression of Hes3 (Androutsellis-Theotokis et al., 2006), a transcriptional and passive repressor (Imayoshi and Kageyama, 2014). We previously demonstrated that glioblastoma cells can grow efficiently under defined conditions that suppress JAK activity and promote Hes3 expression. Under these conditions, Hes3 RNA interference opposes their growth (Park et al., 2013, Androutsellis-Theotokis et al., 2010a). This is of potential clinical interest as Hes3 expressing cells are found in tumor biopsies (Androutsellis-Theotokis et al., 2010a, Park et al., 2013) and www.protein-atlas.org.

In conclusion, current anti-cancer drugs show no or only limited efficacy against target cells, which leads to the fact that there is a high risk for cancer recurrence after a successful treatment of a cancer disease in a subject. Moreover, patients are insufficiently characterized in regard to the presence of target cells and, accordingly, in regard to the selection of an appropriate treatment strategy and prognosis of treatment success.

It is therefore the purpose of the invention to overcame the obstacles of the prior art and to provide methods to characterize and predefine patient groups, which are susceptible to certain treatment strategy for proliferative diseases resulting in a successful and long-lasting alleviation of diseases symptoms.

SUMMARY OF THE INVENTION

As further detailed below, the invention is based on the fact that the presence of target cells in a subject indicates the subject is at increased risk of developing a proliferative disease or recurrence of a previously treated proliferative disease.

In a first aspect, the invention provides a method of screening a subject for a proliferative disease risk factor, comprising detecting the presence or absence of target cells in said subject; the presence of target cells indicating said subject is at increased risk of developing a proliferative disease. Said method of screening a subject for a proliferative disease risk factor enables the characterization and definition of patient subgroups which are susceptible for a selected treatment strategy of a proliferative disease.

A second aspect of the invention relates to a screening method for identifying an anti-proliferative compound for use in the treatment of a subject that has been identified to be at increased risk of developing a proliferative disease, wherein said method comprises the contacting and incubating a tumor cell line, which resembles a CSC state of the target cells, with a test compound, and the selection of a test compound that reduces the cell number of the tumor cell line.

A third aspect of the present invention is a method of screening a compound for efficacy in the treatment of a proliferative disease. The method comprises providing a group of subjects characterized by the presence of target cells. The compound to be tested is then administered to the subjects, and the efficacy of the compound in the treatment of the proliferative disease is determined.

A fourth aspect of the present invention is an in vitro method of screening compounds for efficacy in treating a proliferative disease. The method comprises determining in vitro whether the compound reduces the cell number of a tumor cell line, i.e. kills cells which resemble a CSC state of the target cells, and/or inhibits the growth said tumor cells. The reduction of the cell number of said tumor cell line and/or the inhibition of the growth of said tumor cells indicate the compound is useful in treating the proliferative disease.

In a fifth aspect, the invention provides anti-proliferative compounds or a pharmaceutical composition comprising said anti-proliferative compounds for use in the prevention or treatment of a proliferative disease in a subject, wherein said subject has been preselected for treatment by a screening method comprising the detection of the presence or absence of target cells in a biological sample obtained from the subject, wherein the presence of said target cells is an indicator for the susceptibility of said subject for a positive treatment outcome with said anti-proliferative compound.

The present invention is explained in greater detail in the drawings herein and the specification set forth below.

5

Figure 1:
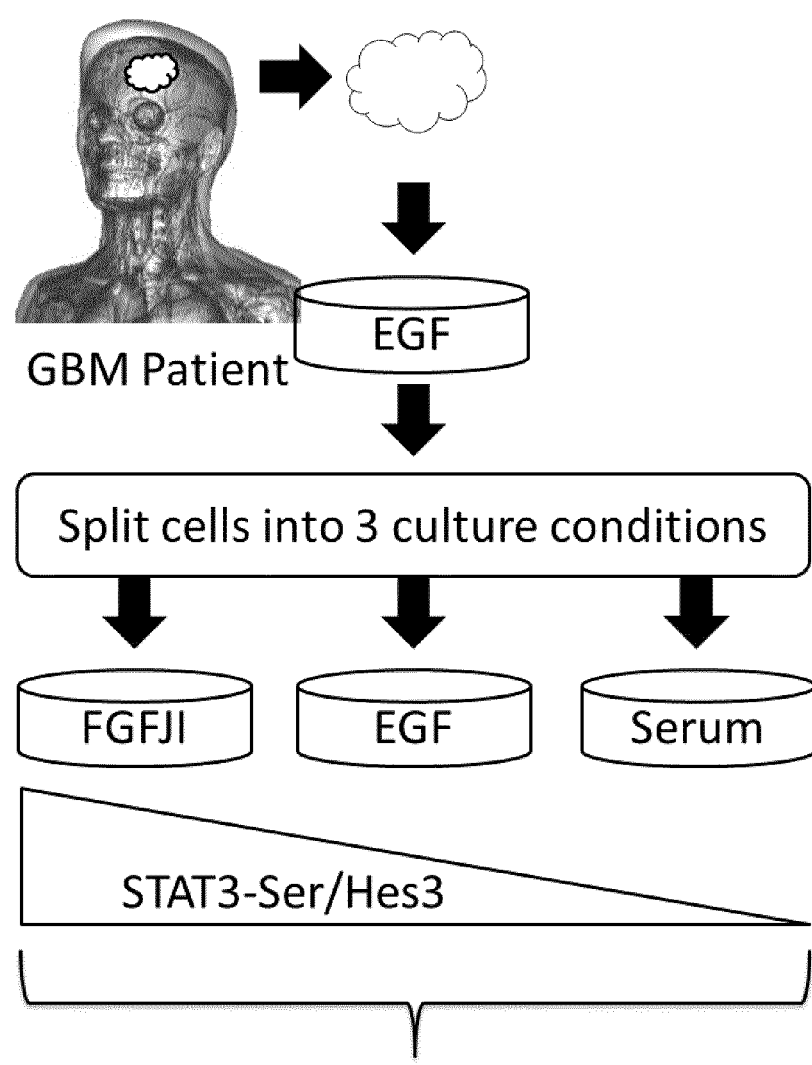
FIG. 1 shows the modelling different cell growth states in vitro. Three different primary brain tumor cell lines (each from a different patient) were established following surgical excision and propagated in serum-free medium containing EGF. Cells were then passaged into new flasks, each containing the same base medium formulation but supplemented with different factors [FGFJI, EGF, or Serum]. After five days, cells were collected for either gene expression profiling or RT-DC. [The human diagram was made on the www.biodigital.com website].

6 from this experiment treated each cell line separately. Therefore, three separate graphs are shown. The graphs are remarkably similar, demonstrating the strength of the data. (Fold expression for the controls is set to "1").

DETAILED DESCRIPTION OF THE INVENTION

The term "target cell" as used herein refers to immature cancer cells. A target cell in the sense of the invention is in particular an immature cancer cell of a certain state, i.e. characterized by low JAK activity, high STAT3-Ser to STAT3-Tyr phosphorylation ratio, and high Hes3 expression; and by physical properties, such as smallness and deformability. In particular, the target cells have properties of a Cancer Stem Cell (CSC) when placed in culture. The target cells are sensitive to Hes3 siRNA. The target cells are in a particular state characterized by high Hes3 expression. This state is further characterized by the absence or low expression of additional biomarkers selected from:

i. TPM4 (tropomyosin 4)
    ii. ASNS (asparagine synthetase (glutamine-hydrolyzing)
    iii. F3 (Coagulation factor III, tissue factor)
    iv. ADAM9 (ADAM metallopeptidase domain 9)
    v. GANAB (glucosidase, alpha; neutral AB)

or a splice variant thereof. The expression of the above biomarkers can be assessed by measuring e.g. mRNA levels, protein levels or by immunohistochemistry in a biopsy.

In a particularly preferred embodiment, this state is characterized by the absence or low expression of the biomarker TPM4 (tropomyosin 4) or a splice variant thereof.

The measurement of mRNA levels delivers a single value of mRNA levels in a biopsy. For Hes3, patients with high expression are selected. Patients with "Hes3 high expression" are defined as the top 50% of patients, preferably top 40% of patients, more preferably top 30% of patients, most preferably top 20% of patients based on the measurement of the Hes3 mRNA level. For the other 5 biomarkers, patients with low Hes3 expression were selected. Patients with "Hes3 low expression" are defined as the bottom 50% of patients, preferably bottom 40% of patients, more preferably bottom 30% of patients, most preferably bottom 20% of patients based on the measurement of the Hes3 mRNA level. Each biopsy can be assessed by comparing expression levels to other biopsies (a series of 10 or more biopsies may be required to standardize the comparison; alternatively, data can be compared to the data published at www.proteinatlas.org).

Immunohistochemistry experiments, when performed on a biopsy, deliver two values:

Incidence of cells; and.
    Intensity of staining per cell.

Both measurements and values are important to characterize a patient to comprise target cells. In a preferred embodiment of the invention, a biopsy comprising intensely stained Hes3+ cells characterizes a patient to comprise target cells. In a further preferred embodiment, a biopsy comprising cells that are completely devoid of expression of the other 5 biomarkers characterizes a patient to comprise target cells. In a further preferred embodiment, a biopsy comprising many cells expressing medium levels of Hes3 characterizes a patient to comprise target cells. In a further preferred embodiment, a biopsy comprising many cells that are mostly (even though not completely) negative for the other 5 biomarkers characterizes a patient to comprise target cells.

Most preferably, in regard to the immunohistochemistry for Hes3 (the Hes3 high cells are targeted):

Biopsies where 1% or more of the cells express high levels of Hes3 characterize a patient to comprise target cells. "High Hes3" in this case means a Hes3 level above the average intensity of each cell in a series of biopsies (or, preferably, at the top of 40%, or 30%, or 20% etc. of biopsies measured).
    Biopsies, in which at least 20% or more of the cells express at least medium Hes3 levels characterize a patient to comprise target cells.

Further most preferred in regard to the immunohistochemistry of the other 5 biomarkers TPM4, ASNS, F3, ADAM9 and GANAB, especially preferred TPM4 (biomarker low expressing cells are targeted):

Biopsies, in which 1% or more of the cells express very low levels of at least one of the 5 biomarkers, preferably of two, three or four, most preferably of all five biomarkers characterize a patient to comprise target cells. "Very low" in this case means significantly below the average intensity of each cell in a series of biopsies (e.g., 30%, or 20% etc.).
    Biopsies where at least 20% or more of the cells express medium or lower levels of at least one of the 5 biomarkers, preferably of two, three or four, most preferably of all five biomarkers characterize a patient to comprise target cells. "Medium or low levels" refer to those cells expressing below average levels of the biomarkers.

The term "risk factor" as used herein indicates subjects that possess the indicated trait or factor and face an increased risk of developing a proliferative diseases than subjects who do not possess the risk factor.

The term "treat" as used herein refers to any type of treatment that imparts a clinical improvement or alleviation in the condition of the patient, or delays the progression of the disease.

The term "proliferative disease" as used herein refers to both cancer and non-cancer disease. Preferably the proliferative disease is one characterized by the presence of target cells in the afflicted patients, in particular by the presence of target cells which do not express TPM4 or a splice variant thereof. Illustrative non-cancer diseases include inflammatory and/or immunoproliferative disorders such as arthritis, fibrosis, asthma and allergies. The invention can be used to screen for risk of and/or treat a variety of different types of cancer cells, particularly malignant (and preferably solid) tumors of epithelial or mesenchymal cells. Said "proliferative disease" is preferably selected from tumor metastasis or tumor recurrence. Examples of cancers that can be screened for risk of and/or treated by the present invention include breast cancer, prostate cancer, pancreatic cancer, adrenal cancer, melanoma, lung cancer, colon cancer, leukemia (a liquid or non-solid tumor), soft tissue and bone sarcomas, neuroendocrine tumors such as islet cell carcinoma or medullary carcinoma of the thyroid, squamous carcinomas (particularly of the head and neck), adenocarcinomas, gliosarcomas such as glioblastoma multiforme etc. The treatment of gliosarcomas is a particularly preferred target for carrying out the present invention. In a further embodiment the treatment of a cancer disease selected from breast cancer, prostate cancer, pancreatic cancer and adrenal cancer is particularly preferred according to the present invention.

In a further preferred embodiment, the proliferative disease is not angiogenesis. Treatments for cancer that exhibit either positive or negative effects on angiogenesis have been explored for many years. Unfortunately for the field of medicine, both approaches have failed to generate treatments with powerful anti-cancer properties. Also, both approaches come with worrisome side effects. Therefore, we prefer treatments that avoid effects on the vasculature and instead, directly target the cancer cell described in this patent application.

Since decades ago, scientists have tried to treat cancer using compounds that have anti-angiogenic effects. The idea was that by reducing the flow of blood to the tumor, the tumor would eventually shrink. The concept was interesting but there was a fundamental problem:

Tumors do fine with reduced blood flow and, in fact, reduced blood flow results in hypoxia which many scientists believe that stimulates cancer stem cell activation, leading to more aggressive tumors. And, anyway, cancer cells are quite able to migrate out of the affected location, if they don't like it, and establish metastases elsewhere. The fundamental problem is that to fight a cancer, you need to kill the cancer cells. Simply making their "home" a bit less comfortable is not the answer. Indicatively: Avastin, a therapeutic with anti-angiogenic properties is having a hard time proving efficacy, especially in certain tumors such as brain tumors Therefore, agents that do not show angiogenic effects are preferred in accordance with the present invention.

The inventors have identified several treatments that could be repurposed in oncology. Several of them can already be used systemically (as they normally are used in this way for their current indication) and others could be reformulated for systemic use. It is an advantage of the invention that the preferred compounds do not show unwanted side-effects in multiple tissues of the patient, which could be caused by angiogenic effects, as other drugs do. This is particularly important when targeting brain tumors where administration methods might increase the concentration of the drug in the brain. The brain is a particularly sensitive organ and side-effects relating to angiogenesis might cause very serious problems (e.g., stroke).

"Stereoisomers": All possible stereoisomers of the claimed compounds are included in the present invention. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and isolation of stereoisomers: Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

"Pharmaceutically acceptable salts": In view of the close relationship between the free compounds and the compounds in the form of their salts or solvates, whenever a compound is referred to in this context, a corresponding salt, solvate or polymorph is also intended, provided such is possible or appropriate under the circumstances. Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4 methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

"Polymorph crystal forms": Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

While the present invention is primarily concerned with the screening and treatment of human subjects, the invention may also be carried out on animal subjects such as dogs, cats, and horses for veterinary purposes.

In order to solve the purpose of the invention, the invention provides in a first aspect a method of screening a subject for a proliferative disease risk factor comprising detecting the presence or absence of target cells. The presence of target cells in the subject indicates the subject is at increased risk of developing a proliferative disease or recurrence of a previously treated proliferative disease.

The method can be carried out whether or not the subject has been previously diagnosed as being afflicted with a proliferative disease, and whether or not the subject has been previously prognosed to be at risk of developing the proliferative disease.

When the subject has previously been diagnosed as afflicted with a proliferative disease, the method may be carried out to monitor the progression of that disease, or monitor the efficacy of drug treatments that the patient has undergone for the treatment of that disease. Decreased cell numbers of target cells would be indicative of efficacy of the drug treatment. The step of detecting whether target cells are present or absent can be carried out by any suitable means. For example, the step may be carried out by detecting the presence of target cells in a biological sample taken from the subject. The biological sample is preferably a tissue sample, more preferably a biopsy obtained from a tissue which is supposed to be in a proliferative disease state.

Cancer cells are plastic, switching between signaling pathways to regulate growth under different conditions. In the tumor microenvironment this likely helps them evade therapies that target specific pathways. One such signaling state is characterized by expression of the transcription factor Hes3 and sensitivity to Hes3 knockdown and can be modeled in vitro by the use of defined culture conditions. Therefore, one method to detect target cells in a tissue sample from a subject is to investigate whether biopsies obtained from a subject co-express Hes3 and/or produce Hes3 in high concentrations. The step of detecting whether the biopsy co-expresses Hes3 can be carried out by any suitable means. For example, the step may be carried out by detecting increased Hes3 mRNA levels in cells of the subject, or by detecting increased levels of the Hes3 protein in cells of the subject. High level Hes3 expression is indicative for the presence of target cells and a subject comprising target cells is at increased risk of developing a proliferative disease.

Surprisingly, it has been found by the inventors that the target cells, independently from Hes3, are characterized by a set of biomarkers, wherein said biomarkers are selected from the group consisting of TPM4 (tropomyosin 4); Ensembl ID: ENSG00000167460;

ASNS (asparagine synthetase (glutamine-hydrolyzing)); Ensembl ID: ENSG00000070669;

F3 (Coagulation factor III, tissue factor); Ensembl ID: ENSG00000117525;

ADAM9 (ADAM metallopeptidase domain 9); Ensembl ID: ENSG00000168615; and

GANAB (glucosidase, alpha; neutral AB); Ensembl ID: ENSG00000089597;

or a splice variant thereof, wherein the absence and/or non-expression or low-level expression of at least one of the above biomarkers is indicating that said subject is at increased risk of developing a proliferative disease. Target cells are preferred that do not express or express on a low level TPM4 or a splice variant thereof.

In a preferred embodiment the biomarker TPM4 (tropomyosin 4); Ensembl ID: ENSG00000167460 is encoded by the gene, which has the nucleic acid sequence of SEQ ID NO: 101.

In a preferred embodiment the biomarker ASNS (asparagine synthetase (glutamine-hydrolyzing)); Ensembl ID: ENSG00000070669 is encoded by the gene, which has the nucleic acid sequence of SEQ ID NO: 102.

In a preferred embodiment the biomarker F3 (Coagulation factor III, tissue factor); Ensembl ID: ENSG00000117525 is encoded by the gene, which has the nucleic acid sequence of SEQ ID NO: 103.

In a preferred embodiment the biomarker ADAM9 (ADAM metallopeptidase domain 9); Ensembl ID: ENSG00000168615 is encoded by the gene, which has the nucleic acid sequence of SEQ ID NO: 104.

In a preferred embodiment the biomarker GANAB (glucosidase, alpha; neutral AB); Ensembl ID: ENSG00000089597 is encoded by the gene, which has the nucleic acid sequence of SEQ ID NO: 105.

Preferably, at least two, at least three or at least four biomarkers selected from TPM4, ASNS, F3, ADAM9 and GANAB are low-level expressed or not expressed and therefore absent in the target cells.

Most preferably, all of the biomarkers TPM4, ASNS, F3, ADAM9 and GANAB are low-level expressed or not expressed and therefore absent in the target cells.

For each of the biomarkers TPM4, ASNS, F3, ADAM9 and GANAB, several splice variants exist, resulting in several mRNA transcripts and expressed polypeptides of different length. The table below shows the known coding sequences for mRNA transcripts and expressed proteins for each of the biomarkers TPM4, ASNS, F3, ADAM9 and GANAB.

TABLE 1

| Coding sequences for known mRNA transcripts and expressed proteins for each of the biomarkers | | | |
|---|---|---|---|
| Name | Transcript ID | Translation ID | Preference |
| TPM-4 (ENSG00000167460) | | | |
| TPM4-201 | ENST00000300933.8 (SEQ ID NO: 1) | ENSP00000300933 (SEQ ID NO: 2) | Preferred |
| TPM4-222 | ENST00000646974.1 (SEQ ID NO: 3) | ENSP00000494125 (SEQ ID NO: 4) | Preferred |
| TPM4-219 | ENST00000643579.1 (SEQ ID NO: 5) | ENSP00000495347 (SEQ ID NO: 6) | Preferred |
| TPM4-202 | ENST00000344824.10 (SEQ ID NO: 7) | ENSP00000345230 (SEQ ID NO: 8) | Preferred |
| TPM4-216 | ENST00000642221.1 (SEQ ID NO: 9) | ENSP00000495135 (SEQ ID NO: 10) | Preferred |
| TPM4-224 | ENST00000647464.1 (SEQ ID NO: 11) | ENSP00000496648 (SEQ ID NO: 12) | Preferred |

TABLE 1-continued

Coding sequences for known mRNA transcripts and expressed proteins for each
of the biomarkers

| Name | Transcript ID | Translation ID | Preference |
|---|---|---|---|
| TPM4-205 | ENST00000586833.6 (SEQ ID NO: 13) | ENSP00000467087 (SEQ ID NO: 14) | Preferred |
| TPM4-221 | ENST00000646575.1 (SEQ ID NO: 15) | ENSP00000496574 (SEQ ID NO: 16) | Preferred |
| TPM4-209 | ENST00000588483.1 (SEQ ID NO: 17) | ENSP00000466106 (SEQ ID NO: 18) | Preferred |
| TPM4-204 | ENST00000586499.5 (SEQ ID NO: 19) | ENSP00000468246 (SEQ ID NO: 20) | Preferred |
| TPM4-215 | ENST00000592138.5 (SEQ ID NO: 21) | ENSP00000466654 (SEQ ID NO: 22) | Preferred |
| TPM4-211 | ENST00000589897.1 (SEQ ID NO: 23) | ENSP00000466158 (SEQ ID NO: 24) | Preferred |
| TPM4-208 | ENST00000588410.1 (SEQ ID NO: 25) | ENSP00000467250 (SEQ ID NO: 26) | Preferred |
| TPM4-210 | ENST00000588507.5 (SEQ ID NO: 27) | ENSP00000467558 (SEQ ID NO: 28) | Preferred |
| TPM4-220 | ENST00000645471.1 (SEQ ID NO: 29) | ENSP00000494867 (SEQ ID NO: 30) | |
| TPM4-223 | ENST00000647037.1 (SEQ ID NO: 31) | ENSP00000495506 (SEQ ID NO: 32) | |
| TPM4-218 | ENST00000643494.1 (SEQ ID NO: 33) | ENSP00000496389 (SEQ ID NO: 34) | |
| TPM4-217 | ENST00000642789.1 (SEQ ID NO: 35) | ENSP00000494589 (SEQ ID NO: 36) | |
| TPM4-207 | ENST00000588032.5 (SEQ ID NO: 37) | ENSP00000467319 (SEQ ID NO: 38) | |
| TPM4-212 | ENST00000590180.2 | — | |
| TPM4-214 | ENST00000591645.2 | — | |
| TPM4-213 | ENST00000591226.1 | — | |
| TPM4-206 | ENST00000587201.5 | — | |
| TPM4-203 | ENST00000586193.5 | — | |
| ASNS (ENSG00000070669) | | | |
| ASNS-201 | ENST00000175506.8 (SEQ ID NO: 39) | ENSP00000175506 (SEQ ID NO: 40) | Preferred |
| ASNS-203 | ENST00000394309.7 (SEQ ID NO: 41) | ENSP00000377846 (SEQ ID NO: 42) | Preferred |
| ASNS-202 | ENST00000394308.7 (SEQ ID NO: 43) | ENSP00000377845 (SEQ ID NO: 44) | Preferred |
| ASNS-205 | ENST00000422745.5 (SEQ ID NO: 45) | ENSP00000414901 (SEQ ID NO: 46) | Preferred |
| ASNS-209 | ENST00000444334.5 (SEQ ID NO: 47) | ENSP00000406994 (SEQ ID NO: 48) | Preferred |
| ASNS-206 | ENST00000437628.5 (SEQ ID NO: 49) | ENSP00000414379 (SEQ ID NO: 50) | Preferred |
| ASNS-214 | ENST00000455086.5 (SEQ ID NO: 51) | ENSP00000408472 (SEQ ID NO: 52) | Preferred |
| ASNS-208 | ENST00000442734.5 (SEQ ID NO: 53) | ENSP00000400422 (SEQ ID NO: 54) | Preferred |

TABLE 1-continued

Coding sequences for known mRNA transcripts and expressed proteins for each
of the biomarkers

| Name | Transcript ID | Translation ID | Preference |
|---|---|---|---|
| ASNS-207 | ENST00000437657.5 (SEQ ID NO: 55) | ENSP00000394242 (SEQ ID NO: 56) | Preferred |
| ASNS-204 | ENST00000414884.1 (SEQ ID NO: 57) | ENSP00000413797 (SEQ ID NO: 58) | Preferred |
| ASNS-210 | ENST00000448127.1 (SEQ ID NO: 59) | ENSP00000402350 (SEQ ID NO: 60) | Preferred |
| ASNS-212 | ENST00000453600.5 (SEQ ID NO: 61) | ENSP00000408797 (SEQ ID NO: 62) | Preferred |
| ASNS-211 | ENST00000451771.5 (SEQ ID NO: 63) | ENSP00000397802 (SEQ ID NO: 64) | Preferred |
| ASNS-213 | ENST00000454046.5 (SEQ ID NO: 65) | ENSP00000401651 (SEQ ID NO: 66) | |
| ASNS-217 | ENST00000495255.1 | — | |
| ASNS-215 | ENST00000462436.1 | — | |
| ASNS-216 | ENST00000487714.1 | — | |
| F3 (ENSG00000117525) | | | |
| F3-201 | ENST00000334047.11 (SEQ ID NO: 67) | ENSP00000334145 (SEQ ID NO: 68) | Preferred |
| F3-202 | ENST00000370207.4 (SEQ ID NO: 69) | ENSP00000359226 (SEQ ID NO: 70) | Preferred |
| F3-204 | ENST00000480356.1 | — | |
| F3-203 | ENST00000478217.5 | — | |
| ADAM9 (ENSG00000168615) | | | |
| ADAM9-209 | ENST00000487273.6 (SEQ ID NO: 71) | ENSP00000419446 (SEQ ID NO: 72) | Preferred |
| ADAM9-206 | ENST00000481513.5 (SEQ ID NO: 73) | ENSP00000417066 (SEQ ID NO: 74) | Preferred |
| ADAM9-203 | ENST00000466936.5 (SEQ ID NO: 75) | ENSP00000420257 (SEQ ID NO: 76) | Preferred |
| ADAM9-201 | ENST00000379917.7 (SEQ ID NO: 77) | ENSP00000369249 (SEQ ID NO: 78) | |
| ADAM9-207 | ENST00000481873.7 (SEQ ID NO: 79) | ENSP00000418437 (SEQ ID NO: 80) | |
| ADAM9-204 | ENST00000468065.5 (SEQ ID NO: 81) | ENSP00000418737 (SEQ ID NO: 82) | |
| ADAM9-208 | ENST00000484143.1 | — | |
| ADAM9-202 | ENST00000463437.2 | — | |
| ADAM9-205 | ENST00000481058.1 | — | |
| GANAB (ENSG00000089597) | | | |
| GANAB-201 | ENST00000346178.8 (SEQ ID NO: 83) | ENSP00000340466 (SEQ ID NO: 84) | Preferred |
| GANAB-216 | ENST00000540933.5 (SEQ ID NO: 85) | ENSP00000442962 (SEQ ID NO: 86) | Preferred |

TABLE 1-continued

Coding sequences for known mRNA transcripts and expressed proteins for each of the biomarkers

| Name | Transcript ID | Translation ID | Preference |
|---|---|---|---|
| GANAB-202 | ENST00000356638.7 (SEQ ID NO: 87) | ENSP00000349053 (SEQ ID NO: 88) | Preferred |
| GANAB-215 | ENST00000534779.5 (SEQ ID NO: 89) | ENSP00000435306 (SEQ ID NO: 90) | Preferred |
| GANAB-204 | ENST00000525994.1 (SEQ ID NO: 91) | ENSP00000434805 (SEQ ID NO: 92) | Preferred |
| GANAB-211 | ENST00000532402.5 (SEQ ID NO: 93) | ENSP00000432181 (SEQ ID NO: 94) | |
| GANAB-214 | ENST00000534613.5 (SEQ ID NO: 95) | ENSP00000434921 (SEQ ID NO: 96) | |
| GANAB-209 | ENST00000529737.5 (SEQ ID NO: 97) | ENSP00000432593 (SEQ ID NO: 98) | |
| GANAB-205 | ENST00000526210.1 (SEQ ID NO: 99) | ENSP00000433799 (SEQ ID NO: 100) | |
| GANAB-213 | ENST00000534422.5 | — | |
| GANAB-212 | ENST00000534419.1 | — | |
| GANAB-207 | ENST00000526732.5 | — | |
| GANAB-203 | ENST00000524437.5 | — | |
| GANAB-208 | ENST00000528503.1 | — | |
| GANAB-210 | ENST00000531563.1 | — | |
| GANAB-206 | ENST00000526392.1 | — | |

In a preferred embodiment of the invention, the TPM-4 biomarker according to the invention is a splice variant encoded by a nucleic acid having a sequence selected from SEQ ID NOs: 1, 3, 5, 7, 9, 11, 13, 15, 17, 19, 21, 23, 25, 27, 29, 31, 33, 35 and 37. More preferably, the TPM-4 biomarker according to the invention is a splice variant encoded by a nucleic acid having a sequence selected from SEQ ID NOs: 1, 3, 5, 7, 9, 11, 13, 15, 17, 19, 21, 23, 25 and 27. Even more preferably, the TPM-4 biomarker according to the invention is a splice variant which is expressed and which has an amino acid sequence selected from SEQ ID NOs 2, 4, 6, 8, 10, 12, 14, 16, 18, 20, 22, 24, 26 and 28.

In a preferred embodiment of the invention, the ASNS biomarker according to the invention is a splice variant encoded by a nucleic acid having a sequence selected from SEQ ID NOs: 39, 41, 43, 45, 47, 49, 51, 53, 55, 57, 59, 61, 63 and 65. More preferably, the ASNS biomarker according to the invention is a splice variant encoded by a nucleic acid having a sequence selected from SEQ ID NOs: 39, 41, 43, 45, 47, 49, 51, 53, 55, 57, 59, 61 and 63. Even more preferably, the ASNS biomarker according to the invention is a splice variant which is expressed and which has an amino acid sequence selected from SEQ ID NOs: 40, 42, 44, 46, 48, 50, 52, 54, 56, 58, 60, 62 and 64.

In a preferred embodiment of the invention, the F3 biomarker according to the invention is a splice variant encoded by a nucleic acid having a sequence selected from SEQ ID NOs: 67 and 69. More preferably, the F3 biomarker according to the invention is a splice variant which is expressed and which has an amino acid sequence selected from SEQ ID NOs: 68 and 70.

In a preferred embodiment of the invention, the ADAM9 biomarker according to the invention is a splice variant encoded by a nucleic acid having a sequence selected from SEQ ID NOs: 71, 73, 75, 77, 79 and 81. More preferably, the ADAM9 biomarker according to the invention is a splice variant encoded by a nucleic acid having a sequence selected from SEQ ID NOs: 71, 73 and 75. Even more preferably, the ADAM9 biomarker according to the invention is a splice variant which is expressed and which has an amino acid sequence selected from SEQ ID NOs: 72, 74 and 76.

In a preferred embodiment of the invention, the GANAB biomarker according to the invention is a splice variant encoded by a nucleic acid having a sequence selected from SEQ ID NOs: 83, 85, 87, 89, 91, 93, 95, 97 and 99. More preferably, the GANAB biomarker according to the invention is a splice variant encoded by a nucleic acid having a sequence selected from SEQ ID NOs: 83, 85, 87, 89 and 91. Even more preferably, the GANAB biomarker according to the invention is a splice variant which is expressed and which has an amino acid sequence selected from SEQ ID NOs: 84, 86, 88, 90 and 92.

Target patients should be LOW or NEGATIVE for the above mentioned biomarkers. Generally, immature cells such as target cells express fewer genes than differentiated cells, such as differentiated Cancer Cells. This is because undifferentiated cells do little more than divide and differentiated cells can assume many different fates, each of which expresses different gene sets. Thus, with the absence or low expression of the above mentioned biomarkers it is possible to define patient subgroups with particularly aggressive tumors.

The step of detecting whether the biopsy co-expresses one or more of the aforesaid biomarkers or not can be carried out by any suitable means. For example, the step may be carried out by detecting mRNA of at least one of a biomarker selected from the group consisting of TPM4, ASNS, F3, ADAM9 and GANAB in cells of the subject, or by detecting increased levels of the proteins of said biomarkers in cells of the subject. Low levels or non-detecting the mRNA and/or the protein of at least one of the foresaid biomarkers indicates that the cells tested in a biopsy obtained from a subject are target cells.

Accordingly, the present invention provides in an advantageous manner a method to detect the presence of target cells and thereby to preselect subjects in need of an effective treatment, i.e. patients who are reasonably likely to show a positive treatment efficacy for an anti-proliferative compound among the entire group of cancer patients or subjects that are prognosed to be afflicted with a proliferative disease. The invention provides a method to distinguish between patients that are reasonably likely to show a positive treatment efficacy for an anti-proliferative compound from patients that are not likely to show a positive treatment efficacy for said anti-proliferative compound. In particular, the method of the invention enables the definition of a patient subgroup that is characterized by the presence of target cells and therefore by a high risk of developing a severe cancer disease.

In a further aspect, the invention provides biomarkers for diagnosing the risk of developing a proliferative disease in a subject, wherein said biomarkers are selected from the group consisting of TPM4 (tropomyosin 4); Ensembl ID: ENSG00000167460;

ASNS (asparagine synthetase (glutamine-hydrolyzing)); Ensembl ID: ENSG00000070669;

F3 (Coagulation factor III, tissue factor); Ensembl ID: ENSG00000117525;

ADAM9 (ADAM metallopeptidase domain 9); Ensembl ID: ENSG00000168615; and

GANAB (glucosidase, alpha; neutral AB); Ensembl ID: ENSG00000089597; or a splice variant thereof. Preferred as a biomarker according to the present invention is TPM4 or a splice variant thereof.

In a further aspect the invention provides a screening method for identifying an anti-proliferative compound for use in the treatment of a subject that has been identified to be at increased risk of developing a proliferative disease, comprising the steps of:

Culturing a mammalian, preferably a human tumor cell line under a first cell culture condition which suppresses the expression of target cells biomarkers; and under a second cell culture condition, which promotes the expression of CSC biomarkers;

Contacting and incubating the tumor cell line under the first and second culture conditions with a test compound for a period of at least 6 hours, preferably 12 hours, more preferably 18 hours, most preferably 24 hours;

Determining the cell number of the tumor cell lines after incubation with the test compound under the first and second culture conditions, and of control without test compound;

Selecting a test compound that reduces the cell number of the tumor cell line cultured under the first culture condition;

wherein a compound that reduces the cell number under first culture condition compared to the control is amenable for use in the treatment of a proliferative disease.

Preferred according to the invention is a test compound that does not reduce or does not significantly reduce the cell number of the tumor cell line under the second culture condition.

The first culture condition of the screening method of the invention preferably comprises culturing the tumor cell line in FGFJI medium. "FGFJI" medium comprises basic Fibroblast Growth Factor (bFGF) including a JAK inhibitor. A JAK inhibitor is for example selected from the group consisting of 2-(1,1-Dimethylethyl)-9-fluoro-3,6-dihydro-7H-benz [h]-imidaz [4,5-f] isoquinolin-7-one;

3-Amino-5-(N-tert-butylsulfonamido-4-phenyl)-indazole;

2-Naphthyl-(N-isopropyl,N-benzyl)-β-aminoethylketone;

9-(3,4-Dichlorophenyl)-2,7-bis (dimethylaminomethyl)-3,4,5,6,7,9-hexahydro-2H-xanthene-1,8-dione;

(3Z)-5-(3-Pyridinyl)-3-(1H-pyrrol-2-ylmethylene)-1,3-dihydro-2H-indol-2-one methanesulfonate;

4-(4'-Hydroxyphenyl)amino-6,7-dimethoxyquinazoline;

N-(Pyridin-4-yl)-3-[1-(4-chlorobenzyl) indol-3-yl]-propanamide;

2-Methyl-1-phenyl-4-pyridin-2-yl-2-(2-pyridin-2-yl-ethyl) butan-1-one;

2-Naphthylvinyl Ketone;

4-[(3'-Bromo-4'-hydroxyphenyl)amino]-6,7-dimethoxy-quinazoline;

10,13-Dimethyl-17-(2-(6-sulfanylidene-3H-purin-9-yl) acetyl)-1,2,6,7,8,9,11,12,14,15,16,17-dodecahydrocy-clopenta[a]phenanthren-3-one;

1,2,3,4,5,6-Hexabromocyclohexane;

(S,E)-3-(6-Bromopyridin-2-yl)-2-cyano-N-(cyclopropyl (phenyl)methyl) acrylamide;

3-(5-(4-(2-Hydroxy-2-methyl-propionyl)-piperazin-1-yl)-2-trifluoromethyl-phenyl)-4-(1H-indol-3-yl)-pyr-role-2,5-dione;

4-Aminobenzoic hydrazide; and

The second culture condition of the screening method of the invention preferably comprises culturing the tumor cell line in serum-supplemented RPMI medium. "RPMI medium" was developed at the Roswell Park Memorial Institute (RPMI) has been found suitable for a variety of mammalian cells, including HeLa, Jurkat, MCF-7, PC12, PBMC, astrocytes, and carcinomas. RPMI medium can be obtained by a number of distributors, such as Sigma-Aldrich, GIBCO and Thermo Fisher Scientific and is distributed as RPMI-1640. "Serum-supplemented RPMI medium" comprises fetal bovine serum, for example 20% fetal bovine serum or lower, preferably 15% fetal bovine serum or lower, more preferably 10% fetal bovine serum or lower, most preferably 10% fetal bovine serum.

In a further embodiment, the screening method of the invention further comprises contacting and incubating the tumor cell line under a third culture condition with a test compound, wherein said third culture condition comprises culturing the tumor cell line in EGF medium.

The tumor cell line used in the screening method of the invention is preferably the cell line U-87.

The differences among human brain tumor cells can be assessed when the cells are cultured under three different monolayer ("2D") conditions: (a) Commonly used conditions induced by serum-containing media that are characterized by high JAK activity and low Hes3 expression (RMPI-medium), (b) Serum-free media containing the mitogen Epidermal Growth Factor (EGF) that maintain cells in an intermediate Hes3 expression level (Park et al., 2013) (this condition is oftentimes used for 3D glioblastoma cell culture systems (Brocard et al., 2015), and (c) Serum-free media containing the mitogen basic Fibroblast Growth Factor (bFGF) and a JAK inhibitor which are characterized by low JAK activity and high Hes3 expression levels (RMPI-medium). This condition is more commonly used with monolayer primary neural stem cell cultures (Androutsellis-Theotokis et al., 2006). Gene expression and mechanical properties (by real-time deformability cytometry) can be assessed in the different culture conditions. Moreover, the response to Hes3 RNA interference in the conditions characterized by high Hes3 expression can be assessed.

Human brain tumor cell line (U-87) is commonly used in drug screening efforts. In the screening method of the present invention, tumor cell line U-87 is used to identify FDA-approved compounds that are effective in cells expressing high Hes3 levels, but not effective in the more commonly used, serum-containing state with low-level or no Hes3 expression, thus focusing the method on potentially overlooked putative therapeutics.

In a further embodiment, the screening method of the invention further comprises the step of investigating the cell morphology and/or mechanical properties of the tumor cell line under the first and the second culture conditions, and optionally under the third culture condition, wherein the cells under the first culture condition show smaller and more neural stem cell-like morphology.

The analysis of the mechanical phenotype can be performed using Real-Time Deformability Cytometry (RT-DC) (Otto et al., 2015) to quantify cell size (cross-sectional area) and deformation under hydrodynamic shear stress in a microfluidic channel in each cell line and in each culture medium. All three cell lines respond to the three different culture conditions in a specific manner. The different cell culture conditions were associated with a specific morphological phenotype, which was similar for the three different cell lines: In FGFJI, cells from all three patients were smaller in size; in EGF, they were larger; in serum-containing media, they were significantly larger still.

Moreover, the data can be plotted as deformation vs. cell area. It has been found that there is an obvious grouping depending on cell culture medium, meaning that cell culture conditions affect the mechanical phenotype of the cells similarly across different cell lines.

Culture conditions affect both gene expression and mechanical phenotype in a specific manner. This correlation can be quantified. Since the size of the cell and its deformation in the channel are not independent, the apparent elastic modulus for each cell (a means of combining size and deformation into one value) can be calculated, assuming an isotropic, homogeneous elastic object, according to Mietke et al. (Mietke et al., 2015). For the RNA-sequence data analysis, a principal component analysis (PCA) can be performed in order to investigate the presence of gene expression patterns related with the experimental culture conditions and the cell lines in a non-biased (unsupervised) manner (Cannistraci et al., 2010). PCA is an unsupervised machine learning method by which original multiple variables (here referring to genes) are converted into a set of linearly uncorrelated orthogonal variables (principal components, or PCs) in such a way that the first principal component (PC1) accounts for the largest variability of the data, and the succeeding principal components (PCs) account for the variance in decreasing order under the constraint that each component is orthogonal to the preceding ones (Ringner, 2008). The average elastic modulus can now be plotted vs. PC1 for each culture condition to determine a possible correlation (linear regression of the normalized PC1 vs. elastic modulus variables). The analysis demonstrated significant correlation between the genomic pattern and cell mechanics. In fact, there was seen a grouping of all three cell lines based upon culture condition.

In a further embodiment, the screening method of the invention further comprises the step of detecting the expression of at least one biomarker by said tumor cell line under the first and the second culture conditions, and optionally under the third culture condition, and compared to a control without test compound, wherein said at least one biomarker is selected from the group consisting of:

TPM4 (tropomyosin 4); Ensembl ID: ENSG00000167460;

ASNS (asparagine synthetase (glutamine-hydrolyzing)); Ensembl ID: ENSG00000070669;

F3 (Coagulation factor III, tissue factor); Ensembl ID: ENSG00000117525;

ADAM9 (ADAM metallopeptidase domain 9); Ensembl ID: ENSG00000168615; and

GANAB (glucosidase, alpha; neutral AB); Ensembl ID: ENSG00000089597; or a splice variant thereof, wherein a test compound is selected that does not promote the expression of said at least one biomarker under the first culture condition and wherein the absence and/or non-expression of said at least one biomarker is indicating that the test compound is amenable for use in the treatment of a proliferative disease. Preferred as a biomarker according to the present invention is TPM4 or a splice variant thereof.

In a further embodiment, the screening method of the invention further comprises the step of detecting the expression of Hes3 by said tumor cell line under the first and the second culture conditions, and optionally under the third culture condition, and compared to a control without test compound, wherein a test compound is selected that decreases the amount of Hes3 in said tumor cell line under the first culture condition and wherein the said Hes3 decreasing activity is indicating that the test compound is amenable for use in the treatment of a proliferative disease.

In a preferred embodiment, Hes3 (ENSG00000173673) is encoded by a gene which has the nucleic acid if SEQ ID NO: 106.

Gene expression profiling of the above biomarkers and/or Hes3 can e.g. be performed by RNA sequencing. Respective methods and materials for RNA sequencing are known to the person skilled in the art.

In a further aspect, the invention provides an anti-proliferative compound or a pharmaceutical composition comprising said anti-proliferative compound for use in the prevention or treatment of a proliferative disease in a subject, wherein said subject has been preselected for treatment by a screening method comprising the detection of the presence or absence of target cells in a biological sample obtained from the subject. The presence of said target cells is an indicator for the susceptibility of said subject for a positive treatment outcome with said anti-proliferative compound.

The invention further provides a method of preventing or treating a proliferative diseases comprising the administering to a subject in need thereof a therapeutically effective amount an anti-proliferative compound or a pharmaceutical composition comprising said anti-proliferative compound to said subject, wherein said subject has been preselected for treatment by a screening method comprising the detection of the presence or absence of target cells in a biological sample obtained from the subject. The presence of said target cells is an indicator for the susceptibility of said subject for a positive treatment outcome with said anti-proliferative compound.

The invention further provides the use of an anti-proliferative compound or a pharmaceutical composition comprising said anti-proliferative compound in the preparation of a medicament for the prevention or treatment of a proliferative disease in a subject, wherein said subject has been preselected for treatment by a screening method comprising the detection of the presence or absence of target cells in a biological sample obtained from the subject. The presence of said target cells is an indicator for the susceptibility of said subject for a positive treatment outcome with said anti-proliferative compound.

In a preferred embodiment, the invention relates to the aforementioned anti-proliferative compound for use, method or use, wherein said preselection method further comprises the step of detecting the expression by said target cells of at least one biomarker selected from the group consisting of:

TPM4 (tropomyosin 4); Ensembl ID: ENSG00000167460;
  ASNS (asparagine synthetase (glutamine-hydrolyzing)); Ensembl ID: ENSG00000070669;
  F3 (Coagulation factor III, tissue factor); Ensembl ID: ENSG00000117525;
  ADAM9 (ADAM metallopeptidase domain 9); Ensembl ID: ENSG00000168615; and
  GANAB (glucosidase, alpha; neutral AB); Ensembl ID: ENSG00000089597;

or a splice variant thereof, wherein the absence and/or non-expression of said at least one biomarker is an indicator for the susceptibility of said subject for a positive treatment outcome with said anti-proliferative compound. Preferred as a biomarker according to the present invention is TPM4 or a splice variant thereof.

In a further preferred embodiment, the invention relates to the aforementioned anti-proliferative compound for use, method or use wherein said preselection method further comprises the step of detecting the expression by said target cells of Hes3, wherein the presence and/or expression of Hes3 is an indicator for the susceptibility of said subject for a positive treatment outcome with said anti-proliferative compound.

The antiproliferative compound according to the invention does preferably not affect angiogenesis.

In a more preferred embodiment, the anti-proliferative compound according to the invention belongs to a group selected from dichlorophenethyl-imidazoles, chlorobenzylphenoles, quinolinoles and macrocyclic lactones.

In a preferred embodiment, said dichlorophenylethyl-imidazole is a 2,4-dichlorophenylethyl-imidazole of formula (I):

(I)

wherein $R_1$-$R_{11}$ independently are H; halogen, such as fluorine, chlorine, bromine; or $C_{1-12}$ alkyl, preferably $C_{1-10}$ alkyl, more preferably $C_{1-8}$ alkyl, most preferably $C_{1-6}$ alkyl, such as methyl, ethyl, propyl, butyl, pentyl or hexyl;

$X_1$, $X_2$, $Y_1$, $Y_2$ independently are C, O, N, S or a bond.

In a preferred embodiment, said chlorobenzylphenol is a compound of formula (II):

(II)

wherein $R_1$-$R_9$ independently are H; halogen, such as fluorine, chlorine, bromine; or $C_{1-12}$ alkyl, preferably $C_{1-10}$ alkyl, more preferably $C_{1-8}$ alkyl, most preferably $C_{1-6}$ alkyl, such as methyl, ethyl, propyl, butyl, pentyl or hexyl; and X is C, O, N, or S.

In a preferred embodiment, said quinolinole is a compound of formula (III):

(III)

wherein $R_1$-$R_7$ independently are H; halogen, such as fluorine, chlorine, bromine; or $C_{1-12}$ alkyl, preferably $C_{1-10}$ alkyl, more preferably $C_{1-8}$ alkyl, most preferably $C_{1-6}$ alkyl, such as methyl, ethyl, propyl, butyl, pentyl or hexyl.

Most preferably, the anti-proliferative compound according to the invention is selected from the group consisting of abamectin, doramectin, quinestrol, benzethonium Cl, ebselen, raloxifene HCl, bisacodyl, econazole nitrate, ramelteon, bithionate Na, escin, ritonavir, broxaldine, hexetidine, selamectin, broxyquinoline, lasalocid Na, sulconazole nitrate, butoconazole, levocetirizine 2HCl, suloctidil, chlorhexidine 2HCl, miconazole nitrate, tioconazole, chloroxine, moxidectin, triclosan, clioquinol, norethynodrel, vinblastine sulfate, clofoctol, oxiconazole nitrate, xylazine, dichlorophen, oxyclozanide, diltiazem HCL, and pimozide.

Even most preferably, the anti-proliferative compound according to the invention is selected from the group consisting of Ramelteon, Quinestrol, raloxifene HCl, diltiazem HCL, levocetirizine 2HCl, Norethynodrel and xylazine.

Even most preferably, the anti-proliferative compound according to the invention is selected from the group consisting of wherein said antiproliferative compound is selected from the group consisting of bithionate Na, broxyquinoline, clioquinol, clofoctol, ebselen, lasalocid Na, ramelteon and triclosan.

The following table contains more detailed information about the specific antiproliferative compounds used herein:

TABLE 2

Detailed information on the specific antiproliferative compounds.

| # | Compound name | Chemical structure | Sample publication, which includes the chemical structure |
|---|---|---|---|
| 1 | ABAMECTIN | | Wang et al., 1982<br>Wright et al., 1987 |
| 2 | BENZETH-ONIUM Cl | | Weiss et al., 1951<br>Pivnick et al., 1963 | benzyl-dimethyl-[2-[2-[4-(2,4,4-trimethylpentan-2-yl)phenoxy]ethoxy]ethyl]azanium chloride TABLE 2-continued Detailed information on the specific antiproliferative compounds.

| Compound name | Chemical structure | Sample publication, which includes the chemical structure |
|---|---|---|
| 3 BISACODYL | <br><br>[4-[(4-acetyloxyphenyl)-pyridin-2-ylmethyl]phenyl] acetate | Wald et al., 2003<br>Dreiling et al., 1959 |
| 4 BITHIONATE Na | <br><br>sodium 2,4-dichloro-6-(3,5-dichloro-2-hydroxyphenyl)sulfanylphenol | Hopper and Wood, 1958 |
| 5 BROX-ALDINE | <br><br>(5,7-dibromo-2-methylquinolin-8-yl) benzoate | Bourquin et al., 1962<br>Sharma et al., 1975 |
| 6 BROXY-QUINOLINE | <br><br>5,7-dibromoquinolin-8-ol | Rodriguez et al., 1968 |

TABLE 2-continued

Detailed information on the specific antiproliferative compounds.

| Compound name | Chemical structure | Sample publication, which includes the chemical structure |
|---|---|---|
| 7 BUTOCONA-ZOLE |  1-[4-(4-chlorophenyl)-2-(2,6-dichlorophenyl)sulfanylbutyl]imidazole | Odds et al., 1984 Droegemueller et al., 1984 |
| 8 CHLORHEX-IDINE 2HCl | Cl—H  Cl—H   (1E)-2-[6-[[amino-[(E)-[amino-(4-chloroanilino)methylidene]amino]methylidene]amino]hexyl]-1-[amino-(4-chloroanilino)methylidene]guanidine dihydrochloride | Davies et al., 1954 Foulkes, 1973 Kenyon et al, 1986 |
| 9 CHLOR-OXINE |  5,7-dichloroquinolin-8-ol | Rohde et al., 1976 Ellenrieder et al., 1970 |
| 10 CLIOQUINOL |  5-chloro-7-iodoquinolin-8-ol | Neldner, 1977 Arnett, 1947 |

TABLE 2-continued

Detailed information on the specific antiproliferative compounds.

| Compound name | Chemical structure | Sample publication, which includes the chemical structure |
|---|---|---|
| 11 CLOFOCTOL | 2-[(2,4-dichlorophenyl)methyl]-4-(2,4,4-trimethylpentan-2-yl)phenol | Danesi et al., 1985 Ghilardi and Casani, 1985 |
| 12 DICHLORO-PHEN | 4-chloro-2-[(5-chloro-2-hydroxyphenyl)methyl]phenol | Lienert et al., 1966 Miller et al., 1966 Idris et al., 1980 |
| 13 DILTIAZEM HCl | HCl [(2S,3S)-5-[2-(dimethylamino)ethyl]-2-(4-methoxyphenyl)-4-oxo-2,3-dihydro-1,5-benzothiazepin-3-yl]acetate hydrochloride | Bevan et al., 1983 Nagao et al., 1973 Sato et al., 1971 |

TABLE 2-continued

Detailed information on the specific antiproliferative compounds.

| Compound name | Chemical structure | Sample publication, which includes the chemical structure |
|---|---|---|
| 14 DORA-MECTIN | | Dutton et al., 1991 Lavy et al., 2003 |
| 15 EBSELEN | 2-phenyl-1,2-benzoselenazol-3-one | Sies et al., 1993 Schewe et al., 1995 Parnham et al., 1990 |
| 16 ECONAZOLE NITRATE | 1-[2-[(4-chlorophenyl)methoxy]-2-(2,4-dichlorophenyl)ethyl]imidazole nitric acid | Heel et al., 1978 Thienpont et al., 1975 Godefroi et al., 1969 |

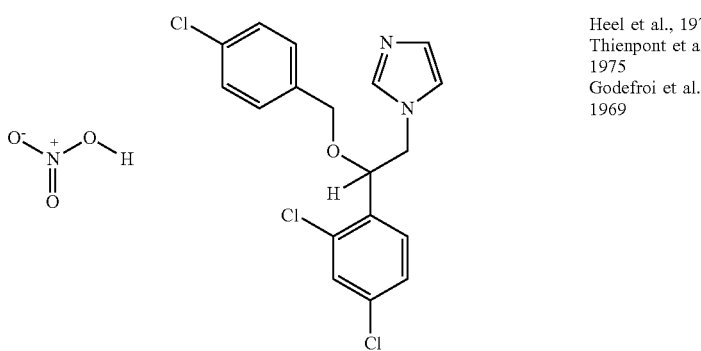

TABLE 2-continued

Detailed information on the specific antiproliferative compounds.

| Compound name | Chemical structure | Sample publication, which includes the chemical structure |
| --- | --- | --- |
| 17 ESCIN Ia | <br><br>(2S,3S,4S,5R,6R)-6-[[(3S,4S,4aR,6aR,6bS,8R,8aR,9R,10R,12aS,14aR,14bR)-9-acetyloxy-8-hydroxy-4,8a-bis(hydroxymethyl)-4,6a,6b,11,11,14b-hexamethyl-10-[(E)-2-methylbut-2-enoyl]oxy-1,2,3,4a,5,6,7,8,9,10,12,12a,14,14a-tetradecahydropicen-3-yl]oxy]-4-hydroxy-3,5-bis[[(2S,3R,4S,5S,6R)-3,4,5-trihydroxy-6-(hydroxymethyl)oxan-2-yl]oxyloxane-2-carboxylic acid | Voigtlander and Rosenberg, 1963 |
| 18 HEXETIDINE | <br><br>1,3-bis(2-ethylhexyl)-5-methyl-1,3-diazinan-5-amine | Moermann and Muehlemann, 1983 |

US 12,590,963 B2

35                                                                                      36

TABLE 2-continued

Detailed information on the specific antiproliferative compounds.

| Compound name | Chemical structure | Sample publication, which includes the chemical structure |
|---|---|---|
| 19 LASALOCID Na |  sodium 6-[(3R,4S,5S,7R)-7-[(2S,3S,5S)-5-ethyl-5-[(2R,5R,6S)-5-ethyl-5-hydroxy-6-methyloxan-2-yl]-3-methyloxolan-2-yl]-4-hydroxy-3,5-dimethyl-6-oxononyl]-2-hydroxy-3-methylbenzoate | Horton and Stockdale, 1981 |
| 20 LEVO-CETIRI-ZINE 2HCl |  Cl—H    Cl—H  2-[2-[4-[(R)-(4-chlorophenyl)-phenylmethyl]piperazin-1-yl]ethoxy]acetic acid dihydrochloride | Klimek, 2009 Mansfield et al., 2010 |

TABLE 2-continued

Detailed information on the specific antiproliferative compounds.

| Compound name | Chemical structure | Sample publication, which includes the chemical structure |
|---|---|---|
| 21 MICO-NAZOLE NITRATE | <br><br>1-[2-(2,4-dichlorophenyl)-2-[(2,4-dichlorophenyl)methoxy]ethyl]imidazole<br>nitric acid | Sawyer et al., 1975<br>Van Cutsem and Thienpont, 1972<br>Godefroi et al., 1969 |
| 22 MOXIDECTIN | | Webb et al., 1991<br>Zimmerman et al., 1992 |
| 23 NORETHY-NODREL | <br><br>(8R,9S,13S,14S,17R)-17-ethynyl-17-hydroxy-13-methyl-1,2,4,6,7,8,9,11,12,14,15,16-dodecahydrocyclopenta[a]phenanthren-3-one | Edgren, 1991<br>Pullen, 1962<br>Paulsen et al., 1962 |

TABLE 2-continued

Detailed information on the specific antiproliferative compounds.

| Compound name | Chemical structure | Sample publication, which includes the chemical structure |
|---|---|---|
| 24 OXICONA-ZOLE NITRATE | (Z)-1-(2,4-dichlorophenyl)-N-[(2,4-dichlorophenyl)methoxy]-2-imidazol-1-ylethanimine nitric acid | Mixich and Thiele, 1979 Polak, 1982 |
| 25 OXYCLO-ZANIDE | 2,3,5-trichloro-N-(3,5-dichloro-2-hydroxyphenyl)-6-hydroxybenzamide | Mrozik et al., 1969 Rajamuthiah et al., 2015 |
| 26 PIMOZIDE | 3-[1-[4,4-bis(4-fluorophenyl)butyl]piperidin-4-yl]-1H-benzimidazol-2-one | Beninger and Hahn, 1983 Janssen et al., 1968 |

TABLE 2-continued

Detailed information on the specific antiproliferative compounds.

| Compound name | Chemical structure | Sample publication, which includes the chemical structure |
|---|---|---|
| 27 QUINESTROL |  (8R,9S,13S,14S,17R)-3-cyclopentyloxy-17-ethynyl-13-methyl-7,8,9,11,12,14,15,16-octahydro-6H-cyclopenta[a]phenanthren-17-ol | Roland et al., 1966 Cohen, 1966 |
| 28 RALOXIFENE HCl |  [6-hydroxy-2-(4-hydroxyphenyl)-1-benzothiophen-3-yl]-[4-(2-piperidin-1-ylethoxy)phenyl]methanone hydrochloride | Buelke-Sam et al, 1998 Cummings et al., 1999 Delmas, 2002 |
| 29 RAMELTEON |  N-[2-[(8S)-2,6,7,8-tetrahydro-1H-cyclopenta[e][1]benzofuran-8-yl]ethyl]propanamide | Kato et al., 2005 Greenblatt et al., 2007 |

TABLE 2-continued

Detailed information on the specific antiproliferative compounds.

| Compound name | Chemical structure | Sample publication, which includes the chemical structure |
|---|---|---|
| 30 RITONAVIR | <br><br>1,3-thiazol-5-ylmethyl N-[(2S,3S,5S)-3-hydroxy-5-[(2S)-3-methyl-2-[[methyl-[(2-propan-2-yl-1,3-thiazol-4-yl)methyl]carbamoyl]amino]butanoyl]amino]-1,6-diphenylhexan-2-yl]carbamate | Lea and Faulds, 1996<br>Nachman et al., 2000<br>Walmsley et al., 2002 |
| 31 SELAMECTIN | | Benchaoui et al., 2000<br>Chailleux and Paradis, 2002 |
| 32 SULCONA-ZOLE NITRATE | <br><br>1-[2-[(4-chlorophenyl)methylsulfanyl]-2-(2,4-dichlorophenyl)ethyl]imidazole nitric acid | Benfield and Clissold, 1988<br>Akers et al., 1989 |

TABLE 2-continued

Detailed information on the specific antiproliferative compounds.

| Compound name | Chemical structure | Sample publication, which includes the chemical structure |
|---|---|---|
| 33 SULOCTIDIL | 2-(octylamino)-1-(4-propan-2-ylsulfanylphenyl)propan-1-ol | Chung et al. 1988 Robertson et al., 2012 |
| 34 TIOCONA-ZOLE | 1-[2-[(2-chlorothiophen-3-yl)methoxy]-2-(2,4-dichlorophenyl)ethyl]imidazole | Clayton et al., 1982 Marriott et al., 1983 |
| 35 TRICLOSAN | 5-chloro-2-(2,4-dichlorophenoxy)phenol | Lyman and Furia, 1969 Mandel, 1994 |

TABLE 2-continued

Detailed information on the specific antiproliferative compounds.

| Compound name | Chemical structure | Sample publication, which includes the chemical structure |
| --- | --- | --- |
| 36 VIN-BLASTINE SULFATE | | Gobbi et al., 1996 Hertz et al., 1960 |
| 37 XYLAZINE | <br>N-(2,6-dimethylphenyl)-5,6-dihydro-4H-1,3-thiazin-2-amine | Clarke and Hall, 1969 |

The present invention is based on a novel signal transduction pathway that regulates plastic cells, including CSC, the so-called "STAT3-Ser/Hes3 Signaling Axis". The use of this unique pathway provides an advantage in drug screening efforts: It can be used as a molecular "blueprint" to devise cell culture conditions that maintain cancer cells in the Hes3 high state (expressing high levels of Hes3), in order to identify drugs that kill them.

Specifically, several FDA-approved drugs were identified with the goal to repurpose them for use in oncology. These drugs as identified herein are not efficient at killing Hes3 low cells (expressing no or only low levels of Hes3), but are very efficient at killing the cells in the Hes3 high state.

The screening methods of the invention enable the introduction/administration of these drugs to a specific patient subgroup that is more likely to respond to the treatments. Thereby, it is avoided prescribing a medication comprising said drugs to patients who may not benefit from the medication. Moreover, there is provided a better therapeutic prediction to those patients who will be prescribed with the drugs. The patient selection rationale is based on the observations that Hes3 high cells behave very differently from Hes3 low cells. More specifically, tumor cells were placed in culture media that lock them in a Hes3 high state vs. a Hes3 low state, which allowed the identification of useful biomarkers that distinguish between the two culture media and cell states. Moreover, cells were placed in culture media that lock them in a Hes3 high state and then Hes3 was knocked down, thereby enabling the identification of additional useful biomarkers.

Biomarkers were identified by experiments and interrogation, using RNA sequencing, of the entire transcriptome of the cells. For the biomarker identification experiments three different primary human brain tumor cell lines were used, each from a different patient. Therefore, the results are generalizable to many patients.

Following data analysis, a number of putative biomarkers was identified that could be used for selecting a patient subgroup. To select the best biomarkers, a number of criteria was applied: The widely used human brain tumor cell line "U-87" was chosen for performing the screening method for suitable anti-proliferative compounds. It was shown that this cell line can be cultured under improved cell culture conditions (grown in FGFIJ medium) and that it behaves like a CSC (i.e., it expresses high levels of the transcription factor Hes3, Hes3 RNA interference opposes growth, cell morphology and global gene expression are different) than when cultured in more commonly-used platforms.

A library of 1,600 FDA-approved compounds was screened on U-87 cells cultured in the improved conditions. Each drug was screened at both 3 micromolar and 10 micromolar concentrations. Cell viability was assessed by measuring ATP levels.

Drugs that opposed cell viability were further investigated. These drugs were re-screened under the more common cell culture conditions (in serum-supplemented RMPI medium, where cells are more differentiated). Some drugs were identified that also opposed growth under the more differentiated conditions. We also identified some drugs that only opposed growth in the improved conditions. It was focused on the latter drugs only as being the target compounds of the present invention.

Altogether 37 compounds opposed cell viability only under the improved (more CSC-like) conditions (when cells were cultured in FGFJI medium).

Overall, 7 compounds have been identified that in the oppose viability of U-87 cells only when these are cultured under the improved conditions (Hes3 high, FGFJI medium). The 7 selected compounds are advantageous because they are orally available and can be administered orally. The relevant lists of compounds is shown in the table below:

TABLE 3

List of the 7 compounds.

| | Compound | Radar | BBB | PGP | Function |
|---|---|---|---|---|---|
| 1 | Ramelteon | YES | YES | YES | Sleep |
| 2 | Quinestrol | YES | YES | NO | Estrogen replacement |
| 3 | RALOXIFENE HCl | YES | ? | ? | Estrogen ag/antag, anti-breast cancer |
| 4 | DILTIAZEM HCl | YES | NO | YES | Ca blocker/vasodilator |
| 5 | LEVOCETIRIZINE 2HCl | YES | YES | YES | antihistamine |
| 6 | Norethynodrel | YES | YES | YES | Contraceptive |
| 7 | XYLAZINE | YES | YES | NO | Vet Med adren alpha-2 agonist |

"Radar" is an indication of oral bioavailability; "BBB" denotes whether the drugs are predicted to cross the blood-brain-barrier; "PGP" denotes whether the drugs are likely to be substrates for exporter mechanisms on cells.

Another selection strategy focused on the drug efficacy scores in the in vitro screening assays. Overall, a list of 8 preferred compounds have been identified that oppose viability of U-87 cells only when these are cultured under the improved conditions (Hes3 high, FGFJI medium) and that exhibit a strong efficacy as measured in the ATP assay. A score between –11 to –3 in the ATP assay is preferred. The relevant list of compounds is shown in the table below:

TABLE 4

List of the 8 compounds.

| | Compound | Radar | BBB | Function | ATP assay score (3 μM, 10 μM) |
|---|---|---|---|---|---|
| 1 | BITHIONATE Na | YES | ? | anthelmintic | –11, –10 |
| 2 | BROXYQUINOLINE | YES | ? | antiprotozoal | –11, –8 |
| 3 | CLIOQUINOL | YES | Y | antifungal | –11, –7 |
| 4 | CLOFOCTOL | YES | ? | antibiotic | –11, –5 |
| 5 | EBSELEN | YES | Y | anti inflammatory | –9 |
| 6 | LASALOCID Na | YES | ? | antibiotic | –10, –5 |
| 7 | RAMELTEON | YES | Y | sleep agent | –5 |
| 8 | TRICLOSAN | YES | Y | antibiotic | –7, –5 |

The invention is now described in more detail and in the following working examples.

Details on the Selected Biomarkers

| TPMA (tropomyosin 4); Ensembl ID: ENSG00000167460 | |
|---|---|
| RNA expression in gliomas: | 55 FPKM |
| How many types of cancer express its RNA: | 17/17 |
| How many types of cancer express its protein: | 20/20 |
| How good is the antibody used above: | "Approved" |
| Favorability of gene expression in gliomas: | None |
| Histopathology expression range: | Broad (i.e., from –ve to +ve patients) |
| Favorability of gene expression in other cancers: | Unfavorable (2 cancer types) |
| Direction of expression in our experiments: | UP after Hes3 siRNA AND regulated by culture conditions |
| Target patient group: | Biomarker negative patients |
| Special attribute: | Biomarker identified by both experiments (i.e., changing culture conditions AND Hes3 siRNA) |

| ASNS (asparagine synthetase (glutamine-hydrolyzing)); Ensembl ID: ENSG00000070669 | |
|---|---|
| RNA expression in gliomas: | 16 FPKM |
| How many types of cancer express its RNA: | 17/17 |
| How many types of cancer express its protein: | 14/20 |
| How good is the antibody used above: | "Approved" |
| Favorability of gene expression in gliomas: | None |
| Histopathology expression range: | Broad |
| Favorability of gene expression in other cancers: | Unfavorable (4 cancer types) |
| Direction of expression in our experiments: | UP after Hes3 siRNA |
| Target patient group: | Biomarker negative patients |
| Special attribute: | Unfavorable in 4 cancer types (this number is quite high) |

| F3 (Coagulation factor III, tissue factor); Ensembl ID: ENSG00000117525 | |
|---|---|
| RNA expression in gliomas: | 67 FPKM |
| How many types of cancer express its RNA: | 17/17 |
| How many types of cancer express its protein: | 17/20 |
| How good is the antibody used above: | "Approved" |
| Favorability of gene expression in gliomas: | None. Tendency for Unfavorable |
| Histopathology expression range: | Broad |
| Favorability of gene expression in other cancers: | Unfavorable (2 cancer types) |
| Direction of expression in our experiments: | DOWN as conditions increase Hes3 |
| Target patient group: | Biomarker negative patients |
| Special attribute: | Strong separation; patients are either –ve or very high. Also, Unfavorable tendency in gliomas, so particularly unexpected biomarker. |

| ADAM9 (ADAM metallopeptidase domain 9); Ensembl ID: ENSG00000168615 | |
| --- | --- |
| RNA expression in gliomas: | 30 FPKM |
| How many types of cancer express its RNA: | 17/17 |
| How many types of cancer express its protein: | Pending from www.proteinatlas.org |
| How good is the antibody used above: | Pending |
| Favorability of gene expression in gliomas: | None from www.proteinatlas.org. |
| A recent publication (PMID: 27571068): | Unfavorable! |
| Histopathology expression range: | Pending |
| Favorability of gene expression in other cancers: | Unfavorable (5 cancer types) |
| Direction of expression in our experiments: | DOWN as conditions increase Hes3 |
| Target patient group: | Biomarker negative patients |
| Special attribute: | This is a new biomarker. Unfavorable in 5 cancers as well as in gliomas (the latter according to a recent publication). |

| GANAB (glucosidase, alpha; neutral AB); Ensembl ID: ENSG00000089597 | |
| --- | --- |
| RNA expression in gliomas: | 84 FPKM |
| How many types of cancer express its RNA: | 17/17 |
| How many types of cancer express its protein: | 19/20 |
| How good is the antibody used above: | "Enhanced" |
| Favorability of gene expression in gliomas: | None |
| Histopathology expression range: | Broad |
| Favorability of gene expression in other cancers: | Unfavorable (2 cancer types) |
| Direction of expression in our experiments: | UP after Hes3 siRNA |
| Target patient group: | Biomarker negative patients |
| Special attribute: | Overall sturdy (many cancer types, good antibody staining) |

Examples of the Invention

Example 1: Cell Culture

Three primary human brain tumor cell lines ("X01", "X04", and "X08") were used in this work. X01 and X04 are from patients with glioblastoma multiforme whereas X08 is from a patient with gliosarcoma (Soeda et al., 2008, Soeda et al., 2009). The cell lines were previously established from acutely resected human tumor tissues. All human tissues in this study were obtained during surgical resections from patients with newly diagnosed or recurrent tumors.

Materials in excess of pathological evaluation were used for research purposes in accordance with protocols approved by the Institutional Review Board of the National Institutes of Health. Written consent was obtained and all research tumor tissues were de-identified (Park et al., 2013). Resected tissue was triturated in N2 medium containing 20 ng/ml EGF with a 1 ml pipette until no tissue clamps were seen; the triturate was allowed to settle for 1 min and the supernatant was collected, diluted in N2 containing EGF and plated. Cells were expanded in serum-free DMEM/F12 medium (Mediatech, 10-090-CV) with $N_2$ supplement and EGF (20 ng/ml, R&D Systems) for 5 days under 5% oxygen conditions and were re-plated fresh or from frozen stocks at 1,000-10,000 cells per cm2. This was repeated for several passages. For the experiments, frozen stocks were thawed and expanded as described before and upon passaging, they were re-plated into different culture conditions as described in the Results section. Gene expression and mechanical analysis were performed after five days in culture. Cell culture experiments were generally performed in accordance with Poser et al, 2013 (Poser and Androutsellis-Theotokis, 2013).

Human brain tumor cell line U-87 MG (ATCC® HTB-14™) was also used. This was propagated in serum-containing RPMI medium. It was then re-plated in different media according to experimental needs.

Results

The primary glioblastoma cell lines used here had never been exposed to serum or other undefined culture media supplements. Their tumorigenic potential was previously established (Soeda et al., 2009). For standard expansion and passaging, cell lines were cultured in monolayer form in the presence of Epidermal Growth Factor (EGF) (FIG. 1), based on previously published methods (Park et al., 2013). Each cell line was split into separate flasks and cultured in three distinct conditions for five days, containing: (a) 10% fetal bovine serum (Serum), (b) EGF, or, (c) basic Fibroblast Growth Factor (bFGF) including a JAK inhibitor (bFGF+ JAK Inhibitor= "FGFJI"), all in a 5% oxygen incubator. The three conditions maintain the cells under different signal transduction states, all of which allow for efficient growth (Park et al., 2013). Serum contains many strong activators of the JAK-STAT signaling pathway which oppose Hes3 expression (Androutsellis-Theotokis et al., 2006); EGF is a relatively mild activator of the JAK-STAT pathway and maintains these cells in a state of intermediate Hes3 expression; FGFJI suppresses the JAK-STAT pathway and strongly promotes Hes3 expression. Following culture under each specific condition, cells were collected for RNA sequencing (Wang et al., 2009) or real-time deformability cytometry (RT-DC) (Otto et al., 2015).

Example 2: Gene Expression Profiling by RNA Sequencing

RNA was extracted using the High Pure RNA Isolation Kit (Roche) and samples were subjected to the standard workflow for strand-specific RNA-Seq library preparation (Ultra Directional RNA Library Prep, NEB). Libraries were equimolar, pooled and sequenced on an Illumina HiSeq 2500, resulting in ca. 26-35 million single-end reads per library. After sequencing, FastQC (http://www.bioinformatics.babraham.ac.uk/) was used to perform a basic quality control on the resulting reads. As an additional control, library diversity was assessed by redundancy investigation in the reads. Reads were aligned to the human reference (GRCh38) using GSNAP (v 2014 Dec. 17) (Wu and Nacu, 2010) and Ensembl gene annotation version 78 was used to detect splice sites. The uniquely aligned reads were counted with featureCounts (v1.4.6) (Liao et al., 2014) and the same Ensembl annotation. Normalization of the raw read counts based on the library size and testing for differential expression between conditions was performed with the DESeq2 R package (v1.6.2) (Love et al., 2014). Experiments addressing the effect of cell culture media composition were performed in triplicates; effects addressing the effect of Hes3 RNA interference were performed in quadruplicates.

Example 3: Systems Biomedical Analysis (Experiments Under Different Culture Conditions)

For the RNA-seq. data analysis, we performed principal component analysis (PCA) in order to investigate the presence of gene expression patterns related with the experimental culture conditions and the cell lines in a non-biased (unsupervised) manner (Cannistraci et al., 2010). PCA is an unsupervised machine learning method by which original multiple variables (here referring to genes) are converted into a set of linearly uncorrelated orthogonal variables (principal components, or PCs) in such a way that the first PC (PC1) accounts for the largest variability of the data, and the succeeding PCs account for the variance in decreasing order under the constraint that each component is orthogonal to the preceding ones (Ringner, 2008). For the heat map generation, PC1 loadings were normalized according to the maximum absolute value to −1 and 1. The top 1% most significantly regulated genes were selected for further analysis. For the x-axis, samples were ordered from X01, X04 and X08 for each culture condition. For the y-axis, the genes were ordered according to an unsupervised machine learning technique, MCE, by using the Euclidean distance (Cannistraci et al., 2013, Cannistraci et al., 2010). The color bar indicates the expression, as the log 10 (1+raw expression read counts).

Results

Figure 2:
FIG. 2 shows a plot of principal component analysis (PCA). Plot of principal component analysis (PCA) shows a patient discriminative pattern of culture condition (PC1) versus patient cell line (PC2). Numbers indicate SVM maximum margin computation values among the three culture conditions groups.
Figure 2:
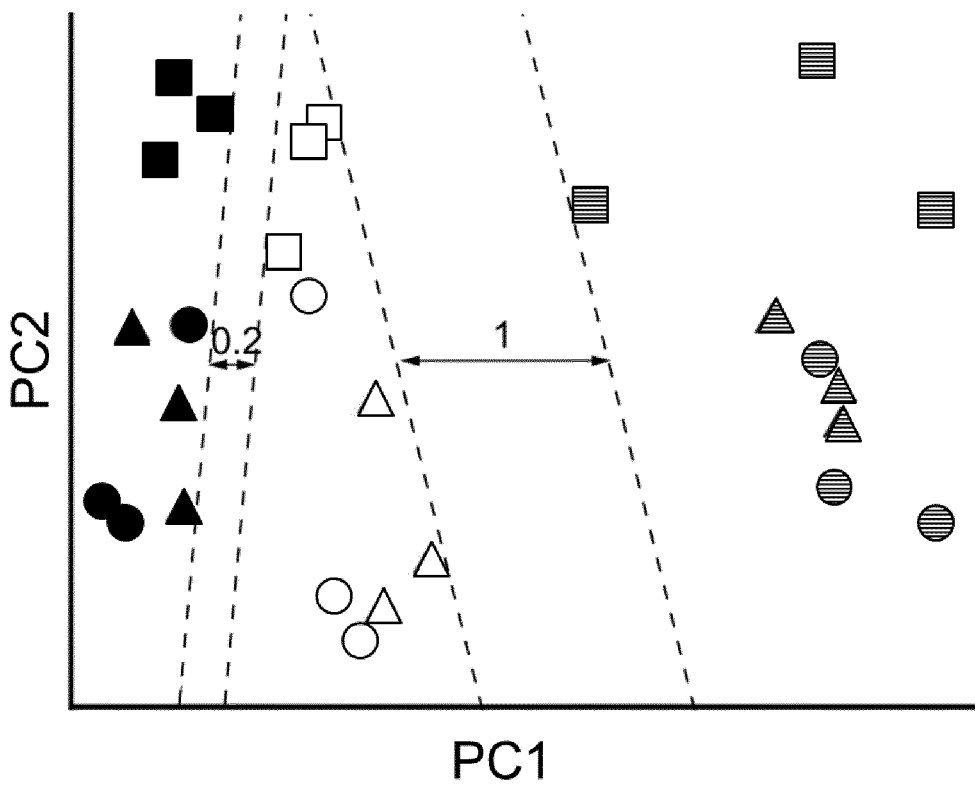

A Principal Component Analysis (PCA) was performed and it was found that PC1 is related with culture condition and PC2 is related with cell line (each cell line is derived from a different patient) (FIG. 2). The data show an undisputable group discrimination (evident linear separations) based upon PC1, suggesting that all three cell lines respond similarly in terms of gene expression when placed under each culture condition. The Serum culture condition is separated from the other two conditions by a larger margin (support vector machine (Cortes and Vapnik, 1995) maximum margin computation values: FGFJI to EGF: 0.2; EFG to Serum: 1.0).

Example 4: Mechanomics Network

In order to determine the main functions related to the top 1% most significantly regulated genes, we performed functional annotation analysis in DAVID (Huang da et al., 2009b, Huang da et al., 2009a) using Ensemble geneID. Then all the significant GO terms and KEGG pathways were considered that achieved a Benjamini corrected p-value lower than 0.05. Since the highest significant GO term (GO: 0008092~cytoskeletal protein binding) and the highest significant pathway (hsa04510: Focal adhesion) were related with cell mechanics, it was decided to further investigate the list of genes contained in the top 20 significant cell mechanics-related GO annotations. To this aim, it was proceeded to the construction of a 'mechanomic' protein-protein interaction (PPI) network where only those genes belonging to the top 20 significant cell mechanics-related GO annotations were considered (201 unique genes were retrieved from the original list of the top 1% regulated genes that were 400). Nearly half of the top 1% most significantly regulated genes are involved with cell-mechanics. STRING was used to build the PPI network (Szklarczyk et al., 2015) and the Cytoscape software for visualizations (Shannon et al., 2003). To select reliable interactions, only links validated by experimental evidence and higher than a 0.7 cut-off were considered to build the networkIn order to correct for the magnitude discrepancy of each gene (forcing an equal contribution of every gene to the final pattern) the expression of every gene is firstly normalized by dividing the sum of this gene's expression in FGFJI or EGF in the investigated module, and then all the composed genes of this module in FGFJI or EGF state are averaged to get the general expression of the particular state.

Results

The GO enrichment analysis of these genes revealed that both the most significant GO term (GO: 0008092~cytoskeletal protein binding, corrected P-Value<0.0001) and the most significant pathway (hsa04510: Focal adhesion, corrected P-Value<0.0001) are related with cell mechanics (Table 5).

TABLE 5

| GO Terms related to mechanical phenotypes derived from the list of top 400 genes. | | | |
|---|---|---|---|
| Term | Count | % | p Value |
| 008092~cytoskeletal protein binding | 53 | 13.58974 | 4.47E−18 |
| GO:0003779~actin binding | 43 | 11.02564 | 3.20E−18 |
| GO:0031012~extracellular matrix | 41 | 10.51282 | 4.26E−15 |
| GO:0005578~proteinaceous extracellular matrix | 38 | 9.74359 | 5.35E−14 |
| GO:0044420~extracellular matrix part | 24 | 6.153846 | 5.29E−14 |
| GO:0015629~actin cytoskeleton | 33 | 8.461538 | 1.38E−12 |
| hsa04510:Focal adhesion | 33 | 8.461538 | 1.40E−12 |
| GO:0005856~cytoskeleton | 82 | 21.02564 | 5.84E−12 |
| GO:0030036~actin cytoskeleton organization | 30 | 7.692308 | 8.19E−13 |
| GO:0044421~extracellular region part | 64 | 16.41026 | 2.27E−11 |
| GO:0030029~actin filament-based process | 31 | 7.948718 | 7.25E−13 |
| GO:0007010~cytoskeleton organization | 40 | 10.25641 | 9.95E−12 |
| GO:0022610~biological adhesion | 52 | 13.33333 | 1.34E−11 |
| GO:0006928~cell motion | 42 | 10.76923 | 8.76E−12 |
| GO:0007155~cell adhesion | 52 | 13.33333 | 1.29E−11 |
| hsa04512:ECM-receptor interaction | 20 | 5.128205 | 1.46E−10 |
| GO:0043062~extracellular structure organization | 21 | 5.384615 | 7.03E−09 |
| GO:0005576~extracellular region | 94 | 24.10256 | 3.98E−08 |
| GO:0032989~cellular component morphogenesis | 32 | 8.205128 | 3.76E−08 |
| GO:0030198~extracellular matrix organization | 16 | 4.102564 | 6.34E−08 |

For the Gene Ontology (GO) Term analysis, the 400 top genes were used for DAVID annotation analysis (using Ensemble geneID). We focused on mechanics-related GO terms which were sorted by Benjamini multiple correction and the top 20 GO terms were chosen for further network construction.

Example 5: Pathway Analysis (Cell Culture Condition Experiments)

Pathway analysis was done using two different methods. First, Gene Ontology (GO) term and KEGG pathway enrichment of differentially expressed genes (adjusted p<0.05) were calculated using DAVID Bioinformatics Resource (Huang da et al., 2009b) based on Ensembl IDs. The background set consisted of all genes passed to DESeq2. Second, the R package fgsea (https://doi.org/10.1101/

060012) was used for a full gene set enrichment analysis based on all genes.-log 10 (p-value)· log 2 (fold-change) was used as rank function and 100,000 permutations were done for enrichment p-value calculation. KEGG pathways were plotted using the R package pathview (Luo et al., 2002).

Example 6: Comparison of Growth Media Experiment with Hes3 Si-RNA Knockdown Experiment Raw gene read counts of all samples were regularized logarithmic transformed (rlog) using DESeq2 R package (Love et al., 2014). Samples were clustered using Spearman rank correlation, Pearson correlation and Euclidean distance based on transformed counts of all genes. Cluster heatmaps were drawn using the ComplexHeatmap R package (Gu et al., 2016). Results Hes3 RNA interference opposes the growth of all three primary cell lines used here, when cultured in FGFJI (Park et al., 2013), pointing to possible core molecular mechanisms that may be targeted in oncology. Here it was set out to identify the genes and signaling pathways affected by Hes3 RNA interference in vitro that are common in all three cell lines, and which may provide therapeutically amenable putative drug targets.

The $X_{01}$, $X_{04}$, and $X_{08}$ cell lines were cultured under FGFJI conditions (i.e., under conditions that maintain high Hes3 expression). Then, RNA interference was performed with an siRNA that has been previously validated to oppose Hes3 expression and cell viability (Park et al., 2013). 24 hours later, we collected RNA for transcriptomics analysis by RNA sequencing methods.

Figure 3:
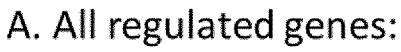
FIG. 3 shows the gene expression regulation following Hes3 RNA interference. (A-C) Number of genes regulated by Hes3 siRNA in each of the three cell lines, compared to control (scrambled) siRNA [abs (log 2-fold change)>1, and p-adjusted <0.05]. Data are split into all genes regulated, up-regulated genes, and down-regulated genes.

Hes3 RNA interference induced gene expression changes in all three cell lines. It was focused on those genes that were significantly regulated at least two-fold from control (scrambled) siRNA (log 2-fold change cut-off, with an adjusted p-value <0.05). There were 290 differentially regulated genes for $X_{01}$, 449 for $X_{04}$, and 56 for $X_{08}$. 25 genes were common to all three cell lines (triple-common) (FIG. 3A-C, Table 6).

TABLE 6

Triple-common regulated genes in the cell lines
X01, X04, and X08, following Hes3
RNA interference (log2 Fold change, p-adj <0.05).

| Ensembl_ID | Gene_Symbol | Description |
|---|---|---|
| | Upregulated by Hes3 siRNA | |
| ENSG00000167460 | TPM4 | tropomyosin 4 |
| ENSG00000254332 | GS1-44D20.1 | |
| ENSG00000089597 | GANAB | glucosidase, alpha; neutral AB |
| ENSG00001171700 | RGS19 | regulator of G-protein signaling 19 |
| ENSG00000204611 | ZNF616 | zinc finger protein 616 |
| ENSG00000213846 | AC098614.2 | |
| ENSG00000101255 | TRIB3 | tribbles pseudokinase 3 |
| ENSG00000158373 | HIST1H2BD | histone cluster 1, H2bd |
| ENSG00000128165 | ADM2 | adrenomedullin 2 |
| ENSG00000139269 | INHBE | inhibin, beta E |
| ENSG00000070669 | ASNS | asparagine synthetase (glutamine-hydrolyzing) |
| ENSG00000272405 | RP11-284F21.10 | |
| ENSG00000100889 | PCK2 | phosphoenolpyruvate carboxy-kinase 2 (mitochondrial) |
| ENSG00000182459 | TEX19 | testis expressed 19 |
| ENSG00000261371 | PECAM1 | platelet/endothelial cell adhesion molecule 1 |
| ENSG00000138678 | AGPAT9 | 1-acylglycerol-3-phosphate O-acyltransferase 9 |

TABLE 6-continued

Triple-common regulated genes in the cell lines
X01, X04, and X08, following Hes3
RNA interference (log2 Fold change, p-adj <0.05).

| Ensembl_ID | Gene_Symbol | Description |
|---|---|---|
| ENSG00000105550 | FGF21 | fibroblast growth factor 21 |
| ENSG00000235513 | RP4-756G23.5 | |
| ENSG00000272068 | RP11-284F21.9 | |
| | Downregulated by Hes3 siRNA | |
| ENSG00000181061 | HIGD1A | HIG1 hypoxia inducible domain family, member 1A |
| ENSG00000160877 | NACC1 | nucleus accumbens associated 1, BEN and BTB (POZ) domain containing |
| ENSG00000171150 | SOCS5 | suppressor of cytokine signaling 5 |
| ENSG00000258016 | HIGD1AP1 | HIG1 hypoxia inducible domain family, member 1A pseudogene 1 |
| ENSG00000072401 | UBE2D1 | ubiquitin-conjugating enzyme E2D 1 |
| ENSG00000248785 | HIGD1AP14 | HIG1 hypoxia inducible domain family, member 1A pseudogene 14 |
| | Downregulated from Serum to EGF AND from Serum to FGFJI | |
| ENSG00000117525 | F3 | coagulation factor III |
| | Downregulated from Serum to FGFJI | |
| ENSG00000168615 | ADAM9 | ADAM metallopeptidase domain 9 |

We found three GO Term categories that were regulated in all three cell lines by Hes3 siRNA (GO: 0005654~nucleoplasm, GO: 0005515~protein binding, GO: 0005737~cytoplasm). Additional GO Terms were found regulated when only the $X_{01}$ and $X_{04}$ cell lines were used in the analysis, of which GO: 0006260~DNA replication, GO: 0051301~cell division and GO: 0006281~DNA repair are noteworthy.

FGF21, one of the 25 triple-common genes, is a well-studied activator of the MAPK signaling pathway.

Unsupervised (non-selected) clustering of all differentially regulated genes shown in FIG. 3A-C was done based on Pearson correlation of rlog transformed expression values.

Example 7: Identification of Biomarkers TPM4, ASNS, F3, ADAM9 and GANAB

Two distinct groups of experiments were performed:

Experiment 1

Cells (3 human brain cancer cell lines, each from a different patient) were cultured under three different cell culture conditions (FGFJI, which maintains cells in a high Hes3 expression state; EGF, which maintains cells in a medium Hes3 expression state; and Serum, which maintains cells in a low Hes3 expression state). Biomarkers were identified that change significantly among these states.

Experiment 2

Cells (3 human brain cancer cell lines, each from a different patient) were cultured under FGFJI conditions (which maintains cells in a high Hes3 expression state) and then we treated them with either control or Hes3 siRNA. Biomarkers were identified whose expression significantly changes due to Hes3 siRNA.

Results

TPM4 was identified using both experiments.
F3 and ADAM9 were identified from experiment 1.
ASNS and GANAB were identified from experiment 2.

Example 8: Real-Time Deformability Cytometry

Real-time deformability cytometry (RT-DC) was per-formed as previously described (Otto et al., 2015, Mietke et al., 2015). Briefly, it allows a marker-free, continuous cell mechanical characterization of large cell populations with analysis rates greater than 100 cells/s. Cells are flowed through a microfluidic channel constriction and deformed without contact by shear stresses and pressure gradients. Cell size and deformation is extracted from the high-speed camera images in real-time and can be transformed into an elastic modulus (of stiffness of a cell) by applying an analytical model relating geometrical parameters to material properties (Mietke et al., 2015). Statistical data analysis was carried out utilizing mixed models (Bates et al., 2014b, Bates et al., 2014a) by assuming random as well as fixed effects for the experimental repeats.

Results

Figure 4:
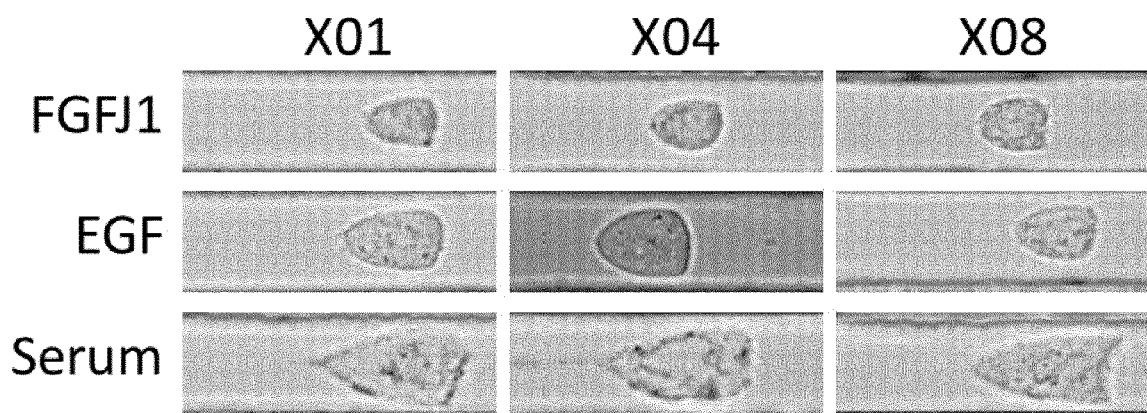
FIG. 4 shows distinct mechanical phenotypes of cells cultured in different conditions. Representative images from the different cell lines in the different culture conditions obtained by RT-DC.

Due to the cell mechanics implications raised by the gene expression data, an analysis of the mechanical phenotype was performed, using Real-Time Deformability Cytometry (RT-DC) (Otto et al., 2015) to quantify cell size (cross-sectional area) and deformation under hydrodynamic shear stress in a microfluidic channel in each cell line and in each culture medium. Example images demonstrate the specific manner by which all three cell lines respond to the three different culture conditions (FIG. 4). The different cell culture conditions were associated with a specific morpho-logical phenotype, which was similar for the three different cell lines: In FGFJI, cells from all three patients were smaller in size; in EGF, they were larger; in serum-contain-ing media, they were significantly larger still.

Figure 5:
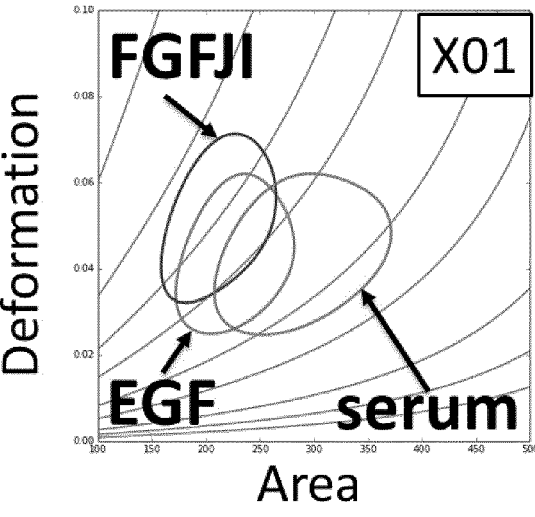
FIG. 5 shows distinct mechanical phenotypes of cells cultured in different conditions. Plots of deformation (1-circularity) vs. cell size (cross sectional area) for each cell line in each of the three culture conditions. Shown are the 50% density lines of the actual distributions.
Figure 5:
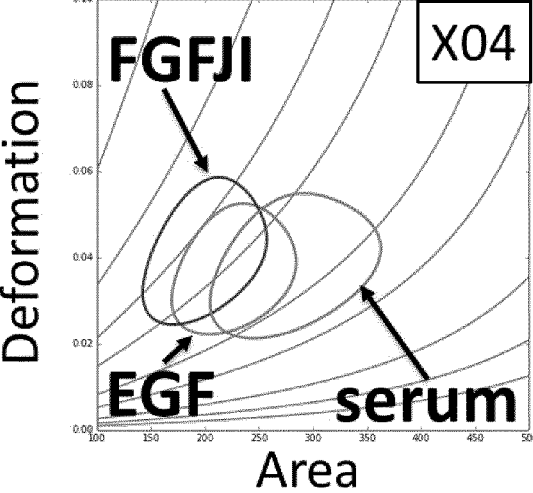
Figure 5:
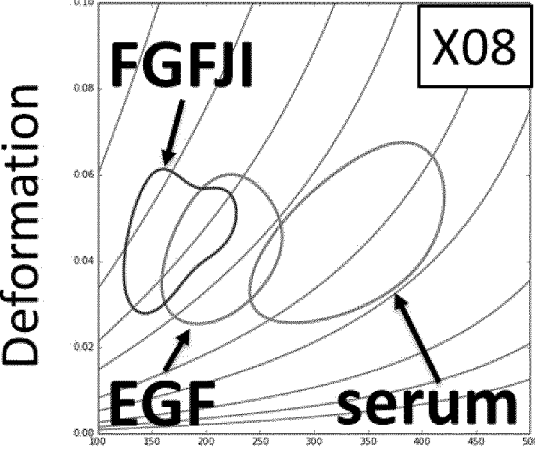
Figure 6:
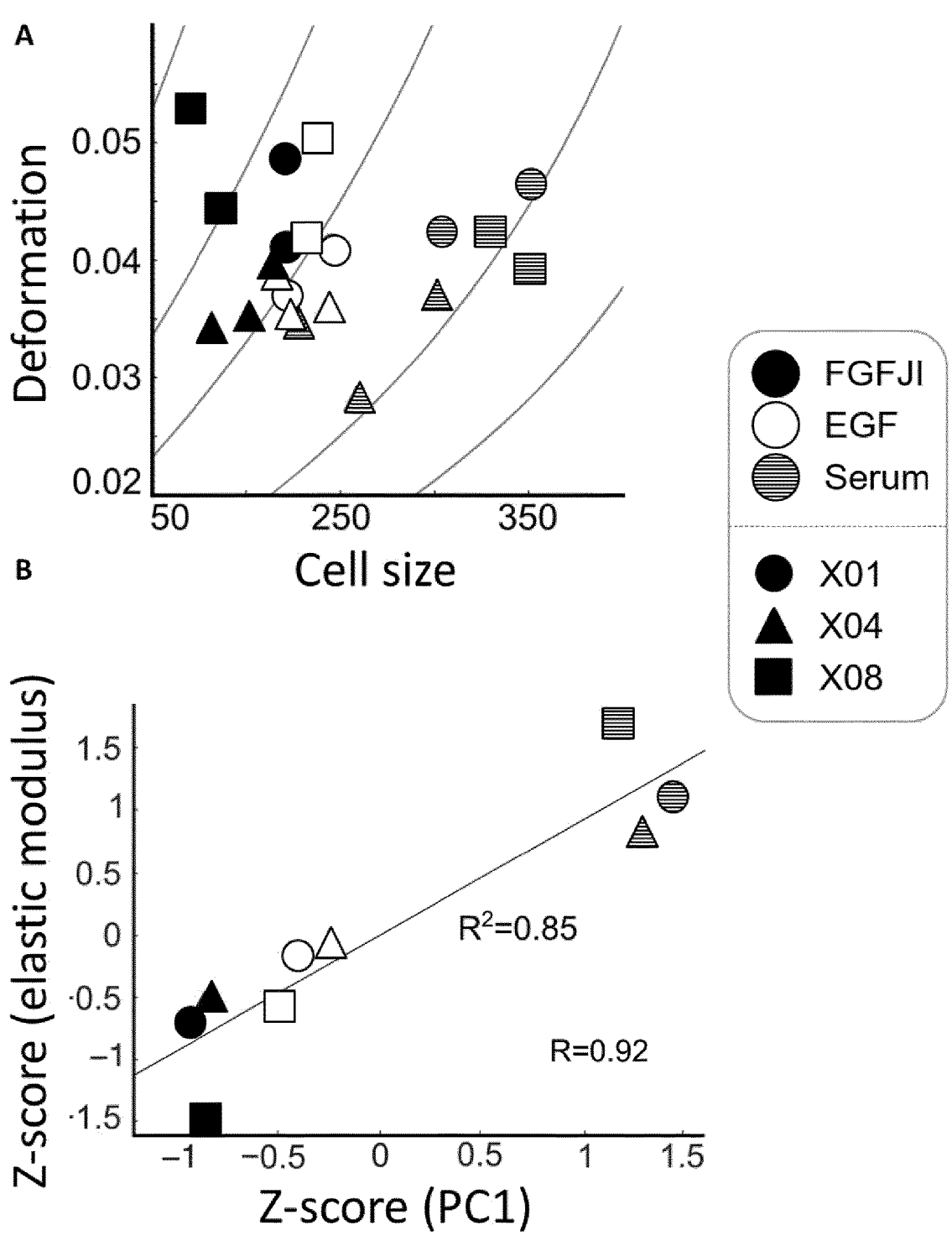
FIG. 6 shows distinct mechanical phenotypes of cells cultured in different conditions. (A) Plot of deformation vs. cell size for each cell line in each culture condition. The data show the mode-values of the distributions of thousands of individual cells analyzed for each condition and patient cell line; isoelasticity lines (grey) show places of equivalent elastic modulus. (B) Linear regression plot of z-score (PC1) and z-score (elastic modulus) for each cell line in each culture condition. The PC1 coordinate of each symbol is obtained as the average of the PC1 coordinates of the same respective symbols in FIG. 1B. The elastic modulus coordinate of 10 each symbol is calculated as the average of the elastic moduli of the respective symbols in panel A. Both coordinates are z-score transformed to adjust for the different physical scales.

When the data is plotted as deformation vs. cell area, again, there is an obvious grouping depending on cell culture medium (FIGS. 5 and 6A), meaning that cell culture con-ditions affect the mechanical phenotype of the cells similarly across different cell lines.

The specific manner in which culture conditions affect both gene expression and mechanical phenotype prompted us to quantify this correlation. Since the size of the cell and its deformation in the channel are not independent, the apparent elastic modulus for each cell was calculated (a means of combining size and deformation into one value), assuming an isotropic, homogeneous elastic object, accord-ing to Mietke et al. (Mietke et al., 2015). We plotted the average elastic modulus vs. PC1 for each condition (FIG. 6B) to determine a possible correlation (linear regression of the normalized PC1 vs. elastic modulus variables). The analysis demonstrates significant correlation (p<0.001; lin-ear regression correlation coefficient R=0.92) between two variables, therefore indicating high correlation between the genomic pattern and cell mechanics. In fact, there was again a grouping of all three cell lines based upon culture condition.

Example 9: Hes3 siRNA Transfection of X0 GBM Cells

Cells were plated into 6 well plates containing N2 medium supplemented with 20 ng/ml FGF and 200 nM Jak inhibitor ("FGFJI"). 48 hours later, cells were transfected with either scrambled control siRNA (Santa Cruz Biotech-nology SC37007) or Hes3 siRNA (Santa Cruz Biotechnol-ogy SC 88003) using Lipofectamine RNAiMax (Thermo Fischer Scientific) transfection reagent as described by the manufacturer. Cells were collected 24 hours post-transfec-tion, and total RNA was isolated using a HighPure RNA isolation kit (Roche). Experiments were performed in qua-druplicates for each cell line and siRNA transfection. RNA quality was assessed using an Agilent 2100 Bioanalyzer.

Example 10: Drug Screening

White Corning 384 well plates (Cat #3570) were coated with 40 ul of 4950 μg/ml polyornithine (Sigma, #P-365) at 370C overnight. The next day the plates were washed 5 times with water using a BioTek EL 406 plate washer. The plates were then coated with 40 ul of 1 mg/ml fibronectin (R&D Systems, #1030-Fn) for 2 hours at 370C and then washed 2 times with PBS. Either 15nl or 50nl of either 10 mM library compounds (MicroSource Pharmakon library) or 100% DMSO as negative control or 1 mM Staurosporine (ACROS #328532500) were dispensed with a Labcyte Echo 550 to screen the library at 3u M and 10 μM respectively. U87 cells were seeded in the plates with a WellMate drop dispenser (ThermoFischer) at a density of 3000 cells per well in 50 μl N2 medium and incubated for 20 hours at 370C in 5% $C_{02}$. Cell viability was assayed using Perkin Elmer ATPLite (Cat 6016731) according to vendor's instructions. For the dose dependent verification assay, cells were seeded in N2 medium with or without serum to test the specificity of compound action. The six compounds that were selected for the dose curve experiment were Ebselen (Abcam, ab142424), Ramelteon (Selleckchen, S1259), Raloxifene HCl (Selleckchen, S1227), Triclosan (Selleckchen, S4541), Clioquinol (Selleckchen, S4601), and Miconazole Nitrate (Selleckchen, S1956).

Results

The different gene expression and mechanomics proper-ties of the cells when placed in different conditions sug-gested that their response to treatment with small molecules may also differ under different culture conditions. Drug screening the same cell line under different culture condi-tions may help reduce the chances of false negatives.

Figure 7:
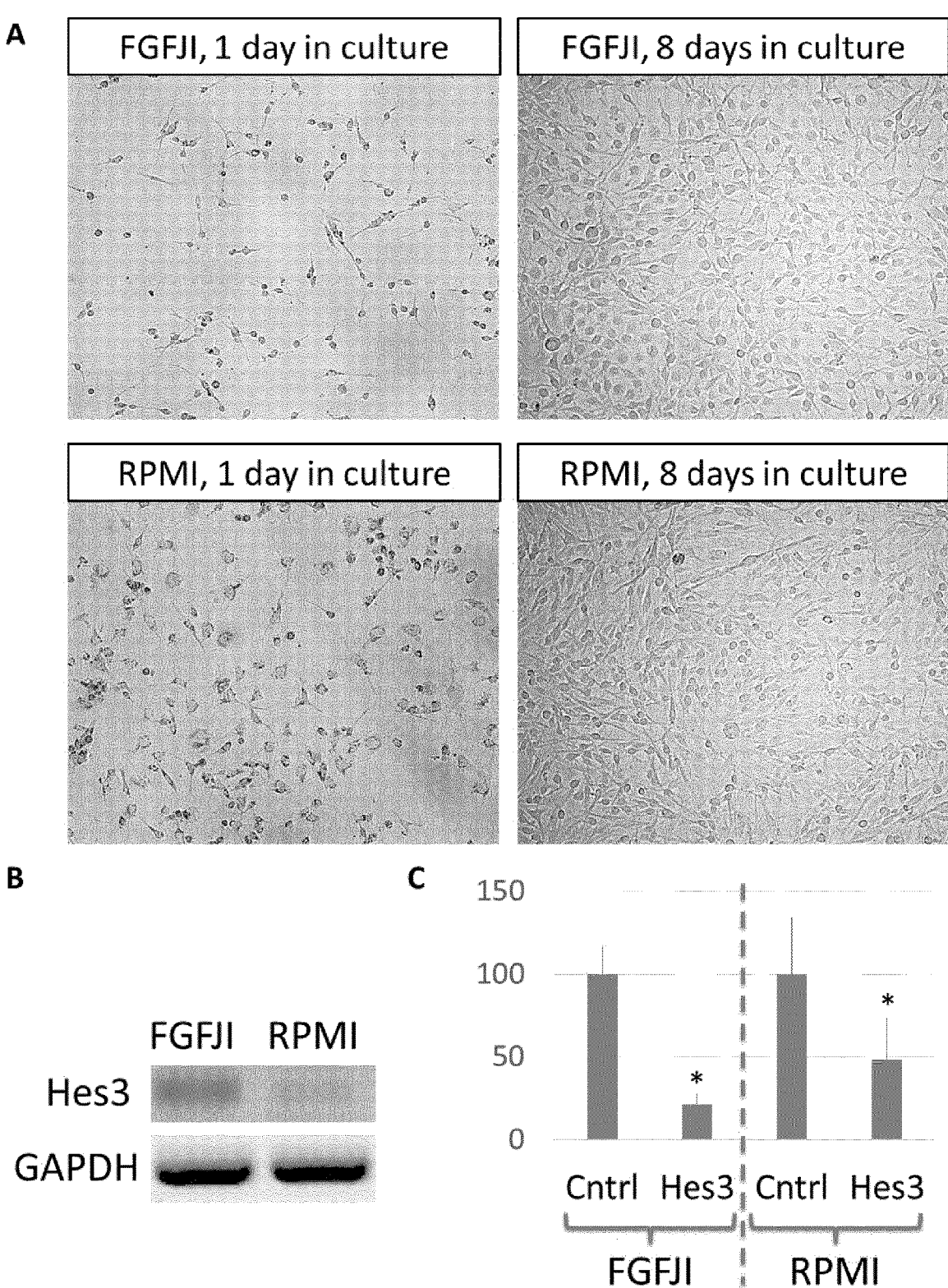
FIG. 7 shows U-87 cells in different culture conditions. (A) U-87 cells grow efficiently in both common media (RPMI supplemented with serum) and FGFJI medium. Images are from days 1 and 8 in culture and show morphological differences in the two media compositions [Image width: 1.22 mm]. (B) PCR analysis shows higher expression of Hes3 in FGFJI than in serum-containing RPMI [Data are from 5 day cultures; GAPDH is used as the housekeeping gene]. (C) Hes3 RNA interference opposes cell number in both FGFJI and serum-containing RPMI medium but more so in FGFJI [Data are from 1 day post-transfection].

To address this hypothesis, the human brain tumor cell line U-87 was used, because it is commonly used in drug screening programs. We chose two cell culture conditions: FGFJI and the commonly used serum-supplemented RPMI medium (i.e., the two culture conditions with the largest difference in Hes3 expression). U-87 cells grow efficiently in both media formulation. FIG. 7A shows image examples from 1-day and 8-day cultures in both media. The morphol-ogy of the cells differs in the two media, with FGFJI inducing a smaller and more neural stem cell-like morphol-ogy. PCR analysis demonstrated that cells in FGFJI express higher levels of Hes3 than in RPMI (FIG. 7B). Cells cultured in FGFJI were also more susceptible to death following Hes3 RNA interference (FIG. 7C; Y-axis is the cell number as a % of cell number of Cntrl siRNA, in each culture condition). One day after transfection, cell number in FGFJI was at 21.0%+6.8, relative to control (scrambled)-trans-fected cells (100%+16.8), with a significance p value (TTEST) of 3.5x10-6. Cell number in RPMI was at 48.3%+

59 60

25.0, relative to control (scrambled)-transfected cells (100%+34.2), with a significance p value (TTEST) of 0.0029.

Figure 8:
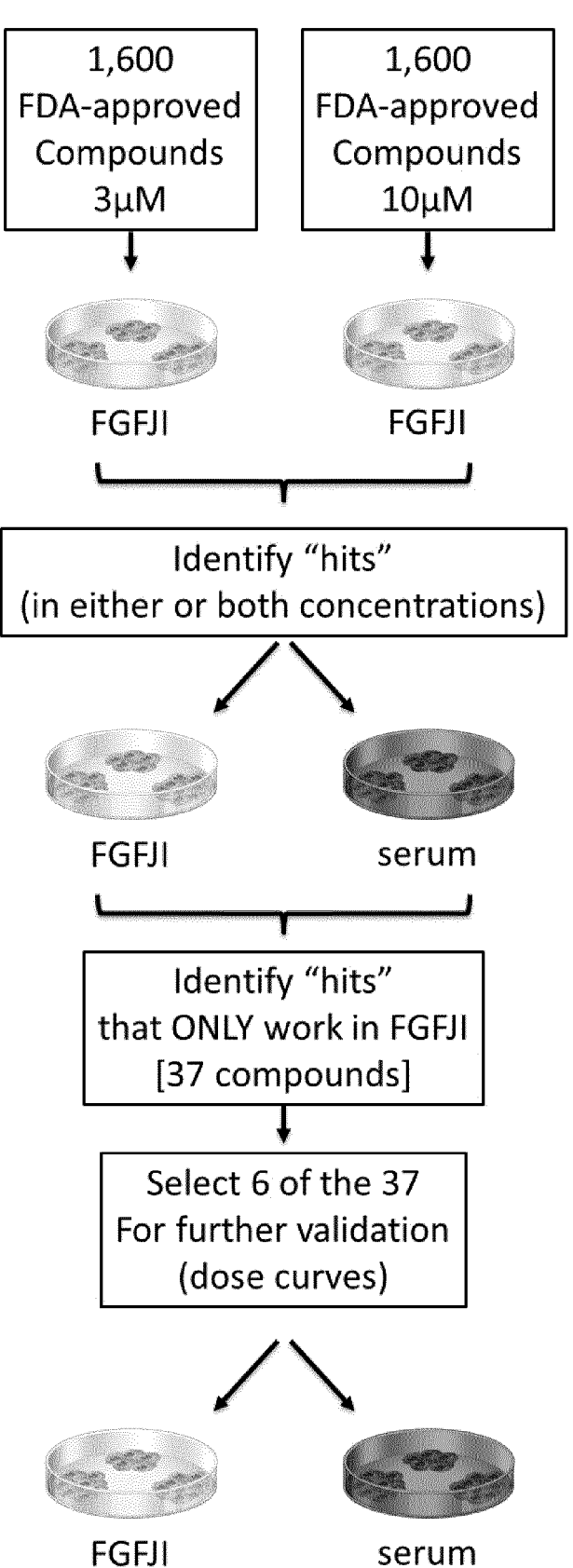
FIG. 8 shows drug screening in different culture conditions and the drug screening strategy.

A library of 1,600 FDA-approved compounds was screened at two different concentrations (10 μM and 3 μM) on U-87 cells cultured in FGFJI (FIG. 8). The compounds that significantly reduced cell number were then re-screened, in parallel, with the U-87 cells cultured in both FGFJI and serum conditions. In this way, we identified 37 compounds that only reduced cell number in FGFJI conditions (Table 7).

TABLE 7

List of 37 compounds (from a library of 1,600 FDA-approved compounds) that reduce cell number in FGFJI but not in serum culture conditions.

| | Compound |
|---|---|
| 1 | ABAMECTIN |
| 2 | BENZETHONIUM Cl |
| 3 | BISACODYL |
| 4 | BITHIONATE Na |
| 5 | BROXALDINE |
| 6 | BROXYQUINOLINE |
| 7 | BUTOCONAZOLE |
| 8 | CHLORHEXIDINE 2HCl |
| 9 | CHLOROXINE |
| 10 | CLIOQUINOL |
| 11 | CLOFOCTOL |
| 12 | DICHLOROPHEN |
| 13 | DILTIAZEM HCl |
| 14 | DORAMECTIN |
| 15 | EBSELEN |
| 16 | ECONAZOLE NITRATE |
| 17 | ESCIN |
| 18 | HEXETIDINE |
| 19 | LASALOCID Na |
| 20 | LEVOCETIRIZINE 2HCl |
| 21 | MICONAZOLE NITRATE |
| 22 | MOXIDECTIN |
| 23 | NORETHYNODREL |
| 24 | OXICONAZOLE NITRATE |
| 25 | OXYCLOZANIDE |
| 26 | PIMOZIDE |
| 27 | QUINESTROL |
| 28 | RALOXIFENE HCl |
| 29 | RAMELTEON |
| 30 | RITONAVIR |
| 31 | SELAMECTIN |
| 32 | SULCONAZOLE NITRATE |
| 33 | SULOCTIDIL |

TABLE 7-continued

List of 37 compounds (from a library of 1,600 FDA-approved compounds) that reduce cell number in FGFJI but not in serum culture conditions.

| | Compound |
|---|---|
| 34 | TIOCONAZOLE |
| 35 | TRICLOSAN |
| 36 | VINBLASTINE SULFATE |
| 37 | XYLAZINE |

Figure 9:
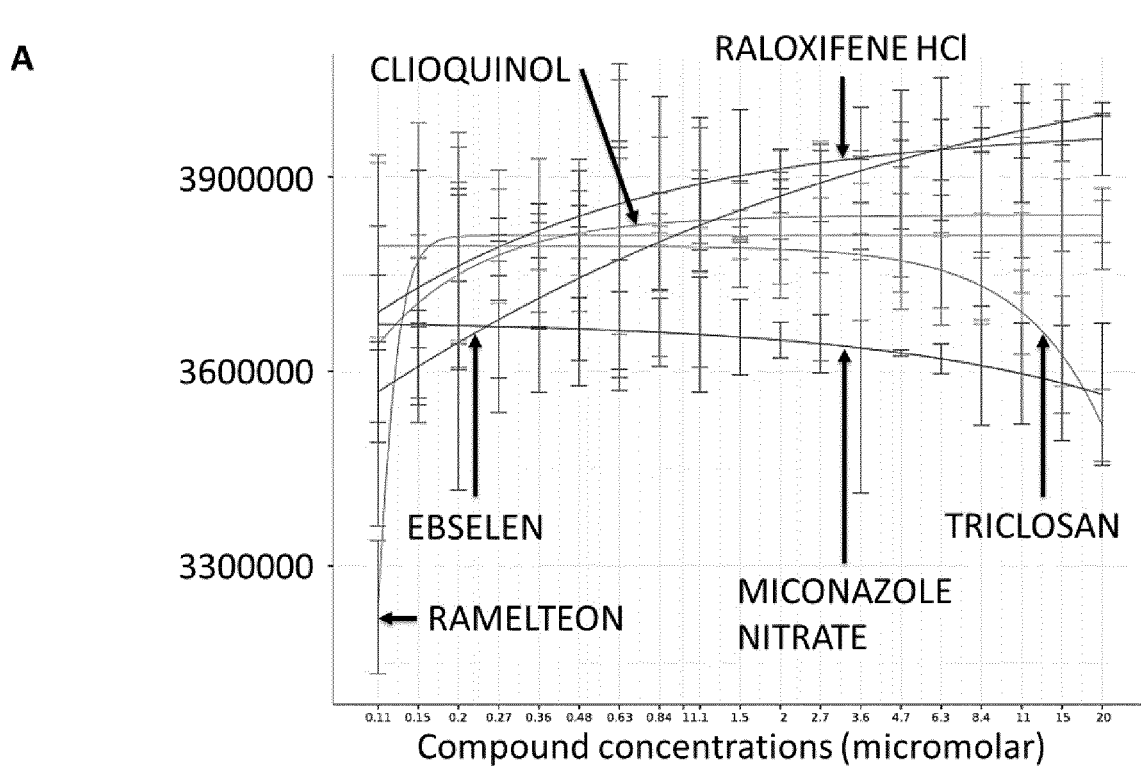
FIG. 9 shows the drug screening in different culture conditions. (A) Dose curves of 6 selected compounds in the serum-containing cell culture condition. (B) Dose curves of the same 6 selected compounds in the FGFJI cell culture condition. [Arrows point to the four of the six compounds used in the dose curve experiment that demonstrated efficacy in FGFJI but not in serum].
Figure 9:
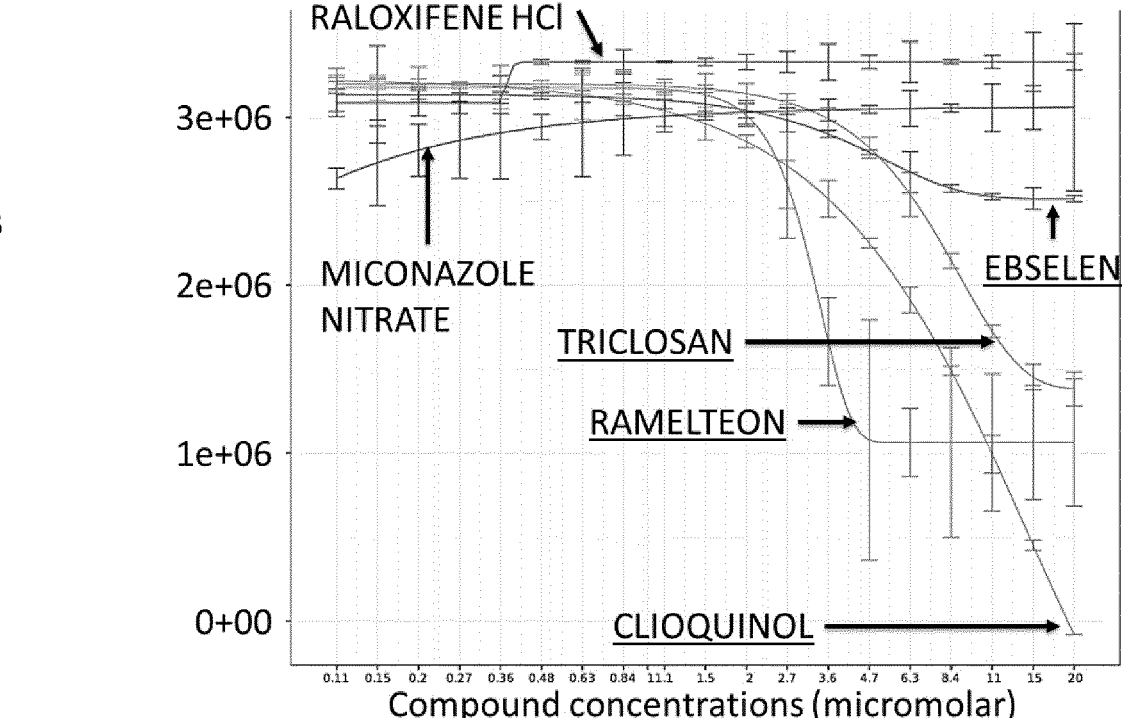

As a final confirmation, six compounds were chosen for dose curve assays in both FGFJI and serum conditions. Of these, four compounds (marked by arrows in the figure) showed a much greater effect in FGFJI than in serum (FIG. 9A-B).

Example 11: Computational Analysis of Selected Compounds

Compound structures were downloaded from PubChem on August 7th of 2017 in SDF format and compared using the Score Matrix Service with standard settings of 2D Tanimoto similarity. The heatmap was generated with the Heatplus package v2.8.0 in R 3.0.2 with hierarchical clustering over average distances. Drug targets were retrieved from Binding DB, drug disease relations from Therpeutic Target Database (TTD), and protein structures from PDB. Data current as of DATE. The corresponding drug-target-disease networks were visualized with Cytoscape v.3.5.1. The drug-target network shows only targets with two or more compounds.

Results

Figure 10:
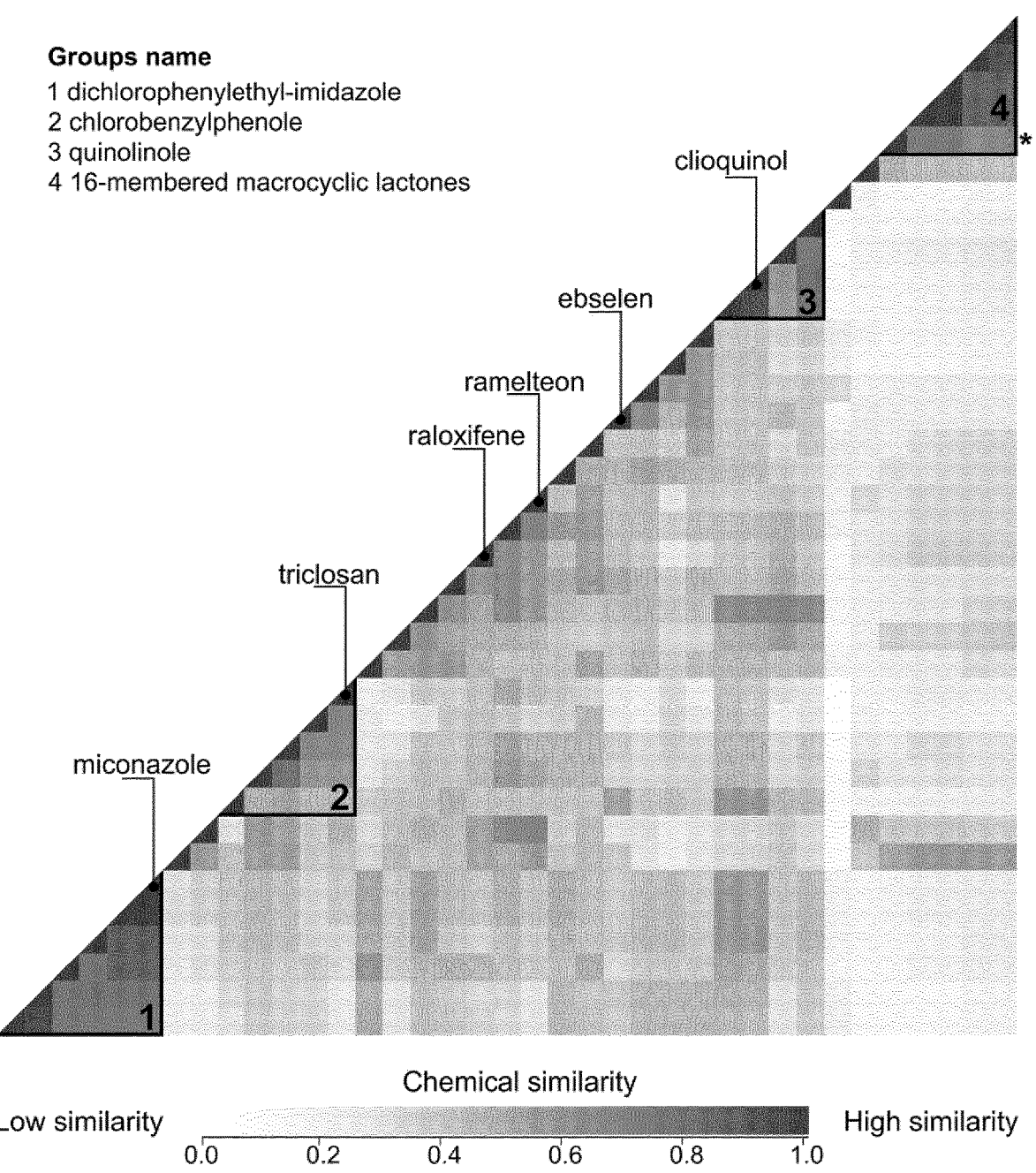
FIG. 10 shows a chemical similarity plot of the 37 hit compounds. Pairwise similarities of compounds reveals four larger groups of related compounds and many singletons. The six selected compounds cover the imidazole, the phenol, and the quinolinole groups as well as three singleton groups thus capturing a great variety of structural scaffolds.

The seven compounds selected for dose curve experiments cover six different chemical scaffolds, thus providing broad diversity. To get an overview of the compounds a clustering was performed based on the structural similarity of the 37 compounds (FIG. 10). The heatmap reveals that the 37 compounds cover structurally very diverse scaffolds and that there are four larger groups of very closely related compounds and many singletons (FIG. 10). For example, the first group, "dichlorophenylethyl-imidazole" comprises six compounds, which contain an imidazole group and some chloro groups (Chemical structures are provided in Table 2). All of these compounds have an antifungal effect and are used in different indications as shown in Table 8.

TABLE 8

List of 37 compounds with disease indication, number of targets, and protein structures.

| | Name | Group | CID | Disease/effect | Targets | Structures |
|---|---|---|---|---|---|---|
| 1 | butoconazole | 1 | 47472 | antifungal | 1 | 0 |
| 2 | sulconazole | 1 | 5318 | antifungal | 12 | 0 |
| 3 | tioconazole | 1 | 5482 | antifungal | 1 | 0 |
| 4 | oxiconazole | 1 | 5353853 | antifungal | 2 | 0 |
| 5 | econazole | 1 | 3198 | antifungal | 20 | 4 |
| 6 | miconazole | 1 | 4189 | antifungal | 27 | 0 |
| 7 | lasalocid | | 5360807 | antibiotic | 0 | 1 |
| 8 | quinestrol | | 9046 | anticancer | 0 | 0 |
| 9 | oxyclozanide | 2 | 16779 | anthelmintic | 0 | 0 |
| 10 | clofoctol | 2 | 2799 | antibiotic | 0 | 0 |
| 11 | dichlorophen | 2 | 3037 | anticestodal | 2 | 0 |
| 12 | Bithionol (bithionate Na) | 2 | 2406 | anthelmintic | 12 | 2 |
| 13 | triclosan | 2 | 5564 | antibiotic | 16 | 31 |
| 14 | ritonavir | | 392622 | antiretroviral | 23 | 15 |
| 15 | vinblastine | | 13342 | anticancer | 13 | 4 |
| 16 | bisacodyl | | 2391 | laxative | 2 | 0 |

TABLE 8-continued

List of 37 compounds with disease indication, number of targets, and protein structures.

| | Name | Group | CID | Disease/effect | Targets | Structures |
|---|---|---|---|---|---|---|
| 17 | diltiazem | | 39186 | blood pressure treatment | 15 | 0 |
| 18 | raloxifene hydrochloride | | 5035 | osteoporosis | 21 | 5 |
| 19 | benzethonium | | 2335 | antimicrobial | 0 | 0 |
| 20 | ramelteon | | 208902 | sleep agent | 2 | 0 |
| 21 | levocetirizine | | 1549000 | anti histamine | 1 | 1 |
| 22 | suloctidil | | 5354 | blood pressure treatment | 0 | 0 |
| 23 | ebselen | | 3194 | anti inflammatory | 26 | 0 |
| 24 | pimozide | | 16362 | anti psychotic | 47 | 0 |
| 25 | chlorhexidine | | 53589 | antimicrobial | 0 | 0 |
| 26 | xylazine | | 5707 | anesthesia | 5 | 0 |
| 27 | chloroxine | 3 | 2722 | antibiotic | 9 | 0 |
| 28 | clioquinol | 3 | 2788 | antifungal | 13 | 1 |
| 29 | broxaldine | 3 | 77262 | antiprotozoal | 0 | 0 |
| 30 | broxyquinoline | 3 | 2453 | antiprotozoal | 1 | 0 |
| 31 | hexetidine | | 3607 | antibiotic | 0 | 0 |
| 32 | norethynodrel | | 6231 | oral contraceptive | 1 | 0 |
| 33 | sodium aescinate | 4 | 3084345 | lung injury treatment | 0 | 0 |
| 34 | abamectin | 4 | 71312393 | anthelmintic | 0 | 0 |
| 35 | doramectin | 4 | 11954226 | anthelmintic | 0 | 0 |
| 36 | milbemycin | 4 | 6436009 | anthelmintic | 0 | 0 |
| 37 | selamectin | 4 | 6445091 | anthelmintic | 0 | 0 |

Figure 11:
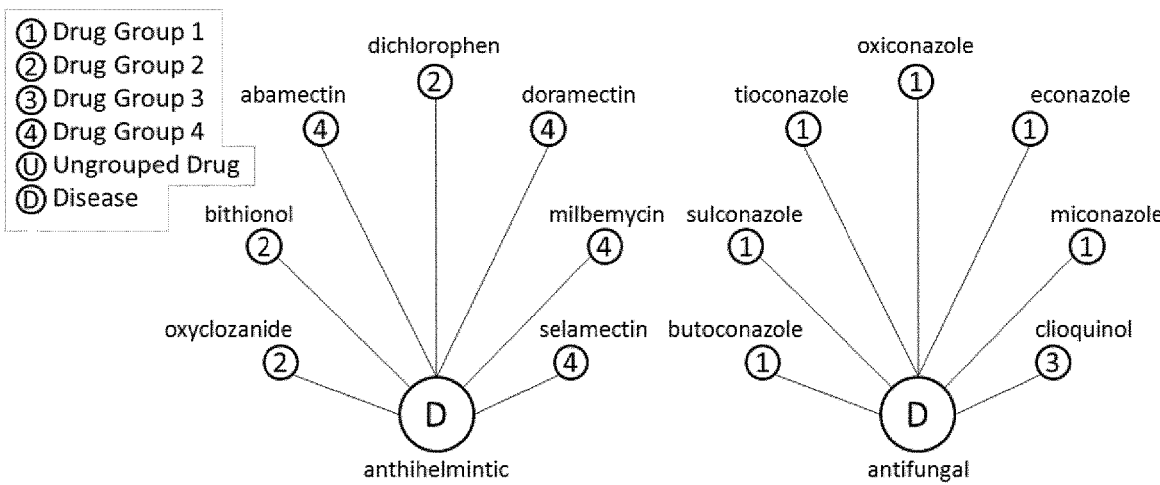
FIG. 11 shows the drug disease network of the 37 hit compounds. Drugs and their disease indications. 19 out of the 37 drugs have an anthelmintic, antifungal, and antibiotic effect.
Figure 11:
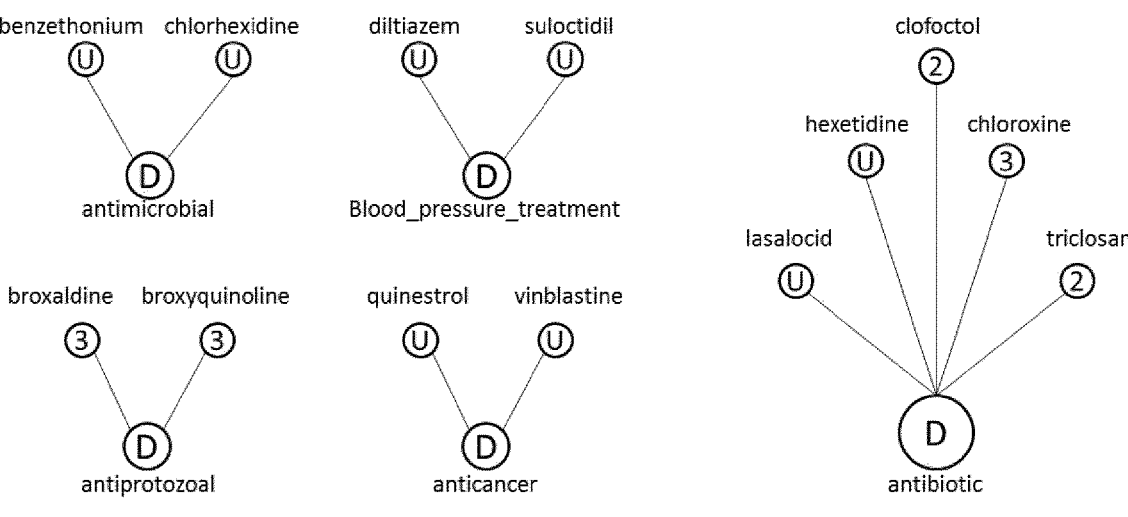
Figure 11:
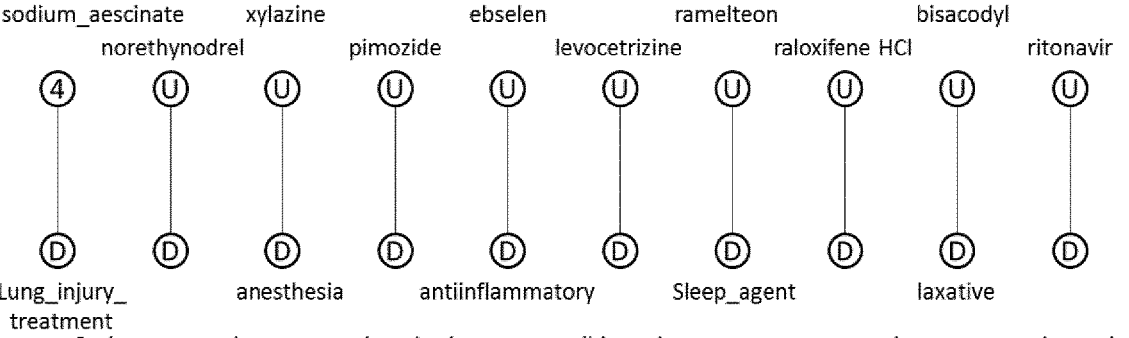

The disease indications of the 37 compounds was analyzed. In total, they cover a broad spectrum including anticancer, antipsychotic, antihistamine, anti-inflammatory, laxative, and sleep agents. However, there was a particular strong focus on anthelmintic, antifungal, and antibiotic actions for 19 of the 37 compounds (FIG. 11). With this analysis a complete drug target-disease network was generated and a drug-drug target network.

Figure 12:
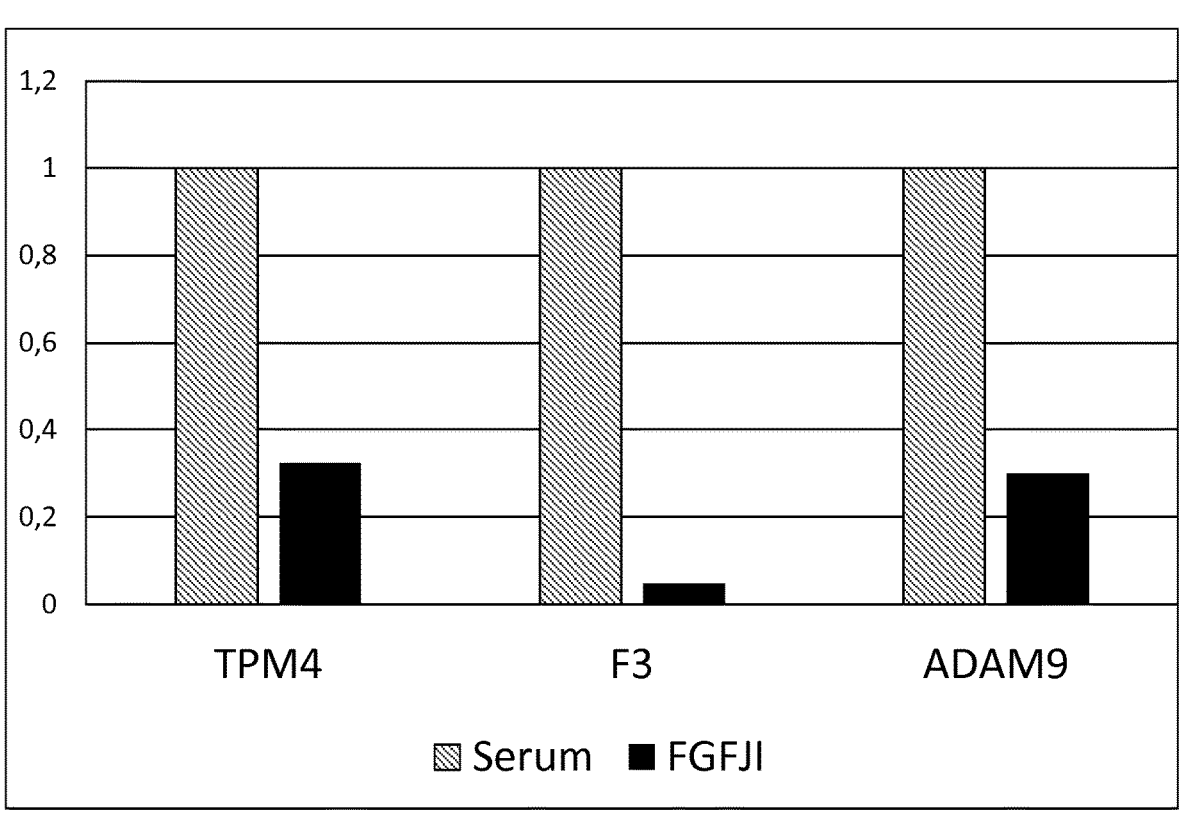
FIG. 12 shows biomarker expression (data from three human cell lines pooled together) for the biomarkers TPM4, F3 and ADAM9. These three biomarkers were identified by placing the cells under different cell culture conditions. Here, the gene expression comparison between the condition "Serum" (set to 1) and the condition "FGFJI") is shown. The data from all three cell lines used were calculated together. Thus, the bar graph represents all three cell lines.
Figure 13:
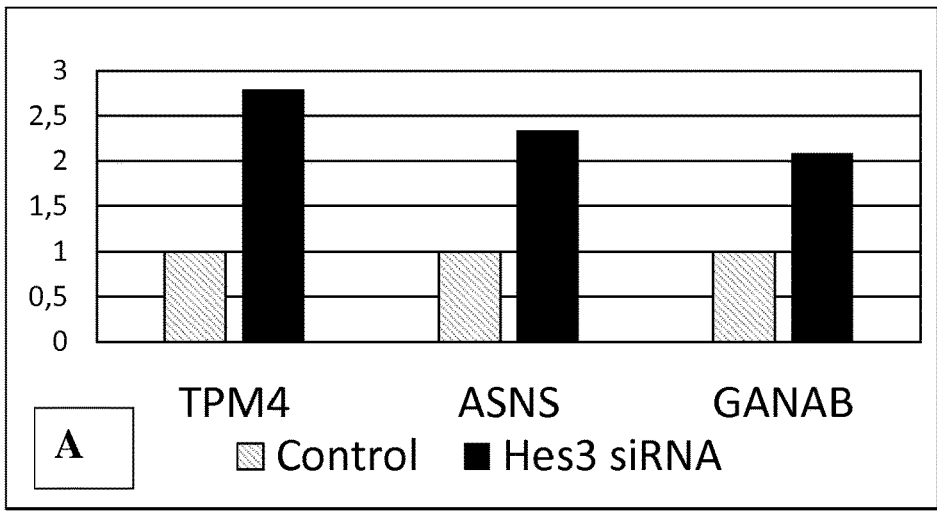
FIG. 13 shows gene expression data for the cell lines X01 (A), X04 (B) and X08 (C) for the biomarkers TPM4, ASNS and GANAB. These three biomarkers were identified by placing the cells under the FGFJI condition and then they were treated with either control or Hes3 siRNA. The data
Figure 13:
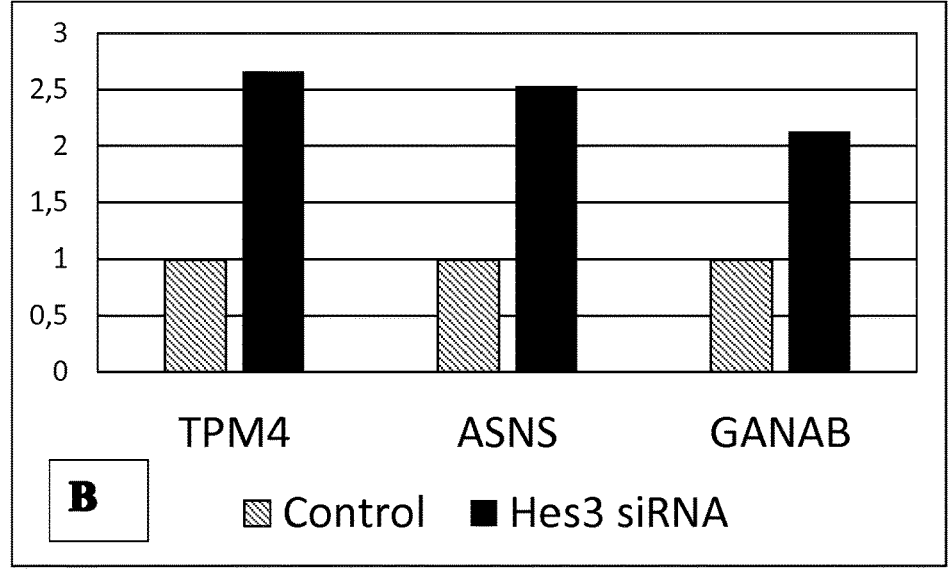
Figure 13:
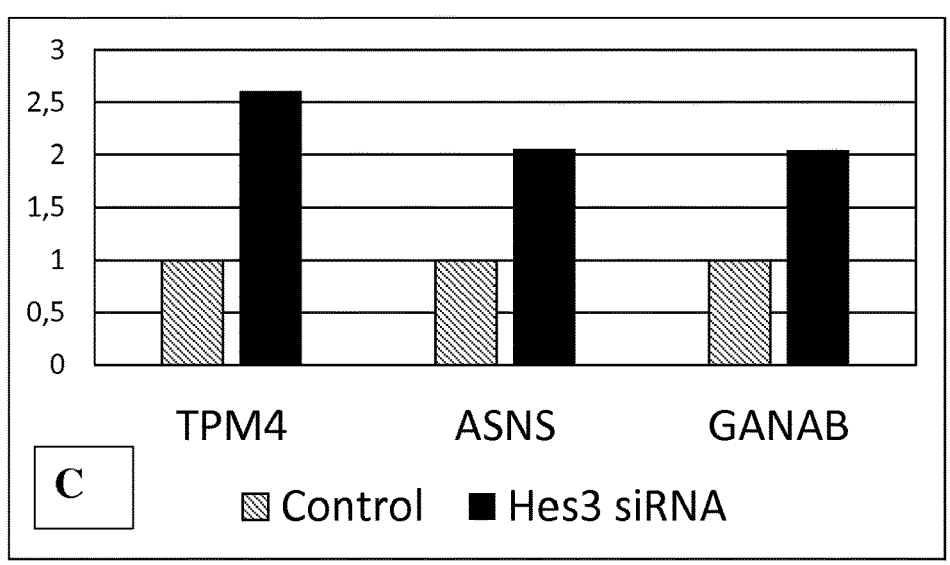

Examples of biomarker regulation in different culture conditions are shown in FIGS. 12 and 13.

REFERENCES

1. Akers, W.A., Lane, A., Lynfield, Y., Greenberg, J., Hall, J., Mangan, C., and Tinker, A. (1989). Sulconazole nitrate 1% cream in the treatment of chronic moccasin-type tinea pedis caused by *Trichophyton rubrum*. Journal of the American Academy of Dermatology 21, 686-689.

2. Androutsellis-Theotokis, A., Leker, R. R., Soldner, F., Hoeppner, D. J., Ravin, R., Poser, S. W., Rueger, M. A., Bae, S. K., Kittappa, R., and Mckay, R. D. (2006). Notch signalling regulates stem cell numbers in vitro and in vivo. Nature 442, 823-826.

3. Androutsellis-Theotokis, A., Rueger, M. A., Park, D. M., Boyd, J. D., Padmanabhan, R., Campanati, L., Stewart, C. V., LeFranc, Y., Plenz, D., Walbridge, S., et al. (2010). Angiogenic factors stimulate growth of adult neural stem cells. PLOS One 5, e9414.

4. Arnett, J. H. (1947). Treatment of carriers of endamoeba *histolytica* and other protozoa with carbarsone, chiniofon and vioform. The American journal of the medical sciences 213, 608-610.

5. Bates, D., Mächler, M., Bolker, B., and Walker, S. (2014a). Fitting linear mixed-effects models using lme4. arXiv preprint arXiv: 14065823.

6. Bates, D., Maechler, M., Bolker, B., and Walker, S. (2014b). lme4: Linear mixed-effects models using Eigen and S4. R package version 1.

7. Benchaoui, H. A., Clemence, R. G., Clements, P. J., Jones, R. L., Watson, P., Shanks, D.J., Smith, D. G., Sture, G. H., Jernigan, A. D., and Rowan, T. G. (2000). Efficacy and safety of selamectin against fleas on dogs and cats presented as veterinary patients in Europe. Veterinary parasitology 91, 223-232.

8. Benfield, P., and Clissold, S. P. (1988). Sulconazole. A review of its antimicrobial activity and therapeutic use in superficial dermatomycoses. Drugs 35, 143-153.

9. Beninger, R. J., and Hahn, B. L. (1983). Pimozide blocks establishment but not expression of amphetamine-produced environment-specific conditioning. Science 220, 1304-1306.

10. Bevan, J. A. (1983). Diltiazem selectively inhibits cerebrovascular extrinsic but not intrinsic myogenic tone. A review. Circ Res 52, 1104-109.

11. Bourquin, J. P., Griot, R., and Schenker, E. (1962). [Synthesis of esters of halogenated quinaldine and quinoline]. Archiv der Pharmazie und Berichte der Deutschen Pharmazeutischen Gesellschaft 295, 383-399.

12. Brocard, E., Oizel, K., Lalier, L., Pecqueur, C., Paris, F., Vallette, F. M., and Oliver, L. (2015). Radiation-induced PGE2 sustains human glioma cells growth and survival through EGF signaling. Oncotarget 6, 6840-6849.

13. Buchert, M., Burns, C. J., and Ernst, M. (2016). Targeting JAK kinase in solid tumors: emerging opportunities and challenges. Oncogene 35, 939-951.

14. Buelke-Sam, J., Bryant, H. U., and Francis, P. C. (1998). The selective estrogen receptor modulator, raloxifene: an overview of nonclinical pharmacology and reproductive and developmental testing. Reproductive toxicology 12, 217-221.

15. Cannistraci, C. V., Alanis-Lobato, G., and Ravasi, T. (2013). Minimum curvilinearity to enhance topological prediction of protein interactions by network embedding. Bioinformatics 29, i199-209.

16. Cannistraci, C. V., Ravasi, T., Montevecchi, F. M., Ideker, T., and Alessio, M. (2010). Nonlinear dimension reduction and clustering by Minimum Curvilinearity unfold neuropathic pain and tissue embryological classes. Bioinformatics 26, i531-539.

17. Chailleux, N., and Paradis, M. (2002). Efficacy of selamectin in the treatment of naturally acquired cheyletiellosis in cats. The Canadian veterinary journal=La revue veterinaire canadienne 43, 767-770.

18. Chung, M. W., Komorowski, R. A., and Varma, R.R. (1988). Suloctidil-induced hepatotoxicity. Gastroenterology 95, 490-491.

19. Clarke, K. W., and Hall, L. W. (1969). "Xylazine"—a new sedative for horses and cattle. The Veterinary record 85, 512-517.

20. Clayton, Y. M., Hay, R. J., McGibbon, D. H., and Pye, R. J. (1982). Double blind comparison of the efficacy of tioconazole and miconazole for the treatment of fungal infection of the skin or erythrasma. Clinical and experimental dermatology 7, 543-549.

21. Cohen, M. R. (1966). Quinestrol therapy in functional infertility. Fertility and sterility 17, 541-546.

22. Cortes, C., and Vapnik, V. (1995). Support-Vector Networks. In Machine Learning, L. Saitta, ed. (Boston: Kluwer Academic Publishers), pp. 273-297.

23. Cummings, S. R., Eckert, S., Krueger, K. A., Grady, D., Powles, T. J., Cauley, J. A., Norton, L., Nickelsen, T., Bjarnason, N. H., Morrow, M., et al. (1999). The effect of raloxifene on risk of breast cancer in postmenopausal women: results from the MORE randomized trial. Multiple Outcomes of Raloxifene Evaluation. Jama 281, 2189-2197.

24. Danesi, R., and Del Tacca, M. (1985). Clinical study on the efficacy of clofoctol in the treatment of infectious respiratory diseases. International journal of clinical pharmacology research 5, 175-179.

25. Davies, G. E., Francis, J., Martin, A. R., Rose, F. L., and Swain, G. (1954). 1:6-Di-4'-chlorophenyldiguanidohexane (hibitane); laboratory investigation of a new antibacterial agent of high potency. British journal of pharmacology and chemotherapy 9, 192-196.

26. Delmas, P. D., Ensrud, K. E., Adachi, J. D., Harper, K. D., Sarkar, S., Gennari, C., Reginster, J. Y., Pols, H. A., Recker, R.R., Harris, S. T., et al. (2002). Efficacy of raloxifene on vertebral fracture risk reduction in postmenopausal women with osteoporosis: four-year results from a randomized clinical trial. J Clin Endocrinol Metab 87, 3609-3617.

27. Dreiling, D. A., Fischl, A., and Fernandez, O. (1959). The therapeutic usefulness of dulcolax (bisacodyl), a new nonpurgative laxative. The American journal of digestive diseases 4, 311-320.

28. Droegemueller, W., Adamson, D. G., Brown, D., Cibley, L., Fleury, F., LePage, M. E., and Henzl, M. R. (1984). Three-day treatment with butoconazole nitrate for vulvovaginal candidiasis. Obstetrics and gynecology 64, 530-534.

29. Dutton, C. J., Gibson, S. P., Goudie, A. C., Holdom, K. S., Pacey, M. S., Ruddock, J. C., Bu'Lock, J. D., and Richards, M. K. (1991). Novel avermectins produced by mutational biosynthesis. The Journal of antibiotics 44, 357-365.

30. Edgren, R. A. (1991). Oral contraception: a review. International journal of fertility 36 Suppl 3, 16-25.

31. Ellenrieder, M., Zeiller, P., Dinter, H., and Sensch, K. H. (1970). [Effect of quinoline derivatives on pathogenic and apathogenic intestinal microorganisms]. Arzneimittel-Forschung 20, 821-824.

32. Foulkes, D.M. (1973). Some toxicological observations on chlorhexidine. Journal of periodontal research Supplement 12, 55-60.

33. Ghilardi, P. L., and Casani, A. (1985). Treatment of ear, nose and throat infections with clofoctol. Drugs under experimental and clinical research 11, 815-818.

34. Gobbi, P. G., Pieresca, C., Frassoldati, A., Carotenuto, M., Di Renzo, N., La Sala, A., Berte, R., Avanzini, P., Federico, M., Silingardi, V., et al. (1996). Vinblastine, bleomycin, and methotrexate chemotherapy plus extended-field radiotherapy in early, favorably presenting, clinically staged Hodgkin's patients: the Gruppo Italiano per lo Studio dei Linfomi Experience. J Clin Oncol 14, 527-533.

35. Godefroi, E. F., Heeres, J., Van Cutsem, J., and Janssen, P. A. (1969). The preparation and antimycotic properties of derivatives of 1-phenethylimidazole. Journal of medicinal chemistry 12, 784-791.

36. Greenblatt, D.J., Harmatz, J. S., and Karim, A. (2007). Age and gender effects on the pharmacokinetics and pharmacodynamics of ramelteon, a hypnotic agent acting via melatonin receptors MT1 and MT2. Journal of clinical pharmacology 47, 485-496.

37. Gu, Z., Eils, R., and Schlesner, M. (2016). Complex heatmaps reveal patterns and correlations in multidimensional genomic data. Bioinformatics 32, 2847-2849.

38. Heel, R. C., Brogden, R. N., Speight, T. M., and Avery, G. S. (1978). Econazole: a review of its antifungal activity and therapeutic efficacy. Drugs 16, 177-201.

39. Hertz, R., Lipsett, M. B., and Moy, R. H. (1960). Effect of Vincaleukoblastine on metastatic choriocarcinoma and related trophoblastic tumors in women. Cancer Res 20, 1050-1053.

40. Hopper, S. H., and Wood, K. M. (1958). Development of a germicidal soap containing bithionol. Journal of the American Pharmaceutical Association American Pharmaceutical Association 47, 317-318.

41. Horton, G. M., and Stockdale, P. H. (1981). Lasalocid and monensin in finishing diets for early weaned lambs with naturally occurring coccidiosis. American journal of veterinary research 42, 433-436.

42. Huang da, W., Sherman, B. T., and Lempicki, R. A. (2009a). Bioinformatics enrichment tools: paths toward the comprehensive functional analysis of large gene lists. Nucleic Acids Res 37, 1-13.

43. Huang da, W., Sherman, B. T., and Lempicki, R. A. (2009b). Systematic and integrative analysis of large gene lists using DAVID bioinformatics resources. Nature protocols 4, 44-57.

44. Idris, M., Rahman, K. M., Muttalib, M.A., and Azad Khan, A. K. (1980). The treatment of fasciolopsiasis with niclosamide and dichlorophen. The Journal of tropical medicine and hygiene 83, 71-74.

45. Imayoshi, I., and Kageyama, R. (2014). bHLH factors in self-renewal, multipotency, and fate choice of neural progenitor cells. Neuron 82, 9-23.

46. Janssen, P. A., Niemegeers, C. J., Schellekens, K. H., Dresse, A., Lenaerts, F. M., Pinchard, A., Schaper, W. K., van Nueten, J. M., and Verbruggen, F. J. (1968). Pimozide, a chemically novel, highly potent and orally long-acting neuroleptic drug. I. The comparative pharmacology of pimozide, haloperidol, and chlorpromazine. Arzneimittel-Forschung 18, 261-279.

47. Kato, K., Hirai, K., Nishiyama, K., Uchikawa, O., Fukatsu, K., Ohkawa, S., Kawamata, Y., Hinuma, S., and Miyamoto, M. (2005). Neurochemical properties of ramelteon (TAK-375), a selective MT1/MT2 receptor agonist. Neuropharmacology 48, 301-310.

48. Kenyon, A. J., Hamilton, S. G., and Douglas, D.M. (1986). Controlled wound repair in guinea pigs, using antimicrobials that alter fibroplasia. American journal of veterinary research 47, 96-101.

49. Klimek, L. (2009). Levocetirizine: from scientific evidence to a potent modern-day treatment of today's allergic patients. Drugs of today 45, 213-225.

50. Kodack, D. P., Askoxylakis, V., Ferraro, G. B., Sheng, Q., Badeaux, M., Goel, S., Qi, X., Shankaraiah, R., Cao, Z. A., Ramjiawan, R. R., et al. (2017). The brain microenvironment mediates resistance in luminal breast cancer to PI3K inhibition through HER3 activation. Science translational medicine 9.

51. Lavy, E., Harrus, S., Mazaki-Tovi, M., Bark, H., Markovics, A., Hagag, A., Aizenberg, I., and Aroch, I. (2003). Spirocerca *lupi* in dogs: prophylactic effect of doramectin. Research in veterinary science 75, 217-222.

52. Lea, A. P., and Faulds, D. (1996). Ritonavir. Drugs 52, 541-546; discussion 547-548.

53. Liao, Y., Smyth, G. K., and Shi, W. (2014). featureCounts: an efficient general purpose program for assigning sequence reads to genomic features. Bioinformatics 30, 923-930.

54. Lienert, E., and Jahn, F. (1966). [Studies on the mechanism of action of anti-trematode agents. II. 2,2-Methylene-bisphenols provided with electron-attracting substitutes are electron acceptors; they have a trematodicide effect because of the strong power of attraction of their oxygen atoms for electrons]. Wiener tierarztliche Monatsschrift 53, 795-802.

55. Love, M. I., Huber, W., and Anders, S. (2014). Moderated estimation of fold change and dispersion for RNA-seq data with DESeq2. Genome Biol 15, 550.

56. Luo, W., and Brouwer, C. (2013). Pathview: an R/Bioconductor package for pathway-based data integration and visualization. Bioinformatics 29, 1830-1831.

57. Lyman, F. L., and Furia, T. (1969). Toxicology of 2, 4, 4'-trichloro-2'-hydroxy-diphenyl ether. IMS, Industrial medicine and surgery 38, 64-71.

58. Mandel, I.D. (1994). Antimicrobial mouthrinses: overview and update. Journal of the American Dental Association 125 Suppl 2, 2S-10S.

59. Mansfield, L. E., Hampel, F., Haeusler, J. M., and Georges, G. (2010). Study of levocetirizine in seasonal allergic rhinitis. Current medical research and opinion 26, 1269-1275.

60. Marriott, M. S., Baird, J. R., Brammer, K. W., Faulkner, J. K., Halliwell, G., Jevons, S., and Tarbit, M. H. (1983). Tioconazole, a new imidazole-antifungal agent for the treatment of dermatomycoses. Antifungal and pharmacologic properties. Dermatologica 166 Suppl 1, 1-7.

61. Mietke, A., Otto, O., Girardo, S., Rosendahl, P., Taubenberger, A., Golfier, S., Ulbricht, E., Aland, S., Guck, J., and Fischer-Friedrich, E. (2015). Extracting Cell Stiffness from Real-Time Deformability Cytometry: Theory and Experiment. Biophysical journal 109, 2023-2036.

62. Miller, T. A. (1966). Anthelmintic activity of toluene and dichlorophen against various stages of *Ancylostoma caninum* in young dogs. American journal of veterinary research 27, 1755-1758.

63. Mixich, G., and Thiele, K. (1979). [A contribution to the stereospecific synthesis of antifungal imidazolyloxime-ethers/Oxiconazole nitrate (Sgd 301-76), a new broad-spectrum antifungal agent (author's transl)]. Arzneimittel-Forschung 29, 1510-1513.

64. Moermann, J. E., and Muehlemann, H. R. (1983). Synergistic inhibitory effect of zinc and hexetidine on in vitro growth and acid production of *Streptococcus mutans*. Journal of dental research 62, 135-137.

65. Mrozik, H., Jones, H., Friedman, J., Schwartzkopf, G., Schardt, R. A., Patchett, A. A., Hoff, D. R., Yakstis, J. J., Riek, R. F., Ostlind, D. A., et al. (1969). A new agent for the treatment of liver fluke infection (fascioliasis). Experientia 25, 883.

66. Mukthavaram, R., Ouyang, X., Saklecha, R., Jiang, P., Nomura, N., Pingle, S. C., Guo, F., Makale, M., and Kesari, S. (2015). Effect of the JAK2/STAT3 inhibitor SAR317461 on human glioblastoma tumorspheres. Journal of translational medicine 13, 269.

67. Nachman, S. A., Stanley, K., Yogev, R., Pelton, S., Wiznia, A., Lee, S., Mofenson, L., Fiscus, S., Rathore, M., Jimenez, E., et al. (2000). Nucleoside analogs plus ritonavir in stable antiretroviral therapy-experienced HIV-infected children: a randomized controlled trial. Pediatric AIDS Clinical Trials Group 338 Study Team. Jama 283, 492-498.

68. Nagao, T., Sato, M., Nakajima, H., and Kiyomoto, A. (1973). Studies on a new 1,5-benzothiazepine derivative (CRD-401). IV. Coronary vasodilating effect and structure-activity relationship. Chemical & pharmaceutical bulletin 21, 92-97.

69. Neldner, K. H. (1977). The halogenated 8-hydroxyquinolines. International journal of dermatology 16, 267-273.

70. Odds, F. C., Webster, C. E., and Abbott, A. B. (1984). Antifungal relative inhibition factors: BAY 1-9139, bifonazole, butoconazole, isoconazole, itraconazole (R 51211), oxiconazole, Ro 14-4767/002, sulconazole, terconazole and vibunazole (BAY n-7133) compared in vitro with nine established antifungal agents. The Journal of antimicrobial chemotherapy 14, 105-114.

71. Otto, O., Rosendahl, P., Mietke, A., Golfier, S., Herold, C., Klaue, D., Girardo, S., Pagliara, S., Ekpenyong, A., Jacobi, A., et al. (2015). Real-time deformability cytometry: on-the-fly cell mechanical phenotyping. Nature methods 12, 199-202, 194 p following 202.

72. Park, D.M., Jung, J., Masjkur, J., Makrogkikas, S., Ebermann, D., Saha, S., Rogliano, R., Paolillo, N., Pacioni, S., Mckay, R. D., et al. (2013). Hes3 regulates cell number in cultures from glioblastoma multiforme with stem cell characteristics. Sci Rep 3, 1095.

73. Parnham, M. J. (1990). Biological activities and clinical potential of Ebselen. Adv Exp Med Biol 264, 193-197.

74. Paulsen, C. A., Leach, R. B., Lanman, J., Goldston, N., Maddock, W. O., and Heller, C. G. (1962). Inherent estrogenicity of norethindrone and norethynodrel: comparison with other synthetic progestins and progesterone. J Clin Endocrinol Metab 22, 1033-1039.

75. Pivnick, H., Tracy, J. M., and Glass, D. G. (1963). Studies of Preservatives of Poliomyelitis (Salk) Vaccine. I. Benzethonium Chloride. Journal of pharmaceutical sciences 52, 883-888.

76. Polak, A. (1982). Oxiconazole, a new imidazole derivative. Evaluation of antifungal activity in vitro and in vivo. Arzneimittel-Forschung 32, 17-24.

77. Poser, S.W., and Androutsellis-Theotokis, A. (2013). Growing neural stem cells from conventional and non-conventional regions of the adult rodent brain. J Vis Exp, e50880.

78. Pullen, D. (1962). "Conovid-E" as an oral contraceptive. British medical journal 2, 1016-1019.

79. Rajamuthiah, R., Fuchs, B. B., Conery, A. L., Kim, W., Jayamani, E., Kwon, B., Ausubel, F. M., and Mylonakis, E. (2015). Repurposing salicylanilide anthelmintic drugs to combat drug resistant *Staphylococcus aureus*. PLOS One 10, e0124595.

80. Ringner, M. (2008). What is principal component analysis? Nature biotechnology 26, 303-304.

81. Robertson, L., Ghouri, M.A., and Kovacs, F. (2012). Antiplatelet and anticoagulant drugs for prevention of restenosis/reocclusion following peripheral endovascular treatment. The Cochrane database of systematic reviews, CD002071.

82. Rodriguez, L. A., and Close, J. A. (1968). The metabolism of the 5-7-dibromo-8-hydroxyquinoline (broxyquinoline) in man. Biochemical pharmacology 17, 1647-1653.

83. Rohde, W., Mikelens, P., Jackson, J., Blackman, J., Whitcher, J., and Levinson, W. (1976). Hydroxyquinolines inhibit ribonucleic acid-dependent deoxyribonucleic acid polymerase and inactivate Rous sarcoma virus and herpes simplex virus. Antimicrobial agents and chemotherapy 10, 234-240.

84. Roland, M., Clyman, M. J., Decker, A., Ober, W. B., and Bronstein, S. B. (1966). Clinical study of quinestrol in infertile women. Fertility and sterility 17, 531-540.

85. Sato, M., Nagao, T., Yamaguchi, I., Nakajima, H., and Kiyomoto, A. (1971). Pharmacological studies on a new 1,5-benzothiazepine derivative (CRD-401). Arzneimittel-Forschung 21, 1338-1343.

86. Sawyer, P. R., Brogden, R. N., Pinder, R. M., Speight, T. M., and Avery, G. S. (1975). Miconazole: a review of its antifungal activity and therapeutic efficacy. Drugs 9, 406-423.

87. Schewe, T. (1995). Molecular actions of ebselen—an antiinflammatory antioxidant. General pharmacology 26, 1153-1169.

88. Shannon, P., Markiel, A., Ozier, O., Baliga, N. S., Wang, J. T., Ramage, D., Amin, N., Schwikowski, B., and Ideker, T. (2003). Cytoscape: a software environment for integrated models of biomolecular interaction networks. Genome research 13, 2498-2504.

89. Sharma, C. S. (1975). Letter: Effect of broxyquinoline and broxaldine in leprosy. Lancet 1,405.

90. Sies, H. (1993). Ebselen, a selenoorganic compound as glutathione peroxidase mimic. Free radical biology & medicine 14, 313-323.

91. Soeda, A., Inagaki, A., Oka, N., Ikegame, Y., Aoki, H., Yoshimura, S., Nakashima, S., Kunisada, T., and Iwama, T. (2008). Epidermal growth factor plays a crucial role in mitogenic regulation of human brain tumor stem cells. J Biol Chem 283, 10958-10966.

92. Soeda, A., Park, M., Lee, D., Mintz, A., Androutsellis-Theotokis, A., Mckay, R.D., Engh, J., Iwama, T., Kunisada, T., Kassam, A. B., et al. (2009). Hypoxia promotes expansion of the CD133-positive glioma stem cells through activation of HIF-1 alpha. Oncogene 28, 3949-3959.

93. Szklarczyk, D., Franceschini, A., Wyder, S., Forslund, K., Heller, D., Huerta-Cepas, J., Simonovic, M., Roth, A., Santos, A., Tsafou, K. P., et al. (2015). STRING v10: protein-protein interaction networks, integrated over the tree of life. Nucleic Acids Res 43, D447-452.

94. Thienpont, D., Van Cutsem, J., Van Nueten, J. M., Niemegeers, C. J., and Marsboom, R. (1975). Bilogical and toxicological properties of econazole, a broad-spectrum antimycotic. Arzneimittel-Forschung 25, 224-230.

95. Van Cutsem, J. M., and Thienpont, D. (1972). Miconazole, a broad-spectrum antimycotic agent with antibacterial activity. Chemotherapy 17, 392-404.

96. Voigtlander, H. W., and Rosenberg, W. (1963). [Prosapogenin GB (beta-aescin). A contribution to the chemistry of horse chestnut saponins]. Arzneimittel-Forschung 13, 385-386.

97. Wald, A. (2003). Is chronic use of stimulant laxatives harmful to the colon? Journal of clinical gastroenterology 36, 386-389.

98. Walmsley, S., Bernstein, B., King, M., Arribas, J., Beall, G., Ruane, P., Johnson, M., Johnson, D., Lalonde, R., Japour, A., et al. (2002). Lopinavir-ritonavir versus nelfinavir for the initial treatment of HIV infection. N Engl J Med 346, 2039-2046.

99. Wang, C. C., and Pong, S. S. (1982). Actions of avermectin Bla on GABA nerves. Progress in clinical and biological research 97, 373-395.

100. Wang, Z., Gerstein, M., and Snyder, M. (2009). RNA-Seq: a revolutionary tool for transcriptomics. Nat Rev Genet 10, 57-63.

101. Webb, J. D., Burg, J. G., and Knapp, F. W. (1991). Moxidectin evaluation against Solenoptes *capillatus* (Anoplura: Linognathidae), *Bovicola bovis* (Mallophaga: trichodectidae), and *Musca autumnalis* (Diptera: Muscidae) on cattle. Journal of economic entomology 84, 1266-1269.

102. Weiss, P., Cordasco, M. G., Carman, W., and Reiner, L. (1951). The effect of ring chlorination on the antibacterial action of aryloxyethoxyethylbenzyl-dimethylammonium chlorides. Journal of the American Pharmaceutical Association American Pharmaceutical Association 40, 267-272.

103. Wright, D.J. (1987). Avermectins: action on target pest species. Biochemical Society transactions 15, 65-67.

104. Wu, T. D., and Nacu, S. (2010). Fast and SNP-tolerant detection of complex variants and splicing in short reads. Bioinformatics 26, 873-881.

105. Zimmerman, G. L., Hoberg, E. P., and Pankavich, J. A. (1992). Efficacy of orally administered moxidectin against naturally acquired gastrointestinal nematodes in cattle. American journal of veterinary research 53, 1409-1410.

The invention claimed is:

1. A method for prevention of treatment of cancer, tumor metastasis or tumor recurrence in a subject, comprising:

obtaining a biological sample from a subject;

detecting in said biological sample target cells that do not express biomarker tropomyosin 4 (TPM4) or a splice variant thereof, detecting in said biological sample target cells that do express biomarker Hes3, wherein the absence and/or non-expression of TPM4 or a splice variant thereof and the presence and/or expression of Hes3, Ensembl ID: ENSG00000173673, is an indicator for the susceptibility of said subject for a positive treatment outcome with an anti-proliferative compound; and if the biological sample from the subject comprises target cells that do not express the biomarker TPM4 or a splice variant thereof and do express the biomarker Hes3, administering to the subject an anti-proliferative compound or a pharmaceutical composition comprising an anti-proliferative compound, wherein said antiproliferative compound is selected from the group consisting of bithionate Na, broxyquinoline, clioquinol, clofoctol, ebselen, lasalocid Na, ramelteon and triclosan.

2. The method according to claim 1, wherein said antiproliferative compound does not affect angiogenesis.

3. A method of screening a subject for a proliferative disease risk factor, comprising detecting the presence or absence of target cells that do not express the biomarker TPM4 (tropomyosin 4) or a splice variant thereof and detecting the presence or absence of target cells that do express the biomarker Hes3 in said subject; the presence of target cells that do not express TPM4 and do express Hes3 indicating said subject is at increased risk of developing a proliferative disease selected from cancer, tumor metastasis or tumor recurrence, characterized in that said detecting the presence or absence of target cells comprises detecting the expression by said target cells of the biomarker TPM4 (tropomyosin 4); Ensembl ID: ENSG00000167460; or a splice variant thereof, and detecting the expression by said target cells of the biomarker Hes3 Ensembl ID: ENSG00000173673, wherein the absence and/or non-expression of the biomarker TPM4 or a splice variant thereof and the presence and/or expression of Hes3 are indicators for the susceptibility of said subject for a positive treatment outcome with said an anti-proliferative compound; and wherein said antiproliferative compound is selected from the group consisting of bithionate Na, broxyquinoline, clioquinol, clofoctol, ebselen, lasalocid Na, ramelteon and triclosan.

4. The method according to claim 3, wherein said subject has been previously diagnosed or prognosed as afflicted with said proliferative disease; or wherein said subject has not been previously diagnosed or prognosed as afflicted with said proliferative disease; or wherein said subject has undergone treatment for said proliferative disease.

5. The method of claim 3, wherein said proliferative disease is cancer and is selected from the group consisting of as malignant tumors of epithelial or mesenchymal cells, breast cancer, prostate cancer, pancreatic cancer, adrenal cancer, melanoma, lung cancer, colon cancer, leukemia, soft tissue and bone sarcomas, neuroendocrine tumors such as islet cell carcinoma or medullary carcinoma of the thyroid, squamous carcinomas, adenocarcinomas and gliosarcomas such as glioblastoma multiforme.

6. The method of claim 3, wherein said proliferative disease is tumor metastasis or tumor recurrence.

* * * * *

SEQUENCE LISTING

<160> NUMBER OF SEQ ID NOS: 106

<210> SEQ ID NO 1
<211> LENGTH: 747
<212> TYPE: DNA
<213> ORGANISM: Homo sapiens

<400> SEQUENCE: 1

```
atggccggcc tcaactccct ggaggcggtg aaacgcaaga tccaggccct gcagcagcag        60
gcggacgagg cggaagaccg cgcgcagggc ctgcagcggg agctggacgg cgagcgcgag       120
```

```
cggcgcgaga aagctgaagg tgatgtggcc gccctcaacc gacgcatcca gctcgttgag      180
gaggagttgg acagggctca ggaacgactg gccacggccc tgcagaagct ggaggaggca      240
gaaaaagctg cagatgagag tgagagagga atgaaggtga tagaaaaccg ggccatgaag      300
gatgaggaga agatggagat tcaggagatg cagctcaaag aggccaagca cattgcggaa      360
gaggctgacc gcaaatacga ggaggtagct cgtaagctgg tcatcctgga gggtgagctg      420
gagagggcag aggagcgtgc ggaggtgtct gaactaaaat gtggtgacct ggaagaagaa      480
ctcaagaatg ttactaacaa tctgaaatct ctggaggctg catctgaaaa gtattctgaa      540
aaggaggaca aatatgaaga agaaattaaa cttctgtctg acaaactgaa agaggctgag      600
acccgtgctg aatttgcaga gagaacggtt gcaaactgg aaaagacaat tgatgacctg      660
gaagagaaac ttgcccaggc caaagaagag aacgtgggct acatcagac actggatcag      720 acactaaacg aacttaactg tatataa                                        747
```

<210> SEQ ID NO 2
<211> LENGTH: 248
<212> TYPE: PRT
<213> ORGANISM: Homo sapiens

<400> SEQUENCE: 2

```
Met Ala Gly Leu Asn Ser Leu Glu Ala Val Lys Arg Lys Ile Gln Ala
1               5                   10                  15

Leu Gln Gln Gln Ala Asp Glu Ala Glu Asp Arg Ala Gln Gly Leu Gln
            20                  25                  30

Arg Glu Leu Asp Gly Glu Arg Glu Arg Arg Glu Lys Ala Glu Gly Asp
        35                  40                  45

Val Ala Ala Leu Asn Arg Arg Ile Gln Leu Val Glu Glu Glu Leu Asp
    50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Met Lys Asp Glu Glu Lys Met Glu Ile Gln Glu Met Gln Leu
            100                 105                 110

Lys Glu Ala Lys His Ile Ala Glu Glu Ala Asp Arg Lys Tyr Glu Glu
        115                 120                 125

Val Ala Arg Lys Leu Val Ile Leu Glu Gly Glu Leu Glu Arg Ala Glu
    130                 135                 140

Glu Arg Ala Glu Val Ser Glu Leu Lys Cys Gly Asp Leu Glu Glu Glu
145                 150                 155                 160

Leu Lys Asn Val Thr Asn Asn Leu Lys Ser Leu Glu Ala Ala Ser Glu
                165                 170                 175

Lys Tyr Ser Glu Lys Glu Asp Lys Tyr Glu Glu Glu Ile Lys Leu Leu
            180                 185                 190

Ser Asp Lys Leu Lys Glu Ala Glu Thr Arg Ala Glu Phe Ala Glu Arg
        195                 200                 205

Thr Val Ala Lys Leu Glu Lys Thr Ile Asp Asp Leu Glu Glu Lys Leu
    210                 215                 220

Ala Gln Ala Lys Glu Glu Asn Val Gly Leu His Gln Thr Leu Asp Gln
225                 230                 235                 240

Thr Leu Asn Glu Leu Asn Cys Ile
                245
```

```
<210> SEQ ID NO 3
<211> LENGTH: 855
<212> TYPE: DNA
<213> ORGANISM: Homo sapiens

<400> SEQUENCE: 3
atggaggcca tcaagaagaa aatgcagatg ctgaagttgg acaaggagaa tgccatcgac        60
cgcgcggagc aggcggaggc ggataagaaa gccgctgagg acaagtgcaa gcaggtggag       120
gaggagctga cgcacctcca gaagaaacta aaagggacag aggacgagct ggataaatat       180
tccgaggacc tgaaggacgc gcaggagaag ctggagctca cggagaagaa ggcctccgac       240
gctgaaggtg atgtggccgc cctcaaccga cgcatccagc tcgttgagga ggagttggac       300
agggctcagg aacgactggc cacggccctg cagaagctgg aggaggcaga aaaagctgca       360
gatgagagtg agagaggaat gaaggtgata gaaaaccggg ccatgaagga tgaggagaag       420
atggagattc aggagatgca gctcaaagag gccaagcaca ttgcggaaga ggctgaccgc       480
aaatacgagg aggtagctcg taagctggtc atcctggagg gtgagctgga gagggcagag       540
gagcgtgcgg aggtgtctga actaaaatgt ggtgacctgg aagaagaact caagaatgtt       600
actaacaatc tgaaatctct ggaggctgca tctgaaaagt attctgaaaa ggaggacaaa       660
tatgaagaag aaattaaact tctgtctgac aaactgaaag aggctgagac ccgtgctgaa       720
tttgcagaga gaacggttgc aaaactggaa aagacaattg atgacctgga agagaaactt       780
gcccaggcca agaagagaa cgtgggctta catcagacac tggatcagac actaaacgaa       840
cttaactgta tataa                                                        855

<210> SEQ ID NO 4
<211> LENGTH: 284
<212> TYPE: PRT
<213> ORGANISM: Homo sapiens

<400> SEQUENCE: 4

Met Glu Ala Ile Lys Lys Lys Met Gln Met Leu Lys Leu Asp Lys Glu
1               5                   10                  15

Asn Ala Ile Asp Arg Ala Glu Gln Ala Glu Ala Asp Lys Lys Ala Ala
            20                  25                  30

Glu Asp Lys Cys Lys Gln Val Glu Glu Glu Leu Thr His Leu Gln Lys
        35                  40                  45

Lys Leu Lys Gly Thr Glu Asp Glu Leu Asp Lys Tyr Ser Glu Asp Leu
    50                  55                  60

Lys Asp Ala Gln Glu Lys Leu Glu Leu Thr Glu Lys Lys Ala Ser Asp
65                  70                  75                  80

Ala Glu Gly Asp Val Ala Ala Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Asn Arg Ala Met Lys Asp Glu Glu Lys Met Glu Ile Gln
    130                 135                 140

Glu Met Gln Leu Lys Glu Ala Lys His Ile Ala Glu Glu Ala Asp Arg
145                 150                 155                 160

Lys Tyr Glu Glu Val Ala Arg Lys Leu Val Ile Leu Glu Gly Glu Leu
                165                 170                 175
```

-continued

---

```
Glu Arg Ala Glu Glu Arg Ala Glu Val Ser Glu Leu Lys Cys Gly Asp
            180                 185                 190

Leu Glu Glu Glu Leu Lys Asn Val Thr Asn Asn Leu Lys Ser Leu Glu
            195                 200                 205

Ala Ala Ser Glu Lys Tyr Ser Glu Lys Glu Asp Lys Tyr Glu Glu Glu
            210                 215                 220

Ile Lys Leu Leu Ser Asp Lys Leu Lys Glu Ala Glu Thr Arg Ala Glu
225                 230                 235                 240

Phe Ala Glu Arg Thr Val Ala Lys Leu Glu Lys Thr Ile Asp Asp Leu
                245                 250                 255

Glu Glu Lys Leu Ala Gln Ala Lys Glu Glu Asn Val Gly Leu His Gln
            260                 265                 270

Thr Leu Asp Gln Thr Leu Asn Glu Leu Asn Cys Ile
            275                 280
```

<210> SEQ ID NO 5
<211> LENGTH: 747
<212> TYPE: DNA
<213> ORGANISM: Homo sapiens

<400> SEQUENCE: 5

```
atggccggcc tcaactccct ggaggcggtg aaacgcaaga tccaggccct gcagcagcag        60
gcggacgagg cggaagaccg cgcgcagggc ctgcagcggg agctggacgg cgagcgcgag       120
cggcgcgaga aagctgaagg tgatgtggcc gccctcaacc gacgcatcca gctcgttgag       180
gaggagttgg acagggctca ggaacgactg gccacggccc tgcagaagct ggaggaggca       240
gaaaaagctg cagatgagag tgagagagga atgaaggtga tagaaaaccg ggccatgaag       300
gatgaggaga agatggagat tcaggagatg cagctcaaag aggccaagca cattgcggaa       360
gaggctgacc gcaaatacga ggaggtagct cgtaagctgg tcatcctgga gggtgagctg       420
gagagggcag aggagcgtgc ggaggtgtct gaactaaaat gtggtgacct ggaagaagaa       480
ctcaagaatg ttactaacaa tctgaaatct ctggaggctg catctgaaaa gtattctgaa       540
aaggaggaca atatgaagaa agaaattaaa cttctgtctg acaaactgaa agaggctgag       600
acccgtgctg aatttgcaga gagaacggtt gcaaaactgg aaaagacaat tgatgacctg       660
gaagagaaac ttgcccaggc caaagaagag aacgtgggct acatcagac actggatcag       720 acactaaacg aacttaactg tatataa                                          747
```

<210> SEQ ID NO 6
<211> LENGTH: 248
<212> TYPE: PRT
<213> ORGANISM: Homo sapiens

<400> SEQUENCE: 6

```
Met Ala Gly Leu Asn Ser Leu Glu Ala Val Lys Arg Lys Ile Gln Ala
1               5                   10                  15

Leu Gln Gln Gln Ala Asp Glu Ala Glu Asp Arg Ala Gln Gly Leu Gln
            20                  25                  30

Arg Glu Leu Asp Gly Glu Arg Glu Arg Arg Glu Lys Ala Glu Gly Asp
            35                  40                  45

Val Ala Ala Leu Asn Arg Arg Ile Gln Leu Val Glu Glu Glu Leu Asp
            50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
```

-continued

```
                      85              90              95
Arg Ala Met Lys Asp Glu Glu Lys Met Glu Ile Gln Glu Met Gln Leu
            100              105              110
Lys Glu Ala Lys His Ile Ala Glu Glu Ala Asp Arg Lys Tyr Glu Glu
        115              120              125
Val Ala Arg Lys Leu Val Ile Leu Glu Gly Glu Leu Glu Arg Ala Glu
    130              135              140
Glu Arg Ala Glu Val Ser Glu Leu Lys Cys Gly Asp Leu Glu Glu Glu
145              150              155              160
Leu Lys Asn Val Thr Asn Asn Leu Lys Ser Leu Glu Ala Ala Ser Glu
            165              170              175
Lys Tyr Ser Glu Lys Glu Asp Lys Tyr Glu Glu Glu Ile Lys Leu Leu
        180              185              190
Ser Asp Lys Leu Lys Glu Ala Glu Thr Arg Ala Glu Phe Ala Glu Arg
        195              200              205
Thr Val Ala Lys Leu Glu Lys Thr Ile Asp Asp Leu Glu Glu Lys Leu
    210              215              220
Ala Gln Ala Lys Glu Glu Asn Val Gly Leu His Gln Thr Leu Asp Gln
225              230              235              240
Thr Leu Asn Glu Leu Asn Cys Ile
            245
```

```
<210> SEQ ID NO 7
<211> LENGTH: 855
<212> TYPE: DNA
<213> ORGANISM: Homo sapiens

<400> SEQUENCE: 7
atggaggcca tcaagaagaa aatgcagatg ctgaagttgg acaaggagaa tgccatcgac      60
cgcgcggagc aggcggaggc ggataagaaa gccgctgagg acaagtgcaa gcaggtggag     120
gaggagctga cgcacctcca gaagaaacta aaagggacag aggacgagct ggataaatat     180
tccgaggacc tgaaggacgc gcaggagaag ctggagctca cggagaagaa ggcctccgac     240
gctgaaggtg atgtggccgc cctcaaccga cgcatccagc tcgttgagga ggagttggac     300
agggctcagg aacgactggc cacggccctg cagaagctgg aggaggcaga aaaagctgca     360
gatgagagtg agagaggaat gaaggtgata gaaaaccggg ccatgaagga tgaggagaag     420
atggagattc aggagatgca gctcaaagag gccaagcaca ttgcggaaga ggctgaccgc     480
aaatacgagg aggtagctcg taagctggtc atcctggagg gtgagctgga gagggcagag     540
gagcgtgcgg aggtgtctga actaaaatgt ggtgacctgg aagaagaact caagaatgtt     600
actaacaatc tgaaatctct ggaggctgca tctgaaaagt attctgaaaa ggaggacaaa     660
tatgaagaag aaattaaact tctgtctgac aaactgaaag aggctgagac ccgtgctgaa     720
tttgcagaga aacggttgc aaaactggaa aagacaattg atgacctgga agagaaactt      780
gcccaggcca agaagagaa cgtgggctta catcagacac tggatcagac actaaacgaa      840
cttaactgta tataa                                                        855
```

```
<210> SEQ ID NO 8
<211> LENGTH: 284
<212> TYPE: PRT
<213> ORGANISM: Homo sapiens

<400> SEQUENCE: 8

Met Glu Ala Ile Lys Lys Lys Met Gln Met Leu Lys Leu Asp Lys Glu
```

-continued

```
1              5               10              15

Asn Ala Ile Asp Arg Ala Glu Gln Ala Glu Ala Asp Lys Lys Ala Ala
            20              25              30

Glu Asp Lys Cys Lys Gln Val Glu Glu Glu Leu Thr His Leu Gln Lys
            35              40              45

Lys Leu Lys Gly Thr Glu Asp Glu Leu Asp Lys Tyr Ser Glu Asp Leu
    50              55              60

Lys Asp Ala Gln Glu Lys Leu Glu Leu Thr Glu Lys Lys Ala Ser Asp
65              70              75              80

Ala Glu Gly Asp Val Ala Ala Leu Asn Arg Arg Ile Gln Leu Val Glu
            85              90              95

Glu Glu Leu Asp Arg Ala Gln Glu Arg Leu Ala Thr Ala Leu Gln Lys
            100             105             110

Leu Glu Glu Ala Glu Lys Ala Ala Asp Glu Ser Glu Arg Gly Met Lys
            115             120             125

Val Ile Glu Asn Arg Ala Met Lys Asp Glu Glu Lys Met Glu Ile Gln
    130             135             140

Glu Met Gln Leu Lys Glu Ala Lys His Ile Ala Glu Glu Ala Asp Arg
145             150             155             160

Lys Tyr Glu Glu Val Ala Arg Lys Leu Val Ile Leu Glu Gly Glu Leu
            165             170             175

Glu Arg Ala Glu Glu Arg Ala Glu Val Ser Glu Leu Lys Cys Gly Asp
            180             185             190

Leu Glu Glu Glu Leu Lys Asn Val Thr Asn Asn Leu Lys Ser Leu Glu
            195             200             205

Ala Ala Ser Glu Lys Tyr Ser Glu Lys Glu Asp Lys Tyr Glu Glu Glu
    210             215             220

Ile Lys Leu Leu Ser Asp Lys Leu Lys Glu Ala Glu Thr Arg Ala Glu
225             230             235             240

Phe Ala Glu Arg Thr Val Ala Lys Leu Glu Lys Thr Ile Asp Asp Leu
            245             250             255

Glu Glu Lys Leu Ala Gln Ala Lys Glu Glu Asn Val Gly Leu His Gln
            260             265             270

Thr Leu Asp Gln Thr Leu Asn Glu Leu Asn Cys Ile
    275             280
```

<210> SEQ ID NO 9
<211> LENGTH: 681
<212> TYPE: DNA
<213> ORGANISM: Homo sapiens

<400> SEQUENCE: 9

```
atggagcgag ccaggcggat tgaaggatgg aattccaacg aggctccccc gcctcgtccc        60
accttggctg aaggtgatgt ggccgccctc aaccgacgca tccagctcgt tgaggaggag       120
ttggacaggg ctcaggaacg actggccacg gccctgcaga agctggagga ggcagaaaaa       180
gctgcagatg agagtgagag aggaatgaag gtgatagaaa accgggccat gaaggatgag       240
gagaagatgg agattcagga gatgcagctc aaagaggcca agcacattgc ggaagaggct       300
gaccgcaaat acgaggaggt agctcgtaag ctggtcatcc tggagggtga gctggagagg       360
gcagaggagc gtgcggaggt gtctgaacta aaatgtggtg acctggaaga agaactcaag       420
aatgttacta caatctgaa atctctggag gctgcatctg aaaagtattc tgaaaaggag       480
gacaaatatg aagaagaaat taaacttctg tctgacaaac tgaaagaggc tgagacccgt       540
```

-continued

```
gctgaatttg cagagagaac ggttgcaaaa ctggaaaaga caattgatga cctggaagag    600
aaacttgccc aggccaaaga agagaacgtg ggcttacatc agacactgga tcagacacta    660
aacgaactta actgtatata a                                              681
```

```
<210> SEQ ID NO 10
<211> LENGTH: 226
<212> TYPE: PRT
<213> ORGANISM: Homo sapiens

<400> SEQUENCE: 10

Met Glu Arg Ala Arg Arg Ile Glu Gly Trp Asn Ser Asn Glu Ala Pro
1               5                   10                  15

Pro Pro Arg Pro Thr Leu Ala Glu Gly Asp Val Ala Ala Leu Asn Arg
                20                  25                  30

Arg Ile Gln Leu Val Glu Glu Glu Leu Asp Arg Ala Gln Glu Arg Leu
        35                  40                  45

Ala Thr Ala Leu Gln Lys Leu Glu Glu Ala Glu Lys Ala Ala Asp Glu
    50                  55                  60

Ser Glu Arg Gly Met Lys Val Ile Glu Asn Arg Ala Met Lys Asp Glu
65                  70                  75                  80

Glu Lys Met Glu Ile Gln Glu Met Gln Leu Lys Glu Ala Lys His Ile
                85                  90                  95

Ala Glu Glu Ala Asp Arg Lys Tyr Glu Glu Val Ala Arg Lys Leu Val
                100                 105                 110

Ile Leu Glu Gly Glu Leu Glu Arg Ala Glu Glu Arg Ala Glu Val Ser
        115                 120                 125

Glu Leu Lys Cys Gly Asp Leu Glu Glu Glu Leu Lys Asn Val Thr Asn
    130                 135                 140

Asn Leu Lys Ser Leu Glu Ala Ala Ser Glu Lys Tyr Ser Glu Lys Glu
145                 150                 155                 160

Asp Lys Tyr Glu Glu Glu Ile Lys Leu Leu Ser Asp Lys Leu Lys Glu
                165                 170                 175

Ala Glu Thr Arg Ala Glu Phe Ala Glu Arg Thr Val Ala Lys Leu Glu
                180                 185                 190

Lys Thr Ile Asp Asp Leu Glu Glu Lys Leu Ala Gln Ala Lys Glu Glu
        195                 200                 205

Asn Val Gly Leu His Gln Thr Leu Asp Gln Thr Leu Asn Glu Leu Asn
    210                 215                 220

Cys Ile
225
```

```
<210> SEQ ID NO 11
<211> LENGTH: 270
<212> TYPE: DNA
<213> ORGANISM: Homo sapiens

<400> SEQUENCE: 11
atgaaggtga tagaaaaccg ggccatgaag gatgaggaga agatggagat tcaggagatg     60
cagctcaaag aggccaagca cattgcggaa gaggctgacc gcaaatacga ggaggtagct    120
cgtaagctgg tcatcctgga gggtgagctg gagagggcag aggagcgtgc ggaggtgtct    180
gaactaaaat gtggtgacct ggaagaagaa ctcaagaatg ttactaacaa tctgaaatct    240
ctggaggctg catctgaaaa gtattctgaa                                     270
```

```
<210> SEQ ID NO 12
```

```
<211> LENGTH: 90
<212> TYPE: PRT
<213> ORGANISM: Homo sapiens

<400> SEQUENCE: 12

Met Lys Val Ile Glu Asn Arg Ala Met Lys Asp Glu Glu Lys Met Glu
1               5                   10                  15

Ile Gln Glu Met Gln Leu Lys Glu Ala Lys His Ile Ala Glu Glu Ala
            20                  25                  30

Asp Arg Lys Tyr Glu Glu Val Ala Arg Lys Leu Val Ile Leu Glu Gly
        35                  40                  45

Glu Leu Glu Arg Ala Glu Glu Arg Ala Glu Val Ser Glu Leu Lys Cys
    50                  55                  60

Gly Asp Leu Glu Glu Glu Leu Lys Asn Val Thr Asn Asn Leu Lys Ser
65                  70                  75                  80

Leu Glu Ala Ala Ser Glu Lys Tyr Ser Glu
                85                  90

<210> SEQ ID NO 13
<211> LENGTH: 744
<212> TYPE: DNA
<213> ORGANISM: Homo sapiens

<400> SEQUENCE: 13
atggtggagg aggagctgac gcacctccag aagaaactaa aagggacaga ggacgagctg      60
gataaatatt ccgaggacct gaaggacgcg caggagaagc tggagctcac ggagaagaag     120
gcctccgacg ctgaaggtga tgtggccgcc ctcaaccgac gcatccagct cgttgaggag     180
gagttggaca gggctcagga acgactggcc acggccctgc agaagctgga ggaggcagaa     240
aaagctgcag atgagagtga gagaggaatg aaggtgatag aaaaccgggc catgaaggat     300
gaggagaaga tggagattca ggagatgcag ctcaaagagg ccaagcacat tgcggaagag     360
gctgaccgca aatacgagga ggtagctcgt aagctggtca tcctggaggg tgagctggag     420
agggcagagg agcgtgcgga ggtgtctgaa ctaaaatgtg gtgacctgga agaagaactc     480
aagaatgtta ctaacaatct gaaatctctg gaggctgcat ctgaaaagta ttctgaaaag     540
gaggacaaat atgaagaaga aattaaactt ctgtctgaca aactgaaaga ggctgagacc     600
cgtgctgaat ttgcagagag aacggttgca aaactggaaa agacaattga tgacctggaa     660
gagaaacttg cccaggccaa agaagagaac gtgggcttac atcagacact ggatcagaca     720
ctaaacgaac ttaactgtat ataa                                          744

<210> SEQ ID NO 14
<211> LENGTH: 247
<212> TYPE: PRT
<213> ORGANISM: Homo sapiens

<400> SEQUENCE: 14

Met Val Glu Glu Glu Leu Thr His Leu Gln Lys Lys Leu Lys Gly Thr
1               5                   10                  15

Glu Asp Glu Leu Asp Lys Tyr Ser Glu Asp Leu Lys Asp Ala Gln Glu
            20                  25                  30

Lys Leu Glu Leu Thr Glu Lys Lys Ala Ser Asp Ala Glu Gly Asp Val
        35                  40                  45

Ala Ala Leu Asn Arg Arg Ile Gln Leu Val Glu Glu Glu Leu Asp Arg
    50                  55                  60

Ala Gln Glu Arg Leu Ala Thr Ala Leu Gln Lys Leu Glu Glu Ala Glu
```

```
65                  70                  75                  80

Lys Ala Ala Asp Glu Ser Glu Arg Gly Met Lys Val Ile Glu Asn Arg
                85                  90                  95

Ala Met Lys Asp Glu Glu Lys Met Glu Ile Gln Glu Met Gln Leu Lys
               100                 105                 110

Glu Ala Lys His Ile Ala Glu Glu Ala Asp Arg Lys Tyr Glu Glu Val
           115                 120                 125

Ala Arg Lys Leu Val Ile Leu Glu Gly Glu Leu Glu Arg Ala Glu Glu
       130                 135                 140

Arg Ala Glu Val Ser Glu Leu Lys Cys Gly Asp Leu Glu Glu Glu Leu
145                 150                 155                 160

Lys Asn Val Thr Asn Asn Leu Lys Ser Leu Glu Ala Ala Ser Glu Lys
                165                 170                 175

Tyr Ser Glu Lys Glu Asp Lys Tyr Glu Glu Glu Ile Lys Leu Leu Ser
                180                 185                 190

Asp Lys Leu Lys Glu Ala Glu Thr Arg Ala Glu Phe Ala Glu Arg Thr
            195                 200                 205

Val Ala Lys Leu Glu Lys Thr Ile Asp Asp Leu Glu Glu Lys Leu Ala
        210                 215                 220

Gln Ala Lys Glu Glu Asn Val Gly Leu His Gln Thr Leu Asp Gln Thr
225                 230                 235                 240

Leu Asn Glu Leu Asn Cys Ile
                245

<210> SEQ ID NO 15
<211> LENGTH: 663
<212> TYPE: DNA
<213> ORGANISM: Homno sapiens
<220> FEATURE:
<221> NAME/KEY: misc_feature
<222> LOCATION: (1)..(2)
<223> OTHER INFORMATION: n is a, c, g, or t

<400> SEQUENCE: 15
nngggcctgc agcgggagct ggacggcgag cgcgagcggc gcgagaaagc tgaaggtgat      60
gtggccgccc tcaaccgacg catccagctc gttgaggagg agttggacag ggctcaggaa     120
cgactggcca cggccctgca gaagctggag gaggcagaaa aagctgcaga tgagagtgag     180
agaggaatga aggtgataga aaaccgggcc atgaaggatg aggagaagat ggagattcag     240
gagatgcagc tcaaagaggc caagcacatt gcggaagagg ctgaccgcaa atacgaggag     300
gtagctcgta agctggtcat cctggagggt gagctggaga gggcagagga gcgtgcggag     360
gtgtctgaac taaaatgtgg tgacctggaa gaagaactca gaatgttac taacaatctg      420 aaatctctgg aggctgcatc tgaaaagtat tctgaaaagg aggacaaata tgaagaagaa     480
attaaacttc tgtctgacaa actgaaagag gctgagaccc gtgctgaatt gcagagaga      540 acggttgcaa aactggaaaa gacaattgat gacctggaag atgagttata cgctcagaag     600
ctcaagtaca aagctatcag cgaggaactg gaccacgctc tcaacgacat gacctctctc     660
tga                                                                    663

<210> SEQ ID NO 16
<211> LENGTH: 220
<212> TYPE: PRT
<213> ORGANISM: Homo sapiens
<220> FEATURE:
<221> NAME/KEY: misc_feature
<222> LOCATION: (1)..(1)
```

```
<223> OTHER INFORMATION: Xaa can be any naturally occurring amino acid

<400> SEQUENCE: 16

Xaa Gly Leu Gln Arg Glu Leu Asp Gly Glu Arg Glu Arg Arg Glu Lys
1               5                   10                  15

Ala Glu Gly Asp Val Ala Ala Leu Asn Arg Arg Ile Gln Leu Val Glu
                20                  25                  30

Glu Glu Leu Asp Arg Ala Gln Glu Arg Leu Ala Thr Ala Leu Gln Lys
        35                  40                  45

Leu Glu Glu Ala Glu Lys Ala Ala Asp Glu Ser Glu Arg Gly Met Lys
    50                  55                  60

Val Ile Glu Asn Arg Ala Met Lys Asp Glu Glu Lys Met Glu Ile Gln
65                  70                  75                  80

Glu Met Gln Leu Lys Glu Ala Lys His Ile Ala Glu Glu Ala Asp Arg
                85                  90                  95

Lys Tyr Glu Glu Val Ala Arg Lys Leu Val Ile Leu Glu Gly Glu Leu
            100                 105                 110

Glu Arg Ala Glu Glu Arg Ala Glu Val Ser Glu Leu Lys Cys Gly Asp
        115                 120                 125

Leu Glu Glu Glu Leu Lys Asn Val Thr Asn Asn Leu Lys Ser Leu Glu
    130                 135                 140

Ala Ala Ser Glu Lys Tyr Ser Glu Lys Glu Asp Lys Tyr Glu Glu Glu
145                 150                 155                 160

Ile Lys Leu Leu Ser Asp Lys Leu Lys Glu Ala Glu Thr Arg Ala Glu
                165                 170                 175

Phe Ala Glu Arg Thr Val Ala Lys Leu Glu Lys Thr Ile Asp Asp Leu
                180                 185                 190

Glu Asp Glu Leu Tyr Ala Gln Lys Leu Lys Tyr Lys Ala Ile Ser Glu
        195                 200                 205

Glu Leu Asp His Ala Leu Asn Asp Met Thr Ser Leu
    210                 215                 220

<210> SEQ ID NO 17
<211> LENGTH: 50
<212> TYPE: DNA
<213> ORGANISM: Homo sapiens

<400> SEQUENCE: 17
atgaaggtga tagaaaaccg ggccatgaag gatgaggaga agatggagat                50

<210> SEQ ID NO 18
<211> LENGTH: 16
<212> TYPE: PRT
<213> ORGANISM: Homo sapiens

<400> SEQUENCE: 18

Met Lys Val Ile Glu Asn Arg Ala Met Lys Asp Glu Glu Lys Met Glu
1               5                   10                  15

<210> SEQ ID NO 19
<211> LENGTH: 511
<212> TYPE: DNA
<213> ORGANISM: Homo sapiens

<400> SEQUENCE: 19
atggggtcct gggctggaag aggggtgacg atcggaccca cccccagcag ggccagtgcg        60
aacaaagtgg aggaggagct gacgcacctc cagaagaaac taaaagggac agaggacgag        120
```

-continued

```
ctggataaat attccgagga cctgaaggac gcgcaggaga agctggagct cacggagaag        180
aaggcctccg acgctgaagg tgatgtggcc gccctcaacc gacgcatcca gctcgttgag        240
gaggagttgg acagggctca ggaacgactg gccacggccc tgcagaagct ggaggaggca        300
gaaaaagctg cagatgagag tgagagagga atgaaggtga tagaaaaccg ggccatgaag        360
gatgaggaga agatggagat tcaggagatg cagctcaaag aggccaagca cattgcggaa        420
gaggctgacc gcaaatacga ggaggtagct cgtaagctgg tcatcctgga gggtgagctg        480
gagagggcag aggagcgtgc ggaggtgtct g                                       511
```

```
<210> SEQ ID NO 20
<211> LENGTH: 170
<212> TYPE: PRT
<213> ORGANISM: Homo sapiens

<400> SEQUENCE: 20

Met Gly Ser Trp Ala Gly Arg Gly Val Thr Ile Gly Pro Thr Pro Ser
1               5                   10                  15

Arg Ala Ser Ala Asn Lys Val Glu Glu Glu Leu Thr His Leu Gln Lys
            20                  25                  30

Lys Leu Lys Gly Thr Glu Asp Glu Leu Asp Lys Tyr Ser Glu Asp Leu
        35                  40                  45

Lys Asp Ala Gln Glu Lys Leu Glu Leu Thr Glu Lys Lys Ala Ser Asp
    50                  55                  60

Ala Glu Gly Asp Val Ala Ala Leu Asn Arg Arg Ile Gln Leu Val Glu
65                  70                  75                  80

Glu Glu Leu Asp Arg Ala Gln Glu Arg Leu Ala Thr Ala Leu Gln Lys
                85                  90                  95

Leu Glu Glu Ala Glu Lys Ala Ala Asp Glu Ser Glu Arg Gly Met Lys
            100                 105                 110

Val Ile Glu Asn Arg Ala Met Lys Asp Glu Glu Lys Met Glu Ile Gln
        115                 120                 125

Glu Met Gln Leu Lys Glu Ala Lys His Ile Ala Glu Glu Ala Asp Arg
    130                 135                 140

Lys Tyr Glu Glu Val Ala Arg Lys Leu Val Ile Leu Glu Gly Glu Leu
145                 150                 155                 160

Glu Arg Ala Glu Glu Arg Ala Glu Val Ser
                165                 170
```

```
<210> SEQ ID NO 21
<211> LENGTH: 307
<212> TYPE: DNA
<213> ORGANISM: Homo sapiens

<400> SEQUENCE: 21
atgaaggtga tagaaaaccg ggccatgaag gatgaggaga agatggagat tcaggagatg         60
cagctcaaag aggccaagca cattgcggaa gaggctgacc gcaaatacga ggaggtagct        120
cgtaagctgg tcatcctgga gggtgagctg gagagggcag aggagcgtgc ggaggtgtct        180
gaactaaaat gtggtgacct ggaagaagaa ctcaagaatg ttactaacaa tctgaaatct        240
ctggaggctg catctgaaaa gtattctgaa aaggaggaca aatatgaaga agaaattaaa        300
cttctgt                                                                  307
```

```
<210> SEQ ID NO 22
<211> LENGTH: 102
<212> TYPE: PRT
```

<213> ORGANISM: Homo sapiens

<400> SEQUENCE: 22

Met Lys Val Ile Glu Asn Arg Ala Met Lys Asp Glu Glu Lys Met Glu
1               5                   10                  15

Ile Gln Glu Met Gln Leu Lys Glu Ala Lys His Ile Ala Glu Glu Ala
                20                  25                  30

Asp Arg Lys Tyr Glu Glu Val Ala Arg Lys Leu Val Ile Leu Glu Gly
            35                  40                  45

Glu Leu Glu Arg Ala Glu Glu Arg Ala Glu Val Ser Glu Leu Lys Cys
        50                  55                  60

Gly Asp Leu Glu Glu Glu Leu Lys Asn Val Thr Asn Asn Leu Lys Ser
65                  70                  75                  80

Leu Glu Ala Ala Ser Glu Lys Tyr Ser Glu Lys Glu Asp Lys Tyr Glu
                85                  90                  95

Glu Glu Ile Lys Leu Leu
            100

<210> SEQ ID NO 23
<211> LENGTH: 209
<212> TYPE: DNA
<213> ORGANISM: Homo sapiens

<400> SEQUENCE: 23
atggaggcca tcaagaagaa aatgcagatg ctgaagttgg acaaggagaa tgccatcgac        60
cgcgcggagc aggcggaggc ggataagaaa gccgctgagg acaagtgcaa gcaggtggag       120
gaggagctga cgcacctcca gaagaaacta aaagggacag aggacgagct ggataaatat       180
tccgaggacc tgaaggacgc gcaggagaa                                        209

<210> SEQ ID NO 24
<211> LENGTH: 69
<212> TYPE: PRT
<213> ORGANISM: Homo sapiens

<400> SEQUENCE: 24

Met Glu Ala Ile Lys Lys Lys Met Gln Met Leu Lys Leu Asp Lys Glu
1               5                   10                  15

Asn Ala Ile Asp Arg Ala Glu Gln Ala Glu Ala Asp Lys Lys Ala Ala
                20                  25                  30

Glu Asp Lys Cys Lys Gln Val Glu Glu Glu Leu Thr His Leu Gln Lys
            35                  40                  45

Lys Leu Lys Gly Thr Glu Asp Glu Leu Asp Lys Tyr Ser Glu Asp Leu
        50                  55                  60

Lys Asp Ala Gln Glu
65

<210> SEQ ID NO 25
<211> LENGTH: 415
<212> TYPE: DNA
<213> ORGANISM: Homo sapiens

<400> SEQUENCE: 25
atgtcttcca tgcctgcaac caagttttct ttccctttcc atatcttttt gtcctgccat        60
ctctcagcca ggcggattga aggatggaat tccaacgagg ctcccccgcc tcgtccacc        120 ttggctgaag gtgatgtggc cgccctcaac cgacgcatcc agctcgttga ggaggagttg       180
gacagggctc aggaacgact ggccacggcc ctgcagaagc tggaggaggc agaaaaagct       240

-continued

```
gcagatgaga gtgagagagg aatgaaggtg atagaaaacc gggccatgaa ggatgaggag       300
aagatggaga ttcaggagat gcagctcaaa gaggccaagc acattgcgga agaggctgac       360
cgcaaatacg aggaggtagc tcgtaagctg gtcatcctgg agggtgagct ggaga           415
```

```
<210> SEQ ID NO 26
<211> LENGTH: 138
<212> TYPE: PRT
<213> ORGANISM: Homo sapiens

<400> SEQUENCE: 26

Met Ser Ser Met Pro Ala Thr Lys Phe Ser Phe Pro Phe His Ile Phe
1               5                   10                  15

Leu Ser Cys His Leu Ser Ala Arg Arg Ile Glu Gly Trp Asn Ser Asn
            20                  25                  30

Glu Ala Pro Pro Pro Arg Pro Thr Leu Ala Glu Gly Asp Val Ala Ala
            35                  40                  45

Leu Asn Arg Arg Ile Gln Leu Val Glu Glu Glu Leu Asp Arg Ala Gln
            50                  55                  60

Glu Arg Leu Ala Thr Ala Leu Gln Lys Leu Glu Glu Ala Glu Lys Ala
65                  70                  75                  80

Ala Asp Glu Ser Glu Arg Gly Met Lys Val Ile Glu Asn Arg Ala Met
                85                  90                  95

Lys Asp Glu Glu Lys Met Glu Ile Gln Glu Met Gln Leu Lys Glu Ala
            100                 105                 110

Lys His Ile Ala Glu Glu Ala Asp Arg Lys Tyr Glu Glu Val Ala Arg
        115                 120                 125

Lys Leu Val Ile Leu Glu Gly Glu Leu Glu
        130                 135
```

```
<210> SEQ ID NO 27
<211> LENGTH: 290
<212> TYPE: DNA
<213> ORGANISM: Homo sapiens

<400> SEQUENCE: 27
atgaaggtga tagaaaaccg ggccatgaag gatgaggaga agatggagat tcaggagatg        60
cagctcaaag aggccaagca cattgcggaa gaggctgacc gcaaatacga ggaggtagct       120
cgtaagctgg tcatcctgga gggtgagctg gagagggcag aggagcgtgc ggaggtgtct       180
gaactaaaat gtggtgacct ggaagaagaa ctcaagaatg ttactaacaa tctgaaatct       240
ctggaggctg catctgaaaa gtattctgaa aaggaggaca aatatgaaga               290
```

```
<210> SEQ ID NO 28
<211> LENGTH: 96
<212> TYPE: PRT
<213> ORGANISM: Homo sapiens

<400> SEQUENCE: 28

Met Lys Val Ile Glu Asn Arg Ala Met Lys Asp Glu Glu Lys Met Glu
1               5                   10                  15

Ile Gln Glu Met Gln Leu Lys Glu Ala Lys His Ile Ala Glu Glu Ala
            20                  25                  30

Asp Arg Lys Tyr Glu Glu Val Ala Arg Lys Leu Val Ile Leu Glu Gly
            35                  40                  45

Glu Leu Glu Arg Ala Glu Glu Arg Ala Glu Val Ser Glu Leu Lys Cys
        50                  55                  60
```

Gly Asp Leu Glu Glu Glu Leu Lys Asn Val Thr Asn Asn Leu Lys Ser
65                  70                  75                  80

Leu Glu Ala Ala Ser Glu Lys Tyr Ser Glu Lys Glu Asp Lys Tyr Glu
                85                  90                  95

<210> SEQ ID NO 29
<211> LENGTH: 747
<212> TYPE: DNA
<213> ORGANISM: Homo sapiens

<400> SEQUENCE: 29
atggccggcc tcaactccct ggaggcggtg aaacgcaaga tccaggccct gcagcagcag      60
gcggacgagg cggaagaccg cgcgcagggc ctgcagcggg agctggacgg cgagcgcgag     120
cggcgcgaga aagctgaagg tgatgtggcc gccctcaacc gacgcatcca gctcgttgag     180
gaggagttgg acagggctca ggaacgactg gccacggccc tgcagaagct ggaggaggca     240
gaaaaagctg cagatgagag tgagagagga atgaaggtga tagaaaaccg ggccatgaag     300
gatgaggaga agatggagat tcaggagatg cagctcaaag aggccaagca cattgcggaa     360
gaggctgacc gcaaatacga ggaggtagct cgtaagctgg tcatcctgga gggtgagctg     420
gagagggcag aggagcgtgc ggaggtgtct gaactaaaat gtggtgacct ggaagaagaa     480
ctcaagaatg ttactaacaa tctgaaatct ctggaggctg catctgaaaa gtattctgaa     540
aaggaggaca atatgaaga agaaattaaa cttctgtctg acaaactgaa agaggctgag     600
acccgtgctg aatttgcaga gagaacggtt gcaaaactgg aaaagacaat tgatgacctg     660
gaagatgagt tatacgctca gaagctcaag tacaaagcta tcagcgagga actggaccac     720
gctctcaacg acatgacctc tctctga                                        747

<210> SEQ ID NO 30
<211> LENGTH: 248
<212> TYPE: PRT
<213> ORGANISM: Homo sapiens

<400> SEQUENCE: 30

Met Ala Gly Leu Asn Ser Leu Glu Ala Val Lys Arg Lys Ile Gln Ala
1               5                   10                  15

Leu Gln Gln Gln Ala Asp Glu Ala Glu Asp Arg Ala Gln Gly Leu Gln
                20                  25                  30

Arg Glu Leu Asp Gly Glu Arg Glu Arg Arg Glu Lys Ala Glu Gly Asp
            35                  40                  45

Val Ala Ala Leu Asn Arg Arg Ile Gln Leu Val Glu Glu Glu Leu Asp
        50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Met Lys Asp Glu Glu Lys Met Glu Ile Gln Glu Met Gln Leu
                100                 105                 110

Lys Glu Ala Lys His Ile Ala Glu Glu Ala Asp Arg Lys Tyr Glu Glu
            115                 120                 125

Val Ala Arg Lys Leu Val Ile Leu Glu Gly Glu Leu Glu Arg Ala Glu
        130                 135                 140

Glu Arg Ala Glu Val Ser Glu Leu Lys Cys Gly Asp Leu Glu Glu Glu
145                 150                 155                 160

```
Leu Lys Asn Val Thr Asn Asn Leu Lys Ser Leu Glu Ala Ala Ser Glu
                165                 170                 175

Lys Tyr Ser Glu Lys Glu Asp Lys Tyr Glu Glu Glu Ile Lys Leu Leu
            180                 185                 190

Ser Asp Lys Leu Lys Glu Ala Glu Thr Arg Ala Glu Phe Ala Glu Arg
        195                 200                 205

Thr Val Ala Lys Leu Glu Lys Thr Ile Asp Asp Leu Glu Asp Glu Leu
    210                 215                 220

Tyr Ala Gln Lys Leu Lys Tyr Lys Ala Ile Ser Glu Glu Leu Asp His
225                 230                 235                 240

Ala Leu Asn Asp Met Thr Ser Leu
                245
```

<210> SEQ ID NO 31
<211> LENGTH: 747
<212> TYPE: DNA
<213> ORGANISM: Homo sapiens

<400> SEQUENCE: 31

```
atggccggcc tcaactccct ggaggcggtg aaacgcaaga tccaggccct gcagcagcag      60
gcggacgagg cggaagaccg cgcgcagggc ctgcagcggg agctggacgg cgagcgcgag     120
cggcgcgaga agctgaagg tgatgtggcc gccctcaacc gacgcatcca gctcgttgag     180
gaggagttgg acagggctca ggaacgactg gccacggccc tgcagaagct ggaggaggca     240
gaaaaagctg cagatgagag tgagagagga atgaaggtga tagaaaaccg ggccatgaag     300
gatgaggaga agatggagat tcaggagatg cagctcaaag aggccaagca cattgcggaa     360
gaggctgacc gcaaatacga ggaggtagct cgtaagctgg tcatcctgga gggtgagctg     420
gagagggcag aggagcgtgc ggaggtgtct gaactaaaat gtggtgacct ggaagaagaa     480
ctcaagaatg ttactaacaa tctgaaatct ctggaggctg catctgaaaa gtattctgaa     540
aaggaggaca aatatgaaga agaaattaaa cttctgtctg acaaactgaa agaggctgag     600
acccgtgctg aatttgcaga gaaacggtt gcaaaactgg aaaagacaat tgatgacctg     660
gaagatgagt tatacgctca gaagctcaag tacaaagcta tcagcgagga actggaccac     720
gctctcaacg acatgacctc tctctga                                        747
```

<210> SEQ ID NO 32
<211> LENGTH: 248
<212> TYPE: PRT
<213> ORGANISM: Homo sapiens

<400> SEQUENCE: 32

```
Met Ala Gly Leu Asn Ser Leu Glu Ala Val Lys Arg Lys Ile Gln Ala
1               5                   10                  15

Leu Gln Gln Gln Ala Asp Glu Ala Glu Asp Arg Ala Gln Gly Leu Gln
                20                  25                  30

Arg Glu Leu Asp Gly Glu Arg Glu Arg Glu Lys Ala Glu Gly Asp
            35                  40                  45

Val Ala Ala Leu Asn Arg Arg Ile Gln Leu Val Glu Glu Glu Leu Asp
        50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Met Lys Asp Glu Glu Lys Met Glu Ile Gln Glu Met Gln Leu
```

-continued

```
                 100                 105                 110
Lys Glu Ala Lys His Ile Ala Glu Glu Ala Asp Arg Lys Tyr Glu Glu
             115                 120                 125

Val Ala Arg Lys Leu Val Ile Leu Glu Gly Glu Leu Glu Arg Ala Glu
         130                 135                 140

Glu Arg Ala Glu Val Ser Glu Leu Lys Cys Gly Asp Leu Glu Glu Glu
145                 150                 155                 160

Leu Lys Asn Val Thr Asn Asn Leu Lys Ser Leu Glu Ala Ala Ser Glu
                 165                 170                 175

Lys Tyr Ser Glu Lys Glu Asp Lys Tyr Glu Glu Glu Ile Lys Leu Leu
             180                 185                 190

Ser Asp Lys Leu Lys Glu Ala Glu Thr Arg Ala Glu Phe Ala Glu Arg
         195                 200                 205

Thr Val Ala Lys Leu Glu Lys Thr Ile Asp Asp Leu Glu Asp Glu Leu
         210                 215                 220

Tyr Ala Gln Lys Leu Lys Tyr Lys Ala Ile Ser Glu Glu Leu Asp His
225                 230                 235                 240

Ala Leu Asn Asp Met Thr Ser Leu
                 245

<210> SEQ ID NO 33
<211> LENGTH: 552
<212> TYPE: DNA
<213> ORGANISM: Homo sapiens

<400> SEQUENCE: 33
atggccggcc tcaactccct ggaggcggtg aaacgcaaga tccaggccct gcagcagcag        60
gcggacgagg cggaagaccg cgcgcagggc ctgcagcggg agctggacgg cgagcgcgag       120
cggcgcgaga aagctgaagg tgatgtggcc gccctcaacc gacgcatcca gctcgttgag       180
gaggagttgg acagggctca ggaacgactg gccacggccc tgcagaagct ggaggaggca       240
gaaaaagctg cagatgagag tgagagagga atgaaggtga tagaaaaccg ggccatgaag       300
gatgaggaga agatggagat tcaggagatg cagctcaaag aggccaagca cattgcggaa       360
gaggctgacc gcaaatacga ggaggtagct cgtaagctgg tcatcctgga gggtgagctg       420
gagagggcag aggagcgtgc ggaggtgtct gaactaaaat gtggtgacct ggaagaagaa       480
ctcaagaatg ttactaacaa tctgaaatct ctggaggctg catctgaaaa gagacggggt       540
ctcactatgt ga                                                         552

<210> SEQ ID NO 34
<211> LENGTH: 183
<212> TYPE: PRT
<213> ORGANISM: Homo sapiens

<400> SEQUENCE: 34

Met Ala Gly Leu Asn Ser Leu Glu Ala Val Lys Arg Lys Ile Gln Ala
1               5                  10                  15

Leu Gln Gln Gln Ala Asp Glu Ala Glu Asp Arg Ala Gln Gly Leu Gln
             20                  25                  30

Arg Glu Leu Asp Gly Glu Arg Glu Arg Arg Glu Lys Ala Glu Gly Asp
         35                  40                  45

Val Ala Ala Leu Asn Arg Arg Ile Gln Leu Val Glu Glu Glu Leu Asp
     50                  55                  60

Arg Ala Gln Glu Arg Leu Ala Thr Ala Leu Gln Lys Leu Glu Glu Ala
65                  70                  75                  80
```

```
Glu Lys Ala Ala Asp Glu Ser Glu Arg Gly Met Lys Val Ile Glu Asn
                85                  90                  95

Arg Ala Met Lys Asp Glu Glu Lys Met Glu Ile Gln Glu Met Gln Leu
            100                 105                 110

Lys Glu Ala Lys His Ile Ala Glu Glu Ala Asp Arg Lys Tyr Glu Glu
        115                 120                 125

Val Ala Arg Lys Leu Val Ile Leu Glu Gly Glu Leu Glu Arg Ala Glu
    130                 135                 140

Glu Arg Ala Glu Val Ser Glu Leu Lys Cys Gly Asp Leu Glu Glu Glu
145                 150                 155                 160

Leu Lys Asn Val Thr Asn Asn Leu Lys Ser Leu Glu Ala Ala Ser Glu
                165                 170                 175

Lys Arg Arg Gly Leu Thr Met
            180
```

```
<210> SEQ ID NO 35
<211> LENGTH: 522
<212> TYPE: DNA
<213> ORGANISM: Homo sapiens
<220> FEATURE:
<221> NAME/KEY: misc_feature
<222> LOCATION: (1)..(2)
<223> OTHER INFORMATION: n is a, c, g, or t

<400> SEQUENCE: 35
nngaagaaac taaaagggac agaggacgag ctggataaat attccgagga cctgaaggac        60
gcgcaggaga agctggagct cacggagaag aaggcctccg acgctgaagg tgatgtggcc       120
gccctcaacc gacgcatcca gctcgttgag gaggagttgg acagggctca ggaacgactg       180
gccacggccc tgcagaagct ggaggaggca gaaaaagctg cagatgagag tgagagagga       240
atgaaggtga tagaaaaccg ggccatgaag gatgaggaga agatggagat tcaggagatg       300
cagctcaaag aggccaagca cattgcggaa gaggctgacc gcaaatacga ggaggtagct       360
cgtaagctgg tcatcctgga gggtgagctg gagagggcag aggagcgtgc ggaggtgtct       420
gaactaaaat gtggtgacct ggaagaagaa ctcaagaatg ttactaacaa tctgaaatct       480
ctggaggctg catctgaaaa gagacggggt ctcactatgt ga                          522
```

```
<210> SEQ ID NO 36
<211> LENGTH: 173
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 36

Xaa Lys Lys Leu Lys Gly Thr Glu Asp Glu Leu Asp Lys Tyr Ser Glu
1               5                   10                  15

Asp Leu Lys Asp Ala Gln Glu Lys Leu Glu Leu Thr Glu Lys Lys Ala
            20                  25                  30

Ser Asp Ala Glu Gly Asp Val Ala Ala Leu Asn Arg Arg Ile Gln Leu
        35                  40                  45

Val Glu Glu Glu Leu Asp Arg Ala Gln Glu Arg Leu Ala Thr Ala Leu
    50                  55                  60

Gln Lys Leu Glu Glu Ala Glu Lys Ala Ala Asp Glu Ser Glu Arg Gly
65                  70                  75                  80
```

```
Met Lys Val Ile Glu Asn Arg Ala Met Lys Asp Glu Glu Lys Met Glu
                85                  90                  95

Ile Gln Glu Met Gln Leu Lys Glu Ala Lys His Ile Ala Glu Glu Ala
            100                 105                 110

Asp Arg Lys Tyr Glu Glu Val Ala Arg Lys Leu Val Ile Leu Glu Gly
        115                 120                 125

Glu Leu Glu Arg Ala Glu Glu Arg Ala Glu Val Ser Glu Leu Lys Cys
    130                 135                 140

Gly Asp Leu Glu Glu Glu Leu Lys Asn Val Thr Asn Asn Leu Lys Ser
145                 150                 155                 160

Leu Glu Ala Ala Ser Glu Lys Arg Arg Gly Leu Thr Met
                165                 170
```

```
<210> SEQ ID NO 37
<211> LENGTH: 333
<212> TYPE: DNA
<213> ORGANISM: Homo sapiens
<220> FEATURE:
<221> NAME/KEY: misc_feature
<222> LOCATION: (1)..(2)
<223> OTHER INFORMATION: n is a, c, g, or t

<400> SEQUENCE: 37
nngctggaga gggcagagga gcgtgcggag gtgtctgaac taaaatgtgg tgacctggaa      60
gaagaactca agaatgttac taacaatctg aaatctctgg aggctgcatc tgaaaagtat     120
tctgaaaagg aggacaaata tgaagaagaa attaaacttc tgtctgacaa actgaaagag     180
gctgagaccc gtgctgaatt tgcagagaga acggttgcaa aactggaaaa gacaattgat     240
gacctggaag agaaacttgc ccaggccaaa gaagagaacg tgggcttaca tcagacactg     300
gatcagacac taaacgaact taactgtata taa                                  333
```

```
<210> SEQ ID NO 38
<211> LENGTH: 110
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 38

Xaa Leu Glu Arg Ala Glu Glu Arg Ala Glu Val Ser Glu Leu Lys Cys
1               5                   10                  15

Gly Asp Leu Glu Glu Glu Leu Lys Asn Val Thr Asn Asn Leu Lys Ser
            20                  25                  30

Leu Glu Ala Ala Ser Glu Lys Tyr Ser Glu Lys Glu Asp Lys Tyr Glu
        35                  40                  45

Glu Glu Ile Lys Leu Leu Ser Asp Lys Leu Lys Glu Ala Glu Thr Arg
    50                  55                  60

Ala Glu Phe Ala Glu Arg Thr Val Ala Lys Leu Glu Lys Thr Ile Asp
65                  70                  75                  80

Asp Leu Glu Glu Lys Leu Ala Gln Ala Lys Glu Glu Asn Val Gly Leu
                85                  90                  95

His Gln Thr Leu Asp Gln Thr Leu Asn Glu Leu Asn Cys Ile
            100                 105                 110
```

```
<210> SEQ ID NO 39
<211> LENGTH: 1686
<212> TYPE: DNA
```

<213> ORGANISM: Homo sapiens

<400> SEQUENCE: 39

```
atgtgtggca tttgggcgct gtttggcagt gatgattgcc tttctgttca gtgtctgagt      60
gctatgaaga ttgcacacag aggtccagat gcattccgtt ttgagaatgt caatggatac     120
accaactgct gctttggatt tcaccggttg gcggtagttg acccgctgtt tggaatgcag     180
ccaattcgag tgaagaaata tccgtatttg tggctctgtt acaatggtga aatctacaac     240
cataagaaga tgcaacagca tttttgaattt gaataccaga ccaaagtgga tggtgagata     300
atccttcatc tttatgacaa aggaggaatt gagcaaacaa tttgtatgtt ggatggtgtg     360
tttgcatttg ttttactgga tactgccaat aagaaagtgt tcctgggtag agatacatat     420
ggagtcagac ctttgtttaa agcaatgaca gaagatggat ttttggctgt atgttcagaa     480
gctaaaggtc ttgttacatt gaagcactcc gcgactccct ttttaaaagt ggagccttt      540 cttcctggac actatgaagt tttggattta aagccaaatg caaagttgc atccgtggaa      600 atggttaaat atcatcactg tcgggatgta ccctgcacg ccctctatga caatgtggag      660
aaactctttc aggtttttga gatagaaact gtgaagaaca acctcaggat cctttttaat     720
aatgctgtaa agaaacgttt gatgacagac agaaggattg gctgcctttt atcaggggc      780 ttggactcca gcttggttgc tgccactctg ttgaagcagc tgaaagaagc ccaagtacag     840
tatcctctcc agacatttgc aattggcatg gaagacagcc ccgatttact ggctgctaga     900
aaggtggcag atcatattgg aagtgaacat tatgaagtcc ttttaactc tgaggaaggc     960 attcaggctc tggatgaagt catatttcc ttggaaactt atgacattac aacagttcgt    1020
gcttcagtag gtatgtattt aatttccaag tatattcgga agaacacaga tagcgtggtg    1080
atcttctctg agaaggatc agatgaactt acgcagggtt acatatattt tcacaaggct    1140
ccttctcctg aaaaagccga ggaggagagt gagaggcttc tgagggaact ctatttgttt    1200
gatgttctcc gcgcagatcg aactactgct gcccatggtc ttgaactgag agtcccattt    1260
ctagatcatc gattttcttc ctattacttg tctctgccac cagaaatgag aattccaaag    1320
aatgggatag aaaaacatct cctgagagag acgtttgagg attccaatct gatacccaaa    1380
gagattctct ggcgaccaaa agaagccttc agtgatggaa taacttcagt taagaattcc    1440
tggtttaaga ttttacagga atacgttgaa catcaggttg atgatgcaat gatggcaaat    1500
gcagcccaga atttcccttt caatactcct aaaaccaaag aaggatatta ctaccgtcaa    1560
gtctttgaac gccattaccc aggccgggct gactggctga ccattactg gatgcccaag    1620 tggatcaatg ccactgaccc ttctgcccgc acgctgaccc actacaagtc agctgtcaaa    1680
gcttag                                                              1686
```

<210> SEQ ID NO 40
<211> LENGTH: 561
<212> TYPE: PRT
<213> ORGANISM: Homo sapiens

<400> SEQUENCE: 40

```
Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45
```

```
Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
                100                 105                 110

Thr Ile Cys Met Leu Asp Gly Val Phe Ala Phe Val Leu Leu Asp Thr
                115                 120                 125

Ala Asn Lys Lys Val Phe Leu Gly Arg Asp Thr Tyr Gly Val Arg Pro
    130                 135                 140

Leu Phe Lys Ala Met Thr Glu Asp Gly Phe Leu Ala Val Cys Ser Glu
145                 150                 155                 160

Ala Lys Gly Leu Val Thr Leu Lys His Ser Ala Thr Pro Phe Leu Lys
                165                 170                 175

Val Glu Pro Phe Leu Pro Gly His Tyr Glu Val Leu Asp Leu Lys Pro
                180                 185                 190

Asn Gly Lys Val Ala Ser Val Glu Met Val Lys Tyr His His Cys Arg
                195                 200                 205

Asp Val Pro Leu His Ala Leu Tyr Asp Asn Val Glu Lys Leu Phe Pro
    210                 215                 220

Gly Phe Glu Ile Glu Thr Val Lys Asn Asn Leu Arg Ile Leu Phe Asn
225                 230                 235                 240

Asn Ala Val Lys Lys Arg Leu Met Thr Asp Arg Arg Ile Gly Cys Leu
                245                 250                 255

Leu Ser Gly Gly Leu Asp Ser Ser Leu Val Ala Ala Thr Leu Leu Lys
                260                 265                 270

Gln Leu Lys Glu Ala Gln Val Gln Tyr Pro Leu Gln Thr Phe Ala Ile
    275                 280                 285

Gly Met Glu Asp Ser Pro Asp Leu Leu Ala Ala Arg Lys Val Ala Asp
    290                 295                 300

His Ile Gly Ser Glu His Tyr Glu Val Leu Phe Asn Ser Glu Glu Gly
305                 310                 315                 320

Ile Gln Ala Leu Asp Glu Val Ile Phe Ser Leu Glu Thr Tyr Asp Ile
                325                 330                 335

Thr Thr Val Arg Ala Ser Val Gly Met Tyr Leu Ile Ser Lys Tyr Ile
                340                 345                 350

Arg Lys Asn Thr Asp Ser Val Val Ile Phe Ser Gly Glu Gly Ser Asp
    355                 360                 365

Glu Leu Thr Gln Gly Tyr Ile Tyr Phe His Lys Ala Pro Ser Pro Glu
    370                 375                 380

Lys Ala Glu Glu Glu Ser Glu Arg Leu Leu Arg Glu Leu Tyr Leu Phe
385                 390                 395                 400

Asp Val Leu Arg Ala Asp Arg Thr Thr Ala Ala His Gly Leu Glu Leu
                405                 410                 415

Arg Val Pro Phe Leu Asp His Arg Phe Ser Ser Tyr Tyr Leu Ser Leu
                420                 425                 430

Pro Pro Glu Met Arg Ile Pro Lys Asn Gly Ile Glu Lys His Leu Leu
                435                 440                 445

Arg Glu Thr Phe Glu Asp Ser Asn Leu Ile Pro Lys Glu Ile Leu Trp
    450                 455                 460

Arg Pro Lys Glu Ala Phe Ser Asp Gly Ile Thr Ser Val Lys Asn Ser
```

-continued

```
465                470                475                480
```

Trp Phe Lys Ile Leu Gln Glu Tyr Val Glu His Gln Val Asp Asp Ala
                485                490                495

Met Met Ala Asn Ala Ala Gln Lys Phe Pro Phe Asn Thr Pro Lys Thr
            500                505                510

Lys Glu Gly Tyr Tyr Tyr Arg Gln Val Phe Glu Arg His Tyr Pro Gly
        515                520                525

Arg Ala Asp Trp Leu Ser His Tyr Trp Met Pro Lys Trp Ile Asn Ala
    530                535                540

Thr Asp Pro Ser Ala Arg Thr Leu Thr His Tyr Lys Ser Ala Val Lys
545                550                555                560

Ala

<210> SEQ ID NO 41
<211> LENGTH: 1686
<212> TYPE: DNA
<213> ORGANISM: Homo sapiens

<400> SEQUENCE: 41
atgtgtggca tttgggcgct gtttggcagt gatgattgcc tttctgttca gtgtctgagt      60
gctatgaaga ttgcacacag aggtccagat gcattccgtt ttgagaatgt caatggatac     120
accaactgct gctttggatt tcaccggttg gcggtagttg acccgctgtt tggaatgcag     180
ccaattcgag tgaagaaata tccgtatttg tggctctgtt acaatggtga aatctacaac     240
cataagaaga tgcaacagca ttttgaattt gaataccaga ccaaagtgga tggtgagata     300
atccttcatc tttatgacaa aggaggaatt gagcaaacaa tttgtatgtt ggatggtgtg     360
tttgcatttg ttttactgga tactgccaat aagaaagtgt tcctgggtag agatacatat     420
ggagtcagac ctttgtttaa agcaatgaca gaagatggat ttttggctgt atgttcagaa     480
gctaaaggtc ttgttacatt gaagcactcc gcgactccct tttaaaagt ggagcctttt     540 cttcctggac actatgaagt tttggattta aagccaaatg gcaaagttgc atccgtggaa     600
atggttaaat atcatcactg tcgggatgta cccctgcacg ccctctatga caatgtggag     660
aaactctttc caggttttga gatagaaact gtgaagaaca acctcaggat ccttttttaat     720 aatgctgtaa agaaacgttt gatgacagac agaaggattg gctgcctttt atcagggggc     780
ttggactcca gcttggttgc tgccactctg ttgaagcagc tgaaagaagc ccaagtacag     840
tatcctctcc agacatttgc aattggcatg gaagacagcc ccgatttact ggctgctaga     900
aaggtggcag atcatattgg aagtgaacat tatgaagtcc tttttaactc tgaggaaggc     960
attcaggctc tggatgaagt catatttttcc ttggaaactt atgacattac aacagttcgt    1020
gcttcagtag gtatgtattt aatttccaag tatattcgga agaacacaga tagcgtggtg    1080
atcttctctg agaaggatc agatgaactt acgcagggtt acatatattt tcacaaggct    1140
ccttctcctg aaaagccga ggaggagagt gagaggcttc tgagggaact ctatttgttt    1200
gatgttctcc gcgcagatcg aactactgct gcccatggtc ttgaactgag agtcccattt    1260
ctagatcatc gattttcttc ctattacttg tctctgccac cagaaatgag aattccaaag    1320
aatgggatag aaaaacatct cctgagagag acgtttgagg attccaatct gatacccaaa    1380
gagattctct ggcgaccaaa agaagccttc agtgatggaa taacttcagt taagaattcc    1440
tggtttaaga ttttacagga atacgttgaa catcaggttg atgatgcaat gatggcaaat    1500
gcagcccaga aatttccctt caatactcct aaaaccaaag aaggatatta ctaccgtcaa    1560
```

-continued

```
gtctttgaac gccattaccc aggccgggct gactggctga gccattactg gatgcccaag    1620
tggatcaatg ccactgaccc ttctgcccgc acgctgaccc actacaagtc agctgtcaaa    1680
gcttag                                                               1686
```

```
<210> SEQ ID NO 42
<211> LENGTH: 561
<212> TYPE: PRT
<213> ORGANISM: Homo sapiens

<400> SEQUENCE: 42

Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45

Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
            100                 105                 110

Thr Ile Cys Met Leu Asp Gly Val Phe Ala Phe Val Leu Leu Asp Thr
            115                 120                 125

Ala Asn Lys Lys Val Phe Leu Gly Arg Asp Thr Tyr Gly Val Arg Pro
    130                 135                 140

Leu Phe Lys Ala Met Thr Glu Asp Gly Phe Leu Ala Val Cys Ser Glu
145                 150                 155                 160

Ala Lys Gly Leu Val Thr Leu Lys His Ser Ala Thr Pro Phe Leu Lys
                165                 170                 175

Val Glu Pro Phe Leu Pro Gly His Tyr Glu Val Leu Asp Leu Lys Pro
            180                 185                 190

Asn Gly Lys Val Ala Ser Val Glu Met Val Lys Tyr His His Cys Arg
        195                 200                 205

Asp Val Pro Leu His Ala Leu Tyr Asp Asn Val Glu Lys Leu Phe Pro
    210                 215                 220

Gly Phe Glu Ile Glu Thr Val Lys Asn Asn Leu Arg Ile Leu Phe Asn
225                 230                 235                 240

Asn Ala Val Lys Lys Arg Leu Met Thr Asp Arg Arg Ile Gly Cys Leu
                245                 250                 255

Leu Ser Gly Gly Leu Asp Ser Ser Leu Val Ala Ala Thr Leu Leu Lys
            260                 265                 270

Gln Leu Lys Glu Ala Gln Val Gln Tyr Pro Leu Gln Thr Phe Ala Ile
        275                 280                 285

Gly Met Glu Asp Ser Pro Asp Leu Leu Ala Ala Arg Lys Val Ala Asp
    290                 295                 300

His Ile Gly Ser Glu His Tyr Glu Val Leu Phe Asn Ser Glu Glu Gly
305                 310                 315                 320

Ile Gln Ala Leu Asp Glu Val Ile Phe Ser Leu Glu Thr Tyr Asp Ile
                325                 330                 335

Thr Thr Val Arg Ala Ser Val Gly Met Tyr Leu Ile Ser Lys Tyr Ile
            340                 345                 350
```

```
Arg Lys Asn Thr Asp Ser Val Val Ile Phe Ser Gly Glu Gly Ser Asp
        355                 360                 365

Glu Leu Thr Gln Gly Tyr Ile Tyr Phe His Lys Ala Pro Ser Pro Glu
        370                 375                 380

Lys Ala Glu Glu Glu Ser Glu Arg Leu Leu Arg Glu Leu Tyr Leu Phe
385                 390                 395                 400

Asp Val Leu Arg Ala Asp Arg Thr Thr Ala Ala His Gly Leu Glu Leu
                405                 410                 415

Arg Val Pro Phe Leu Asp His Arg Phe Ser Ser Tyr Tyr Leu Ser Leu
            420                 425                 430

Pro Pro Glu Met Arg Ile Pro Lys Asn Gly Ile Glu Lys His Leu Leu
        435                 440                 445

Arg Glu Thr Phe Glu Asp Ser Asn Leu Ile Pro Lys Glu Ile Leu Trp
        450                 455                 460

Arg Pro Lys Glu Ala Phe Ser Asp Gly Ile Thr Ser Val Lys Asn Ser
465                 470                 475                 480

Trp Phe Lys Ile Leu Gln Glu Tyr Val Glu His Gln Val Asp Asp Ala
                485                 490                 495

Met Met Ala Asn Ala Ala Gln Lys Phe Pro Phe Asn Thr Pro Lys Thr
                500                 505                 510

Lys Glu Gly Tyr Tyr Tyr Arg Gln Val Phe Glu Arg His Tyr Pro Gly
            515                 520                 525

Arg Ala Asp Trp Leu Ser His Tyr Trp Met Pro Lys Trp Ile Asn Ala
        530                 535                 540

Thr Asp Pro Ser Ala Arg Thr Leu Thr His Tyr Lys Ser Ala Val Lys
545                 550                 555                 560

Ala
```

```
<210> SEQ ID NO 43
<211> LENGTH: 1686
<212> TYPE: DNA
<213> ORGANISM: Homo sapiens

<400> SEQUENCE: 43
atgtgtggca tttgggcgct gtttggcagt gatgattgcc tttctgttca gtgtctgagt        60
gctatgaaga ttgcacacag aggtccagat gcattccgtt ttgagaatgt caatggatac       120
accaactgct gctttggatt tcaccggttg gcggtagttg acccgctgtt tggaatgcag       180
ccaattcgag tgaagaaata tccgtatttg tggctctgtt acaatggtga aatctacaac       240
cataagaaga tgcaacagca ttttgaattt gaataccaga ccaaagtgga tggtgagata       300
atccttcatc tttatgacaa aggaggaatt gagcaaacaa tttgtatgtt ggatggtgtg       360
tttgcatttg ttttactgga tactgccaat aagaaagtgt tcctgggtag agatacatat       420
ggagtcagac ctttgtttaa agcaatgaca gaagatggat ttttggctgt atgttcagaa       480
gctaaaggtc ttgttacatt gaagcactcc gcgactccct ttttaaaagt ggagcctttt       540
cttcctggac actatgaagt tttggattta aagccaaatg caaagttgc atccgtggaa        600 atggttaaat atcatcactg tcgggatgta ccccctgcacg ccctctatga caatgtggag      660
aaactctttc aggttttga datagaaact gtgaagaaca acctcaggat ccttttaat         720 aatgctgtaa agaaacgttt gatgacagac agaaggattg ctgcctttt atcaggggc        780 ttggactcca gcttggttgc tgccactctg ttgaagcagc tgaaagaagc ccaagtacag      840
tatcctctcc agacatttgc aattggcatg gaagacagcc ccgattact ggctgctaga       900
```

-continued

```
aaggtggcag atcatattgg aagtgaacat tatgaagtcc tttttaactc tgaggaaggc      960
attcaggctc tggatgaagt catattttcc ttggaaactt atgacattac aacagttcgt     1020
gcttcagtag gtatgtattt aatttccaag tatattcgga agaacacaga tagcgtggtg     1080
atcttctctg gagaaggatc agatgaactt acgcagggtt acatatattt tcacaaggct     1140
ccttctcctg aaaaagccga ggaggagagt gagaggcttc tgagggaact ctatttgttt     1200
gatgttctcc gcgcagatcg aactactgct gcccatggtc ttgaactgag agtcccattt     1260
ctagatcatc gattttcttc ctattacttg tctctgccac cagaaatgag aattccaaag     1320
aatgggatag aaaaacatct cctgagagag acgtttgagg attccaatct gatacccaaa     1380
gagattctct ggcgaccaaa agaagccttc agtgatggaa taacttcagt taagaattcc     1440
tggtttaaga ttttacagga atacgttgaa catcaggttg atgatgcaat gatggcaaat     1500
gcagcccaga aatttccctt caatactcct aaaaccaaag aaggatatta ctaccgtcaa     1560
gtctttgaac gccattaccc aggccgggct gactggctga gccattactg gatgcccaag     1620
tggatcaatg ccactgaccc ttctgcccgc acgctgaccc actacaagtc agctgtcaaa     1680
gcttag                                                                1686
```

<210> SEQ ID NO 44
<211> LENGTH: 561
<212> TYPE: PRT
<213> ORGANISM: Homo sapiens

<400> SEQUENCE: 44

```
Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45

Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
            100                 105                 110

Thr Ile Cys Met Leu Asp Gly Val Phe Ala Phe Val Leu Leu Asp Thr
        115                 120                 125

Ala Asn Lys Lys Val Phe Leu Gly Arg Asp Thr Tyr Gly Val Arg Pro
    130                 135                 140

Leu Phe Lys Ala Met Thr Glu Asp Gly Phe Leu Ala Val Cys Ser Glu
145                 150                 155                 160

Ala Lys Gly Leu Val Thr Leu Lys His Ser Ala Thr Pro Phe Leu Lys
                165                 170                 175

Val Glu Pro Phe Leu Pro Gly His Tyr Glu Val Leu Asp Leu Lys Pro
            180                 185                 190

Asn Gly Lys Val Ala Ser Val Glu Met Val Lys Tyr His His Cys Arg
        195                 200                 205

Asp Val Pro Leu His Ala Leu Tyr Asp Asn Val Glu Lys Leu Phe Pro
    210                 215                 220
```

-continued

```
Gly Phe Glu Ile Glu Thr Val Lys Asn Asn Leu Arg Ile Leu Phe Asn
225                 230                 235                 240

Asn Ala Val Lys Lys Arg Leu Met Thr Asp Arg Arg Ile Gly Cys Leu
                245                 250                 255

Leu Ser Gly Gly Leu Asp Ser Ser Leu Val Ala Ala Thr Leu Leu Lys
            260                 265                 270

Gln Leu Lys Glu Ala Gln Val Gln Tyr Pro Leu Gln Thr Phe Ala Ile
        275                 280                 285

Gly Met Glu Asp Ser Pro Asp Leu Leu Ala Ala Arg Lys Val Ala Asp
    290                 295                 300

His Ile Gly Ser Glu His Tyr Glu Val Leu Phe Asn Ser Glu Glu Gly
305                 310                 315                 320

Ile Gln Ala Leu Asp Glu Val Ile Phe Ser Leu Glu Thr Tyr Asp Ile
                325                 330                 335

Thr Thr Val Arg Ala Ser Val Gly Met Tyr Leu Ile Ser Lys Tyr Ile
            340                 345                 350

Arg Lys Asn Thr Asp Ser Val Val Ile Phe Ser Gly Glu Gly Ser Asp
        355                 360                 365

Glu Leu Thr Gln Gly Tyr Ile Tyr Phe His Lys Ala Pro Ser Pro Glu
    370                 375                 380

Lys Ala Glu Glu Glu Ser Glu Arg Leu Leu Arg Glu Leu Tyr Leu Phe
385                 390                 395                 400

Asp Val Leu Arg Ala Asp Arg Thr Thr Ala Ala His Gly Leu Glu Leu
                405                 410                 415

Arg Val Pro Phe Leu Asp His Arg Phe Ser Ser Tyr Tyr Leu Ser Leu
            420                 425                 430

Pro Pro Glu Met Arg Ile Pro Lys Asn Gly Ile Glu Lys His Leu Leu
        435                 440                 445

Arg Glu Thr Phe Glu Asp Ser Asn Leu Ile Pro Lys Glu Ile Leu Trp
    450                 455                 460

Arg Pro Lys Glu Ala Phe Ser Asp Gly Ile Thr Ser Val Lys Asn Ser
465                 470                 475                 480

Trp Phe Lys Ile Leu Gln Glu Tyr Val Glu His Gln Val Asp Asp Ala
            485                 490                 495

Met Met Ala Asn Ala Ala Gln Lys Phe Pro Phe Asn Thr Pro Lys Thr
            500                 505                 510

Lys Glu Gly Tyr Tyr Tyr Arg Gln Val Phe Glu Arg His Tyr Pro Gly
        515                 520                 525

Arg Ala Asp Trp Leu Ser His Tyr Trp Met Pro Lys Trp Ile Asn Ala
    530                 535                 540

Thr Asp Pro Ser Ala Arg Thr Leu Thr His Tyr Lys Ser Ala Val Lys
545                 550                 555                 560

Ala
```

<210> SEQ ID NO 45
<211> LENGTH: 1623
<212> TYPE: DNA
<213> ORGANISM: Homo sapiens

<400> SEQUENCE: 45

```
atgaagattg cacacagagg tccagatgca ttccgttttg agaatgtcaa tggatacacc        60
aactgctgct ttggatttca ccggttggcg gtagttgacc cgctgtttgg aatgcagcca       120
attcgagtga agaaatatcc gtatttgtgg ctctgttaca atggtgaaat ctacaaccat       180
```

-continued

```
aagaagatgc aacagcattt tgaatttgaa taccagacca aagtggatgg tgagataatc        240
cttcatcttt atgacaaagg aggaattgag caaacaattt gtatgttgga tggtgtgttt        300
gcatttgttt tactggatac tgccaataag aaagtgttcc tgggtagaga tacatatgga        360
gtcagacctt tgtttaaagc aatgacagaa gatggatttt tggctgtatg ttcagaagct        420
aaaggtcttg ttacattgaa gcactccgcg actccctttt taaaagtgga gccttttctt        480
cctggacact atgaagtttt ggatttaaag ccaaatggca aagttgcatc cgtgaaaatg        540
gttaaatatc atcactgtcg ggatgtaccc ctgcacgccc tctatgacaa tgtggagaaa        600
ctctttccag gttttgagat agaaactgtg aagaacaacc tcaggatcct ttttaataat        660
gctgtaaaga aacgtttgat gacagacaga aggattggct gccttttatc aggggggcttg        720 gactccagct tggttgctgc cactctgttg aagcagctga agaagccca agtacagtat          780 cctctccaga catttgcaat tggcatggaa gacagccccg atttactggc tgctagaaag        840
gtggcagatc atattggaag tgaacattat gaagtccttt ttaactctga ggaaggcatt        900
caggctctgg atgaagtcat attttccttg gaaacttatg acattacaac agttcgtgct        960
tcagtaggta tgtatttaat ttccaagtat attcggaaga acacagatag cgtggtgatc        1020
ttctctggag aaggatcaga tgaacttacg caggggttaca tatattttca caaggctcct       1080
tctcctgaaa aagccgagga ggagagtgag aggcttctga gggaactcta tttgtttgat        1140
gttctccgcg cagatcgaac tactgctgcc catggtcttg aactgagagt cccatttcta        1200
gatcatcgat tttcttccta ttacttgtct ctgccaccag aaatgagaat tccaaagaat        1260
gggatagaaa aacatctcct gagagagacg tttgaggatt ccaatctgat acccaaagag        1320
attctctggc gaccaaaaga agccttcagt gatggaataa cttcagttaa gaattcctgg        1380
tttaagattt tacaggaata cgttgaacat caggttgatg atgcaatgat ggcaaatgca        1440
gcccagaaat ttcccttcaa tactcctaaa accaaagaag gatattacta ccgtcaagtc        1500
tttgaacgcc attcccagg ccgggctgac tggctgagcc attactggat gcccagtgg           1560 atcaatgcca ctgacccttc tgcccgcacg ctgacccact acaagtcagc tgtcaaagct        1620
tag                                                                       1623
```

<210> SEQ ID NO 46
<211> LENGTH: 540
<212> TYPE: PRT
<213> ORGANISM: Homo sapiens

<400> SEQUENCE: 46

```
Met Lys Ile Ala His Arg Gly Pro Asp Ala Phe Arg Phe Glu Asn Val
1               5                   10                  15

Asn Gly Tyr Thr Asn Cys Cys Phe Gly Phe His Arg Leu Ala Val Val
            20                  25                  30

Asp Pro Leu Phe Gly Met Gln Pro Ile Arg Val Lys Lys Tyr Pro Tyr
        35                  40                  45

Leu Trp Leu Cys Tyr Asn Gly Glu Ile Tyr Asn His Lys Lys Met Gln
    50                  55                  60

Gln His Phe Glu Phe Glu Tyr Gln Thr Lys Val Asp Gly Glu Ile Ile
65                  70                  75                  80

Leu His Leu Tyr Asp Lys Gly Gly Ile Glu Gln Thr Ile Cys Met Leu
                85                  90                  95

Asp Gly Val Phe Ala Phe Val Leu Leu Asp Thr Ala Asn Lys Lys Val
            100                 105                 110
```

-continued

```
Phe Leu Gly Arg Asp Thr Tyr Gly Val Arg Pro Leu Phe Lys Ala Met
        115                 120                 125

Thr Glu Asp Gly Phe Leu Ala Val Cys Ser Glu Ala Lys Gly Leu Val
    130                 135                 140

Thr Leu Lys His Ser Ala Thr Pro Phe Leu Lys Val Glu Pro Phe Leu
145                 150                 155                 160

Pro Gly His Tyr Glu Val Leu Asp Leu Lys Pro Asn Gly Lys Val Ala
                165                 170                 175

Ser Val Glu Met Val Lys Tyr His His Cys Arg Asp Val Pro Leu His
                180                 185                 190

Ala Leu Tyr Asp Asn Val Glu Lys Leu Phe Pro Gly Phe Glu Ile Glu
                195                 200                 205

Thr Val Lys Asn Asn Leu Arg Ile Leu Phe Asn Asn Ala Val Lys Lys
    210                 215                 220

Arg Leu Met Thr Asp Arg Arg Ile Gly Cys Leu Leu Ser Gly Gly Leu
225                 230                 235                 240

Asp Ser Ser Leu Val Ala Ala Thr Leu Leu Lys Gln Leu Lys Glu Ala
                245                 250                 255

Gln Val Gln Tyr Pro Leu Gln Thr Phe Ala Ile Gly Met Glu Asp Ser
                260                 265                 270

Pro Asp Leu Leu Ala Ala Arg Lys Val Ala Asp His Ile Gly Ser Glu
                275                 280                 285

His Tyr Glu Val Leu Phe Asn Ser Glu Glu Gly Ile Gln Ala Leu Asp
    290                 295                 300

Glu Val Ile Phe Ser Leu Glu Thr Tyr Asp Ile Thr Thr Val Arg Ala
305                 310                 315                 320

Ser Val Gly Met Tyr Leu Ile Ser Lys Tyr Ile Arg Lys Asn Thr Asp
                325                 330                 335

Ser Val Val Ile Phe Ser Gly Glu Gly Ser Asp Glu Leu Thr Gln Gly
                340                 345                 350

Tyr Ile Tyr Phe His Lys Ala Pro Ser Pro Glu Lys Ala Glu Glu Glu
    355                 360                 365

Ser Glu Arg Leu Leu Arg Glu Leu Tyr Leu Phe Asp Val Leu Arg Ala
    370                 375                 380

Asp Arg Thr Thr Ala Ala His Gly Leu Glu Leu Arg Val Pro Phe Leu
385                 390                 395                 400

Asp His Arg Phe Ser Ser Tyr Tyr Leu Ser Leu Pro Pro Glu Met Arg
                405                 410                 415

Ile Pro Lys Asn Gly Ile Glu Lys His Leu Leu Arg Glu Thr Phe Glu
                420                 425                 430

Asp Ser Asn Leu Ile Pro Lys Glu Ile Leu Trp Arg Pro Lys Glu Ala
    435                 440                 445

Phe Ser Asp Gly Ile Thr Ser Val Lys Asn Ser Trp Phe Lys Ile Leu
    450                 455                 460

Gln Glu Tyr Val Glu His Gln Val Asp Asp Ala Met Met Ala Asn Ala
465                 470                 475                 480

Ala Gln Lys Phe Pro Phe Asn Thr Pro Lys Thr Lys Glu Gly Tyr Tyr
                485                 490                 495

Tyr Arg Gln Val Phe Glu Arg His Tyr Pro Gly Arg Ala Asp Trp Leu
                500                 505                 510

Ser His Tyr Trp Met Pro Lys Trp Ile Asn Ala Thr Asp Pro Ser Ala
    515                 520                 525

Arg Thr Leu Thr His Tyr Lys Ser Ala Val Lys Ala
```

-continued

```
           530              535              540

<210> SEQ ID NO 47
<211> LENGTH: 1623
<212> TYPE: DNA
<213> ORGANISM: homo sapiens

<400> SEQUENCE: 47
atgaagattg cacacagagg tccagatgca ttccgttttg agaatgtcaa tggatacacc      60
aactgctgct ttggatttca ccggttggcg gtagttgacc cgctgtttgg aatgcagcca     120
attcgagtga agaaatatcc gtatttgtgg ctctgttaca atggtgaaat ctacaaccat     180
aagaagatgc aacagcattt tgaatttgaa taccagacca aagtggatgg tgagataatc     240
cttcatcttt atgacaaagg aggaattgag caaacaattt gtatgttgga tggtgtgttt     300
gcatttgttt tactggatac tgccaataag aaagtgttcc tgggtagaga tacatatgga     360
gtcagacctt tgtttaaagc aatgacagaa gatggatttt tggctgtatg ttcagaagct     420
aaaggtcttg ttacattgaa gcactccgcg actccctttt taaaagtgga gccttttctt     480
cctggacact atgaagtttt ggatttaaag ccaaatggca agttgcatc cgtggaaatg     540 gttaaatatc atcactgtcg ggatgtaccc ctgcacgccc tctatgacaa tgtggagaaa     600
ctctttccag gttttgagat agaaactgtg aagaacaacc tcaggatcct ttttaataat     660
gctgtaaaga aacgtttgat gacagacaga aggattggc gccttttatc agggggcttg     720
gactccagct tggttgctgc cactctgttg aagcagctga agaagcccca agtacagtat     780
cctctccaga catttgcaat tggcatggaa gacagccccg atttactggc tgctagaaag     840
gtggcagatc atattggaag tgaacattat gaagtccttt ttaactctga ggaaggcatt     900
caggctctgg atgaagtcat attttccttg gaaacttatg acattacaac agttcgtgct     960
tcagtaggta tgtatttaat ttccaagtat attcggaaga acacagatag cgtggtgatc    1020
ttctctggag aaggatcaga tgaacttacg caggggttaca tatattttca caaggctcct    1080
tctcctgaaa agccgagga ggagagtgag aggcttctga gggaactcta tttgtttgat    1140
gttctccgcg cagatcgaac tactgctgcc catggtcttg aactgagagt cccatttcta    1200
gatcatcgat tttcttccta ttacttgtct ctgccaccag aaatgagaat tccaaagaat    1260
gggatagaaa aacatctcct gagagagacg tttgaggatt ccaatctgat acccaaagag    1320
attctctggc gaccaaaaga agccttcagt gatggaataa cttcagttaa gaattcctgg    1380
tttaagattt tacaggaata cgttgaacat caggttgatg atgcaatgat ggcaaatgca    1440
gcccagaaat ttcccttcaa tactcctaaa accaagaag gatattacta ccgtcaagtc    1500
tttgaacgcc attacccagg ccgggctgac tggctgagcc attactggat gcccaagtgg    1560
atcaatgcca ctgacccttc tgcccgcacg ctgacccact acaagtcagc tgtcaaagct    1620
tag                                                                  1623

<210> SEQ ID NO 48
<211> LENGTH: 540
<212> TYPE: PRT
<213> ORGANISM: Homo sapiens

<400> SEQUENCE: 48

Met Lys Ile Ala His Arg Gly Pro Asp Ala Phe Arg Phe Glu Asn Val
1               5                   10                  15

Asn Gly Tyr Thr Asn Cys Cys Phe Gly Phe His Arg Leu Ala Val Val
                20                  25                  30
```

```
Asp Pro Leu Phe Gly Met Gln Pro Ile Arg Val Lys Lys Tyr Pro Tyr
        35              40              45

Leu Trp Leu Cys Tyr Asn Gly Glu Ile Tyr Asn His Lys Lys Met Gln
    50              55              60

Gln His Phe Glu Phe Glu Tyr Gln Thr Lys Val Asp Gly Glu Ile Ile
65              70              75              80

Leu His Leu Tyr Asp Lys Gly Gly Ile Glu Gln Thr Ile Cys Met Leu
            85              90              95

Asp Gly Val Phe Ala Phe Val Leu Leu Asp Thr Ala Asn Lys Lys Val
            100             105             110

Phe Leu Gly Arg Asp Thr Tyr Gly Val Arg Pro Leu Phe Lys Ala Met
        115             120             125

Thr Glu Asp Gly Phe Leu Ala Val Cys Ser Glu Ala Lys Gly Leu Val
    130             135             140

Thr Leu Lys His Ser Ala Thr Pro Phe Leu Lys Val Glu Pro Phe Leu
145             150             155             160

Pro Gly His Tyr Glu Val Leu Asp Leu Lys Pro Asn Gly Lys Val Ala
            165             170             175

Ser Val Glu Met Val Lys Tyr His His Cys Arg Asp Val Pro Leu His
            180             185             190

Ala Leu Tyr Asp Asn Val Glu Lys Leu Phe Pro Gly Phe Glu Ile Glu
        195             200             205

Thr Val Lys Asn Asn Leu Arg Ile Leu Phe Asn Asn Ala Val Lys Lys
    210             215             220

Arg Leu Met Thr Asp Arg Arg Ile Gly Cys Leu Leu Ser Gly Gly Leu
225             230             235             240

Asp Ser Ser Leu Val Ala Ala Thr Leu Leu Lys Gln Leu Lys Glu Ala
            245             250             255

Gln Val Gln Tyr Pro Leu Gln Thr Phe Ala Ile Gly Met Glu Asp Ser
            260             265             270

Pro Asp Leu Leu Ala Ala Arg Lys Val Ala Asp His Ile Gly Ser Glu
        275             280             285

His Tyr Glu Val Leu Phe Asn Ser Glu Glu Gly Ile Gln Ala Leu Asp
    290             295             300

Glu Val Ile Phe Ser Leu Glu Thr Tyr Asp Ile Thr Thr Val Arg Ala
305             310             315             320

Ser Val Gly Met Tyr Leu Ile Ser Lys Tyr Ile Arg Lys Asn Thr Asp
            325             330             335

Ser Val Val Ile Phe Ser Gly Glu Gly Ser Asp Glu Leu Thr Gln Gly
            340             345             350

Tyr Ile Tyr Phe His Lys Ala Pro Ser Pro Glu Lys Ala Glu Glu Glu
        355             360             365

Ser Glu Arg Leu Leu Arg Glu Leu Tyr Leu Phe Asp Val Leu Arg Ala
    370             375             380

Asp Arg Thr Thr Ala Ala His Gly Leu Glu Leu Arg Val Pro Phe Leu
385             390             395             400

Asp His Arg Phe Ser Ser Tyr Tyr Leu Ser Leu Pro Pro Glu Met Arg
            405             410             415

Ile Pro Lys Asn Gly Ile Glu Lys His Leu Leu Arg Glu Thr Phe Glu
            420             425             430

Asp Ser Asn Leu Ile Pro Lys Glu Ile Leu Trp Arg Pro Lys Glu Ala
        435             440             445
```

-continued

```
Phe Ser Asp Gly Ile Thr Ser Val Lys Asn Ser Trp Phe Lys Ile Leu
    450                 455                 460

Gln Glu Tyr Val Glu His Gln Val Asp Asp Ala Met Met Ala Asn Ala
465                 470                 475                 480

Ala Gln Lys Phe Pro Phe Asn Thr Pro Lys Thr Lys Glu Gly Tyr Tyr
                485                 490                 495

Tyr Arg Gln Val Phe Glu Arg His Tyr Pro Gly Arg Ala Asp Trp Leu
                500                 505                 510

Ser His Tyr Trp Met Pro Lys Trp Ile Asn Ala Thr Asp Pro Ser Ala
            515                 520                 525

Arg Thr Leu Thr His Tyr Lys Ser Ala Val Lys Ala
    530                 535                 540
```

```
<210> SEQ ID NO 49
<211> LENGTH: 1437
<212> TYPE: DNA
<213> ORGANISM: Homo sapiens

<400> SEQUENCE: 49
atgcaacagc attttgaatt tgaataccag accaaagtgg atggtgagat aatccttcat      60
ctttatgaca aggaggaat tgagcaaaca atttgtatgt tggatggtgt gtttgcattt      120
gttttactgg atactgccaa taagaaagtg ttcctgggta gagatacata tggagtcaga      180
cctttgttta aagcaatgac agaagatgga ttttttggctg tatgttcaga agctaaaggt      240
cttgttacat tgaagcactc cgcgactccc tttttaaaag tggagccttt tcttcctgga      300
cactatgaag ttttggattt aaagccaaat ggcaaagttg catccgtgga atggttaaa      360 tatcatcact gtcgggatgt acccctgcac gccctctatg acaatgtgga gaaactcttt      420
ccaggttttg atagaaac tgtgaagaac aacctcagga tccttttttaa taatgctgta      480 aagaaacgtt tgatgacaga cagaaggatt ggctgccttt tatcaggggg cttggactcc      540
agcttggttg ctgccactct gttgaagcag ctgaaagaag cccaagtaca gtatcctctc      600
cagacatttg caattggcat ggaagacagc cccgatttac tggctgctag aaaggtggca      660
gatcatattg gaagtgaaca ttatgaagtc ctttttaact ctgaggaagg cattcaggct      720
ctggatgaag tcatatttttc cttggaaact tatgacatta caacagttcg tgcttcagta      780
ggtatgtatt taatttccaa gtatattcgg aagaacacag atagcgtggt gatcttctct      840
ggagaaggat cagatgaact tacgcagggt tacatatatt ttcacaaggc tccttctcct      900
gaaaaagccg aggaggagag tgagaggctt ctgagggaac tctatttgtt tgatgttctc      960
cgcgcagatc gaactactgc tgcccatggt cttgaactga gagtcccatt tctagatcat    1020 cgatttttctt cctattactt gtctctgcca ccagaaatga gaattccaaa gaatgggata    1080
gaaaaacatc tcctgagaga gacgtttgag gattccaatc tgataccccaa agagattctc    1140 tggcgaccaa aagaagcctt cagtgatgga ataacttcag ttaagaattc ctggtttaag    1200
attttacagg aatacgttga acatcaggtt gatgatgcaa tgatggcaaa tgcagcccag    1260
aaatttcctt tcaatactcc taaaaccaaa gaaggatatt actaccgtca agtctttgaa    1320
cgccattacc caggccgggc tgactggctg agccattact ggatgcccaa gtggatcaat    1380
gccactgacc cttctgcccg cacgctgacc cactacaagt cagctgtcaa agcttag       1437
```

```
<210> SEQ ID NO 50
<211> LENGTH: 478
<212> TYPE: PRT
<213> ORGANISM: Homo sapiens
```

-continued

<400> SEQUENCE: 50

```
Met Gln Gln His Phe Glu Phe Glu Tyr Gln Thr Lys Val Asp Gly Glu
1               5                   10                  15

Ile Ile Leu His Leu Tyr Asp Lys Gly Gly Ile Glu Gln Thr Ile Cys
            20                  25                  30

Met Leu Asp Gly Val Phe Ala Phe Val Leu Leu Asp Thr Ala Asn Lys
        35                  40                  45

Lys Val Phe Leu Gly Arg Asp Thr Tyr Gly Val Arg Pro Leu Phe Lys
    50                  55                  60

Ala Met Thr Glu Asp Gly Phe Leu Ala Val Cys Ser Glu Ala Lys Gly
65                  70                  75                  80

Leu Val Thr Leu Lys His Ser Ala Thr Pro Phe Leu Lys Val Glu Pro
                85                  90                  95

Phe Leu Pro Gly His Tyr Glu Val Leu Asp Leu Lys Pro Asn Gly Lys
            100                 105                 110

Val Ala Ser Val Glu Met Val Lys Tyr His His Cys Arg Asp Val Pro
            115                 120                 125

Leu His Ala Leu Tyr Asp Asn Val Glu Lys Leu Phe Pro Gly Phe Glu
        130                 135                 140

Ile Glu Thr Val Lys Asn Asn Leu Arg Ile Leu Phe Asn Asn Ala Val
145                 150                 155                 160

Lys Lys Arg Leu Met Thr Asp Arg Arg Ile Gly Cys Leu Leu Ser Gly
                165                 170                 175

Gly Leu Asp Ser Ser Leu Val Ala Ala Thr Leu Leu Lys Gln Leu Lys
            180                 185                 190

Glu Ala Gln Val Gln Tyr Pro Leu Gln Thr Phe Ala Ile Gly Met Glu
            195                 200                 205

Asp Ser Pro Asp Leu Leu Ala Ala Arg Lys Val Ala Asp His Ile Gly
        210                 215                 220

Ser Glu His Tyr Glu Val Leu Phe Asn Ser Glu Glu Gly Ile Gln Ala
225                 230                 235                 240

Leu Asp Glu Val Ile Phe Ser Leu Glu Thr Tyr Asp Ile Thr Thr Val
                245                 250                 255

Arg Ala Ser Val Gly Met Tyr Leu Ile Ser Lys Tyr Ile Arg Lys Asn
            260                 265                 270

Thr Asp Ser Val Val Ile Phe Ser Gly Glu Gly Ser Asp Glu Leu Thr
            275                 280                 285

Gln Gly Tyr Ile Tyr Phe His Lys Ala Pro Ser Pro Glu Lys Ala Glu
        290                 295                 300

Glu Glu Ser Glu Arg Leu Leu Arg Glu Leu Tyr Leu Phe Asp Val Leu
305                 310                 315                 320

Arg Ala Asp Arg Thr Thr Ala Ala His Gly Leu Glu Leu Arg Val Pro
            325                 330                 335

Phe Leu Asp His Arg Phe Ser Ser Tyr Tyr Leu Ser Leu Pro Pro Glu
            340                 345                 350

Met Arg Ile Pro Lys Asn Gly Ile Glu Lys His Leu Leu Arg Glu Thr
            355                 360                 365

Phe Glu Asp Ser Asn Leu Ile Pro Lys Glu Ile Leu Trp Arg Pro Lys
        370                 375                 380

Glu Ala Phe Ser Asp Gly Ile Thr Ser Val Lys Asn Ser Trp Phe Lys
385                 390                 395                 400

Ile Leu Gln Glu Tyr Val Glu His Gln Val Asp Asp Ala Met Met Ala
```

-continued

```
              405             410             415
Asn Ala Ala Gln Lys Phe Pro Phe Asn Thr Pro Lys Thr Lys Glu Gly
              420             425             430
Tyr Tyr Tyr Arg Gln Val Phe Glu Arg His Tyr Pro Gly Arg Ala Asp
          435             440             445
Trp Leu Ser His Tyr Trp Met Pro Lys Trp Ile Asn Ala Thr Asp Pro
      450             455             460
Ser Ala Arg Thr Leu Thr His Tyr Lys Ser Ala Val Lys Ala
465             470             475
```

```
<210> SEQ ID NO 51
<211> LENGTH: 1437
<212> TYPE: DNA
<213> ORGANISM: Homo sapiens

<400> SEQUENCE: 51
atgcaacagc attttgaatt tgaataccag accaaagtgg atggtgagat aatccttcat      60
ctttatgaca aaggaggaat tgagcaaaca atttgtatgt tggatggtgt gtttgcattt     120
gttttactgg atactgccaa taagaaagtg ttcctgggta gagatacata tggagtcaga     180
cctttgttta aagcaatgac agaagatgga tttttggctg tatgttcaga agctaaaggt     240
cttgttacat tgaagcactc cgcgactccc tttttaaaag tggagccttt tcttcctgga     300
cactatgaag ttttggattt aaagccaaat ggcaaagttg catccgtgga aatggttaaa     360
tatcatcact gtcgggatgt acccctgcac gccctctatg acaatgtgga gaaactcttt     420
ccaggttttg agatagaaac tgtgaagaac aacctcagga tccttttttaa taatgctgta     480 aagaaacgtt tgatgacaga cagaaggatt ggctgccttt tatcaggggg cttggactcc     540
agcttggttc tgccactct gttgaagcag ctgaaagaag cccaagtaca gtatcctctc     600
cagacatttg caattggcat ggaagacagc cccgattac tggctgctag aaaggtggca     660
gatcatattg gaagtgaaca ttatgaagtc cttttttaact ctgaggaagg cattcaggct     720
ctggatgaag tcatatttc cttggaaact tatgacatta caacagttcg tgcttcagta     780
ggtatgtatt taatttccaa gtatattcgg aagaacacag atagcgtggt gatcttctct     840
ggagaaggat cagatgaact tacgcagggt tacatatatt ttcacaaggc tccttctcct     900
gaaaaagccg aggaggagag tgagaggctt ctgagggaac tctatttgtt tgatgttctc     960
cgcgcagatc gaactactgc tgcccatggt cttgaactga gagtcccatt tctagatcat    1020
cgattttctt cctattactt gtctctgcca ccagaaatga gaattccaaa gaatgggata    1080
gaaaaacatc tcctgagaga gacgtttgag gattccaatc tgatacccaa agagattctc    1140
tggcgaccaa agaagccttt cagtgatgga ataacttcag ttaagaattc ctggtttaag    1200
attttacagg aatacgttga acatcaggtt gatgatgcaa tgatggcaaa tgcagcccag    1260
aaatttccct tcaatactcc taaaaccaaa gaaggatatt actaccgtca agtctttgaa    1320
cgccattacc caggccgggc tgactggctg agccattact ggatgcccaa gtggatcaat    1380
gccactgacc cttctgcccg cacgctgacc cactacaagt cagctgtcaa agcttag       1437

<210> SEQ ID NO 52
<211> LENGTH: 478
<212> TYPE: PRT
<213> ORGANISM: Homo sapiens

<400> SEQUENCE: 52

Met Gln Gln His Phe Glu Phe Glu Tyr Gln Thr Lys Val Asp Gly Glu
```

```
1                 5                  10                 15

Ile Ile Leu His Leu Tyr Asp Lys Gly Gly Ile Glu Gln Thr Ile Cys
            20                 25                 30

Met Leu Asp Gly Val Phe Ala Phe Val Leu Leu Asp Thr Ala Asn Lys
            35                 40                 45

Lys Val Phe Leu Gly Arg Asp Thr Tyr Gly Val Arg Pro Leu Phe Lys
         50                 55                 60

Ala Met Thr Glu Asp Gly Phe Leu Ala Val Cys Ser Glu Ala Lys Gly
65                 70                 75                 80

Leu Val Thr Leu Lys His Ser Ala Thr Pro Phe Leu Lys Val Glu Pro
                85                 90                 95

Phe Leu Pro Gly His Tyr Glu Val Leu Asp Leu Lys Pro Asn Gly Lys
            100                105                110

Val Ala Ser Val Glu Met Val Lys Tyr His His Cys Arg Asp Val Pro
            115                120                125

Leu His Ala Leu Tyr Asp Asn Val Glu Lys Leu Phe Pro Gly Phe Glu
         130                135                140

Ile Glu Thr Val Lys Asn Asn Leu Arg Ile Leu Phe Asn Asn Ala Val
145                150                155                160

Lys Lys Arg Leu Met Thr Asp Arg Arg Ile Gly Cys Leu Leu Ser Gly
                165                170                175

Gly Leu Asp Ser Ser Leu Val Ala Ala Thr Leu Leu Lys Gln Leu Lys
            180                185                190

Glu Ala Gln Val Gln Tyr Pro Leu Gln Thr Phe Ala Ile Gly Met Glu
            195                200                205

Asp Ser Pro Asp Leu Leu Ala Ala Arg Lys Val Ala Asp His Ile Gly
         210                215                220

Ser Glu His Tyr Glu Val Leu Phe Asn Ser Glu Glu Gly Ile Gln Ala
225                230                235                240

Leu Asp Glu Val Ile Phe Ser Leu Glu Thr Tyr Asp Ile Thr Thr Val
                245                250                255

Arg Ala Ser Val Gly Met Tyr Leu Ile Ser Lys Tyr Ile Arg Lys Asn
            260                265                270

Thr Asp Ser Val Val Ile Phe Ser Gly Glu Gly Ser Asp Glu Leu Thr
            275                280                285

Gln Gly Tyr Ile Tyr Phe His Lys Ala Pro Ser Pro Glu Lys Ala Glu
         290                295                300

Glu Glu Ser Glu Arg Leu Leu Arg Glu Leu Tyr Leu Phe Asp Val Leu
305                310                315                320

Arg Ala Asp Arg Thr Thr Ala Ala His Gly Leu Glu Leu Arg Val Pro
                325                330                335

Phe Leu Asp His Arg Phe Ser Ser Tyr Tyr Leu Ser Leu Pro Pro Glu
            340                345                350

Met Arg Ile Pro Lys Asn Gly Ile Glu Lys His Leu Leu Arg Glu Thr
            355                360                365

Phe Glu Asp Ser Asn Leu Ile Pro Lys Glu Ile Leu Trp Arg Pro Lys
         370                375                380

Glu Ala Phe Ser Asp Gly Ile Thr Ser Val Lys Asn Ser Trp Phe Lys
385                390                395                400

Ile Leu Gln Glu Tyr Val Glu His Gln Val Asp Asp Ala Met Met Ala
                405                410                415

Asn Ala Ala Gln Lys Phe Pro Phe Asn Thr Pro Lys Thr Lys Glu Gly
            420                425                430
```

-continued

```
Tyr Tyr Tyr Arg Gln Val Phe Glu Arg His Tyr Pro Gly Arg Ala Asp
        435                 440             445

Trp Leu Ser His Tyr Trp Met Pro Lys Trp Ile Asn Ala Thr Asp Pro
    450                 455             460

Ser Ala Arg Thr Leu Thr His Tyr Lys Ser Ala Val Lys Ala
465                 470             475
```

<210> SEQ ID NO 53
<211> LENGTH: 644
<212> TYPE: DNA
<213> ORGANISM: Homo sapiens

<400> SEQUENCE: 53

```
atgtgtggca tttgggcgct gtttggcagt gatgattgcc tttctgttca gtgtctgagt       60
gctatgaaga ttgcacacag aggtccagat gcattccgtt ttgagaatgt caatggatac      120
accaactgct gctttggatt tcaccggttg gcggtagttg acccgctgtt tggaatgcag      180
ccaattcgag tgaagaaata tccgtatttg tggctctgtt acaatggtga aatctacaac      240
cataagaaga tgcaacagca ttttgaattt gaataccaga ccaaagtgga tggtgagata      300
atccttcatc tttatgacaa aggaggaatt gagcaaacaa tttgtatgtt ggatggtgtg      360
tttgcatttg ttttactgga tactgccaat aagaaagtgt cctgggtag agatacatat       420 ggagtcagac ctttgtttaa agcaatgaca gaagatggat ttttggctgt atgttcagaa      480
gctaaaggtc ttgttacatt gaagcactcc gcgactccct ttttaaaagt ggagcctttt      540
cttcctggac actatgaagt tttggattta aagccaaatg caaagttgc atccgtggaa       600 atggttaaat atcatcactg tcgggatgta cccctgcacg ccct                       644
```

<210> SEQ ID NO 54
<211> LENGTH: 214
<212> TYPE: PRT
<213> ORGANISM: Homo sapiens

<400> SEQUENCE: 54

```
Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45

Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
            100                 105                 110

Thr Ile Cys Met Leu Asp Gly Val Phe Ala Phe Val Leu Leu Asp Thr
            115                 120                 125

Ala Asn Lys Lys Val Phe Leu Gly Arg Asp Thr Tyr Gly Val Arg Pro
        130                 135                 140

Leu Phe Lys Ala Met Thr Glu Asp Gly Phe Leu Ala Val Cys Ser Glu
145                 150                 155                 160

Ala Lys Gly Leu Val Thr Leu Lys His Ser Ala Thr Pro Phe Leu Lys
```

-continued

```
                165                 170                 175
Val Glu Pro Phe Leu Pro Gly His Tyr Glu Val Leu Asp Leu Lys Pro
            180                 185                 190

Asn Gly Lys Val Ala Ser Val Glu Met Val Lys Tyr His His Cys Arg
        195                 200                 205

Asp Val Pro Leu His Ala
    210

<210> SEQ ID NO 55
<211> LENGTH: 487
<212> TYPE: DNA
<213> ORGANISM: Homo sapiens

<400> SEQUENCE: 55
atgtgtggca tttgggcgct gtttggcagt gatgattgcc tttctgttca gtgtctgagt        60
gctatgaaga ttgcacacag aggtccagat gcattccgtt ttgagaatgt caatggatac       120
accaactgct gctttggatt tcaccggttg gcggtagttg acccgctgtt tggaatgcag       180
ccaattcgag tgaagaaata tccgtatttg tggctctgtt acaatggtga aatctacaac       240
cataagaaga tgcaacagca tttttgaattt gaataccaga ccaaagtgga tggtgagata       300
atccttcatc tttatgacaa aggaggaatt gagcaaacaa tttgtatgtt ggatggtgtg       360
tttgcatttg ttttactgga tactgccaat aagaaagtgt tcctgggtag agatacatat       420
ggagtcagac ctttgtttaa agcaatgaca gaagatggat ttttggctgt atgttcagaa       480
gctaaag                                                                  487

<210> SEQ ID NO 56
<211> LENGTH: 162
<212> TYPE: PRT
<213> ORGANISM: Homo sapiens

<400> SEQUENCE: 56

Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45

Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
            100                 105                 110

Thr Ile Cys Met Leu Asp Gly Val Phe Ala Phe Val Leu Leu Asp Thr
        115                 120                 125

Ala Asn Lys Lys Val Phe Leu Gly Arg Asp Thr Tyr Gly Val Arg Pro
    130                 135                 140

Leu Phe Lys Ala Met Thr Glu Asp Gly Phe Leu Ala Val Cys Ser Glu
145                 150                 155                 160

Ala Lys

<210> SEQ ID NO 57
```

-continued

```
<211> LENGTH: 85
<212> TYPE: DNA
<213> ORGANISM: Homo sapiens

<400> SEQUENCE: 57
atgtgtggca tttgggcgct gtttggcagt gatgattgcc tttctgttca gtgtctgagt      60
gctatgaaga ttgcacacag aggtc                                            85

<210> SEQ ID NO 58
<211> LENGTH: 28
<212> TYPE: PRT
<213> ORGANISM: Homo sapiens

<400> SEQUENCE: 58

Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly
            20                  25

<210> SEQ ID NO 59
<211> LENGTH: 356
<212> TYPE: DNA
<213> ORGANISM: Homo sapiens

<400> SEQUENCE: 59
atgtgtggca tttgggcgct gtttggcagt gatgattgcc tttctgttca gtgtctgagt      60
gctatgaaga ttgcacacag aggtccagat gcattccgtt ttgagaatgt caatggatac     120
accaactgct gctttggatt tcaccggttg gcggtagttg acccgctgtt tggaatgcag     180
ccaattcgag tgaagaaata tccgtatttg tggctctgtt acaatggtga aatctacaac     240
cataagaaga tgcaacagca tttttgaattt gaataccaga ccaaagtgga tggtgagata     300
atccttcatc tttatgacaa aggaggaatt gagcaaacaa tttgtatgtt ggatgg         356

<210> SEQ ID NO 60
<211> LENGTH: 118
<212> TYPE: PRT
<213> ORGANISM: Homo sapiens

<400> SEQUENCE: 60

Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
            35                  40                  45

Arg Leu Ala Val Val Asp Pro Leu Phe Gly Met Gln Pro Ile Arg Val
            50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                    85                  90                  95

Asp Gly Glu Ile Ile Leu His Leu Tyr Asp Lys Gly Gly Ile Glu Gln
                100                 105                 110

Thr Ile Cys Met Leu Asp
            115

<210> SEQ ID NO 61
<211> LENGTH: 189
```

```
<212> TYPE: DNA
<213> ORGANISM: Homo sapiens

<400> SEQUENCE: 61
atgaagattg cacacagagg tccagatgca ttccgttttg agaatgtcaa tggatacacc       60
aactgctgct ttggatttca ccggttggcg gtagttgacc cgctgtttgg aatgcagcca      120
attcgagtga agaaatatcc gtatttgtgg ctctgttaca atggtgaaat ctacaaccat      180
aagaaggtg                                                              189

<210> SEQ ID NO 62
<211> LENGTH: 63
<212> TYPE: PRT
<213> ORGANISM: Homo sapiens

<400> SEQUENCE: 62

Met Lys Ile Ala His Arg Gly Pro Asp Ala Phe Arg Phe Glu Asn Val
1               5                   10                  15

Asn Gly Tyr Thr Asn Cys Cys Phe Gly Phe His Arg Leu Ala Val Val
            20                  25                  30

Asp Pro Leu Phe Gly Met Gln Pro Ile Arg Val Lys Lys Tyr Pro Tyr
        35                  40                  45

Leu Trp Leu Cys Tyr Asn Gly Glu Ile Tyr Asn His Lys Lys Val
    50                  55                  60

<210> SEQ ID NO 63
<211> LENGTH: 98
<212> TYPE: DNA
<213> ORGANISM: Homo sapiens

<400> SEQUENCE: 63
atgtgtggca tttgggcgct gtttggcagt gatgattgcc tttctgttca gtgtctgagt       60
gctatgaaga ttgcacacag aggtccagat gcattccg                               98

<210> SEQ ID NO 64
<211> LENGTH: 32
<212> TYPE: PRT
<213> ORGANISM: Homo sapiens

<400> SEQUENCE: 64

Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

<210> SEQ ID NO 65
<211> LENGTH: 1206
<212> TYPE: DNA
<213> ORGANISM: Homo sapiens

<400> SEQUENCE: 65
atgtgtggca tttgggcgct gtttggcagt gatgattgcc tttctgttca gtgtctgagt       60
gctatgaaga ttgcacacag aggtccagat gcattccgtt ttgagaatgt caatggatac      120
accaactgct gctttggatt tcaccggttg gcggtagttg acccgctgtt tggaatgcag      180
ccaattcgag tgaagaaata tccgtatttg tggctctgtt acaatggtga aatctacaac      240
cataagaaga tgcaacagca ttttgaattt gaataccaga ccaaagtgga tggtgagata      300
atccttcatc tttatgacaa aggaggaatt gagcaaacaa tttgtatgtt ggatggtgtg      360
```

-continued

```
tttgcatttg ttttactgga tactgccaat aagaaagtgt tcctgggtag agatacatat    420
ggagtcagac ctttgtttaa agcaatgaca gaagatggat ttttggctgt atgttcagaa    480
gctaaaggtc ttgttacatt gaagcactcc gcgactccct tttttaaaagt ggagcctttt    540 cttcctggac actatgaagt tttggattta aagccaaatg gcaaagttgc atccgtggaa    600
atggttaaat atcatcactg tcgggatgta cccctgcacg ccctctatga caatgtggag    660
aaactctttc caggttttga gatagaaact gtgaagaaca acctcaggat ccttttttaat    720 aatgctgtaa agaaacgttt gatgacagac agaaggattg gctgccttttt atcaggggggc    780 ttggactcca gcttggttgc tgccactctg ttgaagcagc tgaaagaagc ccaagtacag    840
tatcctctcc agacatttgc aattggcatg gaagacagcc ccgatttact ggctgctaga    900
aaggtggcag atcatattgg aagtgaacat tatgaagtcc tttttaactc tgaggaaggc    960
attcaggctc tggatgaagt catatttttcc ttggaaactt atgacattac aacagttcgt   1020
gcttcagtag gtatgtattt aatttccaag tatattcgga agaacacaga tagcgtggtg   1080
atcttctctg gagaaggatc agatgaactt acgcagggtt acatatattt tcacaaggat   1140
tggagaggga gaaagaaaaa ctgctttgtg tgccaaaagc aaaactcttg gtgtttttgt   1200
ttgtga                                                               1206
```

<210> SEQ ID NO 66
<211> LENGTH: 401
<212> TYPE: PRT
<213> ORGANISM: Homo sapiens

<400> SEQUENCE: 66

```
Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45

Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
            100                 105                 110

Thr Ile Cys Met Leu Asp Gly Val Phe Ala Phe Val Leu Leu Asp Thr
        115                 120                 125

Ala Asn Lys Lys Val Phe Leu Gly Arg Asp Thr Tyr Gly Val Arg Pro
    130                 135                 140

Leu Phe Lys Ala Met Thr Glu Asp Gly Phe Leu Ala Val Cys Ser Glu
145                 150                 155                 160

Ala Lys Gly Leu Val Thr Leu Lys His Ser Ala Thr Pro Phe Leu Lys
                165                 170                 175

Val Glu Pro Phe Leu Pro Gly His Tyr Glu Val Leu Asp Leu Lys Pro
                180                 185                 190

Asn Gly Lys Val Ala Ser Val Glu Met Val Lys Tyr His His Cys Arg
            195                 200                 205

Asp Val Pro Leu His Ala Leu Tyr Asp Asn Val Glu Lys Leu Phe Pro
    210                 215                 220
```

```
Gly Phe Glu Ile Glu Thr Val Lys Asn Asn Leu Arg Ile Leu Phe Asn
225                 230                 235                 240

Asn Ala Val Lys Lys Arg Leu Met Thr Asp Arg Arg Ile Gly Cys Leu
                245                 250                 255

Leu Ser Gly Gly Leu Asp Ser Ser Leu Val Ala Ala Thr Leu Leu Lys
                260                 265                 270

Gln Leu Lys Glu Ala Gln Val Gln Tyr Pro Leu Gln Thr Phe Ala Ile
        275                 280                 285

Gly Met Glu Asp Ser Pro Asp Leu Leu Ala Ala Arg Lys Val Ala Asp
        290                 295                 300

His Ile Gly Ser Glu His Tyr Glu Val Leu Phe Asn Ser Glu Glu Gly
305                 310                 315                 320

Ile Gln Ala Leu Asp Glu Val Ile Phe Ser Leu Glu Thr Tyr Asp Ile
                325                 330                 335

Thr Thr Val Arg Ala Ser Val Gly Met Tyr Leu Ile Ser Lys Tyr Ile
                340                 345                 350

Arg Lys Asn Thr Asp Ser Val Val Ile Phe Ser Gly Glu Gly Ser Asp
        355                 360                 365

Glu Leu Thr Gln Gly Tyr Ile Tyr Phe His Lys Asp Trp Arg Gly Arg
        370                 375                 380

Lys Lys Asn Cys Phe Val Cys Gln Lys Gln Asn Ser Trp Cys Phe Cys
385                 390                 395                 400

Leu
```

```
<210> SEQ ID NO 67
<211> LENGTH: 888
<212> TYPE: DNA
<213> ORGANISM: Homo sapiens

<400> SEQUENCE: 67
atggagaccc ctgcctggcc ccgggtcccg cgccccgaga ccgccgtcgc tcggacgctc        60
ctgctcggct gggtcttcgc ccaggtggcc ggcgcttcag gcactacaaa tactgtggca       120
gcatataatt taacttggaa atcaactaat ttcaagacaa tttttggagtg ggaacccaaa      180 cccgtcaatc aagtctacac tgttcaaata agcactaagt caggagattg gaaaagcaaa       240
tgcttttaca caacagacac agagtgtgac ctcaccgacg agattgtgaa ggatgtgaag       300
cagacgtact tggcacgggt cttctcctac ccggcaggga atgtggagag caccggttct       360
gctggggagc ctctgtatga gaactcccca gagttcacac cttacctgga gacaaacctc       420
ggacagccaa caattcagag ttttgaacag gtgggaacaa aagtgaatgt gaccgtagaa       480
gatgaacgga ctttagtcag aaggaacaac actttcctaa gcctccggga tgttttttggc      540 aaggacttaa tttatacact ttattattgg aaatcttcaa gttcaggaaa gaaaacagcc       600
aaaacaaaca ctaatgagtt tttgattgat gtggataaag agaaaactaa ctgtttcagt       660
gttcaagcag tgattccctc ccgaacagtt aaccggaaga gtacagacag cccggtagag       720
tgtatgggcc aggagaaagg ggaattcaga gaaatattct acatcattgg agctgtggta       780
tttgtggtca tcatccttgt catcatcctg ctatatctc tacacaagtg tagaaaggca        840
ggagtggggc agagctggaa ggagaactcc ccactgaatg tttcataa                    888
```

```
<210> SEQ ID NO 68
<211> LENGTH: 295
<212> TYPE: PRT
<213> ORGANISM: Homo sapiens
```

-continued

<400> SEQUENCE: 68

```
Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
        50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
        130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
        210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
            275                 280                 285

Asn Ser Pro Leu Asn Val Ser
    290                 295
```

<210> SEQ ID NO 69
<211> LENGTH: 717
<212> TYPE: DNA
<213> ORGANISM: Homo sapiens

<400> SEQUENCE: 69

```
atggagaccc ctgcctggcc ccgggtcccg cgccccgaga ccgccgtcgc tcggacgctc      60
ctgctcggct gggtcttcgc ccaggtggcc ggcgcttcag gcactacaaa tactgtggca     120
gcatataatt taacttggaa atcaactaat ttcaagacaa ttttggagtg ggaacccaaa     180
cccgtcaatc aagtctacac tgttcaaata agcactaagt caggagattg gaaaagcaaa     240
tgcttttaca acagacacac agagtgtgac ctcaccgacg agattgtgaa ggatgtgaag     300
cagacgtact tggcacgggt cttctcctac ccggcaggga atgtggagag caccggttct     360
```

```
gctggggagc ctctgtatga gaactcccca gagttcacac cttacctgga gacaaacctc      420
ggacagccaa caattcagag ttttgaacag gtgggaacaa aagtgaatgt gaccgtagaa      480
gatgaacgga ctttagtcag aaggaacaac actttcctaa gcctccggga tgttttttggc     540 aaggacttaa tttatacact ttattattgg aaatcttcaa gttcaggaaa gaaatattct      600
acatcattgg agctgtggta tttgtggtca tcatccttgt catcatcctg gctatatctc      660
tacacaagtg tagaaaggca ggagtggggc agagctggaa ggagaactcc ccactga        717
```

<210> SEQ ID NO 70
<211> LENGTH: 238
<212> TYPE: PRT
<213> ORGANISM: Homo sapiens

<400> SEQUENCE: 70

```
Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Tyr Ser Thr Ser Leu Glu Leu Trp Tyr Leu
        195                 200                 205

Trp Ser Ser Ser Leu Ser Ser Ser Trp Leu Tyr Leu Tyr Thr Ser Val
    210                 215                 220

Glu Arg Gln Glu Trp Gly Arg Ala Gly Arg Arg Thr Pro His
225                 230                 235
```

<210> SEQ ID NO 71
<211> LENGTH: 2460
<212> TYPE: DNA
<213> ORGANISM: Homo sapiens

<400> SEQUENCE: 71

```
atggggtctg gcgcgcgctt tccctcgggg accttcgtg tccggtggtt gctgttgctt       60
ggcctggtgg gccagtcct cggtgcggcg cggccaggct ttcaacagac ctcacatctt      120
tcttcttatg aaattataac tccttggaga ttaactagag aaagaagaga agcccctagg      180
```

-continued

```
ccctattcaa aacaagtatc ttatgttatt caggctgaag gaaaagagca tattattcac      240
ttggaaagga acaaagacct tttgcctgaa gattttgtgg tttatactta caacaaggaa      300
gggactttaa tcactgacca tcccaatata cagaatcatt gtcattatcg gggctatgtg      360
gagggagttc ataattcatc cattgctctt agcgactgtt ttggactcag aggattgctg      420
catttagaga atgcgagtta tgggattgaa cccctgcaga acagctctca ttttgagcac      480
atcatttatc gaatggatga tgtctacaaa gagcctctga aatgtggagt ttccaacaag      540
gatatagaga aagaaactgc aaaggatgaa gaggaagagc ctcccagcat gactcagcta      600
cttcgaagaa gaagagctgt cttgccacag acccggtatg tggagctgtt cattgtcgta      660
gacaaggaaa ggtatgacat gatgggaaga aatcagactg ctgtgagaga agagatgatt      720
ctcctggcaa actacttgga tagtatgtat attatgttaa atattcgaat tgtgctagtt      780
ggactggaga tttggaccaa tggaaacctg atcaacatag ttgggggtgc tggtgatgtg      840
ctggggaact cgtgcagtg gcgggaaaag tttcttatca cacgtcggag acatgacagt      900
gcacagctag ttctaaagaa aggttttggt ggaactgcag gaatggcatt tgtgggaaca      960
gtgtgttcaa ggagccacgc aggcgggatt aatgtgtttg gacaaatcac tgtgggagaca     1020 tttgcttcca ttgttgctca tgaattgggt cataatcttg gaatgaatca cgatgatggg     1080
agagattgtt cctgtggagc aaaagagctgc atcatgaatt caggagcatc gggttccaga    1140
aactttagca gttgcagtgc agaggacttt gagaagttaa ctttaaataa aggaggaaac     1200
tgccttctta atattccaaa gcctgatgaa gcctatagtg ctccctcctg tggtaataag     1260
ttggtggacg ctggggaaga gtgtgactgt ggtactccaa aggaatgtga attggaccct     1320
tgctgcgaag gaagtacctg taagcttaaa tcatttgctg agtgtgcata tggtgactgt     1380
tgtaaagact gtcggttcct tccaggaggt actttatgcc gaggaaaaac cagtgagtgt     1440
gatgttccag agtactgcaa tggttcttct cagttctgtc agccagatgt ttttattcag     1500
aatggatatc cttgccagaa taacaaagcc tattgctaca acggcatgtg ccagtattat     1560
gatgctcaat gtcaagtcat ctttggctca aaagccaagg ctgcccccaa agattgtttc     1620
attgaagtga attctaaagg tgacagattt ggcaattgtg gtttctctgg caatgaatac     1680
aagaagtgtg ccactgggaa tgctttgtgt ggaaagcttc agtgtgagaa tgtacaagag     1740
atacctgtat ttggaattgt gcctgctatt attcaaacgc ctagtcgagg caccaaatgt     1800
tggggtgtgg atttccagct aggatcagat gttccagatc ctgggatggt taacgaaggc     1860 acaaatgtg gtgctggaaa gatctgtaga aacttccagt gtgtagatgc ttctgttctg     1920
aattatgact gtgatgttca gaaaaagtgt catggacatg gggtatgtaa tagcaataag     1980
aattgtcact gtgaaaatgg ctgggctccc ccaaattgtg agactaaagg atacggagga     2040
agtgtggaca gtggacctac atacaatgaa atgaatactg cattgaggga cggacttctg     2100
gtcttcttct tcctaattgt tccccttatt gtctgtgcta tttttatctt catcaagagg     2160
gatcaactgt ggagaagcta cttcagaaag aagagatcac aaacatatga gtcagatggc     2220
aaaaatcaag caaacccttc tagacagccg gggagtgttc ctcgacatgt ttctccagtg     2280
acacctccca gagaagttcc tatatatgca aacagatttg cagtaccaac ctatgcagcc     2340
aagcaacctc agcagttccc atcaaggcca cctccaccac aaccgaaagt atcatctcag     2400
ggaaacttaa ttcctgcccg tcctgctcct gcacctcctt tatatagttc cctcacttga     2460
```

<210> SEQ ID NO 72

-continued

```
<211> LENGTH: 819
<212> TYPE: PRT
<213> ORGANISM: Homo sapiens

<400> SEQUENCE: 72

Met Gly Ser Gly Ala Arg Phe Pro Ser Gly Thr Leu Arg Val Arg Trp
1               5                   10                  15

Leu Leu Leu Leu Gly Leu Val Gly Pro Val Leu Gly Ala Ala Arg Pro
                20                  25                  30

Gly Phe Gln Gln Thr Ser His Leu Ser Ser Tyr Glu Ile Ile Thr Pro
            35                  40                  45

Trp Arg Leu Thr Arg Glu Arg Arg Glu Ala Pro Arg Pro Tyr Ser Lys
    50                  55                  60

Gln Val Ser Tyr Val Ile Gln Ala Glu Gly Lys Glu His Ile Ile His
65                  70                  75                  80

Leu Glu Arg Asn Lys Asp Leu Leu Pro Glu Asp Phe Val Val Tyr Thr
                85                  90                  95

Tyr Asn Lys Glu Gly Thr Leu Ile Thr Asp His Pro Asn Ile Gln Asn
            100                 105                 110

His Cys His Tyr Arg Gly Tyr Val Glu Gly Val His Asn Ser Ser Ile
            115                 120                 125

Ala Leu Ser Asp Cys Phe Gly Leu Arg Gly Leu Leu His Leu Glu Asn
    130                 135                 140

Ala Ser Tyr Gly Ile Glu Pro Leu Gln Asn Ser Ser His Phe Glu His
145                 150                 155                 160

Ile Ile Tyr Arg Met Asp Asp Val Tyr Lys Glu Pro Leu Lys Cys Gly
                165                 170                 175

Val Ser Asn Lys Asp Ile Glu Lys Glu Thr Ala Lys Asp Glu Glu Glu
            180                 185                 190

Glu Pro Pro Ser Met Thr Gln Leu Leu Arg Arg Arg Arg Ala Val Leu
            195                 200                 205

Pro Gln Thr Arg Tyr Val Glu Leu Phe Ile Val Val Asp Lys Glu Arg
    210                 215                 220

Tyr Asp Met Met Gly Arg Asn Gln Thr Ala Val Arg Glu Glu Met Ile
225                 230                 235                 240

Leu Leu Ala Asn Tyr Leu Asp Ser Met Tyr Ile Met Leu Asn Ile Arg
                245                 250                 255

Ile Val Leu Val Gly Leu Glu Ile Trp Thr Asn Gly Asn Leu Ile Asn
            260                 265                 270

Ile Val Gly Gly Ala Gly Asp Val Leu Gly Asn Phe Val Gln Trp Arg
            275                 280                 285

Glu Lys Phe Leu Ile Thr Arg Arg His Asp Ser Ala Gln Leu Val
    290                 295                 300

Leu Lys Lys Gly Phe Gly Gly Thr Ala Gly Met Ala Phe Val Gly Thr
305                 310                 315                 320

Val Cys Ser Arg Ser His Ala Gly Gly Ile Asn Val Phe Gly Gln Ile
            325                 330                 335

Thr Val Glu Thr Phe Ala Ser Ile Val Ala His Glu Leu Gly His Asn
            340                 345                 350

Leu Gly Met Asn His Asp Asp Gly Arg Asp Cys Ser Cys Gly Ala Lys
            355                 360                 365

Ser Cys Ile Met Asn Ser Gly Ala Ser Gly Ser Arg Asn Phe Ser Ser
    370                 375                 380

Cys Ser Ala Glu Asp Phe Glu Lys Leu Thr Leu Asn Lys Gly Gly Asn
```

-continued

```
385                   390                   395                   400

Cys Leu Leu Asn Ile Pro Lys Pro Asp Glu Ala Tyr Ser Ala Pro Ser
                405                   410                   415

Cys Gly Asn Lys Leu Val Asp Ala Gly Glu Glu Cys Asp Cys Gly Thr
                420                   425                   430

Pro Lys Glu Cys Glu Leu Asp Pro Cys Cys Glu Gly Ser Thr Cys Lys
                435                   440                   445

Leu Lys Ser Phe Ala Glu Cys Ala Tyr Gly Asp Cys Cys Lys Asp Cys
    450                   455                   460

Arg Phe Leu Pro Gly Gly Thr Leu Cys Arg Gly Lys Thr Ser Glu Cys
465                   470                   475                   480

Asp Val Pro Glu Tyr Cys Asn Gly Ser Ser Gln Phe Cys Gln Pro Asp
                485                   490                   495

Val Phe Ile Gln Asn Gly Tyr Pro Cys Gln Asn Asn Lys Ala Tyr Cys
                500                   505                   510

Tyr Asn Gly Met Cys Gln Tyr Tyr Asp Ala Gln Cys Gln Val Ile Phe
                515                   520                   525

Gly Ser Lys Ala Lys Ala Ala Pro Lys Asp Cys Phe Ile Glu Val Asn
    530                   535                   540

Ser Lys Gly Asp Arg Phe Gly Asn Cys Gly Phe Ser Gly Asn Glu Tyr
545                   550                   555                   560

Lys Lys Cys Ala Thr Gly Asn Ala Leu Cys Gly Lys Leu Gln Cys Glu
                565                   570                   575

Asn Val Gln Glu Ile Pro Val Phe Gly Ile Val Pro Ala Ile Ile Gln
                580                   585                   590

Thr Pro Ser Arg Gly Thr Lys Cys Trp Gly Val Asp Phe Gln Leu Gly
                595                   600                   605

Ser Asp Val Pro Asp Pro Gly Met Val Asn Glu Gly Thr Lys Cys Gly
    610                   615                   620

Ala Gly Lys Ile Cys Arg Asn Phe Gln Cys Val Asp Ala Ser Val Leu
625                   630                   635                   640

Asn Tyr Asp Cys Asp Val Gln Lys Lys Cys His Gly His Gly Val Cys
                645                   650                   655

Asn Ser Asn Lys Asn Cys His Cys Glu Asn Gly Trp Ala Pro Pro Asn
                660                   665                   670

Cys Glu Thr Lys Gly Tyr Gly Gly Ser Val Asp Ser Gly Pro Thr Tyr
                675                   680                   685

Asn Glu Met Asn Thr Ala Leu Arg Asp Gly Leu Leu Val Phe Phe Phe
    690                   695                   700

Leu Ile Val Pro Leu Ile Val Cys Ala Ile Phe Ile Phe Ile Lys Arg
705                   710                   715                   720

Asp Gln Leu Trp Arg Ser Tyr Phe Arg Lys Lys Arg Ser Gln Thr Tyr
                725                   730                   735

Glu Ser Asp Gly Lys Asn Gln Ala Asn Pro Ser Arg Gln Pro Gly Ser
                740                   745                   750

Val Pro Arg His Val Ser Pro Val Thr Pro Pro Arg Glu Val Pro Ile
                755                   760                   765

Tyr Ala Asn Arg Phe Ala Val Pro Thr Tyr Ala Ala Lys Gln Pro Gln
    770                   775                   780

Gln Phe Pro Ser Arg Pro Pro Pro Gln Pro Lys Val Ser Ser Gln
785                   790                   795                   800

Gly Asn Leu Ile Pro Ala Arg Pro Ala Pro Ala Pro Pro Leu Tyr Ser
                805                   810                   815
```

-continued

Ser Leu Thr

<210> SEQ ID NO 73
<211> LENGTH: 387
<212> TYPE: DNA
<213> ORGANISM: Homo sapiens

<400> SEQUENCE: 73
atggggtctg gcgcgcgctt tccctcgggg acccttcgtg tccggtggtt gctgttgctt      60
ggcctggtgg gcccagtcct cggtgcggcg cggccaggct ttcaacagac ctcacatctt     120
tcttcttatg aaattataac tccttggaga ttaactagag aaagaagaga agcccctagg     180
ccctattcaa aacaagtatc ttatgttatt caggctgaag gaaaagagca tattattcac     240
ttggaaagga acaaagacct tttgcctgaa gattttgtgg tttatactta caacaaggaa     300
gggactttaa tcactgacca tcccaatata caggtaatgt atttttctct tgatcccata     360
gcaaatttta aacaattat aatttaa                                          387

<210> SEQ ID NO 74
<211> LENGTH: 128
<212> TYPE: PRT
<213> ORGANISM: Homo sapiens

<400> SEQUENCE: 74

Met Gly Ser Gly Ala Arg Phe Pro Ser Gly Thr Leu Arg Val Arg Trp
1               5                   10                  15

Leu Leu Leu Leu Gly Leu Val Gly Pro Val Leu Gly Ala Ala Arg Pro
            20                  25                  30

Gly Phe Gln Gln Thr Ser His Leu Ser Ser Tyr Glu Ile Ile Thr Pro
        35                  40                  45

Trp Arg Leu Thr Arg Glu Arg Arg Glu Ala Pro Arg Pro Tyr Ser Lys
    50                  55                  60

Gln Val Ser Tyr Val Ile Gln Ala Glu Gly Lys Glu His Ile Ile His
65                  70                  75                  80

Leu Glu Arg Asn Lys Asp Leu Leu Pro Glu Asp Phe Val Val Tyr Thr
                85                  90                  95

Tyr Asn Lys Glu Gly Thr Leu Ile Thr Asp His Pro Asn Ile Gln Val
            100                 105                 110

Met Tyr Phe Ser Leu Asp Pro Ile Ala Asn Phe Lys Thr Ile Ile Ile
        115                 120                 125

<210> SEQ ID NO 75
<211> LENGTH: 444
<212> TYPE: DNA
<213> ORGANISM: Homo sapiens

<400> SEQUENCE: 75
atggggtctg gcgcgcgctt tccctcgggg acccttcgtg tccggtggtt gctgttgctt      60
ggcctggtgg gcccagtcct cggtgcggcg cggccaggct ttcaacagac ctcacatctt     120
tcttcttatg aaattataac tccttggaga ttaactagag aaagaagaga agcccctagg     180
ccctattcaa aacaagtatc ttatgttatt caggctgaag gaaaagagca tattattcac     240
ttggaaagga acaaagacct tttgcctgaa gattttgtgg tttatactta caacaaggaa     300
gggactttaa tcactgacca tcccaatata caggaggtgtg gtcctctctg catcagaaa     360 cagagtactc ctggggacag agctggccag aatacccaaa ataattggca gatgtcaaat     420

-continued

```
ttggctttct gtgtttatta ctag                                              444

<210> SEQ ID NO 76
<211> LENGTH: 147
<212> TYPE: PRT
<213> ORGANISM: Homo sapiens

<400> SEQUENCE: 76

Met Gly Ser Gly Ala Arg Phe Pro Ser Gly Thr Leu Arg Val Arg Trp
1               5                   10                  15

Leu Leu Leu Leu Gly Leu Val Gly Pro Val Leu Gly Ala Ala Arg Pro
            20                  25                  30

Gly Phe Gln Gln Thr Ser His Leu Ser Ser Tyr Glu Ile Ile Thr Pro
        35                  40                  45

Trp Arg Leu Thr Arg Glu Arg Arg Glu Ala Pro Arg Pro Tyr Ser Lys
    50                  55                  60

Gln Val Ser Tyr Val Ile Gln Ala Glu Gly Lys Glu His Ile Ile His
65                  70                  75                  80

Leu Glu Arg Asn Lys Asp Leu Leu Pro Glu Asp Phe Val Val Tyr Thr
                85                  90                  95

Tyr Asn Lys Glu Gly Thr Leu Ile Thr Asp His Pro Asn Ile Gln Arg
            100                 105                 110

Cys Gly Pro Leu Cys Ile Arg Glu Gln Ser Thr Pro Gly Asp Arg Ala
        115                 120                 125

Gly Gln Asn Thr Gln Asn Asn Trp Gln Met Ser Asn Leu Ala Phe Cys
    130                 135                 140

Val Tyr Tyr
145

<210> SEQ ID NO 77
<211> LENGTH: 1968
<212> TYPE: DNA
<213> ORGANISM: Homo sapiens

<400> SEQUENCE: 77
atggggtctg gcgcgcgctt tccctcgggg acccttcgtg tccggtggtt gctgttgctt        60
ggcctggtgg gcccagtcct cggtgcggcg cggccaggct ttcaacagac ctcacatctt       120
tcttcttatg aaattataac tccttggaga ttaactagag aaagaagaga agccctagg        180 ccctattcaa aacaagtatc ttatgttatt caggctgaag gaaaagagca tattattcac       240
ttggaaagga acaaagacct tttgcctgaa gattttgtgg tttatactta caacaaggaa       300
gggactttaa tcactgacca tcccaatata cagaatcatt gtcattatcg gggctatgtg       360
gagggagttc ataattcatc cattgctctt agcgactgtt ttggactcag aggattgctg       420
catttagaga atgcgagtta tgggattgaa cccctgcaga acagctctca ttttgagcac       480
atcatttatc gaatggatga tgtctacaaa gagcctctga atgtggagt ttccaacaag       540 gatatagaga aagaaactgc aaaggatgaa gaggaagagc ctcccagcat gactcagcta       600
cttcgaagaa gaagagctgt cttgccacag acccggtatg tggagctgtt cattgtcgta       660
gacaaggaaa ggtatgacat gatgggaaga aatcagactg ctgtgagaga agagatgatt       720
ctcctggcaa actacttgga tagtatgtat attatgttaa atattcgaat gtgtctagtt       780
ggactggaga tttggaccaa tggaaacctg atcaacatag ttgggggtgc tggtgatgtg       840
ctggggaact cgtgcagtg gcgggaaaag tttcttatca cacgtcggag acatgacagt       900
gcacagctag ttctaaagaa aggttttggt ggaactgcag gaatggcatt tgtgggaaca       960
```

```
gtgtgttcaa ggagccacgc aggcgggatt aatgtgtttg gacaaatcac tgtggagaca    1020
tttgcttcca ttgttgctca tgaattgggt cataatcttg gaatgaatca cgatgatggg    1080
agagattgtt cctgtggagc aaagagctgc atcatgaatt caggagcatc gggttccaga    1140
aactttagca gttgcagtgc agaggacttt gagaagttaa ctttaaataa aggaggaaac    1200
tgccttctta atattccaaa gcctgatgaa gcctatagtg ctccctcctg tggtaataag    1260
ttggtggacg ctgggggaaga gtgtgactgt ggtactccaa aggaatgtga attggaccct    1320
tgctgcgaag gaagtacctg taagcttaaa tcatttgctg agtgtgcata tggtgactgt    1380
tgtaaagact gtcggttcct tccaggaggt actttatgcc gaggaaaaac cagtgagtgt    1440
gatgttccag agtactgcaa tggttcttct cagttctgtc agccagatgt ttttattcag    1500
aatggatatc cttgccagaa taacaaagcc tattgctaca cggcatgtg ccagtattat    1560 gatgctcaat gtcaagtcat ctttggctca aaagccaagg ctgcccccaa agattgtttc    1620
attgaagtga attctaaagg tgacagattt ggcaattgtg gtttctctgg caatgaatac    1680
aagaagtgtg ccactgggaa tgctttgtgt ggaaagcttc agtgtgagaa tgtacaagag    1740
atacctgtat ttggaattgt gcctgctatt attcaaacgc ctagtcgagg caccaaatgt    1800
tggggtgtgg atttccagct aggatcagat gttccagatc ctgggatggt taacgaaggc    1860 acaaatgtg gtgctggaaa gatctgtaga aacttccagt gtgtagatgc ttctgttctg    1920
aattatgact gtgatgttca gaaaaagtgt catggacatg ggaaatga                  1968
```

<210> SEQ ID NO 78
<211> LENGTH: 655
<212> TYPE: PRT
<213> ORGANISM: Homo sapiens

<400> SEQUENCE: 78

```
Met Gly Ser Gly Ala Arg Phe Pro Ser Gly Thr Leu Arg Val Arg Trp
1               5                   10                  15

Leu Leu Leu Leu Gly Leu Val Gly Pro Val Leu Gly Ala Ala Arg Pro
            20                  25                  30

Gly Phe Gln Gln Thr Ser His Leu Ser Ser Tyr Glu Ile Ile Thr Pro
        35                  40                  45

Trp Arg Leu Thr Arg Glu Arg Arg Glu Ala Pro Arg Pro Tyr Ser Lys
    50                  55                  60

Gln Val Ser Tyr Val Ile Gln Ala Glu Gly Lys Glu His Ile Ile His
65                  70                  75                  80

Leu Glu Arg Asn Lys Asp Leu Leu Pro Glu Asp Phe Val Val Tyr Thr
                85                  90                  95

Tyr Asn Lys Glu Gly Thr Leu Ile Thr Asp His Pro Asn Ile Gln Asn
            100                 105                 110

His Cys His Tyr Arg Gly Tyr Val Glu Gly Val His Asn Ser Ser Ile
        115                 120                 125

Ala Leu Ser Asp Cys Phe Gly Leu Arg Gly Leu Leu His Leu Glu Asn
        130                 135                 140

Ala Ser Tyr Gly Ile Glu Pro Leu Gln Asn Ser Ser His Phe Glu His
145                 150                 155                 160

Ile Ile Tyr Arg Met Asp Asp Val Tyr Lys Glu Pro Leu Lys Cys Gly
                165                 170                 175

Val Ser Asn Lys Asp Ile Glu Lys Glu Thr Ala Lys Asp Glu Glu Glu
            180                 185                 190
```

-continued

```
Glu Pro Pro Ser Met Thr Gln Leu Leu Arg Arg Arg Arg Ala Val Leu
        195                 200             205

Pro Gln Thr Arg Tyr Val Glu Leu Phe Ile Val Val Asp Lys Glu Arg
        210                 215             220

Tyr Asp Met Met Gly Arg Asn Gln Thr Ala Val Arg Glu Glu Met Ile
225                 230             235                 240

Leu Leu Ala Asn Tyr Leu Asp Ser Met Tyr Ile Met Leu Asn Ile Arg
                245             250             255

Ile Val Leu Val Gly Leu Glu Ile Trp Thr Asn Gly Asn Leu Ile Asn
                260             265             270

Ile Val Gly Gly Ala Gly Asp Val Leu Gly Asn Phe Val Gln Trp Arg
                275             280             285

Glu Lys Phe Leu Ile Thr Arg Arg His Asp Ser Ala Gln Leu Val
        290             295             300

Leu Lys Lys Gly Phe Gly Gly Thr Ala Gly Met Ala Phe Val Gly Thr
305             310             315             320

Val Cys Ser Arg Ser His Ala Gly Gly Ile Asn Val Phe Gly Gln Ile
                325             330             335

Thr Val Glu Thr Phe Ala Ser Ile Val Ala His Glu Leu Gly His Asn
                340             345             350

Leu Gly Met Asn His Asp Asp Gly Arg Asp Cys Ser Cys Gly Ala Lys
        355             360             365

Ser Cys Ile Met Asn Ser Gly Ala Ser Gly Ser Arg Asn Phe Ser Ser
        370             375             380

Cys Ser Ala Glu Asp Phe Glu Lys Leu Thr Leu Asn Lys Gly Gly Asn
385             390             395             400

Cys Leu Leu Asn Ile Pro Lys Pro Asp Glu Ala Tyr Ser Ala Pro Ser
                405             410             415

Cys Gly Asn Lys Leu Val Asp Ala Gly Glu Glu Cys Asp Cys Gly Thr
                420             425             430

Pro Lys Glu Cys Glu Leu Asp Pro Cys Cys Glu Gly Ser Thr Cys Lys
        435             440             445

Leu Lys Ser Phe Ala Glu Cys Ala Tyr Gly Asp Cys Cys Lys Asp Cys
        450             455             460

Arg Phe Leu Pro Gly Gly Thr Leu Cys Arg Gly Lys Thr Ser Glu Cys
465             470             475             480

Asp Val Pro Glu Tyr Cys Asn Gly Ser Ser Gln Phe Cys Gln Pro Asp
                485             490             495

Val Phe Ile Gln Asn Gly Tyr Pro Cys Gln Asn Asn Lys Ala Tyr Cys
                500             505             510

Tyr Asn Gly Met Cys Gln Tyr Tyr Asp Ala Gln Cys Gln Val Ile Phe
        515             520             525

Gly Ser Lys Ala Lys Ala Ala Pro Lys Asp Cys Phe Ile Glu Val Asn
        530             535             540

Ser Lys Gly Asp Arg Phe Gly Asn Cys Gly Phe Ser Gly Asn Glu Tyr
545             550             555             560

Lys Lys Cys Ala Thr Gly Asn Ala Leu Cys Gly Lys Leu Gln Cys Glu
                565             570             575

Asn Val Gln Glu Ile Pro Val Phe Gly Ile Val Pro Ala Ile Ile Gln
                580             585             590

Thr Pro Ser Arg Gly Thr Lys Cys Trp Gly Val Asp Phe Gln Leu Gly
        595             600             605

Ser Asp Val Pro Asp Pro Gly Met Val Asn Glu Gly Thr Lys Cys Gly
```

-continued

```
            610               615               620
Ala Gly Lys Ile Cys Arg Asn Phe Gln Cys Val Asp Ala Ser Val Leu
625               630               635               640

Asn Tyr Asp Cys Asp Val Gln Lys Lys Cys His Gly His Gly Lys
                  645               650               655

<210> SEQ ID NO 79
<211> LENGTH: 2139
<212> TYPE: DNA
<213> ORGANISM: Homo sapiens

<400> SEQUENCE: 79
atggggtctg gcgcgcgctt tccctcgggg acccttcgtg tccggtggtt gctgttgctt      60
ggcctggtgg gccagtcct cggtgcggcg cggccaggct ttcaacagac ctcacatctt     120
tcttcttatg aaattataac tccttggaga ttaactagag aaagaagaga agccctagg     180 ccctattcaa aacaagtatc ttatgttatt caggctgaag gaaaagagca tattattcac     240
ttggaaagga acaaagacct tttgcctgaa gattttgtgg tttatactta caacaaggaa     300
gggactttaa tcactgacca tcccaatata cagaatcatt gtcattatcg gggctatgtg     360
gagggagttc ataattcatc cattgctctt agcgactgtt ttggactcag aggattgctg     420
catttagaga atgcgagtta tgggattgaa ccctgcaga acagctctca ttttgagcac     480
atcatttatc gaatggatga tgtctacaaa gagcctctga aatgtggagt ttccaacaag     540
gatatagaga agaaactgc aaaggatgaa gaggaagagc ctcccagcat gactcagcta     600
cttcgaagaa gaagagctgt cttgccacag acccggtatg tggagctgtt cattgtcgta     660
gacaaggaaa ggtatgacat gatgggaaga aatcagactg ctgtgagaga agagatgatt     720
ctcctggcaa actacttgga tagtatgtat attatgttaa atattcgaat gtgctagtt     780 ggactggaga tttggaccaa tggaaacctg atcaacatag ttgggggtgc tggtgatgtg     840
ctggggaact cgtgcagtg gcgggaaaag tttcttatca cacgtcggag acatgacagt     900
gcacagctag ttctaaagaa aggttttggt ggaactgcag gaatggcatt tgtgggaaca     960
gtgtgttcaa ggagccacgc aggcgggatt aatgtgtttg acaaatcac tgtggagaca    1020 tttgcttcca ttgttgctca tgaattgggt cataatcttg gaatgaatca cgatgatggg    1080
agagattgtt cctgtggagc aaaagagctgc atcatgaatt caggagcatc gggttccaga    1140
aactttagca gttgcagtgc agaggacttt gagaagttaa ctttaaataa aggaggaaac    1200
tgccttctta atattccaaa gcctgatgaa gcctatagtg ctccctcctg tggtaataag    1260
ttggtggacg ctggggaaga gtgtgactgt ggtactccaa aggaatgtga attggaccct    1320
tgctgcgaag gaagtacctg taagcttaaa tcatttgctg agtgtgcata tggtgactgt    1380
tgtaaagact gtcggttcct tccaggaggt actttatgcc gaggaaaaac cagtgagtgt    1440
gatgttccag agtactgcaa tggttcttct cagttctgtc agccagatgt ttttattcag    1500
aatggatatc cttgccagaa taacaaagcc tattgctaca cggcatgtg ccagtattat    1560 gatgctcaat gtcaagtcat ctttggctca aaagccaagg ctgcccccaa agattgtttc    1620
attgaagtga attctaaagg tgacagattt ggcaattgtg gtttctctgg caatgaatac    1680
aagaagtgtg ccactgggaa tgctttgtgt ggaaagcttc agtgtgagaa tgtacaagag    1740
atacctgtat ttggaattgt gcctgctatt attcaaacgc ctagtcgagg caccaaatgt    1800
tggggtgtgg atttccagct aggatcagat gttccagatc ctgggatggt taacgaaggc    1860
acaaaatgtg gtgctggaaa gatctgtaga aacttccagt gtgtagatgc ttctgttctg    1920
```

-continued

```
aattatgact gtgatgttca gaaaaagtgt catggacatg gggtatgtaa tagcaataag    1980
aattgtcact gtgaaaatgg ctgggctccc ccaaattgtg agactaaagg atacggagga    2040
agtgtggaca gtggacctac atacaatggt cagatggcaa aaatcaagca aaccccttcta   2100 gacagccggg gagtgttcct cgacatgttt ctccagtga                           2139

<210> SEQ ID NO 80
<211> LENGTH: 712
<212> TYPE: PRT
<213> ORGANISM: Homo sapiens

<400> SEQUENCE: 80

Met Gly Ser Gly Ala Arg Phe Pro Ser Gly Thr Leu Arg Val Arg Trp
1               5                   10                  15

Leu Leu Leu Leu Gly Leu Val Gly Pro Val Leu Gly Ala Ala Arg Pro
            20                  25                  30

Gly Phe Gln Gln Thr Ser His Leu Ser Ser Tyr Glu Ile Ile Thr Pro
        35                  40                  45

Trp Arg Leu Thr Arg Glu Arg Arg Glu Ala Pro Arg Pro Tyr Ser Lys
    50                  55                  60

Gln Val Ser Tyr Val Ile Gln Ala Glu Gly Lys Glu His Ile Ile His
65                  70                  75                  80

Leu Glu Arg Asn Lys Asp Leu Leu Pro Glu Asp Phe Val Val Tyr Thr
                85                  90                  95

Tyr Asn Lys Glu Gly Thr Leu Ile Thr Asp His Pro Asn Ile Gln Asn
            100                 105                 110

His Cys His Tyr Arg Gly Tyr Val Glu Gly Val His Asn Ser Ser Ile
        115                 120                 125

Ala Leu Ser Asp Cys Phe Gly Leu Arg Gly Leu Leu His Leu Glu Asn
        130                 135                 140

Ala Ser Tyr Gly Ile Glu Pro Leu Gln Asn Ser Ser His Phe Glu His
145                 150                 155                 160

Ile Ile Tyr Arg Met Asp Asp Val Tyr Lys Glu Pro Leu Lys Cys Gly
                165                 170                 175

Val Ser Asn Lys Asp Ile Glu Lys Glu Thr Ala Lys Asp Glu Glu Glu
            180                 185                 190

Glu Pro Pro Ser Met Thr Gln Leu Leu Arg Arg Arg Arg Ala Val Leu
            195                 200                 205

Pro Gln Thr Arg Tyr Val Glu Leu Phe Ile Val Val Asp Lys Glu Arg
        210                 215                 220

Tyr Asp Met Met Gly Arg Asn Gln Thr Ala Val Arg Glu Glu Met Ile
225                 230                 235                 240

Leu Leu Ala Asn Tyr Leu Asp Ser Met Tyr Ile Met Leu Asn Ile Arg
                245                 250                 255

Ile Val Leu Val Gly Leu Glu Ile Trp Thr Asn Gly Asn Leu Ile Asn
            260                 265                 270

Ile Val Gly Gly Ala Gly Asp Val Leu Gly Asn Phe Val Gln Trp Arg
        275                 280                 285

Glu Lys Phe Leu Ile Thr Arg Arg Arg His Asp Ser Ala Gln Leu Val
        290                 295                 300

Leu Lys Lys Gly Phe Gly Gly Thr Ala Gly Met Ala Phe Val Gly Thr
305                 310                 315                 320

Val Cys Ser Arg Ser His Ala Gly Gly Ile Asn Val Phe Gly Gln Ile
                325                 330                 335
```

-continued

```
Thr Val Glu Thr Phe Ala Ser Ile Val Ala His Glu Leu Gly His Asn
        340                 345                 350

Leu Gly Met Asn His Asp Asp Gly Arg Asp Cys Ser Cys Gly Ala Lys
        355                 360                 365

Ser Cys Ile Met Asn Ser Gly Ala Ser Gly Ser Arg Asn Phe Ser Ser
        370                 375                 380

Cys Ser Ala Glu Asp Phe Glu Lys Leu Thr Leu Asn Lys Gly Gly Asn
385                 390                 395                 400

Cys Leu Leu Asn Ile Pro Lys Pro Asp Glu Ala Tyr Ser Ala Pro Ser
                405                 410                 415

Cys Gly Asn Lys Leu Val Asp Ala Gly Glu Glu Cys Asp Cys Gly Thr
                420                 425                 430

Pro Lys Glu Cys Glu Leu Asp Pro Cys Cys Glu Gly Ser Thr Cys Lys
            435                 440                 445

Leu Lys Ser Phe Ala Glu Cys Ala Tyr Gly Asp Cys Cys Lys Asp Cys
        450                 455                 460

Arg Phe Leu Pro Gly Gly Thr Leu Cys Arg Gly Lys Thr Ser Glu Cys
465                 470                 475                 480

Asp Val Pro Glu Tyr Cys Asn Gly Ser Ser Gln Phe Cys Gln Pro Asp
                485                 490                 495

Val Phe Ile Gln Asn Gly Tyr Pro Cys Gln Asn Asn Lys Ala Tyr Cys
                500                 505                 510

Tyr Asn Gly Met Cys Gln Tyr Tyr Asp Ala Gln Cys Gln Val Ile Phe
            515                 520                 525

Gly Ser Lys Ala Lys Ala Ala Pro Lys Asp Cys Phe Ile Glu Val Asn
        530                 535                 540

Ser Lys Gly Asp Arg Phe Gly Asn Cys Gly Phe Ser Gly Asn Glu Tyr
545                 550                 555                 560

Lys Lys Cys Ala Thr Gly Asn Ala Leu Cys Gly Lys Leu Gln Cys Glu
                565                 570                 575

Asn Val Gln Glu Ile Pro Val Phe Gly Ile Val Pro Ala Ile Ile Gln
                580                 585                 590

Thr Pro Ser Arg Gly Thr Lys Cys Trp Gly Val Asp Phe Gln Leu Gly
            595                 600                 605

Ser Asp Val Pro Asp Pro Gly Met Val Asn Glu Gly Thr Lys Cys Gly
        610                 615                 620

Ala Gly Lys Ile Cys Arg Asn Phe Gln Cys Val Asp Ala Ser Val Leu
625                 630                 635                 640

Asn Tyr Asp Cys Asp Val Gln Lys Lys Cys His Gly His Gly Val Cys
                645                 650                 655

Asn Ser Asn Lys Asn Cys His Cys Glu Asn Gly Trp Ala Pro Pro Asn
            660                 665                 670

Cys Glu Thr Lys Gly Tyr Gly Gly Ser Val Asp Ser Gly Pro Thr Tyr
        675                 680                 685

Asn Gly Gln Met Ala Lys Ile Lys Gln Thr Leu Leu Asp Ser Arg Gly
        690                 695                 700

Val Phe Leu Asp Met Phe Leu Gln
705                 710
```

```
<210> SEQ ID NO 81
<211> LENGTH: 1887
<212> TYPE: DNA
<213> ORGANISM: Homo sapiens
```

-continued

<400> SEQUENCE: 81

```
atggggtctg gcgcgcgctt tccctcgggg acccttcgtg tccggtggtt gctgttgctt    60
ggcctggtgg gcccagtcct cggtgcggcg cggccaggct ttcaacagac ctcacatctt   120
tcttcttatg aaattataac tccttggaga ttaactagag aaagaagaga agccctagg    180 ccctattcaa aacaagtatc ttatgttatt caggctgaag gaaaagagca tattattcac   240
ttggaaagga acaaagacct tttgcctgaa gattttgtgg tttatactta caacaaggaa   300
gggactttaa tcactgacca tcccaatata cagaatcatt gtcattatcg gggctatgtg   360
gagggagttc ataattcatc cattgctctt agcgactgtt ttggactcag aggattgctg   420
catttagaga atgcgagtta tgggattgaa cccctgcaga acagctctca ttttgagcac   480
atcatttatc gaatggatga tgtctacaaa gagcctctga atgtggagt ttccaacaag   540 gatatagaga aagaaactgc aaaggatgaa gaggaagagc ctcccagcat gactcagcta   600
cttcgaagaa gaagagctgt cttgccacag acccggtatg tggagctgtt cattgtcgta   660
gacaaggaaa ggtatgacat gatgggaaga aatcagactg ctgtgagaga agagatgatt   720
ctcctggcaa actacttgga tagtatgtat attatgttaa atattcgaat tgtgctagtt   780
ggactggaga tttggaccaa tggaaacctg atcaacatag ttggggtgc tggtgatgtg   840 ctggggaact tcgtgcagtg gcgggaaaag tttcttatca cacgtcggag acatgacagt   900
gcacagctag ttctaaagaa aggttttggt ggaactgcag gaatggcatt tgtgggaaca   960
gtgtgttcaa ggagccacgc aggcgggatt aatgtgtttg gacaaatcac tgtggagaca  1020
tttgcttcca ttgttgctca tgaattgggt cataatcttg gaatgaatca cgatgatggg  1080
agagattgtt cctgtggagc aaagagctgc atcatgaatt caggagcatc gggttccaga  1140
aactttagca gttgcagtgc agaggacttt gagaagttaa ctttaaataa aggaggaaac  1200
tgccttctta atattccaaa gcctgatgaa gcctatagtg ctccctcctg tggtaataag  1260
ttggtggacg ctggggaaga gtgtgactgt ggtactccaa aggaatgtga attggaccct  1320
tgctgcgaag gaagtacctg taagcttaaa tcatttgctg agtgtgcata tggtgactgt  1380
tgtaaagact gtcggttcct tccaggaggt actttatgcc gaggaaaaac cagtgagtgt  1440
gatgttccag agtactgcaa tggttcttct cagttctgtc agccagatgt ttttattcag  1500
aatggatatc cttgccagaa taacaaagcc tattgctaca cggcatgtg ccagtattat  1560 gatgctcaat gtcaagtcat ctttggctca aaagccaagg ctgcccccaa agattgtttc  1620
attgaagtga attctaaagg tgacagattt ggcaattgtg gtttctctgg caatgaatac  1680
aagaagtgtg ccactgggaa tgctttgtgt ggaaagcttc agtgtgagaa tgtacaagag  1740
atacctgtat ttggaattgt gcctgctatt attcaaacgc ctagtcgagg caccaaatgt  1800
tggggtgtgg atttccagct aggatcagat gttccagatc ctgggatggt taacgaaggc  1860
acaaaatgtg gtgctggaaa gaaatga                                      1887
```

<210> SEQ ID NO 82
<211> LENGTH: 628
<212> TYPE: PRT
<213> ORGANISM: Homo sapiens

<400> SEQUENCE: 82

```
Met Gly Ser Gly Ala Arg Phe Pro Ser Gly Thr Leu Arg Val Arg Trp
1               5                   10                  15

Leu Leu Leu Leu Gly Leu Val Gly Pro Val Leu Gly Ala Ala Arg Pro
            20                  25                  30
```

-continued

```
Gly Phe Gln Gln Thr Ser His Leu Ser Ser Tyr Glu Ile Ile Thr Pro
        35                  40                  45

Trp Arg Leu Thr Arg Glu Arg Arg Glu Ala Pro Arg Pro Tyr Ser Lys
    50                  55                  60

Gln Val Ser Tyr Val Ile Gln Ala Glu Gly Lys Glu His Ile Ile His
65                  70                  75                  80

Leu Glu Arg Asn Lys Asp Leu Leu Pro Glu Asp Phe Val Val Tyr Thr
                85                  90                  95

Tyr Asn Lys Glu Gly Thr Leu Ile Thr Asp His Pro Asn Ile Gln Asn
            100                 105                 110

His Cys His Tyr Arg Gly Tyr Val Glu Gly Val His Asn Ser Ser Ile
            115                 120                 125

Ala Leu Ser Asp Cys Phe Gly Leu Arg Gly Leu Leu His Leu Glu Asn
    130                 135                 140

Ala Ser Tyr Gly Ile Glu Pro Leu Gln Asn Ser Ser His Phe Glu His
145                 150                 155                 160

Ile Ile Tyr Arg Met Asp Asp Val Tyr Lys Glu Pro Leu Lys Cys Gly
                165                 170                 175

Val Ser Asn Lys Asp Ile Glu Lys Glu Thr Ala Lys Asp Glu Glu Glu
            180                 185                 190

Glu Pro Pro Ser Met Thr Gln Leu Leu Arg Arg Arg Arg Ala Val Leu
            195                 200                 205

Pro Gln Thr Arg Tyr Val Glu Leu Phe Ile Val Val Asp Lys Glu Arg
    210                 215                 220

Tyr Asp Met Met Gly Arg Asn Gln Thr Ala Val Arg Glu Glu Met Ile
225                 230                 235                 240

Leu Leu Ala Asn Tyr Leu Asp Ser Met Tyr Ile Met Leu Asn Ile Arg
                245                 250                 255

Ile Val Leu Val Gly Leu Glu Ile Trp Thr Asn Gly Asn Leu Ile Asn
            260                 265                 270

Ile Val Gly Gly Ala Gly Asp Val Leu Gly Asn Phe Val Gln Trp Arg
            275                 280                 285

Glu Lys Phe Leu Ile Thr Arg Arg Arg His Asp Ser Ala Gln Leu Val
    290                 295                 300

Leu Lys Lys Gly Phe Gly Gly Thr Ala Gly Met Ala Phe Val Gly Thr
305                 310                 315                 320

Val Cys Ser Arg Ser His Ala Gly Gly Ile Asn Val Phe Gly Gln Ile
                325                 330                 335

Thr Val Glu Thr Phe Ala Ser Ile Val Ala His Glu Leu Gly His Asn
            340                 345                 350

Leu Gly Met Asn His Asp Asp Gly Arg Asp Cys Ser Cys Gly Ala Lys
            355                 360                 365

Ser Cys Ile Met Asn Ser Gly Ala Ser Gly Ser Arg Asn Phe Ser Ser
    370                 375                 380

Cys Ser Ala Glu Asp Phe Glu Lys Leu Thr Leu Asn Lys Gly Gly Asn
385                 390                 395                 400

Cys Leu Leu Asn Ile Pro Lys Pro Asp Glu Ala Tyr Ser Ala Pro Ser
                405                 410                 415

Cys Gly Asn Lys Leu Val Asp Ala Gly Glu Glu Cys Asp Cys Gly Thr
            420                 425                 430

Pro Lys Glu Cys Glu Leu Asp Pro Cys Cys Glu Gly Ser Thr Cys Lys
            435                 440                 445
```

-continued

```
Leu Lys Ser Phe Ala Glu Cys Ala Tyr Gly Asp Cys Cys Lys Asp Cys
    450             455             460

Arg Phe Leu Pro Gly Gly Thr Leu Cys Arg Gly Lys Thr Ser Glu Cys
465             470             475             480

Asp Val Pro Glu Tyr Cys Asn Gly Ser Ser Gln Phe Cys Gln Pro Asp
                485             490             495

Val Phe Ile Gln Asn Gly Tyr Pro Cys Gln Asn Asn Lys Ala Tyr Cys
                500             505             510

Tyr Asn Gly Met Cys Gln Tyr Tyr Asp Ala Gln Cys Gln Val Ile Phe
            515             520             525

Gly Ser Lys Ala Lys Ala Ala Pro Lys Asp Cys Phe Ile Glu Val Asn
    530             535             540

Ser Lys Gly Asp Arg Phe Gly Asn Cys Gly Phe Ser Gly Asn Glu Tyr
545             550             555             560

Lys Lys Cys Ala Thr Gly Asn Ala Leu Cys Gly Lys Leu Gln Cys Glu
            565             570             575

Asn Val Gln Glu Ile Pro Val Phe Gly Ile Val Pro Ala Ile Ile Gln
            580             585             590

Thr Pro Ser Arg Gly Thr Lys Cys Trp Gly Val Asp Phe Gln Leu Gly
    595             600             605

Ser Asp Val Pro Asp Pro Gly Met Val Asn Glu Gly Thr Lys Cys Gly
    610             615             620

Ala Gly Lys Lys
625
```

```
<210> SEQ ID NO 83
<211> LENGTH: 2901
<212> TYPE: DNA
<213> ORGANISM: Homo sapiens

<400> SEQUENCE: 83
atggcggcgg tagcggcagt ggcggcgcgt aggaggcggt cttgggcgtc tttggtactg      60 gctttttttag gggtctgcct ggggattacc cttgctgtgg atagaagcaa ctttaagacc     120
tgtgaagaga gttctttctg caagcgacag agaagcatac ggccaggcct ctctccatac     180
cgagccttgc tggactctct acagcttggt cctgattccc tcacggtcca tctgatccat     240
gaggtcacca aggtgttgct ggtgctagag cttcaggggc ttcaaaagaa catgactcgg     300
ttcaggattg atgagctgga gcctcggcga ccccgatacc gtgtaccaga tgttttggtg     360
gctgatccac caatagcccg gctttctgtc tctggtcgtg atgagaacag tgtggagtta     420
accatggctg agggaccctta caagatcatc ttgacagcac ggccattccg ccttgaccta     480
ctagaggacc gaagtctttt gcttagtgtc aatgcccgag gactcttgga gtttgagcat     540
cagagggccc ctagggtctc tttctcggat aaggttaatc tcacgcttgg tagcatatgg     600
gataagatca agaacctttt ctctaggcaa ggatcaaaag acccagctga gggcgatggg     660
gcccagcctg aggaaacacc cagggatggc gacaagccag aggagactca ggggaaggca     720
gagaaagatg agccaggagc ctgggaggag acattcaaaa ctcactctga cagcaagccg     780 tatgcccca tgtctgtggg tttggacttc tctctgccag gcatggagca tgtctatggg     840
atccctgagc atgcagacaa cctgaggctg aaggtcactg agggtgggga gccatatcgc     900
ctctacaatt tggatgtgtt ccagtatgag ctgtacaacc caatggcctt gtatgggtct     960
gtgcctgtgc tcctggcaca caaccctcat cgcgacttgg gcatcttctg gctcaatgct    1020
gcagagacct gggttgatat atcttccaac actgccggga agaccctgtt tgggaagatg    1080
```

```
atggactacc tgcagggctc tggggagacc ccacagacag atgttcgctg gatgtcagag      1140
actggcatca ttgacgtctt cctgctgctg gggccctcca tctctgatgt tttccggcaa      1200
tatgctagtc tcacaggaac ccaggcgttg cccccactct tctccctcgg ctaccaccag      1260
agccgttgga actaccggga cgaggctgat gtgctggaag tggatcaggg cttttgatgat      1320 cacaacctgc cctgtgatgt catctggcta gacattgaac atgctgatgg caagcggtat      1380
ttcacctggg accccagtcg cttccctcag ccccgcacca tgcttgagcg cttggcttct      1440
aagaggcgga agctggtggc catcgtagac ccccacatca aggtggactc cggctaccga      1500
gttcacgagg agctgcggaa cctggggctg tatgttaaaa cccgggatgg ctctgactat      1560
gagggctggt gctggccagg ctcagctggt taccctgact tcactaatcc cacgatgagg      1620
gcctggtggg ctaacatgtt cagctatgac aattatgagg gctcagctcc caacctcttt      1680
gtctggaatg acatgaacga accatctgtg ttcaatggtc ctgaggtcac catgctcaag      1740
gatgcccagc attatggggg ctgggagcac cgggatgtgc ataacatcta tggcctttat      1800
gtgcacatgg cgactgctga tgggctgaga cagcgctctg ggggcatgga acgccccttt      1860
gtcctggcca gggccttctt cgctggctcc cagcgctttg gagccgtgtg dacagggac      1920 aacactgccg agtgggacca tttgaagatc tctattccta tgtgtctcag cttggggctg      1980
gtgggacttt ccttctgtgg ggcggatgtg ggtggcttct tcaaaaaccc agagccagag      2040
ctgcttgtgc gctggtacca gatgggtgct taccagccat tcttccgggc acatgcccac      2100
ttggacactg ggcgacgaga gccatggctg ttaccatctc agcacaatga tataatccga      2160
gatgccttgg gccagcgata ttctttgctg cccttctggt acaccctctt atatcaggcc      2220
catcgggaag gcattcctgt catgaggccc ctgtgggtgc agtaccctca ggatgtgact      2280
accttcaata tagatgatca gtacttgctt ggggatgcgt tgctggttca ccctgtatca      2340
gactctggag cccatggtgt ccaggtctat ctgcctggcc aaggggaggt gtggtatgac      2400
attcaaagct accagaagca tcatggtccc cagaccctgt acctgcctgt aactctaagc      2460
agtatccctg tgttccagcg tggagggaca atcgtgcctc gatggatgcg agtgcggcgg      2520
tcttcagaat gtatgaagga tgaccccatc actctctttg ttgcacttag ccctcagggt      2580
acagctcaag gagagctctt tctggatgat gggcacacgt tcaactatca gactcgccaa      2640
gagttcctgc tgcgtcgatt ctcattctct ggcaacaccc ttgtctccag ctcagcagac      2700
cctgaaggac actttgagac accaatctgg attgagcggg tggtgataat aggggctgga      2760
aagccagcag ctgtggtact ccagacaaaa ggatctccag aaagccgcct gtccttccag      2820
catgaccctg agacctctgt gttggtcctg cgcaagcctg gcatcaatgt ggcatctgat      2880
tggagtattc acctgcgata a                                                2901
```

<210> SEQ ID NO 84
<211> LENGTH: 966
<212> TYPE: PRT
<213> ORGANISM: Homo sapiens

<400> SEQUENCE: 84

```
Met Ala Ala Val Ala Ala Val Ala Ala Arg Arg Arg Arg Ser Trp Ala
1               5                   10                  15

Ser Leu Val Leu Ala Phe Leu Gly Val Cys Leu Gly Ile Thr Leu Ala
                20                  25                  30

Val Asp Arg Ser Asn Phe Lys Thr Cys Glu Glu Ser Ser Phe Cys Lys
            35                  40                  45
```

```
Arg Gln Arg Ser Ile Arg Pro Gly Leu Ser Pro Tyr Arg Ala Leu Leu
    50              55              60

Asp Ser Leu Gln Leu Gly Pro Asp Ser Leu Thr Val His Leu Ile His
65              70              75              80

Glu Val Thr Lys Val Leu Leu Val Leu Glu Leu Gln Gly Leu Gln Lys
            85              90              95

Asn Met Thr Arg Phe Arg Ile Asp Glu Leu Glu Pro Arg Arg Pro Arg
            100             105             110

Tyr Arg Val Pro Asp Val Leu Val Ala Asp Pro Pro Ile Ala Arg Leu
        115             120             125

Ser Val Ser Gly Arg Asp Glu Asn Ser Val Glu Leu Thr Met Ala Glu
    130             135             140

Gly Pro Tyr Lys Ile Ile Leu Thr Ala Arg Pro Phe Arg Leu Asp Leu
145             150             155             160

Leu Glu Asp Arg Ser Leu Leu Leu Ser Val Asn Ala Arg Gly Leu Leu
            165             170             175

Glu Phe Glu His Gln Arg Ala Pro Arg Val Ser Phe Ser Asp Lys Val
        180             185             190

Asn Leu Thr Leu Gly Ser Ile Trp Asp Lys Ile Lys Asn Leu Phe Ser
    195             200             205

Arg Gln Gly Ser Lys Asp Pro Ala Glu Gly Asp Gly Ala Gln Pro Glu
    210             215             220

Glu Thr Pro Arg Asp Gly Asp Lys Pro Glu Glu Thr Gln Gly Lys Ala
225             230             235             240

Glu Lys Asp Glu Pro Gly Ala Trp Glu Glu Thr Phe Lys Thr His Ser
            245             250             255

Asp Ser Lys Pro Tyr Gly Pro Met Ser Val Gly Leu Asp Phe Ser Leu
            260             265             270

Pro Gly Met Glu His Val Tyr Gly Ile Pro Glu His Ala Asp Asn Leu
        275             280             285

Arg Leu Lys Val Thr Glu Gly Gly Glu Pro Tyr Arg Leu Tyr Asn Leu
    290             295             300

Asp Val Phe Gln Tyr Glu Leu Tyr Asn Pro Met Ala Leu Tyr Gly Ser
305             310             315             320

Val Pro Val Leu Leu Ala His Asn Pro His Arg Asp Leu Gly Ile Phe
        325             330             335

Trp Leu Asn Ala Ala Glu Thr Trp Val Asp Ile Ser Ser Asn Thr Ala
        340             345             350

Gly Lys Thr Leu Phe Gly Lys Met Met Asp Tyr Leu Gln Gly Ser Gly
        355             360             365

Glu Thr Pro Gln Thr Asp Val Arg Trp Met Ser Glu Thr Gly Ile Ile
        370             375             380

Asp Val Phe Leu Leu Leu Gly Pro Ser Ile Ser Asp Val Phe Arg Gln
385             390             395             400

Tyr Ala Ser Leu Thr Gly Thr Gln Ala Leu Pro Pro Leu Phe Ser Leu
            405             410             415

Gly Tyr His Gln Ser Arg Trp Asn Tyr Arg Asp Glu Ala Asp Val Leu
            420             425             430

Glu Val Asp Gln Gly Phe Asp Asp His Asn Leu Pro Cys Asp Val Ile
        435             440             445

Trp Leu Asp Ile Glu His Ala Asp Gly Lys Arg Tyr Phe Thr Trp Asp
    450             455             460
```

-continued

```
Pro Ser Arg Phe Pro Gln Pro Arg Thr Met Leu Glu Arg Leu Ala Ser
465             470             475             480

Lys Arg Arg Lys Leu Val Ala Ile Val Asp Pro His Ile Lys Val Asp
            485             490             495

Ser Gly Tyr Arg Val His Glu Glu Leu Arg Asn Leu Gly Leu Tyr Val
            500             505             510

Lys Thr Arg Asp Gly Ser Asp Tyr Glu Gly Trp Cys Trp Pro Gly Ser
        515             520             525

Ala Gly Tyr Pro Asp Phe Thr Asn Pro Thr Met Arg Ala Trp Trp Ala
    530             535             540

Asn Met Phe Ser Tyr Asp Asn Tyr Glu Gly Ser Ala Pro Asn Leu Phe
545             550             555             560

Val Trp Asn Asp Met Asn Glu Pro Ser Val Phe Asn Gly Pro Glu Val
            565             570             575

Thr Met Leu Lys Asp Ala Gln His Tyr Gly Gly Trp Glu His Arg Asp
            580             585             590

Val His Asn Ile Tyr Gly Leu Tyr Val His Met Ala Thr Ala Asp Gly
            595             600             605

Leu Arg Gln Arg Ser Gly Gly Met Glu Arg Pro Phe Val Leu Ala Arg
    610             615             620

Ala Phe Phe Ala Gly Ser Gln Arg Phe Gly Ala Val Trp Thr Gly Asp
625             630             635             640

Asn Thr Ala Glu Trp Asp His Leu Lys Ile Ser Ile Pro Met Cys Leu
            645             650             655

Ser Leu Gly Leu Val Gly Leu Ser Phe Cys Gly Ala Asp Val Gly Gly
            660             665             670

Phe Phe Lys Asn Pro Glu Pro Glu Leu Leu Val Arg Trp Tyr Gln Met
            675             680             685

Gly Ala Tyr Gln Pro Phe Phe Arg Ala His Ala His Leu Asp Thr Gly
    690             695             700

Arg Arg Glu Pro Trp Leu Leu Pro Ser Gln His Asn Asp Ile Ile Arg
705             710             715             720

Asp Ala Leu Gly Gln Arg Tyr Ser Leu Leu Pro Phe Trp Tyr Thr Leu
            725             730             735

Leu Tyr Gln Ala His Arg Glu Gly Ile Pro Val Met Arg Pro Leu Trp
            740             745             750

Val Gln Tyr Pro Gln Asp Val Thr Thr Phe Asn Ile Asp Asp Gln Tyr
            755             760             765

Leu Leu Gly Asp Ala Leu Leu Val His Pro Val Ser Asp Ser Gly Ala
    770             775             780

His Gly Val Gln Val Tyr Leu Pro Gly Gln Gly Glu Val Trp Tyr Asp
785             790             795             800

Ile Gln Ser Tyr Gln Lys His His Gly Pro Gln Thr Leu Tyr Leu Pro
            805             810             815

Val Thr Leu Ser Ser Ile Pro Val Phe Gln Arg Gly Gly Thr Ile Val
            820             825             830

Pro Arg Trp Met Arg Val Arg Arg Ser Ser Glu Cys Met Lys Asp Asp
        835             840             845

Pro Ile Thr Leu Phe Val Ala Leu Ser Pro Gln Gly Thr Ala Gln Gly
    850             855             860

Glu Leu Phe Leu Asp Asp Gly His Thr Phe Asn Tyr Gln Thr Arg Gln
865             870             875             880

Glu Phe Leu Leu Arg Arg Phe Ser Phe Ser Gly Asn Thr Leu Val Ser
```

```
                        885                  890                  895

Ser Ser Ala Asp Pro Glu Gly His Phe Glu Thr Pro Ile Trp Ile Glu
            900                  905                  910

Arg Val Val Ile Ile Gly Ala Gly Lys Pro Ala Ala Val Val Leu Gln
        915                  920                  925

Thr Lys Gly Ser Pro Glu Ser Arg Leu Ser Phe Gln His Asp Pro Glu
    930                  935                  940

Thr Ser Val Leu Val Leu Arg Lys Pro Gly Ile Asn Val Ala Ser Asp
945                  950                  955                  960

Trp Ser Ile His Leu Arg
                965
```

<210> SEQ ID NO 85
<211> LENGTH: 2544
<212> TYPE: DNA
<213> ORGANISM: Homo sapiens

<400> SEQUENCE: 85

```
atgactcggt tcaggattga tgagctggag cctcggcgac cccgataccg tgtaccagat      60
gttttggtgg ctgatccacc aatagcccgg ctttctgtct ctggtcgtga tgagaacagt     120
gtggagttaa ccatggctga gggaccctac aagatcatct tgacagcacg gccattccgc     180
cttgacctac tagaggaccg aagtcttttg cttagtgtca atgcccgagg actcttggag     240
tttgagcatc agagggcccc tagggtctcg caaggatcaa aagacccagc tgagggcgat     300
ggggcccagc ctgaggaaac acccagggat ggcgacaagc agaggagac tcaggggaag      360 gcagagaaag atgagccagg agcctgggag gagacattca aaactcactc tgacagcaag     420
ccgtatggcc ccatgtctgt gggtttggac ttctctctgc caggcatgga gcatgtctat     480
gggatccctg agcatgcaga caacctgagg ctgaaggtca ctgagggtgg ggagccatat     540
cgcctctaca atttggatgt gttccagtat gagctgtaca acccaatggc cttgtatggg     600
tctgtgcctg tgctcctggc acacaaccct catcgcgact tgggcatctt ctggctcaat     660
gctgcagaga cctgggttga tatatcttcc aacactgccg ggaagaccct gtttgggaag     720
atgatggact acctgcaggg ctctggggag accccacaga cagatgttcg ctggatgtca     780
gagactggca tcattgacgt cttcctgctg ctggggccct ccatctctga tgtttttccgg     840 caatatgcta gtctcacagg aacccaggcg ttgcccccac tcttctccct cggctaccac     900
cagagccgtt ggaactaccg ggacgaggct gatgtgctgg aagtggatca gggctttgat     960
gatcacaacc tgccctgtga tgtcatctgg ctagacattg aacatgctga tggcaagcgg    1020
tatttcacct gggaccccag tcgcttccct cagccccgca ccatgcttga gcgcttggct    1080
tctaagaggc ggaagctggt ggccatcgta gacccccaca tcaaggtgga ctccggctac    1140
cgagttcacg aggagctgcg gaacctgggg ctgtatgtta aaacccggga tggctctgac    1200
tatgagggct ggtgctggcc aggctcagct ggttaccctg acttcactaa tcccacgatg    1260
agggcctggt gggctaacat gttcagctat gacaattatg agggctcagc tcccaacctc    1320
tttgtctgga tgacatgaa cgaaccatct gtgttcaatg gtcctgaggt caccatgctc     1380
aaggatgccc agcattatgg gggctgggag caccgggatg tgcataacat ctatggcctt    1440
tatgtgcaca tggcgactgc tgatgggctg agacagcgct ctgggggcat ggaacgcccc    1500
tttgtcctgg ccagggcctt cttcgctggc tcccagcgct ttggagccgt gtggacaggg    1560
gacaacactg ccgagtggga ccatttgaag atctctattc ctatgtgtct cagcttgggg    1620
```

-continued

```
ctggtgggac tttccttctg tggggcggat gtgggtggct tcttcaaaaa cccagagcca    1680
gagctgcttg tgcgctggta ccagatgggt gcttaccagc cattcttccg ggcacatgcc    1740
cacttggaca ctgggcgacg agagccatgg ctgttaccat ctcagcacaa tgatataatc    1800
cgagatgcct tgggccagcg atattctttg ctgcccttct ggtacaccct cttatatcag    1860
gcccatcggg aaggcattcc tgtcatgagg cccctgtggg tgcagtaccc tcaggatgtg    1920
actaccttca atatagatga tcagtacttg cttggggatg cgttgctggt tcaccctgta    1980
tcagactctg gagcccatgg tgtccaggtc tatctgcctg gccaggggga ggtgtggtat    2040
gacattcaaa gctaccagaa gcatcatggt ccccagaccc tgtacctgcc tgtaactcta    2100
agcagtatcc ctgtgttcca gcgtggaggg acaatcgtgc ctcgatggat gcgagtgcgg    2160
cggtcttcag aatgtatgaa ggatgacccc atcactctct ttgttgcact tagccctcag    2220
ggtacagctc aaggagagct ctttctggat gatgggcaca cgttcaacta tcagactcgc    2280
caagagttcc tgctgcgtcg attctcattc tctggcaaca cccttgtctc cagctcagca    2340
gaccctgaag gacactttga gacaccaatc tggattgagc gggtggtgat aataggggct    2400
ggaaagccag cagctgtggt actccagaca aaaggatctc agaaagccg cctgtccttc    2460 cagcatgacc ctgagacctc tgtgttggtc ctgcgcaagc ctggcatcaa gtggcatct    2520 gattggagta ttcacctgcg ataa                                          2544
```

```
<210> SEQ ID NO 86
<211> LENGTH: 847
<212> TYPE: PRT
<213> ORGANISM: Homo sapiens

<400> SEQUENCE: 86

Met Thr Arg Phe Arg Ile Asp Glu Leu Glu Pro Arg Arg Pro Arg Tyr
1               5                   10                  15

Arg Val Pro Asp Val Leu Val Ala Asp Pro Pro Ile Ala Arg Leu Ser
            20                  25                  30

Val Ser Gly Arg Asp Glu Asn Ser Val Glu Leu Thr Met Ala Glu Gly
        35                  40                  45

Pro Tyr Lys Ile Ile Leu Thr Ala Arg Pro Phe Arg Leu Asp Leu Leu
    50                  55                  60

Glu Asp Arg Ser Leu Leu Leu Ser Val Asn Ala Arg Gly Leu Leu Glu
65                  70                  75                  80

Phe Glu His Gln Arg Ala Pro Arg Val Ser Gln Gly Ser Lys Asp Pro
                85                  90                  95

Ala Glu Gly Asp Gly Ala Gln Pro Glu Glu Thr Pro Arg Asp Gly Asp
            100                 105                 110

Lys Pro Glu Glu Thr Gln Gly Lys Ala Glu Lys Asp Glu Pro Gly Ala
        115                 120                 125

Trp Glu Glu Thr Phe Lys Thr His Ser Asp Ser Lys Pro Tyr Gly Pro
    130                 135                 140

Met Ser Val Gly Leu Asp Phe Ser Leu Pro Gly Met Glu His Val Tyr
145                 150                 155                 160

Gly Ile Pro Glu His Ala Asp Asn Leu Arg Leu Lys Val Thr Glu Gly
                165                 170                 175

Gly Glu Pro Tyr Arg Leu Tyr Asn Leu Asp Val Phe Gln Tyr Glu Leu
            180                 185                 190

Tyr Asn Pro Met Ala Leu Tyr Gly Ser Val Pro Val Leu Leu Ala His
        195                 200                 205
```

```
Asn Pro His Arg Asp Leu Gly Ile Phe Trp Leu Asn Ala Ala Glu Thr
    210                 215             220

Trp Val Asp Ile Ser Ser Asn Thr Ala Gly Lys Thr Leu Phe Gly Lys
225                 230             235                 240

Met Met Asp Tyr Leu Gln Gly Ser Gly Glu Thr Pro Gln Thr Asp Val
            245             250             255

Arg Trp Met Ser Glu Thr Gly Ile Ile Asp Val Phe Leu Leu Leu Gly
            260             265             270

Pro Ser Ile Ser Asp Val Phe Arg Gln Tyr Ala Ser Leu Thr Gly Thr
        275             280             285

Gln Ala Leu Pro Pro Leu Phe Ser Leu Gly Tyr His Gln Ser Arg Trp
    290             295             300

Asn Tyr Arg Asp Glu Ala Asp Val Leu Glu Val Asp Gln Gly Phe Asp
305             310             315                 320

Asp His Asn Leu Pro Cys Asp Val Ile Trp Leu Asp Ile Glu His Ala
            325             330             335

Asp Gly Lys Arg Tyr Phe Thr Trp Asp Pro Ser Arg Phe Pro Gln Pro
        340             345             350

Arg Thr Met Leu Glu Arg Leu Ala Ser Lys Arg Arg Lys Leu Val Ala
        355             360             365

Ile Val Asp Pro His Ile Lys Val Asp Ser Gly Tyr Arg Val His Glu
    370             375             380

Glu Leu Arg Asn Leu Gly Leu Tyr Val Lys Thr Arg Asp Gly Ser Asp
385             390             395                 400

Tyr Glu Gly Trp Cys Trp Pro Gly Ser Ala Gly Tyr Pro Asp Phe Thr
            405             410             415

Asn Pro Thr Met Arg Ala Trp Trp Ala Asn Met Phe Ser Tyr Asp Asn
            420             425             430

Tyr Glu Gly Ser Ala Pro Asn Leu Phe Val Trp Asn Asp Met Asn Glu
        435             440             445

Pro Ser Val Phe Asn Gly Pro Glu Val Thr Met Leu Lys Asp Ala Gln
    450             455             460

His Tyr Gly Gly Trp Glu His Arg Asp Val His Asn Ile Tyr Gly Leu
465             470             475                 480

Tyr Val His Met Ala Thr Ala Asp Gly Leu Arg Gln Arg Ser Gly Gly
            485             490             495

Met Glu Arg Pro Phe Val Leu Ala Arg Ala Phe Phe Ala Gly Ser Gln
        500             505             510

Arg Phe Gly Ala Val Trp Thr Gly Asp Asn Thr Ala Glu Trp Asp His
        515             520             525

Leu Lys Ile Ser Ile Pro Met Cys Leu Ser Leu Gly Leu Val Gly Leu
    530             535             540

Ser Phe Cys Gly Ala Asp Val Gly Gly Phe Phe Lys Asn Pro Glu Pro
545             550             555                 560

Glu Leu Leu Val Arg Trp Tyr Gln Met Gly Ala Tyr Gln Pro Phe Phe
            565             570             575

Arg Ala His Ala His Leu Asp Thr Gly Arg Arg Glu Pro Trp Leu Leu
            580             585             590

Pro Ser Gln His Asn Asp Ile Ile Arg Asp Ala Leu Gly Gln Arg Tyr
        595             600             605

Ser Leu Leu Pro Phe Trp Tyr Thr Leu Leu Tyr Gln Ala His Arg Glu
    610             615             620

Gly Ile Pro Val Met Arg Pro Leu Trp Val Gln Tyr Pro Gln Asp Val
```

-continued

```
625                 630                 635                 640

Thr Thr Phe Asn Ile Asp Asp Gln Tyr Leu Leu Gly Asp Ala Leu Leu
                645                 650                 655

Val His Pro Val Ser Asp Ser Gly Ala His Gly Val Gln Val Tyr Leu
                660                 665                 670

Pro Gly Gln Gly Glu Val Trp Tyr Asp Ile Gln Ser Tyr Gln Lys His
            675                 680                 685

His Gly Pro Gln Thr Leu Tyr Leu Pro Val Thr Leu Ser Ser Ile Pro
            690                 695                 700

Val Phe Gln Arg Gly Gly Thr Ile Val Pro Arg Trp Met Arg Val Arg
705                 710                 715                 720

Arg Ser Ser Glu Cys Met Lys Asp Asp Pro Ile Thr Leu Phe Val Ala
                725                 730                 735

Leu Ser Pro Gln Gly Thr Ala Gln Gly Glu Leu Phe Leu Asp Asp Gly
            740                 745                 750

His Thr Phe Asn Tyr Gln Thr Arg Gln Glu Phe Leu Leu Arg Arg Phe
            755                 760                 765

Ser Phe Ser Gly Asn Thr Leu Val Ser Ser Ser Ala Asp Pro Glu Gly
            770                 775                 780

His Phe Glu Thr Pro Ile Trp Ile Glu Arg Val Val Ile Ile Gly Ala
785                 790                 795                 800

Gly Lys Pro Ala Ala Val Val Leu Gln Thr Lys Gly Ser Pro Glu Ser
                805                 810                 815

Arg Leu Ser Phe Gln His Asp Pro Glu Thr Ser Val Leu Val Leu Arg
            820                 825                 830

Lys Pro Gly Ile Asn Val Ala Ser Asp Trp Ser Ile His Leu Arg
            835                 840                 845
```

<210> SEQ ID NO 87
<211> LENGTH: 2835
<212> TYPE: DNA
<213> ORGANISM: Homo sapiens
<400> SEQUENCE: 87

```
atggcggcgg tagcggcagt ggcggcgcgt aggaggcggt cttgggcgtc tttggtactg        60
gcttttttag gggtctgcct ggggattacc cttgctgtgg atagaagcaa ctttaagacc       120
tgtgaagaga gttctttctg caagcgacag agaagcatac ggccaggcct ctctccatac       180
cgagccttgc tggactctct acagcttggt cctgattccc tcacggtcca tctgatccat       240
gaggtcacca aggtgttgct ggtgctagag cttcaggggc ttcaaaagaa catgactcgg       300
ttcaggattg atgagctgga gcctcggcga ccccgatacc gtgtaccaga tgttttggtg       360
gctgatccac caatagcccg gctttctgtc tctggtcgtg atgagaacag tgtggagtta       420
accatggctg agggaccccta caagatcatc ttgacagcac ggccattccg ccttgaccta       480
ctagaggacc gaagtctttt gcttagtgtc aatgcccgag gactcttgga gtttgagcat       540
cagagggccc ctagggtctc gcaaggatca aaagacccag ctgagggcga tggggcccag       600
cctgaggaaa cacccaggga tggcgacaag ccagaggaga ctcaggggaa ggcagagaaa       660
gatgagccag gagcctggga ggagacattc aaaactcact ctgacagcaa gccgtatggc       720
cccatgtctg tgggtttgga cttctctctg ccaggcatgg agcatgtcta tgggatccct       780
gagcatgcag acaacctgag gctgaaggtc actgagggtg gggagccata tcgcctctac       840
aatttggatg tgttccagta tgagctgtac aacccaatgg ccttgtatgg gtctgtgcct       900
```

```
gtgctcctgg cacacaaccc tcatcgcgac ttgggcatct tctggctcaa tgctgcagag        960
acctgggttg atatatcttc caacactgcc gggaagaccc tgtttgggaa gatgatggac       1020
tacctgcagg gctctgggga gaccccacag acagatgttc gctggatgtc agagactggc       1080
atcattgacg tcttcctgct gctggggccc tccatctctg atgttttccg gcaatatgct       1140
agtctcacag gaacccaggc gttgcccca ctcttctccc tcggctacca ccagagccgt        1200
tggaactacc gggacgaggc tgatgtgctg gaagtggatc agggctttga tgatcacaac       1260
ctgccctgtg atgtcatctg ctagacatt gaacatgctg atggcaagcg gtatttcacc        1320
tgggacccca gtcgcttccc tcagccccgc accatgcttg agcgcttggc ttctaagagg       1380
cggaagctgg tggccatcgt agaccccac atcaaggtgg actccggcta ccgagttcac        1440
gaggagctgc ggaacctggg gctgtatgtt aaaacccggg atggctctga ctatgagggc       1500
tggtgctggc caggctcagc tggttaccct gacttcacta atcccacgat gagggcctgg       1560
tgggctaaca tgttcagcta tgacaattat gagggctcag ctcccaacct ctttgtctgg       1620
aatgacatga acgaaccatc tgtgttcaat ggtcctgagg tcaccatgct caaggatgcc       1680
cagcattatg ggggctggga gcaccgggat gtgcataaca tctatggcct ttatgtgcac       1740
atggcgactg ctgatgggct gagacagcgc tctgggggca tggaacgccc ctttgtcctg       1800
gccagggcct tcttcgctgg ctcccagcgc tttggagccg tgtggacagg ggacaacact       1860
gccgagtggg accatttgaa gatctctatt cctatgtgtc tcagcttggg gctggtggga       1920
ctttccttct gtggggcgga tgtgggtggc ttcttcaaaa acccagagcc agagctgctt       1980
gtgcgctggt accagatggg tgcttaccag ccattcttcc gggcacatgc ccacttggac       2040
actgggcgac gagagccatg gctgttacca tctcagcaca atgatataat ccgagatgcc       2100
ttgggccagc gatattcttt gctgcccttc tggtacaccc tcttatatca ggcccatcgg       2160
gaaggcattc ctgtcatgag gcccctgtgg gtgcagtacc ctcaggatgt gactaccttc       2220
aatatagatg atcagtactt gcttggggat gcgttgctgg ttcaccctgt atcagactct       2280
ggagcccatg gtgtccaggt ctatctgcct ggccaagggg aggtgtggta tgacattcaa       2340
agctaccaga agcatcatgg tccccagacc ctgtacctgc ctgtaactct aagcagtatc       2400
cctgtgttcc agcgtggagg gacaatcgtg cctcgatgga tgcgagtgcg gcggtcttca       2460
gaatgtatga aggatgaccc catcactctc tttgttgcac ttagccctca gggtacagct       2520
caaggagagc tctttctgga tgatgggcac acgttcaact atcagactcg ccaagagttc       2580
ctgctgcgtc gattctcatt ctctggcaac acccttgtct ccagctcagc agaccctgaa       2640
ggacactttg agacaccaat ctggattgag cgggtggtga taataggggc tggaaagcca       2700
gcagctgtgg tactccagac aaaaggatct ccagaaagcc gcctgtcctt ccagcatgac       2760
cctgagacct ctgtgttggt cctgcgcaag cctggcatca atgtggcatc tgattggagt       2820
attcacctgc gataa                                                       2835
```

<210> SEQ ID NO 88
<211> LENGTH: 944
<212> TYPE: PRT
<213> ORGANISM: Homo sapiens

<400> SEQUENCE: 88

```
Met Ala Ala Val Ala Ala Val Ala Ala Arg Arg Arg Arg Ser Trp Ala
1               5                   10                  15

Ser Leu Val Leu Ala Phe Leu Gly Val Cys Leu Gly Ile Thr Leu Ala
            20                  25                  30
```

-continued

```
Val Asp Arg Ser Asn Phe Lys Thr Cys Glu Glu Ser Ser Phe Cys Lys
        35                  40                  45

Arg Gln Arg Ser Ile Arg Pro Gly Leu Ser Pro Tyr Arg Ala Leu Leu
    50                  55                  60

Asp Ser Leu Gln Leu Gly Pro Asp Ser Leu Thr Val His Leu Ile His
65                  70                  75                  80

Glu Val Thr Lys Val Leu Leu Val Leu Glu Leu Gln Gly Leu Gln Lys
                85                  90                  95

Asn Met Thr Arg Phe Arg Ile Asp Glu Leu Glu Pro Arg Arg Pro Arg
            100                 105                 110

Tyr Arg Val Pro Asp Val Leu Val Ala Asp Pro Pro Ile Ala Arg Leu
            115                 120                 125

Ser Val Ser Gly Arg Asp Glu Asn Ser Val Glu Leu Thr Met Ala Glu
        130                 135                 140

Gly Pro Tyr Lys Ile Ile Leu Thr Ala Arg Pro Phe Arg Leu Asp Leu
145                 150                 155                 160

Leu Glu Asp Arg Ser Leu Leu Leu Ser Val Asn Ala Arg Gly Leu Leu
                165                 170                 175

Glu Phe Glu His Gln Arg Ala Pro Arg Val Ser Gln Gly Ser Lys Asp
            180                 185                 190

Pro Ala Glu Gly Asp Gly Ala Gln Pro Glu Glu Thr Pro Arg Asp Gly
            195                 200                 205

Asp Lys Pro Glu Glu Thr Gln Gly Lys Ala Glu Lys Asp Glu Pro Gly
        210                 215                 220

Ala Trp Glu Glu Thr Phe Lys Thr His Ser Asp Ser Lys Pro Tyr Gly
225                 230                 235                 240

Pro Met Ser Val Gly Leu Asp Phe Ser Leu Pro Gly Met Glu His Val
                245                 250                 255

Tyr Gly Ile Pro Glu His Ala Asp Asn Leu Arg Leu Lys Val Thr Glu
            260                 265                 270

Gly Gly Glu Pro Tyr Arg Leu Tyr Asn Leu Asp Val Phe Gln Tyr Glu
        275                 280                 285

Leu Tyr Asn Pro Met Ala Leu Tyr Gly Ser Val Pro Val Leu Leu Ala
    290                 295                 300

His Asn Pro His Arg Asp Leu Gly Ile Phe Trp Leu Asn Ala Ala Glu
305                 310                 315                 320

Thr Trp Val Asp Ile Ser Ser Asn Thr Ala Gly Lys Thr Leu Phe Gly
                325                 330                 335

Lys Met Met Asp Tyr Leu Gln Gly Ser Gly Glu Thr Pro Gln Thr Asp
            340                 345                 350

Val Arg Trp Met Ser Glu Thr Gly Ile Ile Asp Val Phe Leu Leu Leu
            355                 360                 365

Gly Pro Ser Ile Ser Asp Val Phe Arg Gln Tyr Ala Ser Leu Thr Gly
    370                 375                 380

Thr Gln Ala Leu Pro Pro Leu Phe Ser Leu Gly Tyr His Gln Ser Arg
385                 390                 395                 400

Trp Asn Tyr Arg Asp Glu Ala Asp Val Leu Glu Val Asp Gln Gly Phe
                405                 410                 415

Asp Asp His Asn Leu Pro Cys Asp Val Ile Trp Leu Asp Ile Glu His
            420                 425                 430

Ala Asp Gly Lys Arg Tyr Phe Thr Trp Asp Pro Ser Arg Phe Pro Gln
            435                 440                 445
```

-continued

```
Pro Arg Thr Met Leu Glu Arg Leu Ala Ser Lys Arg Arg Lys Leu Val
    450                 455                 460

Ala Ile Val Asp Pro His Ile Lys Val Asp Ser Gly Tyr Arg Val His
465                 470                 475                 480

Glu Glu Leu Arg Asn Leu Gly Leu Tyr Val Lys Thr Arg Asp Gly Ser
                485                 490                 495

Asp Tyr Glu Gly Trp Cys Trp Pro Gly Ser Ala Gly Tyr Pro Asp Phe
                500                 505                 510

Thr Asn Pro Thr Met Arg Ala Trp Trp Ala Asn Met Phe Ser Tyr Asp
                515                 520                 525

Asn Tyr Glu Gly Ser Ala Pro Asn Leu Phe Val Trp Asn Asp Met Asn
    530                 535                 540

Glu Pro Ser Val Phe Asn Gly Pro Glu Val Thr Met Leu Lys Asp Ala
545                 550                 555                 560

Gln His Tyr Gly Gly Trp Glu His Arg Asp Val His Asn Ile Tyr Gly
                565                 570                 575

Leu Tyr Val His Met Ala Thr Ala Asp Gly Leu Arg Gln Arg Ser Gly
                580                 585                 590

Gly Met Glu Arg Pro Phe Val Leu Ala Arg Ala Phe Phe Ala Gly Ser
                595                 600                 605

Gln Arg Phe Gly Ala Val Trp Thr Gly Asp Asn Thr Ala Glu Trp Asp
    610                 615                 620

His Leu Lys Ile Ser Ile Pro Met Cys Leu Ser Leu Gly Leu Val Gly
625                 630                 635                 640

Leu Ser Phe Cys Gly Ala Asp Val Gly Gly Phe Phe Lys Asn Pro Glu
                645                 650                 655

Pro Glu Leu Leu Val Arg Trp Tyr Gln Met Gly Ala Tyr Gln Pro Phe
                660                 665                 670

Phe Arg Ala His Ala His Leu Asp Thr Gly Arg Arg Glu Pro Trp Leu
                675                 680                 685

Leu Pro Ser Gln His Asn Asp Ile Ile Arg Asp Ala Leu Gly Gln Arg
    690                 695                 700

Tyr Ser Leu Leu Pro Phe Trp Tyr Thr Leu Leu Tyr Gln Ala His Arg
705                 710                 715                 720

Glu Gly Ile Pro Val Met Arg Pro Leu Trp Val Gln Tyr Pro Gln Asp
                725                 730                 735

Val Thr Thr Phe Asn Ile Asp Asp Gln Tyr Leu Leu Gly Asp Ala Leu
                740                 745                 750

Leu Val His Pro Val Ser Asp Ser Gly Ala His Gly Val Gln Val Tyr
                755                 760                 765

Leu Pro Gly Gln Gly Glu Val Trp Tyr Asp Ile Gln Ser Tyr Gln Lys
    770                 775                 780

His His Gly Pro Gln Thr Leu Tyr Leu Pro Val Thr Leu Ser Ser Ile
785                 790                 795                 800

Pro Val Phe Gln Arg Gly Gly Thr Ile Val Pro Arg Trp Met Arg Val
                805                 810                 815

Arg Arg Ser Ser Glu Cys Met Lys Asp Asp Pro Ile Thr Leu Phe Val
                820                 825                 830

Ala Leu Ser Pro Gln Gly Thr Ala Gln Gly Glu Leu Phe Leu Asp Asp
                835                 840                 845

Gly His Thr Phe Asn Tyr Gln Thr Arg Gln Glu Phe Leu Leu Arg Arg
    850                 855                 860

Phe Ser Phe Ser Gly Asn Thr Leu Val Ser Ser Ser Ala Asp Pro Glu
```

-continued

```
865            870            875            880

Gly His Phe Glu Thr Pro Ile Trp Ile Glu Arg Val Val Ile Ile Gly
                885                        890                895

Ala Gly Lys Pro Ala Ala Val Val Leu Gln Thr Lys Gly Ser Pro Glu
            900                        905                910

Ser Arg Leu Ser Phe Gln His Asp Pro Glu Thr Ser Val Leu Val Leu
            915                        920                925

Arg Lys Pro Gly Ile Asn Val Ala Ser Asp Trp Ser Ile His Leu Arg
        930                        935                940
```

```
<210> SEQ ID NO 89
<211> LENGTH: 2559
<212> TYPE: DNA
<213> ORGANISM: Homo sapiens

<400> SEQUENCE: 89
atggcggcgg tagcggcagt ggcggcgcgt aggaggcggc tttctgtctc tggtcgtgat      60
gagaacagtg tggagttaac catggctgag ggaccctaca agatcatctt gacagcacgg     120
ccattccgcc ttgacctact agaggaccga agtctttgc ttagtgtcaa tgcccgagga     180
ctcttggagt ttgagcatca gagggcccct agggtctctt tctcggataa ggttaatctc     240
acgcttggta gcatatggga taagatcaag aaccttttct ctaggcaagg atcaaaagac     300
ccagctgagg gcgatggggc ccagcctgag gaaacaccca gggatggcga caagccagag     360
gagactcagg ggaaggcaga gaaagatgag ccaggagcct gggaggagac attcaaaact     420
cactctgaca gcaagccgta tggccccatg tctgtgggtt tggacttctc tctgccaggc     480
atggagcatg tctatgggat ccctgagcat gcagacaacc tgaggctgaa ggtcactgag     540
ggtggggagc catatcgcct ctacaatttg gatgtgttcc agtatgagct gtacaaccca     600
atggccttgt atgggtctgt gcctgtgctc ctggcacaca accctcatcg cgacttgggc     660
atcttctggc tcaatgctgc agagacctgg gttgatatat cttccaacac tgccgggaag     720
accctgtttg ggaagatgat ggactacctg cagggctctg gggagacccc acagacagat     780
gttcgctgga tgtcagagac tggcatcatt gacgtcttcc tgctgctggg gccctccatc     840
tctgatgttt ccggcaata tgctagtctc acaggaaccc aggcgttgcc cccactcttc     900
tccctcggct accaccagag ccgttggaac taccgggacg aggctgatgt gctggaagtg     960
gatcagggct ttgatgatca caacctgccc tgtgatgtca tctggctaga cattgaacat    1020
gctgatggca gcggtatttt cacctgggac cccagtcgct tccctcagcc ccgcaccatg    1080
cttgagcgct tggcttctaa gaggcggaag ctggtggcca tcgtagaccc ccacatcaag    1140
gtggactccg gctaccgagt tcacgaggag ctgcggaacc tggggctgta tgttaaaacc    1200 cgggatggc ctgactatga gggctggtgc tggccaggct cagctggtta ccctgacttc    1260
actaatccca cgatgagggc ctggtgggct aacatgttca gctatgacaa ttatgagggc    1320
tcagctccca acctctttgt ctggaatgac atgaacgaac atctgtgtt caatggtcct    1380 gaggtcacca tgctcaagga tgcccagcat tatgggggct gggagcaccg ggatgtgcat    1440
aacatctatg gcctttatgt gcacatggcg actgctgatg gctgagaca gcgctctggg    1500 ggcatggaac gcccctttgt cctggccagg gccttcttcg ctggctccca gcgctttgga    1560
gccgtgtgga cagggggacaa cactgccgag tgggaccatt tgaagatctc tattcctatg    1620
tgtctcagct ggggctggt gggacttttcc ttctgtgggg cggatgtggg tggcttcttc    1680
aaaaacccag agccagagct gcttgtgcgc tggtaccaga tgggtgctta ccagccattc    1740
```

```
ttccgggcac atgcccactt ggacactggg cgacgagagc catggctgtt accatctcag      1800
cacaatgata taatccgaga tgccttgggc cagcgatatt ctttgctgcc cttctggtac      1860
accctcttat atcaggccca tcgggaaggc attcctgtca tgaggcccct gtgggtgcag      1920
taccctcagg atgtgactac cttcaatata gatgatcagt acttgcttgg ggatgcgttg      1980
ctggttcacc ctgtatcaga ctctggagcc catggtgtcc aggtctatct gcctggccaa      2040
ggggaggtgt ggtatgacat tcaaagctac cagaagcatc atggtcccca gaccctgtac      2100
ctgcctgtaa ctctaagcag tatccctgtg ttccagcgtg gagggacaat cgtgcctcga      2160
tggatgcgag tgcggcggtc ttcagaatgt atgaaggatg accccatcac tctctttgtt      2220
gcacttagcc ctcagggtac agctcaagga gagctctttc tggatgatgg gcacacgttc      2280
aactatcaga ctcgccaaga gttcctgctg cgtcgattct cattctctgg caacaccctt      2340
gtctccagct cagcagaccc tgaaggacac tttgagacac caatctggat tgagcgggtg      2400
gtgataatag gggctggaaa gccagcagct gtggtactcc agacaaaagg atctccagaa      2460
agccgcctgt ccttccagca tgaccctgag acctctgtgt tggtcctgcg caagcctggc      2520
atcaatgtgg catctgattg gagtattcac ctgcgataa                             2559
```

<210> SEQ ID NO 90
<211> LENGTH: 852
<212> TYPE: PRT
<213> ORGANISM: Homo sapiens

<400> SEQUENCE: 90

```
Met Ala Ala Val Ala Ala Val Ala Ala Arg Arg Arg Arg Leu Ser Val
1               5                   10                  15

Ser Gly Arg Asp Glu Asn Ser Val Glu Leu Thr Met Ala Glu Gly Pro
            20                  25                  30

Tyr Lys Ile Ile Leu Thr Ala Arg Pro Phe Arg Leu Asp Leu Leu Glu
        35                  40                  45

Asp Arg Ser Leu Leu Leu Ser Val Asn Ala Arg Gly Leu Leu Glu Phe
    50                  55                  60

Glu His Gln Arg Ala Pro Arg Val Ser Phe Ser Asp Lys Val Asn Leu
65                  70                  75                  80

Thr Leu Gly Ser Ile Trp Asp Lys Ile Lys Asn Leu Phe Ser Arg Gln
            85                  90                  95

Gly Ser Lys Asp Pro Ala Glu Gly Asp Gly Ala Gln Pro Glu Glu Thr
            100                 105                 110

Pro Arg Asp Gly Asp Lys Pro Glu Glu Thr Gln Gly Lys Ala Glu Lys
        115                 120                 125

Asp Glu Pro Gly Ala Trp Glu Glu Thr Phe Lys Thr His Ser Asp Ser
    130                 135                 140

Lys Pro Tyr Gly Pro Met Ser Val Gly Leu Asp Phe Ser Leu Pro Gly
145                 150                 155                 160

Met Glu His Val Tyr Gly Ile Pro Glu His Ala Asp Asn Leu Arg Leu
                165                 170                 175

Lys Val Thr Glu Gly Gly Glu Pro Tyr Arg Leu Tyr Asn Leu Asp Val
            180                 185                 190

Phe Gln Tyr Glu Leu Tyr Asn Pro Met Ala Leu Tyr Gly Ser Val Pro
            195                 200                 205

Val Leu Leu Ala His Asn Pro His Arg Asp Leu Gly Ile Phe Trp Leu
    210                 215                 220
```

```
Asn Ala Ala Glu Thr Trp Val Asp Ile Ser Ser Asn Thr Ala Gly Lys
225                 230                 235                 240

Thr Leu Phe Gly Lys Met Met Asp Tyr Leu Gln Gly Ser Gly Glu Thr
            245                 250                 255

Pro Gln Thr Asp Val Arg Trp Met Ser Glu Thr Gly Ile Ile Asp Val
            260                 265                 270

Phe Leu Leu Leu Gly Pro Ser Ile Ser Asp Val Phe Arg Gln Tyr Ala
            275                 280                 285

Ser Leu Thr Gly Thr Gln Ala Leu Pro Pro Leu Phe Ser Leu Gly Tyr
    290                 295                 300

His Gln Ser Arg Trp Asn Tyr Arg Asp Glu Ala Asp Val Leu Glu Val
305                 310                 315                 320

Asp Gln Gly Phe Asp Asp His Asn Leu Pro Cys Asp Val Ile Trp Leu
                325                 330                 335

Asp Ile Glu His Ala Asp Gly Lys Arg Tyr Phe Thr Trp Asp Pro Ser
            340                 345                 350

Arg Phe Pro Gln Pro Arg Thr Met Leu Glu Arg Leu Ala Ser Lys Arg
            355                 360                 365

Arg Lys Leu Val Ala Ile Val Asp Pro His Ile Lys Val Asp Ser Gly
    370                 375                 380

Tyr Arg Val His Glu Glu Leu Arg Asn Leu Gly Leu Tyr Val Lys Thr
385                 390                 395                 400

Arg Asp Gly Ser Asp Tyr Glu Gly Trp Cys Trp Pro Gly Ser Ala Gly
                405                 410                 415

Tyr Pro Asp Phe Thr Asn Pro Thr Met Arg Ala Trp Trp Ala Asn Met
            420                 425                 430

Phe Ser Tyr Asp Asn Tyr Glu Gly Ser Ala Pro Asn Leu Phe Val Trp
            435                 440                 445

Asn Asp Met Asn Glu Pro Ser Val Phe Asn Gly Pro Glu Val Thr Met
    450                 455                 460

Leu Lys Asp Ala Gln His Tyr Gly Gly Trp Glu His Arg Asp Val His
465                 470                 475                 480

Asn Ile Tyr Gly Leu Tyr Val His Met Ala Thr Ala Asp Gly Leu Arg
                485                 490                 495

Gln Arg Ser Gly Gly Met Glu Arg Pro Phe Val Leu Ala Arg Ala Phe
            500                 505                 510

Phe Ala Gly Ser Gln Arg Phe Gly Ala Val Trp Thr Gly Asp Asn Thr
            515                 520                 525

Ala Glu Trp Asp His Leu Lys Ile Ser Ile Pro Met Cys Leu Ser Leu
    530                 535                 540

Gly Leu Val Gly Leu Ser Phe Cys Gly Ala Asp Val Gly Gly Phe Phe
545                 550                 555                 560

Lys Asn Pro Glu Pro Glu Leu Leu Val Arg Trp Tyr Gln Met Gly Ala
            565                 570                 575

Tyr Gln Pro Phe Phe Arg Ala His Ala His Leu Asp Thr Gly Arg Arg
            580                 585                 590

Glu Pro Trp Leu Leu Pro Ser Gln His Asn Asp Ile Ile Arg Asp Ala
            595                 600                 605

Leu Gly Gln Arg Tyr Ser Leu Leu Pro Phe Trp Tyr Thr Leu Leu Tyr
    610                 615                 620

Gln Ala His Arg Glu Gly Ile Pro Val Met Arg Pro Leu Trp Val Gln
625                 630                 635                 640

Tyr Pro Gln Asp Val Thr Thr Phe Asn Ile Asp Asp Gln Tyr Leu Leu
```

-continued

```
              645             650             655
Gly Asp Ala Leu Leu Val His Pro Val Ser Asp Ser Gly Ala His Gly
         660             665             670

Val Gln Val Tyr Leu Pro Gly Gln Gly Glu Val Trp Tyr Asp Ile Gln
         675             680             685

Ser Tyr Gln Lys His His Gly Pro Gln Thr Leu Tyr Leu Pro Val Thr
     690             695             700

Leu Ser Ser Ile Pro Val Phe Gln Arg Gly Gly Thr Ile Val Pro Arg
705             710             715             720

Trp Met Arg Val Arg Arg Ser Ser Glu Cys Met Lys Asp Asp Pro Ile
             725             730             735

Thr Leu Phe Val Ala Leu Ser Pro Gln Gly Thr Ala Gln Gly Glu Leu
         740             745             750

Phe Leu Asp Asp Gly His Thr Phe Asn Tyr Gln Thr Arg Gln Glu Phe
         755             760             765

Leu Leu Arg Arg Phe Ser Phe Ser Gly Asn Thr Leu Val Ser Ser Ser
     770             775             780

Ala Asp Pro Glu Gly His Phe Glu Thr Pro Ile Trp Ile Glu Arg Val
785             790             795             800

Val Ile Ile Gly Ala Gly Lys Pro Ala Ala Val Val Leu Gln Thr Lys
             805             810             815

Gly Ser Pro Glu Ser Arg Leu Ser Phe Gln His Asp Pro Glu Thr Ser
         820             825             830

Val Leu Val Leu Arg Lys Pro Gly Ile Asn Val Ala Ser Asp Trp Ser
         835             840             845

Ile His Leu Arg
     850

<210> SEQ ID NO 91
<211> LENGTH: 357
<212> TYPE: DNA
<213> ORGANISM: Homo sapiens

<400> SEQUENCE: 91
atggcggcgg tagcggcagt ggcggcgcgt aggaggcggc tttctgtctc tggtcgtgat      60
gagaacagtg tggagttaac catggctgag ggaccctaca agatcatctt gacagcacgg     120
ccattccgcc ttgacctact agaggaccga agtcttttgc ttagtgtcaa tgcccgagga     180
ctcttggagt ttgagcatca gagggcccct agggtctctt tctcggataa ggttaatctc     240
acgcttggta gcatatggga taagatcaag aaccttttct ctaggcaagg atcaaaagac     300
ccagctgagg gcgatggggc ccagcctgag gaaacaccca gggatggcga caaggca       357

<210> SEQ ID NO 92
<211> LENGTH: 119
<212> TYPE: PRT
<213> ORGANISM: Homo sapiens

<400> SEQUENCE: 92

Met Ala Ala Val Ala Ala Val Ala Ala Arg Arg Arg Arg Leu Ser Val
1               5              10              15

Ser Gly Arg Asp Glu Asn Ser Val Glu Leu Thr Met Ala Glu Gly Pro
             20              25              30

Tyr Lys Ile Ile Leu Thr Ala Arg Pro Phe Arg Leu Asp Leu Leu Glu
         35              40              45

Asp Arg Ser Leu Leu Leu Ser Val Asn Ala Arg Gly Leu Leu Glu Phe
```

-continued

```
            50                    55                    60
Glu His Gln Arg Ala Pro Arg Val Ser Phe Ser Asp Lys Val Asn Leu
65                    70                    75                    80

Thr Leu Gly Ser Ile Trp Asp Lys Ile Lys Asn Leu Phe Ser Arg Gln
                85                    90                    95

Gly Ser Lys Asp Pro Ala Glu Gly Asp Gly Ala Gln Pro Glu Glu Thr
            100                   105                   110

Pro Arg Asp Gly Asp Lys Ala
        115

<210> SEQ ID NO 93
<211> LENGTH: 159
<212> TYPE: DNA
<213> ORGANISM: Homo sapiens

<400> SEQUENCE: 93
atggcggcgg tagcggcagt ggcggcgcgt aggaggcggt cttgggcgtc tttggtactg      60 gctttttag gggtctgcct ggggattacc cttgctgtgg atagaagcaa ctttaagacc     120
tgtgaagaga gttctttctg caagtgttgc tggtgctag                            159

<210> SEQ ID NO 94
<211> LENGTH: 52
<212> TYPE: PRT
<213> ORGANISM: Homo sapiens

<400> SEQUENCE: 94

Met Ala Ala Val Ala Ala Val Ala Ala Arg Arg Arg Arg Ser Trp Ala
1               5                   10                  15

Ser Leu Val Leu Ala Phe Leu Gly Val Cys Leu Gly Ile Thr Leu Ala
            20                  25                  30

Val Asp Arg Ser Asn Phe Lys Thr Cys Glu Glu Ser Ser Phe Cys Lys
        35                  40                  45

Cys Cys Trp Cys
    50

<210> SEQ ID NO 95
<211> LENGTH: 159
<212> TYPE: DNA
<213> ORGANISM: Homo sapiens

<400> SEQUENCE: 95
atggcggcgg tagcggcagt ggcggcgcgt aggaggcggt cttgggcgtc tttggtactg      60 gctttttag gggtctgcct ggggattacc cttgctgtgg atagaagcaa ctttaagacc     120
tgtgaagaga gttctttctg caagtgttgc tggtgctag                            159

<210> SEQ ID NO 96
<211> LENGTH: 52
<212> TYPE: PRT
<213> ORGANISM: Homo sapiens

<400> SEQUENCE: 96

Met Ala Ala Val Ala Ala Val Ala Ala Arg Arg Arg Arg Ser Trp Ala
1               5                   10                  15

Ser Leu Val Leu Ala Phe Leu Gly Val Cys Leu Gly Ile Thr Leu Ala
            20                  25                  30

Val Asp Arg Ser Asn Phe Lys Thr Cys Glu Glu Ser Ser Phe Cys Lys
        35                  40                  45
```

-continued

```
Cys Cys Trp Cys
    50

<210> SEQ ID NO 97
<211> LENGTH: 231
<212> TYPE: DNA
<213> ORGANISM: Homo sapiens

<400> SEQUENCE: 97
atggcggcgg tagcggcagt ggcggcgcgt aggaggcggt cttgggcgtc tttggtactg      60 gctttttttag gggtctgcct ggggattacc cttgctgtgg atagaagcaa ctttaagacc     120
tgtgaagaga gttctttctg cgacagagaa gcataccggcc aggcctctct ccataccgag     180
ccttgctgga ctctctacag cttggtcctg attccctcac ggtccatctg a               231

<210> SEQ ID NO 98
<211> LENGTH: 76
<212> TYPE: PRT
<213> ORGANISM: Homo sapiens

<400> SEQUENCE: 98

Met Ala Ala Val Ala Ala Val Ala Ala Arg Arg Arg Arg Ser Trp Ala
1               5                   10                  15

Ser Leu Val Leu Ala Phe Leu Gly Val Cys Leu Gly Ile Thr Leu Ala
            20                  25                  30

Val Asp Arg Ser Asn Phe Lys Thr Cys Glu Glu Ser Ser Phe Cys Asp
        35                  40                  45

Arg Glu Ala Tyr Gly Gln Ala Ser Leu His Thr Glu Pro Cys Trp Thr
    50                  55                  60

Leu Tyr Ser Leu Val Leu Ile Pro Ser Arg Ser Ile
65                  70                  75

<210> SEQ ID NO 99
<211> LENGTH: 159
<212> TYPE: DNA
<213> ORGANISM: Homo sapiens

<400> SEQUENCE: 99
atggcggcgg tagcggcagt ggcggcgcgt aggaggcggt cttgggcgtc tttggtactg      60 gctttttttag gggtctgcct ggggattacc cttgctgtgg atagaagcaa ctttaagacc     120
tgtgaagaga gttctttctg caagtgttgc tggtgctag                             159

<210> SEQ ID NO 100
<211> LENGTH: 52
<212> TYPE: PRT
<213> ORGANISM: Homo sapiens

<400> SEQUENCE: 100

Met Ala Ala Val Ala Ala Val Ala Ala Arg Arg Arg Arg Ser Trp Ala
1               5                   10                  15

Ser Leu Val Leu Ala Phe Leu Gly Val Cys Leu Gly Ile Thr Leu Ala
            20                  25                  30

Val Asp Arg Ser Asn Phe Lys Thr Cys Glu Glu Ser Ser Phe Cys Lys
        35                  40                  45

Cys Cys Trp Cys
    50

<210> SEQ ID NO 101
<211> LENGTH: 37185
```

```
<212> TYPE: DNA
<213> ORGANISM: Homo sapiens

<400> SEQUENCE: 101
ggtcaaggag atggacggca caaaggcctg ggggtgggaa aactggagta cagggggtcca        60 gtgtggagag agttgggggc agagtcttaa gcgggggagct aaggcactaa ggccgtctcc       120
tgttctttgg gaactgggga gccacacctt gattcccagc acaagaggga ggaaaggaag       180
acctgagatc tagagaggac agcaggagcc tgccctgggc tccaagagtt tcagagatgg       240
cccagatcag ttgattgagt ggccttctcc ctgtcatgag ccacaagcag tagaagccac       300 agggggggcag aagagatgga gagatggaga gagacacagc gacagtcacc agaagagaga       360
caggggcatg gcagaaagag gtgggagaaa tccaggaagg ctccctgggg gtggtggccg       420
gaaatagggt ggaggcctaa tccctgatac tagagaggca ggacctagag gggaggagaa       480
agcttgatgc taggcaggaa gtccaaaagt ctgtctagga atccaggacg gcttcctgaa       540
ggaggggcca ttggatctgg gccttgaaag ataaatagac gtttcctaca tttcctaggc       600
agagaaaagt gtgtgtgtgg gcggtggggg aggggggaaa cggggaattg ctcattttac       660
ttaacaagta ctttcccatt tttaggggac caggtactca gtgggccaca gacaagacca       720
aggcagaaaa gacaggcgcc tccccacatt gcagcaccgg gaccccgagc ccacccacag       780
ccctcttcat tcctcccaac gatggatggg gaaactgagg cagcccagag cagccccac       840 cctaggtcct gcccgggaca cgcccacgcg ggacctgtgt caccaggtta aaaatggaaa       900
cagctaggac ctttttttttt tcttccttta agaaaatcct aggtccaaat aaggcgaggg       960
ctgccgggag cacggtgagc tggccaagtc ctcctgagca agcgagtggc ggctggcccg      1020
gccggcctgg gcttgggcct cctccaagac tcgcctggca ggaggcgga ggcaccccgg      1080 gaggctataa ggccctctcc tccaccctgc caggctcact ctgccccaca gccacagccc      1140
ctgactgccg cagcccccac agagcccgcc gcgcacccca cgtccccccac gccagcgcccc      1200 agccatggag gccatcaaga agaaaatgca gatgctgaag ttggacaagg agaatgccat      1260
cgaccgcgcg gagcaggcgg aggcggataa gaaagccgct gaggacaagt gcaagcaggt      1320
gaggtgccct ccgctgggcc gctccgggct gctgggagtc ctctctgtgc ggaaggccgg      1380
ggtctggagc ccagttgggg gtcgcagaca cctgcgggag gataggaggc tgatgctttg      1440
gcggaggaag agcgagggga ccattgcctt ccttggatgg ggtcctgggc tggaagaggg      1500
gtgacgatcg gacccacccc cagcagggcc agtgcgaaca aagtgagttt gacagagaga      1560
gagttggcgg gggagggaga gtgagaacgt tcgtgagcga ggtgtcgttt gcgctgggag      1620
gttgtgtact agatagggcg gttggggaca tgctgtgtgt gtgtatttgc gtgtgtttga      1680
gcgtatgtgt gtgtacgtgt gtgtgtacgt gtgtgcgtgt ttgcctctgg tgtgtgtgtg      1740
catgtgtgcg tgtgtgtgtg tgtgtgtgtg tgtttgagac agagtctcgc tctgtggccc      1800
aggctggagt gcagtggccc aatctcggat cactgcaacc tccgcctcct gcgttcaggc      1860
gattctcctg cctcagcctc cgagtagctg ggattacagg cacccaccat cacacccggc      1920
taattttgta tttttagtag agaccggatt tcgccatgtt ggccggactg gtctcaaact      1980
cctgacctca agtgatccgc ccgcgtctgc ctcccaaagt gctgggatta caggcatgag      2040
ccactgcgcc cggccatttg tgtgtgtttg agcaattctc tgtgtgtgtg cgtgagcatt      2100
tctgtgtgtg tctgtgtgtg tatctgcatg tttgagcatt tgtgtctgtg tgtacatgta      2160
ttgtgtatgt ttgagcgtgt gtctgtgtgt atctatgtgt ttaagcattt ctgcacatgt      2220
```

```
ctgtgtgtgt acacatattt gtgtgtttga gcaattctct gtgcgtgtat ctgtatgtgt    2280
ttaagcattt ctgcgtgtgt gtgtacacat atttgtgtgt gtgagagcag ttctgtgtgt    2340
gtgtgagtgt atctgtgtgt gtttgagcct ttctgtgtgt gcacatgtgt tgtatgtgtc    2400
tgttttacgt gtctatctgt acatgcacat atgtttcagc tgaaaagagt gcggaggggt    2460
aaaggtgact gtgagaatga gtgtgtacta ggagagctgt gtgtgggacg ctgcgtgcgg    2520
ctgttggaaa gtaggtgtga aagagtgtgg gtgtgtttgt gagcctgtgt gtagatggtg    2580
ggggtctgtg agggtagcgg gacaggctga ctgtgtgtgt gcttgagcaa acgctggtat    2640
gacagtgatt gaaagtacat gttgatgtgg ctatgtttgt gttggcatct gtgtatcagg    2700
gtgatgggtt tctgatggcg tgtgtgtgtg cacccacgca catgtttgga tgtgtgtttc    2760
tgttgtgtgt attggtgact gtgcttctgt tggggtgtgt gtgcatgttt agatgagtgt    2820
gtgtttctgt tggtgtgttt atgtgtatga gtgtgtttct gttggtgtgt gtgaatgtgt    2880
atggatgagt gtgtgtttct gatggggtgt gtgtatggtt gtgtgtttct attggtgtgt    2940
atgtgtgtgg atgagtgtgt gtttctattg gtgtgtgtgt atgagtgtgt gtttctgttg    3000
gtgtgtatgt gtgtgaatga gtgtgtgtttt ctattggtgt gtgaatgtgt atggatgagt    3060
gtgtgtttct gatggggtgt gtgtatgatt gtgtgtttct attggtgtgt atgtgtgttg    3120
tgtgtggatg agtgtgtgtt tctattggtg tgtgtgtttc tattggtgtg tgtggatgaa    3180
tgtgtgtttc tgttgctgtg tgtgtgtggg tgagtgtgtg tttctgttgg tgtgtgtgtg    3240
gatgagtgtg tgtttctgtt ggggtgtgtg tgtggataag tgtgtgtttt tatggggttg    3300
cgtgtatgag tgtgtttcta ttggggggtg tgtgcatgtg tggatgagtg tgtgtttcga    3360
ttggtgtgtg tgtgaatgag tgtgtgtttc tgtcggggtg agtgtgtgtg tcagtgactg    3420
tttctgctgg cgtgtgcata tggatgtgag ggggtctgtg cgaacctgtg tgtgcgtgta    3480
ggtgacacta tgcccctgga tcaggaagcc tccactgtga cagaagcccg ctgtctcatg    3540
ggcacctgcc caggagaatg gcacggcatg tgtgtgtgtg tgtgtggtgg gggcccaggg    3600
ctgtgacctg ctgcaggggt gactgggtgg ggtctgggga ctgggatggg agtagagttg    3660
agagtgagtc tgagaatctc attgtgtatg tgggggtgtc cctgctaaaa gcctggaggc    3720
cggggcaggt gggctgcccg tggtggacgg aggagaggga ggccatttcc catctcctgg    3780
cagccaagag cccacacaga cccagaactt tggagacaag agtcctggga accctggcaa    3840
tgagaatgca ttggagttcc aaggccgtgg ccatggtttg gggcagagca gacaggagca    3900
gtgggtggga ggaaggaagg gagtcccctc ccacagagcc atgttcccca caatgtttat    3960
ccacaccccg atgtcaactg ccaagccctg gggagcatcc aggtctccga taaaccctgg    4020
gagatgccta ggaccatggc accgagtgcc cagccccacc caggccagga gccaggccag    4080
cccggcagct aaaggcgaaa gctcggagct cagactggcc atgtttgagt catggctcag    4140
tcgctaggtg tcccggacgc ctgcatgagt gagatacgga agtgacagta gggcctccct    4200
tgccacccca tgacaggatt agaggtgact gtacaggtgg aacccttggc ccggagccta    4260
gctcagagta agcactcaat aaatgtaggt tgatttcctg ccccgcccta cttcccttt    4320 gggcctcccc agccccccgt gccccagggc tgccctaaga gtatgtggca cattcgtgca    4380
ggccaagccc cacccagtg ttccctgcca caagctctct ccgccttctc tgtgcccctc    4440
cctggcaaac acagacattc atcctgtgct gggccagctt ctagccatca tttagccctc    4500
accatgaggg acttagccag agattcggag agaaacaagt ttatagcact aattcttact    4560
aaggtgtgag tggctatctc ccaggacagc cacaagttca aaaaggaaga atcctcaaag    4620
```

```
cctccagcca gctgcgtggc caaggaggtt atgccttttt tgtcccacaa agatgcccac   4680
tggagtagac ttgggctcaa agcaagtcta cacagactag ctttcaggca aacctccata   4740
gactagcaca tactttgtgt atatcagtct ttaaatgtat ttttattttt tagagatggg   4800
ggtctcactc tgttgcccag gctggagtgc agtggtgcaa tcacagctta ctgcagcctc   4860
aaactcctag ggctcaagcg atcctcccac ctcagcctcc ccagtggagg tgcacacctc   4920
cacgcccagc tagttatttt attttttagta gagacagggt ctcactattg cccaggctag   4980
tcttgaactc ctgggctcaa gtgatccttc cacctcaacc tcccaaagtg ctgggatcac   5040
agacttgagc cacggagcct ggtctttgtg actctcctag cttcatgact gaggacacgt   5100
tcctgcacat ttctgagccc tcagtgtcct catctgtgaa atgggaacac gtgaggcctt   5160
ctgaagttca ggtgtggaac tcaagatccc agaattccga agcagaagcc agcgccccac   5220
aggagctaac ggccagtcct gctggggaat agaggcactt agagcgcctg acgctgcagg   5280
aggccagaga gagcagctct cgggccagcc tgatcccagc agccaagcac tgatttctgg   5340
ccctgcttac ccagtgtggg aaaaggacaa agaggcccag cccggccgct tcctgcccac   5400
tcccctccca gggcagcaac atcctccacc actggccttt gacccacat cctgcctcag   5460 ccctgcccca aggccccatt tgcagggact aaggtaatcc tatgacagat agggaaactg   5520
aggctcacag agggacaatg acgggcacgc gccaccaggc ccggctaatt tttgtatttt   5580
tagtaaagac ggggtttcac catgttggtc tggctggtct caaactcctg acctcgtgat   5640
ccgcccgcct cggcctcccg tagtgctgga attacaggcg tgagccactg cgcccagctc   5700
tcatttattt tttatcctca ctgcctacca ctgaagggtt tggggttgtg tcttcgattc   5760
atcccaaaca cttcctacag tgttctaatg ctgggggcca tagtggcctc agtcccagaa   5820
ctgaccctca agaaactcca agctgaggga gacagaccat gaataccccc agctcagagg   5880
tcagggccgg accagaggga gggacagagg ctgggacagc tgtaggcgtg gcgaaagctc   5940
tgctcagggc agcagagcag gccaccaggg ttggggagcc ttgggactga gcatggaggg   6000
acggtagatg ccctcccagt gaaaagtaga aagtcattct tagcagtggg tccagcatgg   6060
tctagaagtc aagcaaacca gctttggaat cagactaaca aagattcaaa tcccccatct   6120
gtgtggcatc aggcaagtcc cttccccttt cagagactca gtttgcccct ctgtagtatg   6180
gggcttccct gagacaatat ttgtaacacg ccctggccag gcatagtggc tcacacctgt   6240
aatcccagca cttcaggagg ctgaggtggg ggatcacctg aggtcaggag ttcgagacca   6300
gcctggcaaa accctgtctc tacaaaaaat acaaaaatta actgggcttg gtggcatgag   6360
cctgtaatcc cagctactag ggaggttgag gcaggagaag cacttgagcc agggaggtgg   6420
aagttgcagt gagctgagat ccagccacta cactccagcc taggcaacag agcaagactc   6480
tgtctcaaaa aatatatcaa aacaaattgt aacacgccca acacattcta aatgccagat   6540 agcccctgt cggccttatc cctgtcctca catgttcttg cccaaacatt tcccccaaaa   6600
aagtagtcaa aaccccaaac caaacaaaaa aaccccaaac cagccaggtg gggtggctca   6660
tgcctgttgt cccagctact cgggaggctg aagtgggagg atcccttgag cccaggagtt   6720
cgagaccagc ctgataaca cagcgagatc ctatctcaaa aaaacaaaaa caaaaacaaa   6780
acaaaacacc caaaccatct tcataccctg atgagtccat gctgtcagat ttgctctcac   6840
tcttcctaca tgttaggaga gtcctgtgtt gggcacacag ttggcaccca ataaatgctg   6900
tgatccacag atctggaagg aagtcaggtg gatgctgtag gtcagggttg acctatgaaa   6960
```

-continued

```
cgtctttaag gaaactggct cattttctca gtcaaggcag aagttcaaaa gcagctgccg      7020
gaatgctcag agaccagcat gtcaaggttt ctgttctgca gatggagaat ctgaggccag      7080
aaaaggggac gggggtcgca gagcttggat ttggagtcag gcttccaggc tccccacccg      7140
gaggtcaagg tcaggcccta tagactctga ccctgccctg atcagctggc caccctggat      7200
tgggccctgt catctcccca tagcttggga tgctcctgag gacttcagac aggatagccc      7260
tccctgctct ctgtcacatc tcagctagag acccttgcag gtcacctcag tgacatcagc      7320
tgaacctcca gctgccagcc tccaccccat cctccagctg acacccagca ggccgcaaga      7380
tgggaagcct ggagttcaca ctttccagct actcaggagg ctgaggcggg aggatcgctt      7440
gagccgagga ggtcaaggct gcagtaagct atgatcacac cactgcactc cagcctggga      7500
gacacaggaa gaccatgtaa aaaaaaaaaa aaaaaaaaa cgcaaaaaaa aaaaataatg      7560
cacacacaca cacagcaaga tcaggttaaa aaaaaaaag gcaaaaaaaa aacatacaca      7620
cacacacaca tatggggcac ctggtacatt ttgcacatcc actcaggggt gagcacgtag      7680
cccagacagg attcagagct cagtctagaa gccacgggca cagcagcttt tttaacatac      7740
cctcttcaag aaaaaaaga agagaagcaa gtcagagagg gaggaaggga agctggccta      7800
gtgtgaggaa cagggccaag ggctttgtct ttgtcagctc aggcagttat aacaaaacac      7860
catagactgg gtagcttcag taatagacat ttattgttta cagtctggag gctagatgtc      7920
caagatcaag atgctggcag attaaatgtc tggtgagcgc tctctagcta gcttgcagac      7980
agccaccttc ttgctgtgtc ctcacattgg aagaggataa ccaagttctg gcctcttctc      8040
ataagggcct taatcccatc atggtgggtc aaccctcatg acctcaccca aacctcatca      8100
tcttccaaag gccccatcac caattaccat cacatggaga tgagggcttc aacacatgaa      8160
ttggagaggg ggcaaaagca agcattcagt tcattatagg cttatattcc agaagacctg      8220
ggctcaaacc ctgtgctgtg tgacctgggg aaagtcatcc cacctctctg agcctcctgc      8280
tgtggggagg aagcaggaga atgaagctgg gctcagtggg ggctgtctgc ccaccctggg      8340
agcaggaaca agatcagtgt caaaccatct aaggcaaaag tcagatccaa gccaggtgtg      8400
gcgactcacg cctgcaatcc cagcaatttg ggaggccgag gcgggcagat cacttgaggt      8460
caggagtttg agacctgcct ggccaatatt gcaaaccct gtctctactg aaaatacaaa      8520
aattagtcag tcgtggtggt gtgcacctgt agtaccagct accggggagg ttgaggcagg      8580
agaatcactt gaacccagga ggcggaggtt gcagtgagct gagatcgtgc cactgcactc      8640
cagccttggt gacagagcga gactctcaaa aaaaaaagtc agatccaggc atgagctgga      8700
tatgatcacc ctaatccaga gttgggggcc cagggaggga gtttcagcct ggaggtgaca      8760
gaaaagtctt cttgagccaa ctctagaccg gtgtggtggg gggtgacaaa gagaggtgat      8820
ggggtctgtg gtttgtaatc cataggcctg agcttctcaa actaggagtg atgggaggat      8880
aggactcttg ggataaacag aggactgaaa atttagggaa agtaggggac atttttatta      8940
aaatgaacat ggcctatatg caaaaatttt aaagatttaa cccgagcctt caaagaaagt      9000
gatcctgtag gggcgagtct cttctagcca agctccccaa agcccagaaa tgagggacta      9060
ggtctgagcc cttcagccct tcagagtatt ttggtaagac agtctaagaa ccactgcctt      9120
gggccatagg gagccatagc aggttctagg cagaaagagg gcaggcgtat ttgttagaaa      9180
gtttctctga ccccgtgttg gggtcagaac cagagggaga aaggctgggg acagggatgg      9240
gcggagggat ccacgcgcag agaatgagat tgcttaactc cagatcatgg tgaggctgca      9300
cctctgaaac tggaatgtgt gtatttctgg aaaacatttg gagtcttcag tttcccaaaa      9360
```

-continued

```
gctgccattg atctccctag agtactgggg accccaataa gcccaaaaca gctggtcctc      9420
aggacgaggg aaagatgtga aaatcccact atcaggtagc atggatggcg tggtgcatgc      9480
tatcgcaacc cctgttctac agataaggaa actgatgccc agagagagac ggaggactct      9540
tgtgaatatt ggggggggacc gccctgcac ctcgggacg tgacccccc cccaggctga       9600 cccgttcctc gctctgtcgt ccccaggtgg aggaggagct gacgcacctc cagaagaaac      9660
taaaagggac agaggacgag ctggataaat attccgagga cctgaaggac gcgcaggaga      9720
agctggagct cacggagaag aaggcctccg acgtacgtgt gcagggatgc gggagcccgc      9780
ggcggggcca ggccggagcc ccggggccgg gaaggcgggg agagccgcag ggggaggagg      9840
aagaggagga ggagaaggcg gcgcctccca gcgctttctc caaataagtc ccgaaaaggg      9900
gcactttcca gcagctgtgg ccagcggtgc cgacgtcagg ccctcccca gcggtgctga       9960 cgtcggcggt ccggccgggt gacctcatcg ccccgacggc agccggcccg gggggcgggg     10020
agaggcgggg gcgcccccg cgcaggcaaa ggcttggggg gccgggggcgc ggctgtgcag     10080 ctctcgccgg agccgagccc agccgagcgt ccgccgctgc ccgtgcgcct ctgcgcctcc     10140
gcgccatggc cggcctcaac tccctggagg cggtgaaacg caagatccag gccctgcagc     10200
agcaggcgga cgaggcggaa gaccgcgcgc agggcctgca gcgggagctg gacggcgagc     10260
gcgagcggcg cgagaaagtg agcgccccgg cctcgggccc cgcacccgca gcctcctccc     10320
ccgcgcgccc tcctttcttc ccggcttccc gcgctgcccg cccgcgcgca gtcctcgggc     10380 cgcctttta cgccctcgga cgccgatcgc cgacccacat ccctgcgccc gcagccagga     10440 cccctactt cctccgccgt cctccttcct gggcctggga caggggaggg ggcgccgcct     10500
ccgggtcggg cggggccggc caagcgggaa atgggggggat ggggcggagg gggtgagcga    10560
tctccgggtg gagaagtgga gcggcgggag ggggcgtatc gtgcaggctc cgactccggg     10620
gctggcgccg gggtcccggg ccgaggggaa cccgcgaccg gacttgtggg ggagaatgag     10680
gatgaaaacg tggagcttcc attgtctagg gtttgaccgg ccgacaggga tttcgacggg     10740
ggaccgggga tctggggagg gggtcgcact ttctcgcctc tttcgcggct tcccggcttc     10800
tgcttgcttc cctgaccgtt cccaggggcg cggcggcgac gtgtctgctc caggcggcgg     10860
gggggatggg gggtggagga agttcagccc caagccgccc gcctttctcc agctgattcc     10920
tgcgggaacc ggggcggcgg gaccctgcct ctctccagaa ggccccggga acgctggcgc     10980
ggggccctga acccacgatc gtttgagcgc ctgctgtgcg cctccgccgc gagtcgcagg     11040 gccccgagata aacaatgggt ctgaaaaagg agggagtttc accatcctct ctgcatcatc    11100
ctcctggctg tccctcggga cagatggtgg caccgccagg gtctggggac agatttggat     11160
tctggtccca tatcatgcca cccacaggct tcatgacttg gtatttgctc tctaggagct     11220 ttttcccat ctgcgagtag gactgataag aatcccgacc ccccagagta gcagggaggg      11280
tcccaggagt aaatctcagg cgtggagcct ggcgctttgt aaataatcaa ttgtgttgtt     11340 gtttttgtt gtttgttttt tgaggcagtc tcactctgtc gcccaggctg gagtgcagtg      11400
gtgcgatctc ggctcgctgc aacctccacc ccccgagttc aagagattct cctgcttcag     11460
cctcccgagt agctgggatt acaggtgccc gccaccacgc ccagctaatt tttttttttt     11520
tattttggat ttttagtaga gacagtgtct caccatgctg gccaggctgg tctcgaactc     11580
ctgacctcgt gatctgccca ccttggcctc ccaaagttct gggattacaa gcgtgagcca     11640
cggcgcccag cctcaattgt gttttctctg ccctgggaag agctcataga caaatggagg     11700
```

-continued

```
caggggagct gactcactga tggagcgagg tctgcattcc acgggttttc tgtgcagtta   11760
tgggagcatg acaggggagg ctccaaaatg gaggttgagc tgggtcttat agaataaata   11820
agtttgctgg gaccagagac atgggtgtgc acagactcag aggcaagaaa gttgtatgat   11880
gagggtgggg gggtgtgcgg atagaggttg aagcccaaaa gccctgaaag ttcagtgttg   11940
aggctcaggg tggggaccct agagaggcaa aagatgccca gccagatgga attggtggtg   12000
tgaattgcca ggactggaaa gagcccagat gggggctgca gcatgggcct tggttgaagc   12060
ctctaatcct gtaagggctg ctttggccca agaggcctta gaaacccggt gtaagcctca   12120
atcggtagcc ggtctggcct ctttctcaca cttaaccgac acagctcttg ctctgatctc   12180
atcccaagtc atctcgctgg aggacaatta actcggcttc aaaatggccc tcagcctgga   12240
gccaagattt aggagcaaga ccgtctagtt gggagagaag atgtttttgg agagttgaag   12300
acttcttgaa aaagttcgaa aagttcttga aaaagcaaag gatgcttctt tccgtctggg   12360
agagggaaaa cctctcccag ggcaaaagga actaagacca ggggtgggtt aaaaaaaaaa   12420
aaaaaaaaac ctttcactct tgtagaataa gccaggagcc ggcgtgtggt agacttctgg   12480
gcctgtttcc cgacagctgg tttcgtttag attttttgtgt gattaactga catcttcctg   12540
ttcctttgcc acatgtatct agcaagcctc ttttacctta taagggaaat cctttgtagc   12600
gtgtggaagg ctttgattgc aggaaggggt ggaacccaaa atgactcggc cgtgactagc   12660
agtttttcaa aaatacatat atatgtatgc atgtacagat atgcgtgtat ctcccaactc   12720
cagacagctg aaaatctgcc aaaagcgttg tttgccagga ttcagaattt cccacataag   12780
ggctactcac ttcttaaaag acaactcatg aatcaagcac ctctgtttga tctttaaaat   12840
caattcctcg actgctaatg ggtacacagt tttttgtttg tttgtttgtc tttggcgggt   12900
tatgaaaatg tcctggaatt cgataatggt gttggttgca gagtgttttt gcaacatcag   12960
ttcctggccc agttactgaa ggtggtagga ggagttaaga tctaggcaat taaaaagaat   13020
gaaaggcacc cattcatggg aaggcctcag tgacgtttct taagacagtt tcatcagtgg   13080
ttttcacaat tctctgcatt tggtgtttca gaggacactg caatacgaaa cacctgtggg   13140
agtgccctct ttctgcttct aggaatctga ggctgagaaa ccttcctgac tctatttgtg   13200 tagttttttcg gccacgttag cctcattcta tttttttttc ccccagtatg aactcagggc   13260
aggagaggga gtggtttcct aataattttt tttttttgag acggaatctt gctctgttac   13320
ccaggctgga gtgcagtggc gcgatctcgg ctcattgcaa ccttcacctc ccgggttcaa   13380
gcgattctcc tgcctcagcc tcccaagtag ctgggattac aggcgcctgc ccccacaccc   13440
aactgatttt tttgtatttt tagtagagat gcggtttcac catgttggcc aggctggtct   13500
cgaactcctg acctcatgtg atccacccac ctccgcctcc caaagtgtta ggattacgga   13560
tgtgagccac cgcgcccggc cttcctaata attttgatag ccttccccag ttcagggatt   13620
cttcatttgt tctgatagga aaagctagc gtggcttccc ttttcctctc ggttgaggcc   13680
cgtttgaccc gttctcaata ttccttccaa agagcaggca tcgctggaaa actcgccttg   13740
cctcgtagcc ctggcaggac ctaggggaca ggttctgaca aggaagagcc ctgggtgggt   13800
cttaagaggc cattcatttc ttaccaattc tgagtcactg aataaaacca cttccccag    13860 tggggcccct cggtttcttc acctgtaaaa tgggtgcgat gtgtgaggat gaaattgcag   13920
taaaataaaa ccgtggcagt aagagatgcc tttctctggc acatcccacc tgctgggcat   13980
aagcggcgcc accctctgga gttacagcct caaggcagtc cggtaactaa tcaggctttg   14040
ggatggagag ggccaggatg aggaagcaac cttcccaaca ccacgtggct gtgaaaatga   14100
```

-continued

```
caaagcacgg tcgggcgcag tggctcacgc ctgtaatccc agtactttgg gagaccaagg   14160
cgggtggatc acgtgaggcc aggagtttga gaccagcctg accaacaaga cgaaaccctg   14220
tctctactaa aaatacaaaa aaatagcaag gcgtggtggt gtccgtctgt aatcccagct   14280
actcaggagg ctgaggcaga attgcttgaa cccgggaggt agaagttgca gcaagccgag   14340
atcatgccat tgcactccag ccttggtgac ggcgcaagac tccatctcaa aaaaaaaatt   14400
aaaaagaaaa tgacaaagcg gggattccag cccagcactt tttggccctg gagttcctgg   14460
tttaatgctt cccattgtac ttcctttctt gtaggtaaaa acaccttgaa aagccaataa   14520
cactattggg gtatgtcttc catgcctgca accaagtttt cttttcccttt ccatatcttt   14580 ttgtcctgcc atctctcagc caggcggatt gaaggatgga attccaacga ggctcccccg   14640
cctcgtccca ccttggtaat tgcatggcca acatttaact gagggctcca tagtcttgca   14700
tttatcttgc cattcaggtg aatgggagcg gaactcacag gacacaatga gccgggtcac   14760
tgatggcctt gctttctaag aatctcacag tgagccctag aactctctac gtggtaacac   14820
tgtgtgcctt tttcagagaa gagcctatct tagatcttag cctaacgttg ggtctattgt   14880
gttgctggag agaccagcac tgacattcat ctcaaagcac atggtatgtt tgactcctat   14940
gttgactcaa ctacccatct tgtactggga cactcgcttt tttttttttt ttttgagacg   15000
gagtcttgct ctgtcaccag gctggagtgc agtggcacga tctcagctca cggcaacctc   15060
cgcctcccgg gttcaagtga ttcttctgcc tcagcctcct gagcatgtgg aactacaggc   15120
acgtgccacc acactcagct aattttttcta tttttagtag agacagggtt tcaccacgtt   15180
ggccaggatg gtctcgatct cttgaccttg tgatacaccc acctcagcct cccaaagtgc   15240
tgggattaca ggcatgagcc accacgcttg gcgatgctca tcttttgcta tggagtggta   15300 gatgttttc ccagacattt tccgggaaga tcatactgaa attttggtat gagtgtaaat   15360
tccctatggc ctggactcct gggtgggctt tgacggggaa gatcaggtta acagagggca   15420
ggacatgggg gaggctccca ctggtggctg gcctgatact tcttaacatg gctgcacctc   15480
cgacctcccc aggctgaagg tgatgtggcc gccctcaacc gacgcatcca gctcgttgag   15540
gaggagttgg acagggctca ggaacgactg gccacggccc tgcagaagct ggaggaggca   15600
gaaaaagctg cagatgagag tgagaggtaa ggacgctttg aatctggtgg catccgtgtt   15660
tgcttttaga aaatggggat catgctgccg acctcgcaga gctggtgtga aagtaaacaa   15720
ggtcacaagg acatgcatgt gtccacaaaa aagtgcatga cagcactttg taaaccatca   15780
ctccatgggt agagatgttt atccgtggcc aggcacggtg gctcatgcct gtaatcccag   15840
cactttggga ggccaaggcg gacggatcac ctgaggttgg gagtttgaga ccagcctggc   15900
caacatggtg aaaccccgtc tttcctaaaa gtacaaaaaa attagcctgc catggtggcg   15960
ggcacctgta atcccagcta ctcaggaggc tgaggcaaga gaatctcttg aacccaggag   16020
gcagaggctg cagtgagccg agatcgtgcc attgcactcc agcctgggca acaagagcaa   16080
aactccatct caaaataaag tgaggggtgt ttatccttac ggtaaccatg aaaagaaact   16140
tccgacagac agaaaggcaa acagaacggg cagatgtgag actgcaagta tgactgtcca   16200
tggtggtcag tttgcaaagc actgcttctc gtatttttctc tgaaagccac agtgcctctt   16260
agtgttctct agacaccaaa tttcaggtag gccggatgca gtgattcctg cctgtgctcc   16320
cagcactttg ggaggcagag gcgggcaaat cgcctgagct caggagttca agaccaactg   16380
gggcaatgtg gtgagaccct gtctctacaa aaaatacaaa aattagccgg gtgtggtggt   16440
```

-continued

```
gcacgcctgt actcctggct actcaagagg ctgaggtggg aggatcactt gaccccaaga    16500
gtttgaagct gcagtgaggc aagattgtgc cactgcactc cagcctcagt gacagatgag    16560
attctgtctc aaaaaaaaaa aaaaaaaaaa aaaagcagag tactgtggag aggaggaaag    16620
gaaacttggg atgcacaggt gattgttagc agagctgtca ggctttaggc ttttggacgg    16680
tgacagctat ttcagggaca gttgcaaacc agcatggtta atgtacttgc aactgaccat    16740
gcaccaggtg ccgtggctca cgcctataat cccagcactt tgcgatgacg aggcgggtgg    16800
atcaactgag gtcaggtgtt tgagaccaga ctggccaaca tggtgaaacc ccgtctctat    16860
taaaaataca caaattagct gggcgtggtg gcgggcacct gtaatcccac ctactcagga    16920
ggctaaggca agatccccca gcttgaaccc aggaggcaga gggtgcagtg agccaagatc    16980
gcaccactgc actccagcct gggcaacaga gtgagactct gtctcaaaaa gaaactgacc    17040
acgttcctca cccgcccatg gtatctgtgc tgcaacccag ccaccagtag ggtgccttct    17100
cctcggtagc cagatcattc tctggcacgc cttggcacag gctctctgga agactgaggg    17160
tagattgtgt aattcacaga agcagcagtc tgtgtgtggt ggaaaaggag ttccttgtgt    17220
ggcaatggtg tgggcccgac cagtgatcat cgcgtctgcc cctcattcac accggagttc    17280
tcacttgagc cagccaccat gcttttgcag tataaacacc tcccaaagat tcatttcttt    17340
tttttttttt tttttgaga cagggtctta ctctatcacc caggctggaa tgtagtggtg    17400
cgatcacagc tcactgcagc ctcgacctcc tgggctcaag cgatcctccc gccacggcct    17460
ccagagttcc agagtaaagc tgggactaca ggcgcatgcc atcatgccca gctaattttt    17520
ttttgagaca gagtctcgct ctgtcgccca ggctggagtg cactggcgtg atctcagctc    17580
actacaagct tcacctcctg ggttcacgac attctcctgc ctcagcctcc caagtagctg    17640
ggactacagg cacccgccac cacacccggc taattttttt gtattttttag tagagacagg    17700 gtttcaccgt gttagccacg atgttctcaa gctcctgacc ttgtaatcca cctgccttgg    17760
cctcccaaag tgctggcacg cctagctaat ttaagatgca tttctggttg tgctgctgtg    17820
accactaacc agagattaga aaccagctaa ggaatcttgg agattgcatg tcacccaagc    17880
tggaaatttc ttcccaagta gtggaacagc caggcagag ggaacagacg ctactgcaga    17940
ctctgcttca gccactgaat caagggagag agtggcagct ccggcagcca cggggcagtg    18000
gaaggaccca gtcacgagag ttcctggctg tgcctgtggc ctgggttagc tgctgttcac    18060
agtcagacca gcctggctgg atgctgacgt tgagggctcc catattggca aaccaaggga    18120
ggctgcgaag gccagtctct tgtttgcacc atgtccccag aggcctttgg tgacacccct    18180
gttaaagact gctgtgtctc agtagaaaga attatatact tgaagcttgg ggatctagag    18240
tcagcttcta ccactggcac tttctatgga gccttaggca agtcactttg atctcttggg    18300
tactacaagg ggttttgggg caataaataa cccagagagc ttgctcacat gctgagggtg    18360
agacctcgta caggtggggg agggtgtttt gagacttagc tgagaacggg tgacacccca    18420
cgtgaacata tttattggac agcaagaagc atatggtctc tgtgctgggt gggaatgata    18480
catatcaatg acacattatc ccaggctggc ctcttctttt cttttctttt cttgtttttaa    18540 atacacaagt tcttggcagg gtgcggtggc tcacacctgt aatcccagcc ctttgggagg    18600
cgggcggatc gcttgagccc aggagtttga accagcctg cgcaacatag tgagacccca    18660
tctctacaaa aaaatattaa aaattagcca ggcatggtag tgcatgctgg tagtcccagc    18720
cactcaaggg actgaggtgg gagaatcacc tgatcccagg aaggcaaggt tgcagtgagc    18780
tatgattaca ccactacact ccagcctggg caacagagtg agaacctgtc tcaagaaaaa    18840
```

-continued

```
aaataaataa atacacaacg tcttgctctg tcacccaggc tggagagcag tggtgcaatc   18900
acgactcacc gcagccttga actcctgggc tcaagcgatc ctcctacctc agcaacattg   18960 caaaacccc acctccacaa aaaatttttt tttagtttag ctgggtgcag tggtgcacac    19020
ctatagtccc agctactcag gaggccgagg caacaggatt gcttgagcct gagaggacaa    19080
ggctgccgtg agctctcagg gcaccactgc actccaacct gggcaacaga gtgagacacc    19140
atctctcaaa ataaaagaaa aagaaagggg gcacagactc tggagtcaga ctgccaaggg    19200
ctgagcctca gctctaccac ttaccagctc tgtaacctta agttacttac cctctctcta    19260
tgccttagtt tcttcatttg taaaatgtgg ataatttacc tgctccatag ggcagttgtg    19320
aaagtgaagg cacttagaaa agtgcctggt agtaaagatg aagggaggct gggcgcggtg    19380
gctcacacct gtaatcccag cactctggga ggtcaaggcg ggcagatcac ttgaggtcag    19440
gagttccaga ccagcctggc caacatggcg aaacccctc tctactaaaa atataaaagt     19500
tagccggtca cggtggtgca tgcctatagt cccggctatg ctggaggctg agacaggaga    19560
attgcttgaa cccaggagat ggaggctgca gtgagctgag atcacactac tgcactccag    19620
cctgggtgac agagcgagac tccatctcaa aaaaaaaaa aaaaaccaag atgaaggaaa     19680
tgtgtgcaca gagttccatc tttgcagtgt gttacagtgc tcagtagatt cagagactca    19740
tttagatgag agatgggact aggggtggtg tctcacgcaa ttagccagac atggtgacgg    19800
gtgcctgtaa ttccagctac tcaggaggct gaggcaggag aatcgcttga acccgggagg    19860
tggaggttgc agtgagctga gatcgtgcca ctgcactcca gcctggatga cagagcgaga    19920
ctccatctga aagaaaagat agatgagagg tgggtggagg ggtgtgagtg aacggccgtc    19980
ctgatgagat tgctccttgc agaggaatga aggtgataga aaaccgggcc atgaaggatg    20040
aggagaagat ggagattcag gagatgcagc tcaaagaggc caagcacatt gcggaagagg    20100
ctgaccgcaa atacgaggag gtgagtgggg ctggcagatg gcgcagcagc aggaagtggg    20160
aggaaatgca tctgctgaga tagggaggac accgggggcca acgaaaggaa gctctcggtt    20220
aggtcagctg tcctcctgcg tgaacatatg tttgtccaga gacaaccact ggctaggaa     20280 actatctccc acgatgccag aaagtgctgc ggacgcttgt ctaacgtaat gggaaaaccg    20340
aatgatcagc tcacttgtgt cgttagctgg gagttttggc acagttgggc aaaaatggag    20400
gattgtggtc ccaagccatg gagtttcaga ccatgcaagc tcaggccctc ctttgcctcc    20460
ctcgatggct cggctcttcc ctcccgcctc ttgtctgcct cgctcctcag gcttgaggaa    20520
gagaatcagg atttcctcca ggccccagga tggctctttc agttgaagcg ccagcaaaag    20580
gccaggcgcg gtggctcgta cctgtaaccc cagcacttcg accgaggcgg gaggatcacc    20640
tgaggccagg agtttgagac cagcctgggc aacatagtga cacccatttt ctaaaaataa    20700
taataataat aattagctgg gtgtggtggc atgcacctgt agtcccagct acttgggagg    20760
ctgaggcagg aggatcgctt gaacctggga agtcaaggct gcagtgagct ctgaccacgc    20820
cactgcactc cagccttgga gacagagcaa gaccctctgt caaaaacata aaagggctgg    20880
gcatggtggc tcacgccggt aatcccagca ctttgggagg ccaaggcagg cagatcacct    20940
gaggtcagga gttcatgacc agcctggcca acgtggtgaa accctgtctc tacaaaaaat    21000
acaaaaatta gccgggcatg gtcgtgcatg cctgtaagcc cagctatttg gaaggctgag    21060
acaggagatt cacttgaacc caggaggcag aggttgcagt gagtcaaggt tgagccactg    21120
catttcagcc tgggtgatgg agcgagactc tgtctcaaaa gaataaaaaa ataaaaaaga    21180
```

-continued

```
ggccaggtgt ggtggctcat gcctataatc ccagcactct gggaggccga ggtaggtgga    21240
tcaggaggtc aggaattcga gaccagcctg gccactacgg tgaaacccca tctcgactga    21300
aaatacaaaa attagctggg cgtggtggca cgcgcctgta gtcccagcta cttggaaggc    21360
tgaggcagga gaatcgcttg aacccaggag gtggaggttg cagtgagccg agactgtgcc    21420
actgcactcc agcctgggca acagagggag actccgtccc cctgcaaaaa aaagaaacac    21480
cagaaaaacc catgttgcag ctggtctagg ggtctgggtg gggcatcatt gggggctgtc    21540
tgcagtggat gggagaggac acggctggtg gggatcgggc tcagctgggc ctttctgtct    21600
ctgcaggtag ctcgtaagct ggtcatcctg gagggtgagc tggagagggc agaggagcgt    21660
gcggaggtgt ctgaactgtg agtggcagaa caggactgag cgaggctggc tcgattcctg    21720
gggcggagtg ggaaggagct ggctgtgttg ggaattggct ctgaccgggg tctctgctca    21780
agtggacggg cgtcaggggc tcatggctca tcttttctct tggcttctgt gacaaagagg    21840
tggtgacttg ttcttactgc catgggaagc actgcccacg tgttgaccct ttctgcaaag    21900
atatgaggaa ataggagtga gacaggaggc agcaggaag cccagaagtc ccattttccc     21960
agagaggata tctcaggggg ctgtgccatc ttaacagaac actgacctgc tccagaaggc    22020
aggctccccc ggtcagtatg taaatgcttt tgctcctgtc agtgtttggc cgtgacacat    22080
tcctggcggg aaggtgagaa gcttaaccag aatcccacaa gcaagcaccg aaaaacaaaa    22140
cacctgtcct cttggcccg ggtgaggaat tcagccccac agagcatccg ggagtgctga     22200
gagagatctg gtttcacaaa tccactccgg gcttccttcc cggagtgtcc cctgcaaact    22260
cccattgctc tctgcccgcc ttctgccctc agtcccattc ttacaccttc cggagtcggc    22320
ctcatcaatc atagatttca caagtccttg cagccttacc cttggcaaaa gaccaggagt    22380
gttttccaag ccctccaaat actcttcggg cgcacctcgc ctctgcctgg tatgataagc    22440
ctttgataag cccatagtat cacactgcag aaaaatccat taacatttc tccccacatt     22500 ccttctgccc cccaccgggg gagctgtgta ggtttctcct ttggaaaatt tattgttggg    22560
gcgattgcta ttattgccgg ctgtaaggga agataagaca caaaaatcct ttgtctttgt    22620
gcagaaaatg tggtgacctg gaagaagaac tcaagaatgt tactaacaat ctgaaatctc    22680
tggaggctgc atctgaaaag gtaggtggtt ggcttgagct ggagggtggc ttgctggact    22740
ttgttctttt cttctcccga gggatgcagg agcctgtcag gttatgggga atctgccctt    22800
tatttaacag tagcgttggt gcctggcagc cagggttttt cccctacaga aagagctgga    22860
tttctcctgc acactcttga gtcctcttcc atggggtctg agcaccatct ttgatctcca    22920
tctcaggagg atagagatag aacatgaggc tcttcttagc gagatctgag catagttgta    22980
taaataaata cagagcctgc ctctcacctg attccctgg ttcctccaga aataccatct     23040
caaaggtata gcaatgatca gaggtggaat tgggcttttt agtttgaaac agcacccaaa    23100
gcagttgcta cgtggcagct acgtcgggaa caaaggacac acttccacgg ccgaacccca    23160
ctgaatttcc cagcctcttc ctcattcttg ctcctgcttt tgcagtttca cagacattct    23220
ttgttctccc atcacctcca cccccactt tttttttttt tttttgaga cagagcttcg     23280 ctctgttgcc caggctggaa ttcagtggca tgatcatagt tcattgcagc cttgaactcc    23340
caggctcaag cgatcctccc acctcagcca ccacctgcta ttcactcaac tgggtgtggc    23400 tttcctttg cttgataaac ccctattcag cctttttttt tcttttcttt ttttttgaga    23460
cagggtctca ctctgtcacc caggctggag tgaagtggcg tgatctcagc ttactgcagc    23520
cttcgactcc caagttcaag caattctccc acctcagcct cccgattaca cgctaatttt    23580
```

-continued

```
tataattttt ggtagagatg aggtttcacc acattggcca ggctggtctc gaactcctga   23640
tctcaagtga tctgcccgcc tcgccctccc aaagtgctgg gattacaggc atgacccact   23700
gcacctggcc tagagatgag atcttgctct gttgcttagg ctggaagtgt agtggcgtga   23760
tcatagctca ctgcaggccc caaactcctg ggcttaaata atcctatcac ctcagcttcc   23820
tgagtagcta ggacttgcag gcatgtgcca ctactccaaa actgtatttt tttttttttt   23880
tttatagagc acagtctatg ttgcctaggc tggtcttaaa ctcctggcct caagtgatcc   23940
tcccacctta gcctcccaaa gtgctgggat tacaggcgtg ggccaccgtg cctggctaat   24000
ttttctagtt tttggtagag acaaggtttc atcatgttgg ccaggctggt cttgaactcc   24060
tggcctcaag tgatcctccc accttggcct cccaaagtgc tgggattact ttgggaggcc   24120
gccgagcctg gcctcctgtt catcctttga gcttctgctt aaacatcact tctgagagtc   24180
cttctctgat ttctcatcta ggttaggtat ttctctgctg tgtagccctg tctatacttt   24240
tgctggcatt atgatttctt acatttatta tagttactcc attaattgca tgccttcctt   24300
gctagattgt aagttgtaag gacaggaacc atgtcatctt gttcagagtt gtgtccctag   24360
tactagcatt gtgcctggca tatatctgta gtgtgtgtgt gtaatttttt tttttttttt   24420 tttttttagta gagatggtgt ttcaccatgt tgcccaggct gatctcaaac tcctggcctc   24480
gagtgatcca cctgcctctg tctcccatat gtgccagccc tggcatatat ctgatactag   24540
gatgtgtaag gaatgaatcc agttggtgtg tgtatgccag acactgcccc gggccagggg   24600
gatagatgta acaccactaa tacctcagct gctttgtttt gttttgtttt gagatggagc   24660
cttgctctgt cgcccaggct ggagtgcaga ggcacgatct cagctcactg caacctccac   24720
ctcctaggct caagcaattc tcctgcctca gcctcctgag taactgggaa tacaggcgca   24780
cacaccacgc ccagctaatt tttgtatttt tagtagagac ggagtttcac catgttggcc   24840
aggctcgtct caaactcctg acctcaagtg atccacccac ctcggcctcc caaagggctg   24900
ggattacagg tgtgagccac tgtgcccagc ctggcatctg ctcttgaaga gctcagagtc   24960
gagtctagtg gaagggattg acaaagtcac agagtgcttt gggaatacaa tagagggacc   25020
ttggtaggtt gtgaacggtg tcaccaagga ggcgacattt aaaacagctg taggtccagc   25080
acggtggctc atgcctgtaa ttccagcact ttaggaagcc gaggcgggag gatcgcttga   25140
gctcagaagt tcgagaccag cctgggcaac atggagagat cccgtctcta ccaaaaatac   25200
aaaaactagc tgggcatggt ggtgcatgct tgtgatccta gctacttggg aggctgaggt   25260
gagaggatca cttgagcctg gagggcggag gttgcattga gccaagattg ccccactgca   25320
ctccagagtc aggcttcagt catgacttga tcacttaata gccatgtgac cctaggcaaa   25380
ataataactt cacctttctg tgaccctttc ctccctata aaatgggatt acagatacca   25440
ggctgtgatg ccattaacta tgtctggccc atggtaagca gctaataagt gttagttatt   25500
attgggaggc cgaggcaggc ggatcacctg aggtcaggag ttcgagagca gcctggctgg   25560
ccatcgtagc gaaaccccat ctctgctaaa aataacaaaa attagctggg catggtggtg   25620
ggcgcctgta ggcccagcta cttgggaggc tgagtcaggg gaattgcttc agcctgggag   25680
gcagaagttg caagtcacag tgagccgaga tcgtaccact gcactccagc ctgggtgaca   25740
gagcaagatt ctgtctgaaa aaaaaaaaa agaaaagaaa agtataattt ctgatgggtc   25800
atcatgggga ggggaacatt ccatgctaag gggtgcattc atggacaggg actgggactc   25860
aggagtccac agattatgat cagggagtgc ctgtcaccct ggggaaggtg gtggagaatg   25920
```

-continued

```
gggttggaaa tacagagggg gccttgagta acagattccc agttatctcc ctttcttcgc   25980
catacttttt atctcaagtt ctcagtttag gccttctgat caataccatc ctacaggact   26040
ctccccaaca tcctccacat ttcacacata tttcttctgc tggggaaagg tgcctgcctc   26100
tactctgcct actttttttt tttttttcttt ttgagatgga gtctcactcc atcgccccag   26160
gctggagtgc ggtggcgcca tctggcctca ctacagcctc cacctcctgg gtttaagcaa   26220
ttctcatgcc ttagcctcct gagtagctga gattacaggc acccaccacc acacctggct   26280 aattttgta tttttagtaa agacagcgtt tcgccatgtt ggccaggctg gtctcgaact   26340
cctgacctca agcgatccac ccgccttggc ctcccagagt actgggatta caggcgtgag   26400
ccaccgtgcc tggcctgctt acttcttttt atgcttcttc ctccttttttt ttgagatggg   26460 gtcctgccct gttgcccagg ctagagtgta gtggtccaat cagagctctc tgcagccttg   26520
aattccaggg ttcaagccat cttccctcct cagcgtcccc attagctggg actacaggtg   26580
ctcaccacca tgactggcta atttttaaat tctttgtaga gacggggtct cactatgtga   26640
cccaggttgg tctcaaattc ctgggctcaa gtaattctcc caccatggtc ccccaaaaca   26700
ctggaatcac aggtgagagc caccacaccc agccctcctt ttctttcttt ctgttttttt   26760 tttgttttg ttgttgttgt tgtttgtttt tttgagatgg agtcttactc tgtcacccag   26820
gctggagtgc agtggcgtga tctcggctca ctgcaacctc cacctcccag gttcgagtga   26880
gtcttctgcc tcatcctccc cagtagctgg gactacagct gcatgccacc aagcctggct   26940 aattttgta tttttagtag agacggggtt tcaccatgtt ggccaggctg gtctcgaact   27000
cctgaccttg tgatccacca gcctcaggct cccaaagtgc caggattcca ggcatgagcc   27060
accatgcctg gctgggcctc cttttcttaa agcagtgttt tggtttctcc cacagtattc   27120
tgaaaaggag gacaaatatg aagaagaaat taaacttctg tctgacaaac tgaaagaggt   27180
gagtgtggtg gcacccagcg agctctggtt tctcctgggg ctggtcttga agccatgata   27240
gtaactcctt tcttcttatc taggctgaga cccgtgctga atttgcagag agaacggttg   27300
caaaactgga aaagacaatt gatgacctgg aaggtatgag gttaccatct aaatgtttgc   27360
cttgccctgc cttcccctct gggacacatc cacggacagt tggggaatgt ttgtggaggg   27420
gctgggttgg gctttgtttg ccttaggaaa gtaaagcgca tagtgatgtc atatctggat   27480
gtcctggaac actggaatag gataatgcaa agcattcagg cttgaatggc ccttttttttt   27540 tttttttttt ttttctatga gacggagtct ggctctgtct cccaggctgg atggagtgca   27600
gtggcgccat ctcggctcac tgcaacctgc gcctcccggg ttcaagtgat tctcctgcct   27660
cagcctccca ggtagctggg actacaggcg tgtgccgcca cacctggcta attgaattgc   27720
cactttcagg aggtaaaata tctctgctta gttagtccca tgagcaagta tagagaaaag   27780
agtatggctc tctctgatta aaaaaatatt aataataaat taaaaatctc aggccaggcg   27840
cagtggctca agcctgtaat cctagcactt tgggaggccg aggcgggcgg atcacttgaa   27900
atcaggagtt tgagactaac ctggccaaca tggtgaaacc ccgtctctac caaaaataga   27960
aaaaattagc caggcgtggt ggtgcacgcc tgtaatccta gctactgggg aggctgaggc   28020
agggagaatc ccttgaacct gggaggcgga ggttgcagta agccaagatc acgccacagc   28080
tctccagcct gggtgacaga gccagactcc gtctcaaaaa aaaaaaaact tcacaatttc   28140
cttctgtttg ctcatttctg atagatgcct tgcattttt ttttacatgc cttgcatttt   28200
tgcagaagct ctgtcccagg gagctcaaag cttatcatag tatttaaaaa aaaaaacaga   28260
aatacagaaa gtgtagggac tgcaataaag actagtctgc aagtctgggg cccacttctc   28320
```

-continued

```
ccagaatttt ttcaagagtt ccagtgttta acattcggcc tcagaaattc cagaatcttg   28380
gggttcaaat ggaatcttcc aaactgccca tcccacccag aaaggacaca ttcttcagac   28440
catatcttcc aatgtttttt tggggaagtg aggttcccat ataagggaaa atgccccatt   28500
ccaaaatacg acctttggac agggtgacgt cattggaaat ccgaaataaa ctgagggggtg  28560 gggaccagtg gggggaagct ctgtcacttc tggttaccac tgttttgaag cttcattgtg   28620
gctaatcccc ctgcagaacc tcaaaccact tagagatcaa ctccatagat ctttggtttt   28680
cttcatctgt ttcacatgga acacagcttt ctcctagtct gtgctttgtt tgctcacgtg   28740 ttttttttctt cctcttgtgg ttcatctgtg gcactccatt ccgacccttg ccttctgtcc   28800
cctgtacttc tgaactgtct ccctggggac ctccgccctc tagatgagtt atacgctcag   28860
aagctcaagt acaaagctat cagcgaggaa ctggaccacg ctctcaacga catgacctct   28920
ctctgagagg cagccaggtc gctgccctct gtccttctca catggtgcct cctacgcccc   28980
tgtgggcttc taggagctcc ggtggcctgc cttctggttt gaacgtcaga gccttcttct   29040
gatgtgtctg tgactctaca accgaaataa agacgggcag tcctcctctt catgcccccct  29100 cattctcatt ttctccactt gctgcctttg agctgtagct gtgtgcccctt aaccatagcc   29160 tgaaacacaa agtgggtggt tagcctctct cactcacaaa tgaaaagctt attacaaaaa   29220
gaaaattatg cctacaggat gcttttctga agacgtgaaa acaaaagcaa actgggcatg   29280
tgctctcaga taccgctgtt agctaacggc atctgcatgc caataatttt tttttgtttt   29340
tttgttttga dacagggtct tgctttgtca cccaggctgg agtgcagtga caccatcata   29400
gttcactgca acctccacct acaaggctca agctatcctc ccacctcgac ctcccaagta   29460
gctggaacta caggtgtgca ccaccacaca aggctaattt ttgtactttt tttttttttt   29520
tttgaggcgg agtctcacta tgtcgcccag gctggagtgc agtggtgcaa tctcggctca   29580
ctgcaacctc cgcctcccgg gttcaagcaa ttctcctgcc tcagcctccc aagtagctga   29640
gattacaggc atacaccacc acacctggct aattttttctt ttggattttt agtagagaca   29700
gggtttcacc atgttggtca ggctggtctc aaactcctga ccttgtgatc cgcctgcctt   29760
ggcctcccaa agtgcaggga ttacaggctt gagccatcac gcctggccat ttttgtactt   29820
tttgtagaag cgggagggtt tcactatgtt gcccaggctg gtcttgaact gctgggctca   29880
ggcagtctgc ccacctcacc ctcccagggt gctgcaatta caggcatgag ccaccgcgcc   29940
catccccaat ggtttttcct taaatagaaa ttgttgtgaa tggaggctca tccttgtaaa   30000
ccgcttaggc agcttaagag tcaacaggga tttggaaaaa ccagcaagcc tgtgtcaaaa   30060
atgaggctcc ccttgaatgg ggcttgagct acagattcaa acagcggcag tgacattttg   30120
atctccattt cctcctttttc ttgtgtcttt tctctgtgtt acactgtgag tgtggtgact   30180
ggggcttccc gtggctttac tcttcactgt tcatccagct cccagtcctg ggaggaagtt   30240
cacctccacg ccctgcccctt agaaaactga ctgtacaagg agtgaacggg cctccatgaa   30300
cagggaaagt gctgtgacgt cagaagacgt gaatttagaa ttctttttccc gaattccaga   30360 attgcctgag actgctaaca tcaatctcca ttcatatttc agttagttat aacaggaacc   30420
ttgctttagt ttagaatagc tcttaaggtt gacctgtggg taataaaagg tcatgctttt   30480
tcctacatga ggaatatgga gaaaacaagg tcactctttt tttttttttt tttttttttt   30540
tttttttttt caagacaggg tctcactctg ttgcccgggc tggagtgcag tggcgccatc   30600
ttggctcact gcaacctccg cctcctgggt tcaagtgatt ctcatgcctc agcctcccga   30660
```

-continued

```
gtagctggga ttacagtcgc ggaccaccac actcagctaa tttttgtact ttcagtagag   30720
atggggtttc accatgttag ctaggctggt ctgaaactcc tggcctcaac tgatccgccc   30780
acctcagctt ccaaaaatgc tgggattaca ggcgtgagcc actttgcccg gcccaggcta   30840
tgctttgctt ttttttttct tctttctttt tgagacggag tttcgctctt gttgcccacg   30900
ctggagtgca gtggcgccat ctctgctcac tgcaacctct gcctcacggg ttcaagcaat   30960
tctcctgcct cagcctccca agtagctggg actacaggca tgcgccacca tgcctggcta   31020
attttgtatt tttagtagag acagggtttc accatgttgg ccaggctggt tttgaacccc   31080
tgacctcagg tgatccaccc gcctcggcct cccaaagtgc tgggattaca ggtgtgagcc   31140
actgcacctg gcccaagcta tgcttttcta atgatcaaaa acataccaat ttgtcccaaa   31200
atttcaaata gtgcatctgg ttctcccctg catcctacca ccactaccac ctcaaattat   31260
cacagataat tgacatttag atgttcaagc cacatcttcc agactacccc ttgaacctgg   31320
aaatggcatg aaaatctcca actagatcct gaattttcgg tatccattgt tattcctcat   31380
cctatttttt tgtccaggtg ggaagctctg tccccattac tctctctatt catccattcc   31440
tccaaaatgc acctcccta aaccacctcc acctttccac cctcagcctc tccctgctcc   31500
taactgccgt ccatcctgaa cttctgcaaa aaccattccc ctcacacatt gccatatata   31560
tgcccttgga aagattacag actgtgtagg gggctggttt ttgtttggag tctgtgtgtt   31620
tgtccctgga atttctccag gcatttctgg actccaccct ttgaagtaac tatgcagcct   31680
gtctatccag ttattctacc taactaagca cataagtgga atttcagaga ttagtgctat   31740
ggccgggcac ggtggctcac gcctgtaatc ccaacacttt gggaggccaa ggcaggcagg   31800
tcacttgagg tcagaagttc aggaccaacc tggtcaacat ggtgaaactc tgtctctact   31860
aaaaatgcaa aaattagccg ggcatggtca tgggggcctg taatcccagc tactgggag   31920 gctgaggtgg gaaaatcaat cacttgaacc tgggaggcgg agcttgctgt gagccaaggt   31980
cgaacctttg tactccagcc tgggcgacag agtgagactc cgcctcaaaa aaaagaaaa   32040 gaaaagaaaa gagattagca ctatggaggt ctacactatc tgttgatagt ctgtgagcct   32100
tgtcgtgatt ctcaagggca gttaacactt tcagggaaag tcattttatc tcagacctaa   32160
taacaaaata gatgctaaag catctgagtg acaagatgaa gcgaagtcag gatttgtagt   32220
caagagacca gggtttaagg cctggcgcag tggctcacac ttgtaatccc agcactttgg   32280
gaggccaagg caggcggatc acttgagctc aggagtttga gaccaatctg ggcaatatgg   32340
caagacccca tctctaaaat tattcataat aatattttat ttttaaaaaa tttttttaata   32400 aaataataaa taaagagacc aggatttaaa atcctagctc tactacttta accatgccaa   32460
cgtgaacaag ctgcttaggt tttctgcaaa ataaaggtga tatctctgtt atgaggatta   32520
aatgagataa tggagaaact ggctcgtcca acatagtcag cattcagtta acatctattc   32580
acccagactg gataggccca ggtcactgat ctgtctgata gaatcctccc aggtcatagt   32640
cacttgactc tgtgtgtgtg tgtgtgtgtg tgtgtgtgtg atggagtccc actctgtcac   32700
ccaggctgga gggcagtgac gcaatctcgg ctcactgcag tgtccgcctc ccgggttcaa   32760
gtgattctcc tgcctcagcc tcctgtgtag ctgggattac aggtgtgcgc caccacaccc   32820
ggctaatttt ttgtattttt aagtagagat ggggtttcgc catgttggcc aggctggtct   32880
cgaactcctt acatcaagga tccatggtgt ctcatgccag taatcccagc actttgggag   32940
gccgaggtgg gtggattgca tgagaccagc ttgggcaaca tggcgaaacc ccatctctac   33000
taaaaataca agaattggct gggtgtagtg gcacgcactt gtagtcccag ctacttggga   33060
```

-continued

```
ggctgaggta gaaggatcac ttgagcccag gaggtcaagg ctgcagtgag ctatgatcat   33120
gccactgcac tccagcctgg gcaacagagc aagaccctgt ttaaaaataa ataaataaga   33180
aaggctgcca tcttctgcag tcattttttt ctttctgtaa atttccaggc tgatgatatc   33240
acattttatg aggcattttg ctttccccca gcattttaat gagtcttggc cttgtccctt   33300
atcagccatc acttactgca aactaagttc tctctcgtgc tctgtcacgc atagctctaa   33360
atggcgtctt ttttctctct ctctttcttt tttaatttaa attgtttcat cagctcagtt   33420
acttaataac atgcctgtag aatggcttaa atttcgcatt tacctggggt ttgtctccgt   33480
tctcctggat tcatagacag ttacacaatt atgtgtataa tttaaacagc cattcccaga   33540
agctccgaag gaaagatggg ttacaggatt ttagatttaa ctatcaaagg ctcaggggct   33600
aattaactag cacttgggtg gaaatttata ttaagtcaca catatctagg actgaaatct   33660
tcatgtagca gcacgtcata ggttctgaag tatttctcct ttattcctca tcataacccc   33720
cacaccacgc attgatatcg ttacccccat ttgacagacg gggaaaacag acctaggaag   33780
gttagatgct tacttaagtg atacaactgg agcttaagtt caggtattct gactcagggg   33840
ttaccagagt tcacaaggaa aaatacagga caccaactta aatctgagtt tcagataagc   33900
aatgaataat tttttaatca taagtatatc tcttgcataa gtacatctca tgcaacattt   33960
gggatatact tacactaaaa tattatttgt ggtttatctg aaattcaatt taactgggcg   34020
ccctgcattt tatcttacaa ctgtgactcc caaatttggt gcttgttcct tagtattctg   34080
tgatgttctg ctgtaattaa aaatacaaag tactggacag gcatggtggc tataacccac   34140
ctgtattccc agcactttgg gaggctgagc agatgggttc cttgagccca ggagctcaag   34200
accagcctgg gtaacatggt gagaccctgt ctctagaaaa aatgcaaaaa ttggccaggt   34260
ggtggcatgc acctgcagtc ccagctatgc gggaggctga ggtgggagga tcacctgagc   34320
ccagggaggt caaggctacg gtgattcgtg attacgccac tgcacttcag cctggacaac   34380
agagtgagac cctgtctcaa aaaaaaagta ctttctctct tgtgactttc accctggcag   34440
tttcaggttt agaaatcttt ggggggggtgc tgggcatggt ggctcacacc tgtaatccca   34500
gcactttagg aggccaaggt gggtggatca cttgaggtca agagctcgag accagcctgg   34560
ctaacatggt gaaaccccat ctctactaaa aatacaaaaa ttagccgggt ggtggtggca   34620
cgcgtctgta atcccagcta ctcgggaggc tgaggcagga gaattgcttg agcctggcag   34680
gtgaaggttg cagtgagcca agatcgcgcc actgcactcc agcctgggtg acagaatgag   34740
accctgtctc aagaagaaga aaaaaaaaca aatctttttt tttctttcat ttaacaaaga   34800
cgcttattaa tttatctttc cccatactct taatcctcac cagagaaact tgcccaggcc   34860
aaagaagaga acgtgggctt acatcagaca ctggatcaga cactaaacga acttaactgt   34920
atataagcaa aacagaagag tcttgttcca acagaaactc tggagctccg tgggtctttc   34980
tcttctcttg taagaagttc cttttgttat tgccatcttc gctttgctgg aaatgtcaag   35040
caaattatga atacatgacc aaatattttg tatcggagaa gctttgagca ccagttaaat   35100
ctcattcctt cccttttttt ttcaaatggc accagctttt tcagctctct tattttttcc   35160
ttaagtagca tttattccta aggtaggcag ggtatttcct agtaagcata ctttcttaag   35220
acggaggcca tttggttcct gggagaatag gcagccccac actttgaaga atacagaccc   35280
cagtatctag tcgtggatat aattaaaacg ctgaagacca taaccttttg ggtcaactgt   35340
tggtcaaact ataggagaga ccagggacca tcacatgggt agggattttc catccagagc   35400
```

```
caataaaagg actggtgggg gccggggtg gctattgtgg gaagtcataa cccacagata   35460
gatcaaccta agaatcctgg cccttctcca ctctccacca tgcaggacaa acatcttctc   35520
aagcagtcaa cgtagaatgc ttgggaaata gtcataatta cccacatata gtaattaata   35580
gatggtaatt aattgatcct tgatgtgatg ttcttttgca tatttccttc attctaaagt   35640
tgttccctgg ccgggagcgt tggctttcgc ctgtaatccc aacactttgg gaggccagga   35700
cagatcactt gaggtcagga gttcgagacc agcccagcca acatggcgaa accatgtctc   35760
tactaaaaat acaaaaatta tggtgacgcc tgcctgtagt cccagctact cgggaggctg   35820
aggcaggagg atcgcttgaa cccaggaagt ggagactgca gtgagccgat atcgcaccac   35880
agcgctccag cctggtcgac agagtgagac tccatctcaa gaaaaaataa aaataaagtt   35940
gttctctgaa gagcaaatgt ctcattccag taatgaccca ctcagcagga atatggtgga   36000
gttcagtcca attcaggtca gccatatcca aaagaccaca agtcattact aagttgagca   36060
aaagagtttt tatctattag cagaaagggc ctctctggca gcagagatta aaaactggcc   36120
caacttcatt tccatacttc agggaacagc aaattgagga tttacttatc taggacttga   36180
attccttctt tgggaccaag ttaataaaag accaagaaac tcctgattaa actggataat   36240
gaaggattct gtagacaggg ctgcacgtat cggctttgtt tgacttctct tttctcagtt   36300
aacatctcag agctagaaca ttccacattc cccagcagcg tgtgggggct gactaaagtt   36360
tacaattcca actaaaaatc accctgcttc tggcttatct gaatcccta cccaccccac   36420 cccaccaccc tactcctatt tattcagcac cacactaccc aggaaataca ctagcaaatt   36480
gtgcaatgga ataaaatcca cactttagat tcttgcaact gtatcatatg taatagtatc   36540 acttttcta cattttggtc aaataaattt ttacataaac tacaatttgc gtgaatttta   36600
gaatgtgtgg gggtacacag agcatttgg ttcaacaaat gttaaaggga tggaaaggga   36660
aaataaccag agccaagaat gtagacaagg ttatctattt gctttatact gtgacttcat   36720
gatacaagga tattacagtc tcattgcagg cgagagcact cagcctcggt cactcgaaaa   36780
ctcctggcct tccttatccc ctacgctgcc taagccaggc tgtgaagaat gagtaggatt   36840
ttaagagata aaagcaggga aaatcatctc tgttgcctga gttaggaaga tctgcctagc   36900
taaggctgag ttacacatac aaaggaaagc agaccagcat gggcaccata gtgagacccc   36960
gtctacaaac aataacaaaa atttggccag gtacagtggc caaattacac ctgtaatccc   37020
agcactttgg gaggccgagg ctggcggacc gcttagggcc aggagttcag gaccagcctg   37080
gccaacattg tgaaacccca tctctactaa aaacacaaaa atgagctggg catggtggtg   37140
cacacctata atcccagcta cccgggaggc ggaggttgca gtgag              37185
```

<210> SEQ ID NO 102
<211> LENGTH: 21625
<212> TYPE: DNA
<213> ORGANISM: Homo sapiens

<400> SEQUENCE: 102

```
gtacttaaaa tgtttaagga ccactgatgt attttggctt catgtatcaa ttagatttag     60
attttattgt tttagagatg ggggtctccc tttgtcgccc aggctggagt tgagctcacc    120
tcagcctcaa acgcctgggc tcaaactatc cttctgcctc agcctcctga gttgctggga    180
ctaccatggt gtgccaccaa tttttataga gatgtgatct cgctgtgttt cccaggctgg    240
tcttgaactc ctggtttcaa gtgatcctct tgccttggct tcccaaagtg ttgggattac    300
aggcgtgagc caccgctcct ggccccgatt tattaataga tcttataagg acattttagg    360
```

```
cctcacgcat cagtttctta ggacaagctt ttctctgcac tgcataataa atcagacggc        420
agtgcaacaa aaaaacggtg atgatttccc gaagaacaaa ccaagttcag aagcctccct        480
aattgtcaga acagcaggta gcctgggcgg agctctgagg ctatccttaa acaggcgcac        540
tgagacgcaa ggcgctggaa acaaaagagc tcctccttgc gcccttccgc cgccccactt        600
agtcctgctc cgccccggac accccgcggc cccgcccctg tgcgcgctgg ttggtcctcg        660
caggcatgat gaaacttccc gcacgcgtta caggagccag gtcggtataa cgccagcgg        720 cctcgccgcc cgtcaagctg tccacatccc tggcctcagc ccgccacatc accctgacct        780
gcttacgccc aggtgagccg ggtcctgcgc cccgtgccct gcgccccgcg ccagcatcct        840
cctcgcgtgc cctggggctg ctccggaagg aagggggtgga ggatgcggtc ttcagcctgg        900
cacccggcag acgcggttcg cgggcgcctg ctgatgctgc ggctcctgcg gtagggaggg        960
cggggcggac gcctagcgat tgttacgcac ctgacagcta gcggaaggac ctttctgtcc       1020
tggttccctg aagcatcgag agggaaccgc ggccggcagg ccggaccgct ccggagagga       1080
ggcagcggca gtttgagccc ctgtaaatgt tatatgtgta ctttttttta ctatgtggcg       1140
tcgaagcctg tggacatttt cgcggtccgg gtccctgcgg cggacgggtc ggatcgtgct       1200
cgtggccagg gcgcagtcag gtgtcgcgtg gtcctgatct aggaagagac tgcggcctta       1260
tcaccgtctc ggtgtctgct ttcaccttca actgcccccc tcctcacctg gaccgctcac       1320
cctcctcctc ccctctcacc ccgccatccc caccagtccc cacctgtctc tgtagactgc       1380
aagactcatc aagtgacttg ctgagcaaac cctgccgaga gaggtctgt ttagggacac       1440 aggcgaccaa gtacagaaaa aggcaaaaga actagcatgc ctttttcaat ggctgtcatt       1500
ttgcagggct ggcttcagat gattgttata gctttaaata aaaaggacag ttttcatctc       1560
ggcccgtggc ctacattatt tctttactgt ccattgccct gggcgcttga ctaataattt       1620
aacagcagtt tttttttta aattttaaat catgattcat agcattgctg taagagtaat       1680
tagaggtaaa gtagggcttg aacctgtctg tagttggtta cttactgaga tcttaatata       1740
aaagtaaagg gagagggtga agttgtaagt agcactaagt ggaatagaaa ttaaatgcac       1800
tgaaactgcc atgtccagtt cggtaggcgc tagccacctg taactgttga gcacttgaag       1860
tgctggctag tcctaactga gatgtattgt gttaaataca ctggattttg tcgttggagt       1920
aggaagaaca gtgtaaaata tctgctcgat aatattttat attgattaca tatatgttaa       1980
aatgttacta tttgggacat actgagttaa gtttatttaa aattaatttc acctttttct       2040
tttaatgggg ctactagtat atttaaaatt acatatgtgg cttacatata tatttattgg       2100
acagcactgt tctagaagtt taggaagaaa taagaaaaat attgagaaca ggtagcggca       2160
gtaggaactt tgccctccta taagactgat tccaataaaa ataataggtt atagttttaa       2220
ttggcttttt cctactagaa aaaataagtg tactttacat gcctctttgt tctcccttt        2280 tcccctccag tttagtggtt agaatgtatt tattatagca ggattaatac agggattcac       2340
taagcagcgt taagaagact taggtaactg attccctgat gaccatactt gattttcaaa       2400
gcactttcct aacccgtttt aaattgatat agagtcaaag gcagatggct tattagtagt       2460
catctcattt aaatcttatg gaattttttcc agtaaatctc aaataaatttg ttataggcta       2520 tttgggctat ttggtcaagt gcatggaaga gacagcatag gacatgtggt acttcatttc       2580
caaattgctt gagatgattt tcattctaac catatattat ttggttctgg ttttccggaa       2640
aagccagcta aacctttggt tcttttagat ataaatgaaa tatcatcaaa gaatagctca       2700
```

-continued

```
aagtgactta tgcaacttga atgtatattt tttccttagg gtgtttatcc caaactattt    2760
gggcatttgc tgcaattcgc agttttttta aaaaaaacac caaaatagtt atttttcaag    2820
ttagagatgt tttaattaaa acatcttgtt tttggtgtat ccattgacat tctcaaaacg    2880
gaatgtatct ggacctctgt gtacaatctt cgtagcactc agacactgaa cagaaaggca    2940
gtcatcactg ccaaacaggg cccaaatgcc acacatggtg caatgtgtca ttttgagctg    3000
gcagcagcca aataaaacag ccctttattt cacagttgag aatttgaaat tggaaagtaa    3060
ttaacgtatg taagggtgat ttatttgctt ccgggcttat agggatgagc taagtttttt    3120
attagggatg ttgttggtgt atatgtctca cctactttgc ttccttactg aacaatgcaa    3180
ctttgagaca gaaatatttg agaacatttt tgtcagtgag gacattttga tagtgaatat    3240
tttgtatctt ctattaactt gaaatgtttt atttgttata aagccaggat atctgatatc    3300
aaattaaatt gttttttttt tccctttaga ttttcttcaa tcacatctga ataaatcact    3360
tgaaggtaac ctagatgtaa tatagtgaaa tgcttgaaag agctgcgtat cttttacact    3420
tacagcagta tgattttctg ttgtacccat tatatggtac ctgcagctag ttcagataaa    3480
gagggcattt aactgtcaag ggaacctgag aggagactct agtaatctgg aaagtctgtt    3540
ggatctttga gggattttgg gatggtgaga gtggggctag gatctctggc taggttggag    3600
ccagcctgca tttgtatctg tatcttggaa gcaaacttag aatgcagaga cagatgtggc    3660
atggacgctg tcagctctag ccaaccacta aatcctaagg tgggagagat gcaggctttg    3720
gctaggtgct aagctgctgt agccggttga atgtagaggt cactatcttt tccgaatacc    3780
tgtaagtaaa ttaaatcatt ctctactccc atgtgcctgc caacctaatg ggaaatcgct    3840
atagaaaaga tggtttaaat tttagtcttt gaagtggttt atgcacgttt ccggaatcaa    3900
gatttaatgc agagttggat tggatattga atatttttga tttgtctgct tttctctcca    3960
tagaaagctt atagcttcat tgcaccatgt gtggcatttg ggcgctgttt ggcagtgatg    4020
attgcctttc tgttcagtgt ctgagtgcta tgaagattgc acacagaggt ccagatgcat    4080
tccgttttga gaatgtcaat ggatacacca actgctgctt tggatttcac cggttggcgg    4140
tagttgaccc gctgtttgga atgcagccaa ttcgagtgaa gaaatatccg tatttgtggc    4200
tctgttacaa tggtgaaatc tacaaccata agaaggtgag gagaaagaaa ccagatgtct    4260
ggatgcgatt aaacttcaga gtttgttggt tacgatgatg ttacatattc tgtatcatgc    4320
tttttccttt gcaaagcact ctatgttcgt tatctcattt gctctaagta tgtaaatagg    4380
gaactgatga ataaaaaggt gagtgaaatg acttggtcac aaaaaaagtg ataaaaatgg    4440
ggattacagt tcagtttcat tgactcttag aattttttct ccttctcccc agcttttcat    4500
tttgaaaaaa ttcctaacat acagtaaaga acagaacaac aagcacctag attaaatagt    4560
cattaatgtt ttgccatagt tgcttgattt ttctttctac acacacacac acacacacac    4620
acatgttttt gctgaatcat ttgagagtac agtgcagata ttatgacact cctaaatata    4680
taagcattta tctcctaaga ataaggacat tcttctacat aacatcaatg ccattattaa    4740
acctaagagt ccataatacc acctaatatc cagttaatac ttaaatgaaa tttccctaag    4800
tgtcccaaga atatttttat ttatttattt attttgagac agagtctcat tctgtcaccc    4860
aggctggagt gcagtggtgc gatctcggct tactgcaacc tctgcctccc aggttcaagc    4920
aattctcctg cctcagcctc ccaagtagct gggactacag gcacctgcca ccatgcccag    4980
ctaatttttt gtattttagt aaagacaggg tttcaccatg ttgcccaggg tggtctggaa    5040
ctcctgagct caggtaatct gcccaccttg acctctcaaa gtgctaccaa gaatatcttt    5100
```

-continued

```
atagctggtt cttgtttgtt ttgagccaga tttcattcaa ggttcatgca tttggttggt    5160
atgtttcttg gtattttttg agacttcttg atagatacct gtcaggcatt gatagagatt    5220
tacatcctaa tcacattttg gacattttta tctgtgaaca atagcttttg tcattgtttg    5280
ttgcctgctc ataggaagac tcttaataat agtcttctca tttaaaaagt tttaaaatag    5340
ttattcagga aattcctttt acacatttct ttattccttt attaagggtc tactatgcac    5400
cagacatcat ttttctaggt gattggagat gaaatggtga aaaggaaagg caagaatgga    5460
atttcctgct agtgggaggt agaagaagag agtattaaaa attttttcta agtcaaataa    5520
tgtcatatac atgagaacgc taggtggtat tatggcatta tcagcttggc tttcccctta    5580
aatgaaatag gaagtgccct gtttcacttg aacagtgtta tttcttttat taaaaagtta    5640
caagaagtta aatattttga aaataattaa tttctattct aaattagcca aatgttatat    5700
ttgtaaaagt agagaagttt gttccattgc ttctaccaag catctaagtt tatgtagttg    5760
gggcagctag cagtctgtct aatgagcaga atgtatactt taggcttata taaagtattc    5820
agaaatcccc cccacacctc cttttttggta aaaataaagt ttaccactac aataaaatac    5880
agccagaggt gtactgggag tagaaggaga ctgaatgaaa gaaaggagga atggggtaaa    5940
ggctggggca aagagcaggc cctctccctg caggggagta tcagggcctg cagccaagtc    6000
aaatgacagc atgacgtcag gaggcaagat ttgagggctt ttatttaagg tgcagcattg    6060
gagtttggtt ttaggagagt aggaagtaat acatccgtta cccaaaggac ccttctcctt    6120
tttaaataag ttacctgcaa agtttaggcc aaagaggtgg gtaaggtaga tttgggaagc    6180
tgttgcttac taatatcacc gaatgcttta tggtcactaa cccttcaggc agttcagccc    6240
agaagagtca gcagaagact gtttacaggc ccccacctgc tagttacaga tcatccctga    6300
tagagcagag aggggtgacc aggtagtgac tttgtagtca ctggaggcaa agcccatttt    6360
tggacagttc agtgaggact tatagacaaa agattcacaa attatggagt gagttggatg    6420
gagtgtgaag catatttatg ggtcatgcac atacataata ggtttacttt ttgaaatttg    6480
aaagcatgtt ttaagcttat ctaggatttc cacctgattt aaacctcttc tttctctaat    6540
gtcagccaaa aacccgagta caaagaagaa agaggaatac atcaaggact tttcatcctc    6600
atagtttgcc attaatggct catagtttgc cgttgatggt ggagagtgtc agaattgggg    6660
agtagcctaa tcaaaccttc ttactctgca tgcagtggca gacagtccct ttgctgttct    6720
tttggggaat gcagactaat aaagcgccac cgtcattta tctatcagta aggagtagct    6780
ttaatgctgc tgcagtggtg gaagcactgg gcattgtcat ccacccctgg ggaccagcag    6840
ctttgttttg gatcatgtat ctgttattgt gatggagcca tttattttc agggaatgat    6900 gccaaatgat gtttgtccct ttgctttaca tttttatagc taggactttg aagctgaact    6960
ggaggaactt cttagccaat actatcttct caaatcaaaa gtttatagtt gcaaaagaca    7020
cgttttttag tgtcatggca accaggcaac ctattatctt aacttaaatt tagaggttga    7080
gcatccctaa tctgaaaatc tgaaatttga aatgctccaa aatctgaaac tttttgagca    7140
ctgacatgac attacatgtg cattttgatg tcacagtcaa aatgcaggtg taaaacacgc    7200
agtttatttg gcgttcccta gggaaaaaag accctctcag cccgcttcag ctgcagtata    7260
acttttctac acatgcccgg atttccccat gcaagcacgc ccacaaaggg taatagaatg    7320
gcacatgttc aagctggata cgccattggc aggatcccca cagatgggac ttatgtgcat    7380
tatccattgt gtattttttgc ttattttctg ctctgtggtg ttaagatact gaaaatgtca    7440
```

-continued

```
aaaagacctg tagatatttc tatgagcagc agtgataagg aaaagtagaa acacttataa   7500
cacagaaagt caagctgtag gagaaactgg actgtagtat aaaggtatag atgacatggt   7560
gaaaatgtgt gatagagata ttgaaggact agagctacct gcattcataa cagaacaaga   7620
ggtcatgtca gtttataaaa tcaaagagag ccttccaaga caaaagccat tgttaatgaa   7680
gcagatgact ctggagaaac atttaaaagt catctggccg aatgcctctt caatctcaga   7740
ggacccgctt cctagttgct cagctgcttc tgatgtttct tctcacctga aaaaggaaaa   7800
aaaaatacag tgtatagtaa cctttttaatc aaaacgcagc attgtaggtg gagtctgaaa   7860
gcctgccatt gtttgtacag ctgtttaaca gctgatgcag gtattctggt gattctacta   7920
tgctacttat tactttctta ctgtattaat ggtatgtcat attttataag catatgaaaa   7980
tgattgctca tcagcagcat aataaattca gagtcaggaa tgatggtcaa tgatgtcaaa   8040
cagccacaga ttttccacat ggtagctgag atagtgaccc ctttgctttc tgatggttcc   8100
atgtatgcaa actttgtttc atgcacaaaa ttatttgaaa tattatataa aattacctttt   8160 aggtttgtg tataagatat atgaaacata aatgaagttc atgtttagac ttgggtctca   8220
tgcccaagat atctcacata tatgcaaata ttccaaagtc caaaacacaa aacacttctg   8280
gttccaaaca tttcagataa gggatactca atctgtatat atataaatat atgtatgtat   8340
tacatatatg gtatgtatat aatatacatt tccatccctc cacaggttac tgttctggca   8400
cattcccatt atgttctgtt tatcagactg caactaaaat tttcatgggt tcggctttat   8460
gttgaacaga atttgcagaa tatgagttga agcgaaccat agtttaataa tgctgtgatt   8520
ctcctaaatc accaaagtgc atgaaaggat tatagagctc agaaatactg aagcatcttt   8580
gcaataaaaa attattagtg aatgtacaag gagtctaaca ttttggtttt gctttcgctt   8640
cctaagatgc aacagcattt tgaatttgaa taccagacca aagtggatgg tgagataatc   8700
cttcatcttt atgacaaagg aggaattgag caaacaattt gtatgttgga tggtgtgttt   8760
gcatttgttt tactggatac tgccaataag aaagtgttcc tgggtagaga tacatatgga   8820
gtcagacctt tgtttaaagc aatgacagaa gatggatttt tggctgtatg ttcagaagct   8880
aaaggtaata ataaatttttt ctatagattt tcattattgt cttggttgta cgttttctttt   8940 taaattatat ttgaaaatct cttagagagc aatccagaat tttacaagtg actaagttat   9000
gagtctttac ctttttttaa aaaaacagag gagttgtact ctcctttttca gcacttaaat   9060 tctgtaatcc ttgaaggatg attctttagt gcagtcgttt attttttgct gtgctaatat   9120
gctctacatc tagcttgatc ttaagtgcag ttttaagttt tcctgtgtca tactataatc   9180
gtagggttga ctctgcaatt attgcattgt ggtactttgc gcagttatag cacagcaagt   9240
gttaggattt ctaaaacagc tttattgata attcacatac catgtaattc acccacttga   9300
agtatacagt tcagtggttt ttagtatatt cacagatgtt ggtaaacaac actccaatca   9360
gttttaggat tgttttttcca cctcaaaaaa aaccaaatca aatcctatgc cctttacctt   9420 agttttttgct ggcaggatca actaggtttt tgtttgtttg tttgtttgaa gagatggggt   9480
cttgctcagt cgcccagccc aggctggagt gcggtggttt gatagctcag tgcagccttg   9540
aactcgtggg ctcaagcgat tctcccacct cagcctccct agtagctagg agtataggca   9600
tgcaccacaa caccctgcct cctgtgccct ttagctttga attccatctc tccatatcca   9660
tcagctgcac ccctgcagtt gtagcccgg caatcaccag tctttctgcc tctggattcc   9720
ctattctgta tgtttcatat gaacgggatt atatatcata ccggctttttg tgactggatt   9780 cttttcacttg gtatagtgct ttcaagatttt gtctatgccg tagcatgtat cagtacttac   9840
```

-continued

```
ttcttatggc caaatgatat tccattacat ggatacactg cattttgttt attcgcttgt    9900
cagttgatgg acatttagga cattatttac cccttttggc tattatgaat aatgctgcta    9960
taaacattgg tgtacaagtt tttgtgtgga catttccctt gggtgtatat ctaggagtag   10020
aattgctggg acacatgata actatgttca gttgaagaac tgccagacta atttttgaaa   10080
tggctgcatc attttttatt cactccagca gtgtattaaa atttctgttt ctccacatct   10140
tcacaaacag tgtgtgactt taattctagc cattctagtg tatgtgaagt ggtatctcat   10200
tgtgattttg atttgtattt tcctgttgac agtgatgtcc agcatcttat cttatgctta   10260
ttggccattt gtatatcttc tttggagaaa tatttgttca gatcctttgc cattttttt    10320 tcctgttagg gatcatttta ttttaaaaac ataatagact ttattttttt ttttgagcag   10380
ttttagaaaa aattgagagg aaagtgcaga gagttcacat atgctcccc tacagtgccc     10440 ctgcccagtt ttccccactc ttaacatctt gcattactgt gctacattta ttagatttga   10500
tgaactgata cttatatatt aactgaagtt catagtttac ataagggttc actcttttgtg 10560 ttttatagat ttttggattt gacaaatgtt taatgccatg tacccaccat tacagtatta   10620
tgtagaacag tttcattgcc ctaaaaatct cctgtgctcc acttattctt tcctcccgtc   10680
ctcttcctcc taacccccca gtcattactg atctttttgc tttctctctc actttgcctt   10740
tcccagaatg tcgtataata gttgtaatca tatagtatgt agcttttttca gactggcttc  10800 tttcacctag cagtatacat ttatagttct tctgtgtttt ttcatggctt gatagctcat   10860
ttattattat tattattata ctttaagttc tagggtacat gtgcataacg tgcaggtttg    10920
ttacatatgt atacatgtgc catgttggtg tgcttgctga ataatattcc atttgtttgc   10980
atgcaatgca atttgtttat ccattcttga attacccatt tctaattgag ttattttgtc   11040
tttttattac tgaattgtaa tagttcctta tgtattctag atacaaatcc cttctgttca   11100
tcagggttgc aggatacaag atgaatatac aaaaatcaat ggtatttgac acactttaac   11160
tgaatactac atacttaaaa tgagcaatca aaatgaaatt aagaaagcaa cttcatttat    11220
aatagcatca aaaagaataa aatacttaga aataaattta agaagtgtaa aacttgtact    11280
ctgaaaacta taaaatgttg ttgaaagaaa tgagaggaga tctaaataaa tggaaaagta    11340
tcccatgatc atgatttgaa ggcttaacat tgttaagatg gcagtcctcc ctaaactgat    11400
ttacagattt aacttgatcc ctatcagaat cccagatgag ttctttgtga aatctacaag    11460
ctgactctca aattcatatg gaattgcaag agactaagaa tagccaaaac aatcttttga    11520
aaatgaagaa caaagtagga gacctcatat taactgattt taaaacttac tacaagacaa     11580
tggtaataag gacaatataa tactgacaga aggatagatg tatagactag tgggatagaa     11640
ttgagagtca gaaatgaacc catacatata tgatcaactt attttttgaca agggtgccaa     11700 gattattcag tggagaaaga agtttgaaaa ctggcacagg ggcaaccaga tatgtaacca     11760
tatgcaaaac ttggagttga atctttaccc aacatcgtat acaaaaatta tggatacaga    11820
aaaatggatc aggccaggcg cgatggctta tgcctgtaat cccagcactt tgggaggccg    11880
aggcgggtgg atcacgaggt caggagatcg agaccatcct ggctaacaca gtgaaacccc    11940
gtctctacta aaaattagcc gggcgtggtg gcgggcgcct gtagtcccag ctactcagga    12000
ggctgaggca ggagaatggc gtgaacccgg gagacggagc ttgcggtaag ccgagatcgc    12060
gcaactgcac tccagcctga gtgacagagc gagactcatc tcaaaaaaaa aaaaaaaaag    12120
gatcaaatga atcagttttg aactaatcca cttaaatgta agggctaaaa ctataaaatc    12180
```

-continued

```
ccgagaagca aacatagaag taaattgtca tgaccctgga tttggcaaag ctttcttaaa    12240
tatgagacca gcaacaataa taaaaatcaa tgaattggac ttcatcaaaa ttaaacattt    12300
ttgcacatca aaggacacca tcaagaaagt gaaaagacgg cccacaagtt ggaagaaaat    12360
acttgcaaat catgcatagc actttttgat ggtaaacttg aggaagacat ttatctttta    12420
tcccttacct gtgcagcagt aacatcctaa tatctctctc cctgcctctt tttgccattc    12480
tttaaattct ttctcactta attttcagat ttaatattgg ctgaagcagg gataatgaga    12540
tcaatcaaag gggtccttag gacactagtc acagtgtttg tactaatact ggaactggct    12600
tattttcagg catttctagt gtgatcagat ggcaaagaac aagcatatat atatgtcagt    12660
tgccaggact gctgggaaag cctggtaaag agaacactgg ggaaaagcag cctcctgctc    12720
ccctgggcct tctttgagcc tgatgatcac ttgatatgga acttaccctc tgaaattcct    12780
taattgttct tttctatatc cttgacactg tccttttcca gaccaaatta tctcatctgg    12840
aatactgcaa caattttctt ttctcagtgc ttttagaata acctgtcaaa atctcatctg    12900
attatagtat tgcctgctta aaaccttta attactcccc attccctatc cgggttgtgt    12960
agctcacttg agctctgctg ctggtgagg gaatctgggt cctttttctg gtatttgaat    13020
tcagtgctac acaggttact ggctgggtag acaatctcaa attgtaaatc acgagtattc    13080
catgtagata gtccattacg atctacaata aaacattgat gtttgtatca aagatcatgg    13140
tgatgagagg ttgggtactg tactgtctgt gagaatttat tgaggaaatt taagttatat    13200
ggttttattc acatatagtg tataacaact agttaaggga tagatgtctt cttatctgac    13260
tttaaagtag gtaaaagtgg atcattgtac ttgttaaagg tctgggaacc atggctgtgt    13320
tctgaaaata cctcagtgat gacaaataaa tgactcccag cctatcataa cattaggact    13380
ccagttcatc cctttgcttc ataagtgtgt ctttttcctt tgtgtatttg ctttagtata    13440
gaaaataggt tttcttgatt agaaatctaa gaagaagaaa ttgaacactg gagatttttc    13500
tatttctttg aattacgaaa agttagtgta atttggcagt atatccctgt gccattattg    13560
tctctcaggt aagtagatgg tagggcttag gaaaatagaa aatttttttt cctattttgc    13620
ttatttaatg ggtatgtgtt tgtattaaaa agggaaaata ggaatgtaga tgatgttaac    13680
taatcgtgaa agttattggg aagggttacc taatttgaat aaaggtatca ttgtgaattt    13740
ctaggtcttg ttacattgaa gcactccgcg actccctttt taaaagtgga gccttttctt    13800
cctggacact atgaagtttt ggatttaaag ccaaatggca aagttgcatc cgtggaaatg    13860
gttaaatatc atcactgtcg ggatgtaccc ctgcacgccc tctatgacaa tgtgggagaaa    13920 ctctttccag gtagcagaca cccacccacc tattccccat ccttctccaa gggaaaaaaa    13980
ttttaagttg tattctccca tcatttgaat gatttttagtt tcaagaccta cttcctattt    14040
tgtttggagg gaacacatta agatttggca cactccacca ttgagtaaat accatcatga    14100
tagatgttga tgattgtgta tttcatttca ataactaatc cagcccaaga ttttctggag    14160
ctgtttgatt tactgctgtg tttataggtt ttgagataga aactgtgaag aacaacctca    14220
ggatcctttt taataatgct gtaaagaaac gtttgatgac agacagaagg attggctgcc    14280
ttttatcagg tgaagtcaat taaaaaaacc taattatatt tcatgtgtgt ttaattgaaa    14340
tgatttgtag ccatcccttt ggttttttact ataaaatatt tactgtatga tttactcttt    14400
ccttcattat aggatggaaa tgattttttta taagctgtat ttaatagtca tagtcatact    14460
ccaacttgag ttacactata gctatgttat tggtgttaag agtgagtcag tgaatgttct    14520
ttagaattct gtgtagtgat ttttaaccaa ttcaaatact actattatca cagtttatat    14580
```

-continued

```
attttttctct tgttgaagtt gatttcagtt tataaaactt ggcggatttt aaatagtaaa  14640
actatgatct tggtgtttat caggaatata catcttctgt ccctgtctta tgcaaggcac  14700
ataactagga cacttccact tcctcttttg catgtagggg gcttggactc cagcttggtt  14760
gctgccactc tgttgaagca gctgaaagaa gcccaagtac agtatcctct ccagacattt  14820
gcaattggca tggaagacag ccccgattta ctggctgcta gaaaggtaag gtgctgtctc  14880
tgtcccttgt gtagtgtagt tagagtagac ttgttattag aatgaaaatg gagtcaataa  14940
tgggtgattc tactgctgct gtattgactg ggtcaattgt tttaaattga ttgtattaaa  15000
atagaatgaa atggctgttg gatatgcact gtgttgtaca ctgtcctctg tgtactttta  15060
tctgttatga cccatgcaat tctcacaaag accctatgat gataagtatg ctcttttgaa  15120
agtaaaggtg tctgggcatg gtggcctaca cctgtaatcc cagcacttta cgaggctgag  15180
ggaggtagat tacctgaggt caggagtttg aaaccagcct gagcaacata atgaaactcc  15240
atctctacaa aaaaatacaa aaactagcca ggcttggtga cgcatgcctg tagtcttagc  15300
cttatgggag cctgggtgac agagtgagac cttgtctcaa aaaaaaaga aagtaaaggc  15360 ataagtcagg tgcagtggca cacacctata gtcccagata cttgggaggc tgtgggggga  15420
ggtctgagct caggagttca agtccaggct gggcaacgta gcaagacccc atcttgaaaa  15480
attaaaaaaa cgggtttttt gttcgttttt tttttttttt ttttttaaac gtaaaggcat  15540
agtatcatgg ctaagactgc agactttgga acctgacttg tggtttgaaa tcctggctct  15600
actcatttat gtaaccaaaa taatagtgtc tgctatgggg aaattttaag gtgaaatgat  15660
ataattcatg taaagtaagt agggtagaac ttagcatgta gtaagtactt aatgagtgtt  15720
agctgttatt attattttg aaagtactgt atttagaata ctgtgggcag agggcagctt  15780
gtctgtattc agtgagcggg agacctagtt cccactatgg aggactttcg tagcatggat  15840
gagaaaaagc tagagagcag tctcagtgca aggtaatcaa tgccgagaga atccaaaata  15900
gccaaggaaa gcagaatgag gggaagggcc attctatata agaataacat cctggatata  15960
aaattaggca tttaagaagg accaaaaaag accaagctta gcgtgggacc atgttggact  16020
agagagagat gaggtgggtt aggtaaaata ggtagagagg gaggtgccaa ctgggagaat  16080
ggttgaagcc ttggcaccag aggagctgag gggagactta cttcctggtg gtggagttga  16140
agcaggcgag ggaacagtgc tggatggggc ttgtatgtgg tgggctgtaa agtcattttt  16200 cttttttttcc cttgtttagt tttcaccatt gttaattcat aaagctttgt gaactcccat  16260
catgtttgat tttcaaggga agttattttc tttaacaagt aaatgggtat ttctttatat  16320
aataaggtgg cagatcatat tggaagtgaa cattatgaag tccttttaa ctctgaggaa  16380 ggcattcagg ctctggatga agtcatattt tccttggaaa cttatgacat tacaacagtt  16440
cgtgcttcag taggtaaggt attatgatat tcttaaataa aaagctttt ttaatactga  16500 aaaaaatgta aggtttaaaa aaattatttc aagccatagt tttaaaatgt tatttaagga  16560
tgaatgcaaa ttaaatccct atgttactga ttatttaaga ccacttaaga attctctgaa  16620
tctcttttgg agtgaaggga atagtaaata cgtagttcaa cctccacatt gttggtgtca  16680
ctgttggtgt ttcccagggg agcagataca tattttctgc cctctacctc ccatttctct  16740
tatagtttct tgggctacag tctatataca gtgaggaaat aggtcttttt ggtaatgcat  16800
ttttgataag aaatagtcat tttagatata ttccatcaca caacttacca gtcactagct  16860
atcattgctc tgcaaacaat actaattta tcttgtagat aatgtatcta ctgagattgg  16920
```

-continued

```
aagtatacccc caaatcagac tgatccagtg ttattgagcc tttatatgct actgcctccc  16980
ttgagagact tgccttggaa ggcaaaaata tcttaggtat tacaatggtt tatggccctc  17040
caaaacatca cagtaaataa gcagatagac aggatagctc tggtattgga atttcatggg  17100
gctggggtga ggttaggaaa ataagtgtct aaaaaggctc tctagctgag gtgataataa  17160
aaacaaggtt gagaagaaac actggtttag agagatgtgg tgcaggacca aggaggcaag  17220
tttaataact tatatagtct ccccagcttt atgtgaaatc tggtaaatgg ggagtggcag  17280
ggggaaaata cccatcaaaa ttaacactaa accaccaaaa cggttattct tattttttgtg  17340 tcataatacc actatgaaag gcatgatttt taggtatttg agtcattgtt cagcttagca  17400
aagttttgag gtggacattc ttggtctaaa aacattagaa ttttaaaacc tgtttagaaa  17460
atgacaaaat ggttccgggt tattttattt tacagtagta ctttttggatt aagtacatat  17520 aaatggctta taaatacaag gtcattattg tggaaactac tttatattaa tatgaagtcc  17580
agtatagtag taaagctttc aattatttcc aaaaatcaaa tcaaaggcat ttttggtgga  17640
aggttatgtt gacattaaag ttaatttctc tctctcattt aaggtatgta tttaatttcc  17700
aagtatattc ggaagaacac agatagcgtg gtgatcttct ctggagaagg atcagatgaa  17760
cttacgcagg gttacatata tttttcacaag gtaaccactc tgaagtggag ggatattcat  17820
gctatattaa gaaaagtatg aattgtttga ctattttcta tcatctttca gtatgacagt  17880
gatatttttg agtatcttgt gaggttacaa aagggaatct gatagtgttt gctttctatc  17940
tcttggggaa gaaagaaatt ttaatgtgtc agataatttt tattctttaa aactagttac  18000
agctgggtat gagggctcat gctcataccc ccagctgctg aggaggctga ggtgggagga  18060
tcacctgaac ccaggagatt gaggctgcag tgagctgtga ttgcaccact gcactcctgc  18120
ctggttgaca gagtaagacc ccgtctctta aaaaaaaaaa aaaaaaagtt aaaaataaat  18180
aaataaaact acttaagctt gagaatcccc tttctgccat ttcttagcat cctgtggaat  18240
tatgactgtt gcccattgtg ttcattttat tctaatatta gcagtttggt aggaaggaag  18300
gcatgttttg tgaagcattg cttacctctg ttcagttatt tactcccttc cctaaatttg  18360
tttaactttt tgtcttatcc acctttagga ttggagaggg agaaagaaaa actgctttgt  18420
gtgccaaaag caaaactctt ggtgtttttg tttgtgaaat aggctccttc tcctgaaaaa  18480
gccgaggagg agagtgagag gcttctgagg gaactctatt tgtttgatgt tctccgcgca  18540
gatcgaacta ctgctgccca tgggtaatat ttttagaggc tattgtaaaa caaaaacaaa  18600
aaaacaccaa aaacaaaaca aaacaaaaag ctcaatacccc tgagaaaata aaaatcaata  18660
gctgattggc tatatgttac atatagttgg ctatatgtta caaagtgtga cttttataga  18720
gaaaatgaag ctgtttctta actttgtccc aaaaggatta ggccacattt caaagtggtg  18780
ttgtggtata tggagagaag tcttcttcca taggttgttt gaggtggagt tttcacctt  18840 aaagggtaac aacattctgc tcacatctga acaaccaaga tggaagaggc aaggctgcta  18900
cagcagctac cgttaagtgt tttaaagaga agtaaagatc gtaaacatca tgtgacaagt  18960
agtgagtgcc caccatgccc atgtggtgct gtagtgaccc tgagggaata gagtagtgaa  19020
gatacaaggg gtttgattac attataaaga accaggtttc tttggttatc atttctagtt  19080
gtctaaagtt atgttgaaga actgaagact tttactgtac aggataaaca actgacatta  19140
aatgtcttag ttgcctctgc tgaatcacac ctagataagg atataattaa atatgggttt  19200
gaggaatgaa ctgaatctgg tcattatcct ctctgcttgt cctaactaga gtcactaggc  19260
ttcaggaaac cggtgatttg gaatttgatg aaatatagtg ggacactggt ttatatcgca  19320
```

-continued

```
tattgtatgt gaatttttaa tcagtggcaa aaaaatactg tatcgtcatc acaattgtta   19380
gaagagatgg tctcacctag taaacactga gttaggtcta ggcaaggtat tttcttaatg   19440
attgggtcac tcatgttttg taacttttttc tgcttttttga aatatgcatt taactattcc   19500
tagaagggaa agtaaaagta atagtctcag ttagttttac tccctagatg acatgatata   19560
tgtattattt taaatgaaga tttatttttt gtatctattc attagtgtag ggcagtcatt   19620
aggaggcttg tatgtgactg tatgacctta acatttctta agatctggtt gaattgatgg   19680
gaaactgaat cagaacctaa cctggcaggc actaaatacc cattttaatt tagattttct   19740
tcttttctcc tttaagtctt gaactgagag tcccatttct agatcatcga ttttcttcct   19800
attacttgtc tctgccacca gaaatgagaa ttccaaaggt aggtaaatca actcaaggta   19860
aaactgtcca ttgccatcag attatatttg taattttttac ctgatgctcc ttttttttgtc   19920 acgtcagaat gggatagaaa aacatctcct gagagagacg tttgaggatt ccaatctgat   19980
acccaaagag attctctggc gaccaaaaga agccttcagt gatggaataa cttcagttaa   20040
gaattcctgg tttaagattt tacaggaata cgttgaacat caggtataat gtctttaaaa   20100
acattttcag gaataagaca gtttggatgc agagctgtca ttgctgttca ttttgtattt   20160
agtttgaatg atacatgtat ttagtttgaa tgatacatgt atttagtttg aatgatacat   20220
acatcagata tctctctgat aggatgtccc tatcagagag attcagagtc tctgtaaaca   20280
attatctctt ttgtaagaat tacgtaagaa ttaagtagca tgaaggatta taaagtagca   20340
tctagaatcg agagagagag gagacttact actaatcatc actgattttc atttatcaga   20400
tttttgggca cctgctgggt gccagatctt gttaggcaca aatgactaaa acagagccac   20460
caagtattaa aaatatgcat atgagtgttc tttaaaaggc actgcagcta tccatattat   20520
gaatacttta gcattttcta agtgatgggt gattcaaagg gtctcataca agttacagtc   20580
acgtcttaac attttctgtt tcgtgaaatg agactaaaca caagtatttc ctgccatttt   20640
aagccatttt gctcttatat gcttattctt acaggttgat gatgcaatga tggcaaatgc   20700
agcccagaaa tttcccttca atactcctaa aaccaaagaa ggatattact accgtcaagt   20760
ctttgaacgc cattacccag gccgggctga ctggctgagc cattactgga tgcccaagtg   20820
gatcaatgcc actgacccct ctgcccgcac gctgacccac tacaagtcag ctgtcaaagc   20880
ttaggtggtc tttatgctgt aatgtgaaag caaatatttc ttcgtgttgg atggggactg   20940
tgggtagata ggggaacaat gagagtcaac tcaggctaac ttgggtgtga aaaaaataaa   21000
agtcctaaat ctaaaccatt gctgtagtca tttatgttca tgcagtctct tcataagagg   21060
taactagaac tgttttgctg tatcacagta aagtggaggg taagctagga aaagggaaaa   21120
tgatcagatg tctgcaagaa ctcacagccc tctcctggca gagctgcttt agatgacatt   21180
tgcatcttgt gcccgtgtgg cttccttcca gtccttgcct catcttaggg acgtcatcaa   21240
aggactacac tatttttgtt ctgcctacat tcctaacagc tgcctaggca gactcagact   21300
tgaatcttct ataggagttc atcacagctc tattttgcaa gatagtagtt cattttttttc   21360 tcttttatgt tgagccaaag ccacttctgg agacttgtcc tagagcaggg gtcaggcttt   21420
ttttgaattt ttaatttgtt tttaataaag agccagatag taaatatttt aggctttgtg   21480
gacctctttt ggaactgttc agctctgcca ttatagtgca aaagcagtta cataggcaat   21540
atgtaaacaa acgagcgtgg ccatgttcta ttaaaagtta cttatgaaag cagatggtgg   21600
gccagatacg gcctgtgggc catag                                        21625
```

<210> SEQ ID NO 103
<211> LENGTH: 13776
<212> TYPE: DNA
<213> ORGANISM: Homo sapiens

<400> SEQUENCE: 103
gtgcgacccg ctaagggccc cgcgaggtgg gcaggccagg tattcttgac cttcgtgggg        60
tagaagaagc caccgtggct gggagagggc cctgctcaca gccacacgtt tacttcgctg       120
caggtcccga gcttctgccc caggtgggca aagcatccgg gaaatgccct ccgctgcccg       180
aggggagccc agagcccgtg ctttctatta aatgttgtaa atgccgcctc tcccacttta       240
tcaccaaatg gaagggaaga attcttccaa ggcgccctcc ctttcctgcc atagacctgc       300
aacccaccta agctgcacgt cggagtcgcg ggcctgggtg aatccggggg ccttggggga       360
cccgggcaac tagacccgcc tgcgtcctcc agggcagctc cgcgctcggt ggcgcggttg       420
aatcactggg gtgagtcatc ccttgcaggg tcccggagtt tcctaccggg aggaggcggg       480 gcagggtgt ggactcgccg ggggccgccc accgcgacgg caagtgaccc gggccggggg        540
cggggagtcg ggaggagcgg cggggcgggg cgccgggggc gggcagaggc gcgggagagc       600
gcgccgccgg ccctttatag cgcgcggggc accggctccc caagactgcg agctccccgc       660 acccctcgc actccctctg gccggcccag ggcgccttca gcccaacctc cccagcccca        720
cgggcgccac ggaacccgct cgatctcgcc gccaactggt agacatggag accctgcct        780 ggccccgggt cccgcgcccc gagaccgccg tcgctcggac gctcctgctc ggctgggtct       840
tcgcccaggt ggccggcgct tcaggtgagt ggcaccagcc cctggaagcc cggggcgcgc       900
cacacgcagg agggaggcga cagtcctggc tggcagcggg ctcgccctgg ttccccgggg       960
cgcccatgtt gtccccgcg cctacgggac tcggctgcgc tcacccagcc cggcttgaat       1020
gaaccgagtc cgtcgggcgc cggcgggagt tgcaggagg gagttggcgc cccagacccc       1080
gctgcccctt ccgctggaga gttttgctcg gggtgtccga gtaattggac tgttgttgca      1140
taagcggact tttagctccc gctttaactc tggggaaagg gcttcccagt gagttgcgac       1200
cttcaatatg ataggacttg tgcctgcgtc tgcacgtgtt ggcgtgcaga ggtttggata       1260
ttatctttca ttatatgtgc atcttccctt aataaagagc gtccctggtc ttttcctggc      1320
catctttgtt ctaggtttgg gtagaggcaa tccaaaaggg ctggattgct gcttagattg       1380
gagcaggtac aacgttgtgc atgccccgta tttctacgag gtgttcggga cggcgtagag       1440
actgggacct gctgcgtact ggcaaagcag accttcataa gaaataatcc tgatccaata       1500
cagccgacgg tgtgacaggc cacacgtccc cgtgggtctc tgtggaagtt tcagtgtagc       1560
gacatttcag ataaaagtgg aaaaagtgaa gtttggcttt tttcatttgt atgcagtcct       1620
aactcttgtc acacgtgtgg gatttatctt tttccataac ttactgaaaa cccttcctgg       1680
cgggctgaac ctgactcttc ctgagctgag tcctggactg gcacactgat ggctctgggc       1740
tcttcccggt caagttataa caaggctttg cccatgaata atttcaaacg aaaatgtcaa       1800
gatccttgcc ggtgtcctgg gattacaagg tgaatcttgt catgaagaaa ttctaggtct       1860
agaaaaaatt tgaagattct tttttctcttg ataattcact aatgaagctt ttgtggttga      1920
aaaataaaaa gtgaggttta tggtgatgtc aggtgggaag gtgtttata catcaataca       1980 ttcgagtgct ctgaagtgca tgtaataata gctgtttctc tgttgtttaa aggcactaca      2040
aatactgtgg cagcatataa tttaacttgg aaatcaacta atttcaagac aattttggag      2100
tgggaaccca aacccgtcaa tcaagtctac actgttcaaa taaggtaagc tgggtacaga      2160

-continued

```
aaaagaaaat taaggtcttt gatgtttcta ctgtcctatg ctgaacaaga atgtctttaa   2220
agctgattac tggatgaaat tatttaacag atgacgaaga agaagggatt cttggcaatt   2280
cgctggccgg tgtcatactc tattaggcct gcaacatttc cagaccttaa actgatagaa   2340
cattttaatt gttttaattg ttttttggaaa tgatgggaga gttcctaagt ggagtataaa   2400
ctgtggagag atgaaccatc ttgagtaggc actgaagtgt gctttgggtc atgatagatt   2460
aattaatctc atctaaacat tgatgtcttt ttctgttgct gtctagactg tgaacaatgt   2520
ctaacacctt agggaagagg tggggaggaa tcccaatgta tacattgccc ttaagcagtg   2580
tttgattcat tcatctttgg actccatgaa tcgaaatctg gtagaataca tgatcttagt   2640
ggaggaggcc aaatgcgtga ctcactgagc ctggcagagc agaaatactc tgctgtctgc   2700
accctctggg tctggtgtgg ctctgcttct tggtgcctca actctgactg gcagctgtcc   2760
ccaggaggcg ataattcagc atgttcaatc taaaggttat gacttccttg atggttttca   2820
ccatattctt ggcaagtttt tggttttttga aatgttctag gaggcttggt agagatctta   2880
tgaaatagag aatagctgct gtggaaatta ttttaatgct aattacataa aagtacaaaa   2940
gtagcactag ctaaaacaaa aggtattttg ctgttctgtt ttgtttttagc ttgtgccagg   3000 cctttttacag cattaggaat gcaacttcta gataacgatg catcttttaa gtgaatgttc   3060 ttgttttttca aaatgaactt catgacagta gttgccaaac cagcaaggag aacttgcatg   3120
catacgtgca tgcatgtgtg gatatgtatg ggggtggggg gagagaaaga tgaaggaatt   3180
tcataacatg aaataatgat tacagttctg gtcaaacttg tcaattcaga tttcaccaat   3240
tgagaattag taagtaattt ctctgataca ggcctgaagt ttaccttagt aaacacttta   3300
cttccatatg gtaaaaatta gattttggga ggaatgctta cctcctaaat atattcaatc   3360
taatatttga gggacacatg ggaatatatt tatgattcat ctgcttttta aacataagcc   3420
tttgttaact gtaagttctt gaactttata aggctgctgt tatttaaatg agcacagctc   3480
ctgatctgca aacagcagag cgcagggcta cagcttgggg gatgccagcc gactcagggt   3540
ggtcctatgg actgaacaat ctcttgctgc tgtactggag ggcctgggag cttttccatc   3600
agcctcggcc tgaggtgtgc actcttctcc tgcccacccc aggaataaat gagattcctg   3660
gttaaaaagg accagagcag tcattttaca gttgaggaaa ctgttgctct gagaagtgag   3720
ggatttattc atgactacac tgatggtgag tgcccatgtc aggtctggaa ccaaagtcta   3780
cccagtatcc acacaccacc atccctcagg tggctctgcc acagtctgat gggaggctcc   3840
aaagcgggag gaagaaggaa agtcttgccc actgcatctc ctcagttggc cttcctctct   3900
gcctgttttc cctccctaca gttagcatct taagcagctg ccctcttcc ctcccgactg   3960 ctctcactac tgcagcctgg ctccagccgc aggacactac tgctgtgcag aagcccctac   4020
ttggaactcc aactgcattt ttcacctttg ctaacagttt tcagtggtgg ttgggaaatg   4080
ttattggctt aagccttagc acaaaccgtc accggtgata ttcattccat ggaaatgttc   4140
tgaattctaa agctgaattt acaaagcttc tggaaaacaa cctgcaacca aattagtgac   4200
tgaatttttt agttaactca aaattccaaa tcagagggtt ttgcaatgcc tggaggaacc   4260
ttggaggctt ttaaagtgtt aatgctatta atggcattca gagggatttt ctacagaatt   4320
gtcccttcat tacctgttta tacagtttta ctacttacca gggtactgta taaatccttg   4380
tgctaaattt tgctatagag tatgtggtcc ctgctgtgag ctgggaggaa ccaaatactg   4440
tatctctatg ttacatagaa agccctagga gactttctcc tgttatctga acaactattt   4500
```

-continued

```
gctgtactga taaaaaggaa acagcatagt ctcattcact ttttgaaatg gaaatgataa   4560
aataaaacac attttggtca ttcgggaaca aaatacccte tctactttta tcacataaaa   4620
ttaaataaat agaaaccaaa atatttcagt atcaatctta gtttgtgcac tttaggataa   4680
agaatgtgtt tacccaaatc cttttggcct ggttacttag ttcagatttt gaaagaaaat   4740
atatttgtgg cttttatgtg tgaatttaga caatggaatc catgtggtgc ctcgtttttcc   4800 ctgagattat gtattaattc aacctgtaaa tgcaaaccat ctaatagtca gcgagaccct   4860
atagccctgc tgcttaatgg gggcacacaa gggcatgcag ccctcgtacc aggcagactg   4920
tgttcatatt aacagcatcg tggagaaact catgctgggg gacaggggag ggagatgtaa   4980
atgctcagca gggagatctg gagattcctg gagcaggtgg agttgggacc tggccttgaa   5040
cgatgggtct ggctctggca gtcagtaatg ccaaagggaa gagcagcata actgtcactt   5100
tccatgggac agaagtgtgt gaatcaagtt gcagtgacgc ttcacctatt tattattttg   5160
gtcatttaga agaatttcat tgtcagtaga agtcctttaa atcatttccc cttcagtgac   5220
gtctcacaaa agaaagatct gtctttagct ttttagtctc agactttatt agacagatac   5280
tacctgtact cttattctgt aatctttgtt gggatggatt cacatcttgc aaaggaaggg   5340
aggcatgtag tataatgggg caaacagacc cagctctgcc actcgttaga tatgtgacct   5400
tctgcaagtt gcttagtgcc tgtgagcttc agtgtcctca tggataagaa agatccaaca   5460
ccttcttgga aggattatat caaatgaagt aacatgagta aagggtccag cagaatacct   5520
ggcatatagt ggagtcaatg aatgattaat aatattatta atagtggtca tgagagaata   5580
tatgtataac atgttattat gtagactcac tatatagact ctattctaca tagaatatag   5640
aacattatat aacaaacaac tataataagt agactatagt aaacaacctc actttgtctc   5700
agttgcctca tcttgatgga aaactgctct ttctctcctg ttaccctgac agagagcgtc   5760
tacattctaa aagaaagata tttaacaaaa tggttgagta cagatccaag agtcaaatag   5820
ctgtctggtt caaagtccag ctgtgtgatt ttgagctagt cacccaatct cactttgtct   5880
cagtagcctt atttgtaaaa acaaggcaaa ttacagagcc atccctgggg ttgctatgag   5940
gactcaaaca tgcatcccaa gtgctcggtg ttgctaggta tgatggctca cacctgtaca   6000
ttcagcactt tgggaggccg aagcagaagg atcagcctgg gcaacatagc aggacccccat   6060 ctctacaaaa caatgtttaa aaaaaagcaa agtgctcagc acagtgactg catcattagg   6120
attgattgta gggctcctga tgttagcaca gaacaccaca gccaggaagc agtctatctt   6180
gttgggtgca aattgtaaca ttccatttat gtttcttcct tcttttctttt ctttagcact   6240 aagtcaggag attggaaaag caaatgcttt tacacaacag acacagagtg tgacctcacc   6300
gacgagattg tgaaggatgt gaagcagacg tacttggcac gggtcttctc ctacccggca   6360
gggaatgtgg agagcaccgg ttctgctggg gagcctctgt atgagaactc cccagagttc   6420
acaccttacc tggagagtaa gtggcttggg ctgtaatacc gttcattctt gttagaaacg   6480
tctgaacatt ctcgtgatct tgtgcctttta ggggctacaa aattaaaaat atttattctt   6540
tttttctcag aaactggtat gtatcacagc cctcttcaca cattccagat gtggtaggag   6600
gttcacagaa tgtgaacttt ggagctgatg acagtgtcat caagtaactt tctccccag   6660 tctgtcccca gaccctgtta ctgtcctcag taaccggctg aatgtgtgtt gggagagggc   6720
gggccaggga agcgggtagg gataggaaat ccaccaaggc cggggtttta gctttttccct   6780 atatatatat catgtatcct gatttttctg tcccgttatc acactaaaaa tcccagttga   6840 ggattttttcc caaacggtca taaatcaatg aggaaagtcc atggtttccc tctgagccca   6900
```

-continued

```
taattagcct aattatgctg acctttttcta atcagttggc catgatttga gttccgtgat   6960
gtgccagcac ctgcccagcc atctgcctgt caccctcgtt ctggttttgg aaaggtggaa   7020
tactttcctc ctcagccttt gccctgtaa gctggcccta ggagccagta aaagaatgaa    7080
gagaattcct gtcaagtagg agatttattc ttttgccgca actgtggctc tgagctaggc   7140
aatttagata aatgcatgta gcacattgag tagagtgaaa ttagcttctc ttgtaaggcc   7200
agctggttag aatgaaggtg ttgtgtgagt gttaggccca gcgagagaga acagtttctc   7260
aaggtaggaa tggtgaaaag aaggggtgga cggacaacca accaaccatc ctcctctggt   7320
atctactttg agggttgaaa tagggggcct gaccccaggt gaatgtggct gccttcccag   7380
agcccccatt tgcaagaccc tccagacccc caggtgcttc tgcttgtgtc ttttgtggca   7440
ccaggcaaga atgtagcagc gtcagcagcc cctctggtga ctgtggcatg gttgacattc   7500
atttcccccc taattaatgg catcctcatg attctctttt atattaatag ttcttgagtt   7560 ttttgtaag ctacttcaaa tcctttgttg gtgcaagata gaagatattt tatgtgtttg    7620
ttttgcatgt gcacacacat atttggcctg tgaattgatg tttgtttttcc tgtcatttaa   7680 ccaaagcaca tgagataatt gagccattgc agagaccccg tggttaaatc cggcttctcg   7740
aggtaccaag gacatttcct gggctttctc acagccctac atatttttga acctaaaata   7800
tcgtagttta tgctaccacc ctgttcagta tagtagccac tagccacatg tggctgttga   7860
ccacttgaaa tatggctaat gctctaagta taaagtacac actggaattt aagaagtgta   7920
gaatatctca aaacttttttt atattgatta cacattaaaa tgattatatt ccagatatat   7980
gcagttgact caagcaatgc atggctgaga ggcaccgact ccctgtgcag ttgaaaatcc   8040
gagtataact tgactcccca aaaacttaac tactaatagc ctacctatcg gttgactgtt   8100
gactgcagcc ttaccaataa gataaacagt caattaacac acatttttca tgttgcgtgt   8160
attatatact gtattcttac aataaagtaa gctagaggaa agaaaatgtt attaagaaaa   8220
ttataaggaa aagaggctgg gcatggtggc tcgtgcctgt aatctcagaa ctttgggatg   8280
ctaaggcggg tggatcactt gaggtcagga gttcaagacc agcctggcca acatggtgaa   8340
accccatctc tactaaaaat acaaaaatta gccaggcgtg gttgtgggtg cctgtaatcc   8400
cagctacttg ggaggctgag gcaggagaat cacttcaacc caggtggagg aggttgcagt   8460
gaactgagat tgcgccactg cactccggcc tgggtgacag agcgagactc tgtctaaaaa   8520
agaaagggaa agaaagaaaa aaaagaaaag aaaagaaaag aaagaaggaa ggaagagaaa   8580
gaattataag gaagagaaaa tatatttact attgataaag tggaagtgga tcatcataaa   8640
ggtgttcatc ctcgtcatct tcatgttgag taggctgagg aggaggagga ggaggaagag   8700
caggggccac ggcaggagaa aagatggagg aagtaggagg cggcacactt ggtgtaactt   8760
ttatttaaaa aaatttgcat acaagtggat ccacagagtt caaacccatg ttgttcaggg   8820
gtcaactgtc tttggttaaa taaaatatat tattaaaatt aatttcacct gttcctttttt   8880 acttttttcta atgtgactac tagaaaactt aaaatgacat ctgaggctcc attgtcttcc   8940
ccttgggcca gcactaccac agaatgtctt aggattcagc tccaggccgc cacgcctgct   9000
tctttcaggg agctggttct atgcacatgt tttatatgag agataattaa gttgtcaatt   9060
gtgataacaa aacaggattt gactttgtac agaattcttt ggttccaacc aagctcattt   9120
cctttgtttc agcaaacctc ggacagccaa caattcagag ttttgaacag gtgggaacaa   9180
aagtgaatgt gaccgtagaa gatgaacgga ctttagtcag aaggaacaac actttcctaa   9240
```

-continued

```
gcctccggga tgttttttggc aaggacttaa tttatacact ttattattgg aaatcttcaa      9300
gttcaggaaa ggtgagcatt tttttaatttg tttttatgac ctgtttttaaa ttgtgaatac      9360 ttgggtttta caacccattt cttccccaat tcaaaaatag cagaacagag ttgttgagaa      9420
ggtgatggag tagaaggggg agcgcgcact gtggggaggg gtggacaaca ggcctggtcc      9480
tacctgtgac tctgcactac cctgtgactc tgggcagggc cccctcggag acccaggttc      9540
ctcagccaac cggctggatc aggtcatctc taaaggtccc gccatgctca catttctccc      9600
tctattgagg atcccaggca caaaatttgt ttttggttca atgcataata ctcccttcct      9660
ttttctttta ctgcagatat cttctaaagg ggctcaatag ggttcaatat gcctaaattg      9720
gatcttctca gtcttggaaa aggcattttt agcagtgatc aagggaaact gattagcgaa      9780
gtcacttcta atccttcacg tgtcagctgt gttcttgtag gctttgctta gaacctaggt      9840
ttttacttcc acagtgactt aataaagggg aaagaattga ctcagagccc agatgaatta      9900
agaactctat cttttttacag aaaacagcca aaacaaacac taatgagttt ttgattgatg      9960
tggataaagg agaaaactac tgtttcagtg ttcaagcagt gattccctcc cgaacagtta     10020
accggaagag tacagacagc ccggtagagt gtatgggcca ggagaaaggg gaattcagag     10080
gtgagtggct ctgccagcca tttgcctggg ggtatgggtg ctgtgggtga cttctggagg     10140
agtagctcca ccctcagggc tgggatatac ttccttggtt aaatattcag gaaaacaaac     10200
tgcctggagg tttttttgttg ttatttgttt gttttggttt tgattttgct ttggtacaaa     10260
aaagattttg gacatttaga aatgtttctg tgttgattgt gcccttgtat tagcaggtgt     10320
tttcttgagc acctgtcatg tgctaagccc tctgctgagc actggataca caaactgtgt     10380
ttaggattta gcaacaagtc acagatttcc ctgggcattt tttcatgctt aaattctaat     10440
tctgggggtg gcttctggac cagctgcagc aggacacagt agacattcgt gagtacccac     10500
tgtgggctgt tgccacagag gctgtagagt ctaacccatc aagggaaggg attgagtata     10560
tcaaatatac ccacatgcat gcatgtgtgt atatggcgga cacgtgtgtg tacatgcatg     10620
tgcatatgtt gggagctcag gcccattgtg cgaggaacag tccctaaccg gaagtgctgt     10680
gggccttcag actcttgcag gaagctgcaa gcctgtgtgt ctcgatccat gccttacagg     10740
gaaagtattc tgagtacttc cagtgaagaa aagagtcagg ggatataaac gatggcttac     10800
gctgggtgtg gtggctcacg cctgtagtcc ctgcactttg ggaggcccag acaggcaaat     10860
cacttgaggt caggagtttg ggaccagcct ggccaacatg gtaaaagccc atctctactc     10920
aaaatacaaa aagtagctgg gtgtggttgc acgtgtctgt agtcccagct actcaggagg     10980
ttgaggcagg agaattgctt gaacctggga ggcggaggct gaagtgagct gagattggac     11040
cactgtactc cagcctgggt gacagagcga gattccatct caaaaaaaaa aaaaaaagaa     11100
acaacgaaaa aagaaatgat ggcttagctc catgtgaaga tgatatttga acattttaaa     11160
acactttaaa taaactgttc tctcctgttt attgccactg acaggagagg tttctctttta     11220 cctctggtcc tgcaccccctc tgagccatcc tacccacagc cttcagtcat tgtcctaaag     11280
cctagctcta attccactgc ctctccttttt gtgcacacac acttctctgc ttccctggcc     11340
gttctctatc ttggagaggc atttcaaacg ccacttccac cagaaggcct tgctactgca     11400
ccaactagtt actatctctt cttcacccaa atcctggtag cactttggat ctcccacttt     11460
gcacttaggg ttcaccttcc gttataatca ttgccatcaa tctcagcatc gttttttaggc     11520 acttctttcc agccattgtt cttacctcca actacatatc ttttctggac tgtgcattat     11580
tcagtttatt aaatgcccat taaatgtgtt tagccattgt caattactct gaaacgttca     11640
```

-continued

```
ggttttgaca aattctttcc taatgtaagt gtggtggaaa gagtgaaaga aagtcaaatt    11700
gcacaaaaat aggatggtgt aatttggggt tatgccgtca attttgtcca ctgataaatg    11760
ggatttgagc tctccaagtt gactagatgc cctttatttt tcagaaatat tctacatcat    11820
tggagctgtg gtatttgtgg tcatcatcct tgtcatcatc ctggctatat ctctacacaa    11880
gtgtagaaag gcaggagtgg ggcagagctg gaaggagaac tccccactga atgtttcata    11940
aaggaagcac tgttggagct actgcaaatg ctatattgca ctgtgaccga gaacttttaa    12000
gaggatagaa tacatggaaa cgcaaatgag tatttcggag catgaagacc ctggagttca    12060
aaaaactctt gatatgacct gttattacca ttagcattct ggttttgaca tcagcattag    12120
tcactttgaa atgtaacgaa tggtactaca accaattcca agtttttaatt tttaacacca    12180 tggcaccttt tgcacataac atgctttaga ttatatattc cgcactcaag gagtaaccag    12240
gtcgtccaag caaaaacaaa tgggaaaatg tcttaaaaaa tcctgggtgg acttttgaaa    12300
agcttttttt ttttttttt tttttttgag acggagtctt gctctgttgc ccaggctgga    12360
gtgcagtagc acgatctcgg ctcactgcac cctccgtctc tcgggttcaa gcaattgtct    12420
gcctcagcct cccgagtagc tgggattaca ggtgcgcact accacgccaa gctaattttt    12480
gtatttttta gtagagatgg ggtttcacca tcttggccag gctggtcttg aattcctgac    12540
ctcaggtgat ccacccacct tggcctccca aagtgctagt attatgggcg tgaaccacca    12600
tgcccagccg aaaagctttt gaggggctga cttcaatcca tgtaggaaag taaaatggaa    12660
ggaaattggg tgcatttcta ggactttct aacatatgtc tataatatag tgtttaggtt    12720 ctttttttt tcaggaatac atttggaaat tcaaaacaat tggcaaactt tgtattaatg    12780
tgttaagtgc aggagacatt ggtattctgg gcaccttcct aatatgcttt acaatctgca    12840
ctttaactga cttaagtggc attaaacatt tgagagctaa ctatattttt ataagactac    12900
tatacaaact acagagttta tgatttaagg tacttaaagc ttctatggtt gacattgtat    12960
atataatttt ttaaaaaggt tttctatatg gggattttct atttatgtag gtaatattgt    13020
tctatttgta tatattgaga taatttattt aatatacttt aaataaaggt gactgggaat    13080
tgttactgtt gtacttattc tatcttccat ttattattta tgtacaattt ggtgtttgta    13140
ttagctctac tacagtaaat gactgtaaaa ttgtcagtgg cttacaacaa cgtatctttt    13200
tcgcttataa tacatttttgg tgactgtagg ctgactgcac ttcttctcaa tgttttctca    13260
ttctaggatg caaaccaatg gagaagcccc taattagatc agggcagagg gaaaaacaaa    13320
aaactggtag aaaccggcaa ccacagcttc aagctttaag cccatctcct acacttctgc    13380
tctgtaggtg cccattgtca cttctgttca catgctactg tcccaagcaa gtgaccaagc    13440
ctgacaatac tttgtctact ggagtcactg caaggcacat gacggggcag ggatgtcgtc    13500
ttacagggaa gagaaaagat aatgctctct actgcagact tggagagatt tcttcccatt    13560
ggcagtagtt tgactaattg gagatgagaa aaaaagaaac attcttggga tgattgtatt    13620
gaaacaaaat taggtaaaag gacaatatag gataggggaga gatataagtg gaatgagatc    13680
tctagagtcc attaaaagca agctagattg agagctcttg gagggcaggg actgggccta    13740
gctcatggtt tacagctctt gagggtgact gcacag                              13776
```

<210> SEQ ID NO 104
<211> LENGTH: 109476
<212> TYPE: DNA
<213> ORGANISM: Homo sapiens -continued

```
<400> SEQUENCE: 104
acccccgggg ccctccggct gggcggcgcc agcggatgtg agctcaggct cagcggtcgc      60
attttgcgag tggctccgag acacacaatg cagcagaagt aaattcccca gcagcaaagc     120
cgcctggccg cacagaagta agtaactaac cgggcaacca cctagcacca tcttcccggg     180
cacaggagcg gagacccggc ctcaaccaca accccaggcc agcagcacag acccaagaac     240
tgcgtggtca ggcctttccg cgtagccccg cccgcgtagc cccgccaaac agccaatgga     300
cgcgcagctc gacgctccgc gcacctccgc caaccaacta gaaaaggtcg agcagacggg     360
cggggctact ccgccctctg cttctgcttc tcgattcctc ttctgggtct catgctcctc     420
cttcttttgc gccgaatgcg ttctccaatc ggatccgtcg acccccctag gtgggcgtgc     480
ccggcagccg acggggcggg gcggatatga ctggcgggcc gactagtgct ggttgccacc     540
gccggtttag aaatcctatt ctcgcgccgg ggactggatt tttccctacg tcagcgcagc     600
taggcgatgt cgggagcgag ctcggaccga gggctcagtt gcgtcagtgc cgcgcgcgtg     660
ctcgtcgggc gcgcgtgctc gtcggcgcg cgcgcttccc ggccagactt ggggccccgg     720
cagggttgga aaatgatgga agaggcggag gtggaggcga ccgagtgctg agaggaacct     780
gcggaatcgg ccgagatggg gtctggcgcg cgctttccct cggggaccct tcgtgtccgg     840
tggttgctgt tgcttggcct ggtgggccca gtcctcggtg cggcgcggcc aggtgggtgt     900
ccgcgccccg ggtcggttgg gacggctgct tcctagggac ggggcgctcg gagtgaacct     960
gtggtgcctg ggagtggagg ggcccggcct ggggatcgga cccggggtcg gggggcgcgg    1020
ccgctccagg tgtgtgcgga ccggggtcgc acccgaggcg cggggtttgg cgccccaagc    1080
ccttcttggc ccgggtcctc tgcccggcac cgcttcctcc gtgtcctgtt cgatggagcc    1140
gttcccagcg tccccccatc cctcgccgcc tcgcgcgacc ccgggtcccc cagacgcccc    1200
gaaacccgct ctggggcggg cgctgacctc ggcgggccgg agccctgcag gctgggcgcg    1260
cccgcgggcg ttcagtcctc caaacgcctg caggagggga gctggctctc gctcgtggag    1320
ttaatgtcgc ttggaaagag actgagagat gaaacttttg ctgcaggtta taatttgaaa    1380
ttttgacgtt catggtatcc ttgggtcaac acagctaaat ttaatggtgg aataaaggtg    1440
ggtgggagga cgctcatttc tcttgggtca tttttgtagt aagaatattt tgtaaacgat    1500
gtgctacctt tctatagcca aaccattctt aaaaaatctg tgtttttatt gggttcgtac    1560
tgtgttaaat ccggacagat aatccctgct cttttgaact cacaggatta ttgtaggaat    1620
taaatcattt gtgtgaaatc gttttttgaat tgtgaaactg cccttgacta tgtaagatac    1680
ttgtattgga gatgcccaaa catagtggaa gcagattgtc agcacgctgg cgtctttctg    1740
gaaacaagtt gtttattttg gattttgtat gatataattg tttgcatggc tgtattttct    1800
ctatcagcga cagaggatga tggagaatgg gagtttttac taaatcattg attgaaagtt    1860
attcaaaggt gatgatagaa gatttcaacg caggactgtt gaccttcagg aaactaatta    1920
cttgtttttc ttatctttgg ctgctttatt tgaaattaag taaatttgcc ccagtgtgga    1980
aatgttgaaa ctctgacaat gttttgaatg ggaagttgcc aaatttcttc tggttaaaac    2040
tacttttccg gtggtattct agatggttaa cactcaccga tgtttaaggt gaagacgatt    2100
atacatccgg agtttatta atctgtgatt ttttttttgtg tttgtaaatg taaataagac    2160 tgtatttta aatgttaata taaattgtca gtcattaccg acctgcatta ggtgagtgga    2220
atatcctgat ggtctttaac tgtggttttg gccagctcct cacttcggca tgtgtatgcc    2280
ccttcaaagt ttagccaccg tttatggaac tcctataaac accacacagt tgattgtaga    2340
```

-continued

```
ggggcagaag gtgaccaaat atgctaagcg catctgagag atgttgggga agatttttag    2400
agaaaataat atttgaactg ggctacatcg gtgatttttc aagtagaata gtagatacat    2460
tctaagcaga ggaaagtttt tgcaagagta tggtggggcg ggggcgtat  gaaagaacat    2520 gacttttttag gaaatgataa aaatgtcaat atgtcttcat gcagactata aaagggaggg    2580
atggaagatc aaactaaggt aggttgttac cagttgggaa gagtcttcta tgctgaacta    2640
aggggtttgg acttcacccc gtaggaagtt ctttgggcag tggaggtttt aagtaggggt    2700
gcgacctaat ctcattttct gttaagaaaa cgggcaacac ggtggaggat agaatctagg    2760
agggagagac tagaggctgg gacaccggtt aagaggcttt tgtaatagtg tgcagtgagt    2820
caactcttgt ttctctcggg gaacgttcat acaaaatcag ctgaccacat ttttgcagta    2880
taaggtgttt aaaacgtgca ctgaaacatt ttccaggatc gaaagaggaa tttgaggtac    2940
caggcacacg tcagttacat taggagttaa ttaggtttta taggattttt actacctttt    3000
ataacattgt ctcaatgagg aaatgcagta taatttccaa acagctaact ttcagtaaac    3060
tttttttttt tttttaaact gacaaaggta actgtgtcat tgtaaaaaat aagcggaatc    3120
aggtatgaaa cctcttctga ttttctaagg tagtaattat gaggaacaga tttagaattt    3180 tttttttaaac aaagactggc attctaaaga aaatgacttt gaaagcttac tcatggtgag    3240
tcactgtaaa atcatttgtg tagtaagaac ttaggtccat actaatctcg ttttcagatg    3300
ccagcaaaat atttgaattt gatatgtttg tgtttgtgcc gataggagaa tgtagccttt    3360
tacatttaag aatgatttgg ttttcaacct tttaagtaaa aaagaaagca tatataatta    3420
aaatatgtac aaacctagtt cctggtttcc aagacagttt tcaaaaagca cttgaagctt    3480
taacttacca aatttatatt tgctctttgt aaaaaatctg ggtttataat agaatttatt    3540
atggaatccc ccaaaagatg caagctctaa gtaactggaa gctttttctt gggaatatcc    3600
gcaagctcaa acatatgaca tagcctcata tttcttttc  cttttttggta tgtaacatat    3660 actggaggct tggagtcatg ccatcctttt gagtcagcgc tatggaactg cctcataaat    3720
gaatgcagtc cttttgtatc tcagtagcta atccctcaca gtcttttttt ttttgagatg    3780
gagtcttgct gtgtcgccca ggctggagtg cagtggcacg atctcggccc actgcaacct    3840
tcacctcccg agttcaagca attctcctgc ctcagcctta tgcctggcta gttttttgta    3900
tttttagtag agatggagtt tcacggtatt agccaggatg gtctcgacct cctgacctcg    3960
tgatccgccc acctcagcct cccaaagcgc tgagactaca ggcatgagcc accgcgcccc    4020
agcctctctc acagtctttg aatgggtcta atgtggaccc aactaaagtt gggtagcaca    4080
atgttgtttg tatattgaga gattattgta gtttattttc catttcatgt tgttatttta    4140
atcagattat tttccctaag tgatcatatg tgggacactt cttgagtcac atcttttttt    4200
tttctttctg agagacaggg tcttgctctg ttgcccaggc tggagtgcag tggaacagtc    4260
atagatcact gtaacctcga attcctgggc tgaagcaatc ctcctgccta agcctcctga    4320
gtagctggga ctgcaggggt gtgtcaccat gcttggctaa ttaaaaactt ttttttgtgtg    4380 tggagaggca atcttgctct gttgcccagg ctggtctcga actcctgggc tcaagtgttc    4440
ctcctgcatc agcctcccaa agtgctggga ttacaggtgt gaaccaccac acctggcctt    4500
aaatcacatc ttttaagagt gagctaggga accttagaaa ttaacttggt ccgtttttaaa    4560 atatgcagtt ctgtttgtat ttatttatgt ttatggtaat gtaagtattg tgttactaaa    4620
ccttactgga agaaaagaaa atgatatcac ccccagacat gttataatgt agggcagaac    4680
```

-continued

```
tcaaagggaa tgggacgttc cctttgatga attgttcttt taatgagatt tttcatgatt    4740
taagtcattt taggatgatt ttaacgtctt ccttctagta gtgtagaatc ttcatatgag    4800
tagaccccag gagagcctga ttctaatcag tcttattgaa aggctgagaa tcctgttgtg    4860
aagatatctt gggcctaacc tcccatccca gccacttaag agaagtgatt aagcagtctg    4920
tggatagcaa tacaatgaaa tacgattttg ctatcaaaat gacaaatgtg taggctatgt    4980
agatttgtag aaaagttgat acaaaagatg ttaatcataa aaagtaaggt tcactttaag    5040
tcatatgtga taattacaac tatcagaact atgtttgttt agctgtaacc atcagaagag    5100
gttatttatt caacacatat tttattgaat acgtactgta ccagtgcagg aagtacatga    5160
tgaataagat accgtccttg atctcaaaga acttaaattc tttgctggag gaacttaaat    5220
tgtctagggc attaaatctt agaaatgggt ggtgttttc ccaaagggac acttaaacaa    5280
acaacagaag ccatttcttt ttaaatgtaa agatgggtaa atatttaaga aaagtgtaac    5340
actaaaaaaa gtaagagtgt agacctagca gtagaaatta taattaagta tgtttgaagg    5400
tagttttttt tttttttgag atggagtctc acactgttgc ccagactgga gtgcaatggc    5460
tcgatctcag ctcactgcaa cctctgcctc ccaggttcaa gcgatccttc tgcctcagcc    5520
tcctgagtag ctgggattac aggcgcgtgc gccaccacac ctggctaaat tttgtatttt    5580
tagtagagac agggtttcac catgttggca aggctggtct tgaactcctg accttgtgat    5640
ccacccgcct cggcctccca aagtgctggg attacaggca tgagccacca cgcccagccc    5700
aaaggtagtt attaatatac ggtatgtatt tatctggaat tgacctggcg aatactagaa    5760
tgattaaaaa aaaaaaaaaa aaaaaggcaa aaactgcaat tactttgca ccaacctatt    5820 atatggctcg aaataatagt gctttgtaga tctaattgaa acaatttctc tacaagaaat    5880
actttggaaa cagaattatc ttatttatcc tgaatgtgga ggccaggttt attttttattt    5940 tctacagtgg aagtacttaa aagtggctgt ttgtttatgt agtaggcagg agaagcccat    6000
ggtttggagt tcacatttgt ttgctttgca attaggtaga attctttttt ttttttttttt    6060 ttttttttga dacagagtct cactctgttg cccagactgg ggtgcagtgg cacaatctgg    6120
ggtcactgca acctccacct cccaggttca agtgattctt ctgcctcagc ctcccgagta    6180
gctgggacta caggcacgca ccaccacgcc cggctaattt ttgtattttt ttttagtaaa    6240
gacggggttt caccatattg gccaggctgg tctggaattc ctgacctcgt gatccgcctg    6300
cctcggcctc ccaaattgct gggactatag gcttgagcca ctgtgcccgg ccacaattag    6360
gtagaactct tttaactcac ttccctgtac tacaattact attatgaaaa gtgtgctcag    6420
acttcctcta aaacacacta cagtgtatag aaagatctac ggagttagag aaagaaagaa    6480
gtgcaactaa caccttttcc tttctttaag attagacatg ttaagtttca tgtttcagtg    6540
gttcacgttt tctcttcagg ccgtttttctc tttttctttt tttttagacg gagtctccct    6600
cggaggttgc ccaggctgga gtgcagtggt gcaatctcag ctcactgcaa cctccccctc    6660
ctgggctaaa gtggttctca gctcactgca acctccccat cctggctcaa gtggtctcgt    6720
gcctcagcct cccgagtagc tgggacaaca ggagagcgcc accaggcctg gctaattttg    6780
catgttttgt agaggcaggg tttcaccatg ttggccaggc tggtctcaga ctcttgataa    6840
aataaatgat taattgtggc attttggttt tcaaaatgag aattgtgttt aaaatgcaaa    6900
agagggaaag aaagttatat gtaatcttcc tatatttagc ttttattttta cttcattggc    6960 agtctgggta aaaaattcat agaagacaga agacttggtt tctagtcttg gcctgaaact    7020
tttagctgtc acaactgggg gatgctgttg gcatctagtg ggtggaggcc agggatgctg    7080
```

-continued

```
caaaacattc cacagtacac aggacagcgc ccttacaggt tgaaggttta tacaaataat   7140
attaaagctc ttttttttata ttaatgtgga aaaatgttat tttggttccc atgagaaact   7200
gctactattt ggaatttaaa aaaaaaaaaa acaactaaag ggaatttggg gaaaatctat   7260
gcaggatatg aacaggaaaa aagaaaaaaa cctgacctag agataagaaa ggaattttgg   7320 gaaaaaaca tgggaaggag gattttcata caattagtat gtattatttt gatgacattc    7380
ccccagtatg tgcatttgtt atgatgtttt ggaacttttt atggcatggc tttaattcag   7440
aaagtggttg cttggatttt agaagcaaga tgtcaatatc agaataacag cccttacaca   7500
cagaaattat ttcagggtgc tataattttg aaagtctttt aaaaataagt gattagttac   7560
ggcattttgc ttttcaaatg agaattgtgt ttaaaatgga aaagaaggaa aaaaagttac   7620
gtataatctt cctatattta gctttttattt tacttcattg gcagtctcgg taaaagattc   7680
atagaagaca gaagacttgg tttctagttt tggcctgaaa ctataagtaa agtaaactaa   7740
ctttgcctat aaagtaactg aacctgtttc aaaatgaaag ctctttaaat acctgcctgc   7800
ccataagaac tacagatgct ttatttttgg aggcatttct ttttctctgt tatgtttggt   7860
tctgagttgt aacgaaaaaa cttcagtttg gttctatatt gtttagcttc tagtgtaaca   7920
gttgtctgtg tctatcagca tatgtattct ttattttttt tttttggcag ggtctccctc   7980
tgttgctcag gctggagtgc agttgcataa tcatggctca ctgcagcctt gatctcccag   8040
gctcaggtga tccttccact ttagcctcct gagtagctgg gaccacaggc atgtgccacc   8100
atgccccact aatttttaaa ttttttttgaa gagacagggt cttgctctgt tgctcaggct   8160
ggtcttgagc tcttgggctc aagtgatcct cctgccttgg cctcccaaag tgctaggatt   8220
acagggttga gctaccatgc ctggccagca tatgtaatct tgtctgtaat gatttactta   8280
aagagaattt ttttttaaaa agtgaaagca tgtttattaa gaaagtaaag gaataaaaga   8340
atggctactc cacgagcaga acagtggcac gggctgctca gctgagtata ctgatagttg   8400
cttcttggtt atatgccaaa caaggggtgg attattcatg agtttctgg gaaaggggca    8460 aggatttta gaccatataa ggtaacttct gggcattgcc atggcatttg taaactgtca    8520
tggtgctggt gggagtgtct tttagcatgc taatgtatta taattagcat ataatgagca   8580
gtgaggacga ccagaggtca ctttcctcgc agtcttggtt ttggtgggtt ttagctggct   8640
tctttaccgc aaactgtttt atcagcaaag tctctgtgac ttgtatcttg tactgacctc   8700
ctatctcatt ctgtgactaa gaatgcctaa ccttctggga atgcagccca gtaggtctca   8760
gccttatttt atccagcctc tattcaagtt ggagtcagtc tggtctgagt gctgctgaca   8820
tattttccct catccttta catgggaacc ttaatcctaa agattgtaga gggacaaaga    8880
tctatcttct gtgacttctt caggctgaat aggggcaatc atgttcctgc ctaactatag   8940
ggtatcttgt atccggggta gagaggagct cagtcacaca acgtcattat gctgagggcc   9000
attcacaact ctgagttctg ttgagttcac aacacaaaag gtgatatcta gaagattagt   9060
aagattaata attaataagt gttcaattta agaaaacatt cagtaagctt atcctgcatt   9120
cctacacaaa gattacaata gcaatatatt tcatgacagt atagcaaata agtaaaatta   9180
ttccaagtaa actaaataga aagctgttcc atgaactggg caattgttgg aacccagctg   9240
atatagggtc actaactgat tccaatatat gcccagaatt agaatactga tccagatgtt   9300
aacattagcc atccctcttg tttattctga gctgcagtta gagatcactg attggttcac   9360
tgaaataagc agagtcagtc caaattgcag ggaaaaactc agaaacaact gatgagacta   9420
```

-continued

```
gaatttaatg tcaggtgtac tatagttctt gaaacgtaat tttttccttt cctgtcctcc      9480
attttcatta aaaacaaatc atgataggac tgataggata tgatgggtag caaaataagc      9540
tttagtctta ttatgcttgg cctgattgtt tgaaataatt gcagtaagaa taattatttg      9600
ccacataggc acttttttaat tggctttgat ggaactttgt tccataagga atctcacctg      9660
agatgttttt taaagcagag ctcagccatg ggtttgcaca gttaaataca ggtatgagtt      9720
gggtaaattc ctctcctctt gaggtcccaa gataacttga cacacctggg actgtagata      9780
gtgacagtct ttatttacaa cagatcagga acctcgtaca gggactgtgt agacaaggta      9840
tgtggccagt tttctcaagg ggcttttatc ggttctataa atcaagtttg attccttaaa      9900
ggaaagcaca acattccagt caaaacttgg taaaataacc agtttctcca gttgtgtcct      9960
gtgcaaaaga aaacagattc ttacagaaat ataagggatt gatgggtaaa gagtttaaaa      10020
gctgtttata catgcagtac attggatatg atataatta tggtttcttg tttgcagctg       10080
tttgtatctt tttaatccca aaccagacaa aattataaac attttatata caatgttatc      10140
ttggaaaaag ttagatgtaa ataattcatc ttaatctata tttgagaaat ctgaggggta      10200
ttaggaaact catgagtgaa tgaacatata gattggatca aaggaggaga gtatgagagt      10260
agggagacca ggtaaaaagg tatcatagtc atctagaggt gaggttagta agggttaagc      10320
cattggtaat aatgctggaa gaaaaagagg ttgtgttgga cttatcgaga gactatgtat      10380
tggactccca catggtgtgt cttcctaaga gatttgtgtt ggcaattttg attatactca      10440
atttcaattc aagtgatgac tttagaaccc aagccctgct taagacatca tgattccatg      10500
cggatagact gaacagaatt ggaaatggga gttagtctgc atgactttca gagctcttaa      10560
ctgttaagaa attttgctta aaatttgtgt ttttgtgatg gattaatggc tataatttga      10620
aagcgtggct acattgttga gtatgtattt gtcagagtta acccatcaga tattaaaagt      10680
accttttccc tcttacagtc cttgtccatt taataagtgt cttagtctgt gttgctataa      10740
aggagtacct gagactgggt aatttataaa gaaaagaggt ttatttgatt cactgcaggc      10800
tgtacaggaa gcatggcaca ggcatctgct tctggtgagg gctttaggct gcttccattc      10860
atggcagaag gggaagcgga gctggcgggt acagaggtca taaggcaaga ggaagcaaga      10920
gagatggggg agagaggctc tttttaacaa ccagctcttg agggaactaa tagaacaaga      10980
actctttctc ctaccctggc ccctcaggga tggcattact ctgttcatga gggatcccact     11040 tcaatgaccc caacacctgt tactacaccc cacctcccaa cactggcaca ctgggggtta      11100
aatttcagcg tgagatttgg agaagtcaaa catacaaact gtagcagtaa gtatttagta      11160
gtatcatctg agaggatgtt attcatgctg ggtgagggg aggaatggga gatgagtgaa      11220
gggtgctaga ctctaggatg cctttccccc atttccccac caaaccagtt cttttctttc      11280
ttcttgtgtt tataccttaa gatttctttt gagaaaaaag ggttagggtt tatagctaaa      11340
aatgtttgaa atgattgcta tgtatattta taatgtttgg ataaagactg atattctttt      11400
ttaagaaaat acattttcct ccctcatact tacctaatgc attgctattt tcatgtatta      11460
atacaacttt atatgagtac ttttattata tgcatattgt aatatgggaa tgtcaggtga      11520
tttttctgtg atttgaacat tttgatttt cattatattg tgttcccacg tagtttttca      11580
gtttcactta ttatatttgt ttttgccttt tctgtaggct ttcaacagac ctcacatctt      11640
tcttcttatg aaattataac tccttggaga ttaactagag aaagaagaga agccctagg      11700 ccctattcaa aacaagtaag ttataattgt tgagaaataa tatgtggtta atttttttct      11760
tttctgtttt agcacaaagg tgttatttgt agcagtgatc agttcagtga gttattactt      11820
```

-continued

```
ggctgttact tagaatagca ccatatggta ctgatgtccc ctggatgtta tgctagtaaa   11880
agcaacatat tgagccttaa tatccttttt tttttttttaa aatggagtct tgctctgtcg   11940
cccaggctgg agtgtgcagt ggtgtgatct cggctcactg caacctccac cttctgggtt   12000
caagtgattc tcctgcctca gccttctgag tagctgggac tacaggcatg tgccaccatg   12060
tctggctaat ttttggtat ttttcagtag agacagggtt tcaccatgtt ggccaggctg   12120
atcttgaagt cctgacctca ggtcattcgc ctgcctcggc cttgcaaagt gctgggatta   12180
caggtgtgag ccaccacgcc cagccagtat cttttctttt ttaaagacaa tatgatcaac   12240
tcgaaacata acagaataga atagttaaac aaaattgtat cactagggta ggctgctgat   12300
tatatacatt ttaactgaca ggcaatggtc acagtgattt tattataata agaattataa   12360
ttcttactat aattatataa cctcactcag tttgtgatag ctagaacact ttatactata   12420
tcttcactga cggtggagag tgataatgtg ttaaatgcgt atattttata ttagggaata   12480
tttactaaaa tacaagtttt attttcatat tggaagaaac ctactgtgct gtaaatgggg   12540
taaccagtgc acaaaaatta tttttttctac tattcttttg taaagtttgt tcagaagtaa   12600
tcttatttgg actttaattt tataagtcct tcaactttat agaagtataa ttaaatttta   12660
ttataattta acaatgacag gtaataatgc atagaattta gcttatgaat tgtattaata   12720
tctgaattgc tgatacactc agaaatgtaa ggcagcgtgc ctgtttttta gggagtgggc   12780
attgtaaaaa gaacactgga gttgaggatc aggaactttt agttttggtc ctccctgtga   12840
gtaccaccac ctactagttg ggttggtcac tcaactccat ttacatctct ccaactgagg   12900
agtaaatgac tctaagatct cctctgtaga tgaatttata cattttactt gtttttggtt   12960
tgaactgggc agactaccat ttgattatgt tttgtcttag gatagagtta atcagttaat   13020
ccctgtttgg gtgcgatctt ggctcactgc agcctccgcc tcctgggttc aagtgattct   13080
cgtgcctctg cctcctgagt agctgggact acaggcatgt gccactatac ccagctaatt   13140
tcgtatcttt agttgagatg gggttttgcc atgttggcca ggctggtctc gaactcttgg   13200
cttcaagtga tccacctgct tcagcctccc agagtgctgg gattacaggc atgagccacc   13260 tgtttttcctc cttttctaca gtcaatggta gactttcagc ctagggacca tgtttttctcc   13320 ttttttgtgt ctctgatagt atcttcattt agtacttccc tcattaatac ttgggatcgt   13380
catagataat tgtcatttttt atgctttggt taatatttgg agaagtgata tagtcagtgc   13440
atattgaact ggattttgct cattcaacag tgaatgtaat taactcgtta aaaagtattt   13500
attgagttac tattgtatgc taggcaccat ttaggtattg gggatacggc agtgaacaaa   13560
acagacaaaa atttatgccc ttgcatgaat gcagtcttgt attctatgga gcttgcattc   13620
tagtgatggg ggggggggc agggagagag agagagagag agagacaaaa acaaaaacaa   13680
caacaacaaa aacaaacccc cccccccaaa ccaaaaatgt atattacttc agatggtgat   13740
aagtgctatg gagaaaatta aagcaagaag ggggatagg aggctggaaa tggtgagttg   13800
ctggggagag gattgcattt ttcagtagga tggccaggga aagccttacg agaaggtagc   13860
cctttagtaa agactagaag gagggggggtg aacaatccag gcagatactt ggggggaggag   13920 taaactatca caaacaatc ttcagtttct cagatttctt tttagtagac atagcagtga   13980
tgttattaca tcacgtgatt atctaagagc agaatgagta gaaaggcaca tgacaaagct   14040
gtggcaatag aaagagcttg gtggtttttgc tggcccactg gagactgagg tagatgatga   14100
agggttcttg gattcccatg caggatgtgg aggtggatga caggatccat aggttggtct   14160
```

-continued

```
agcgcttaga agtcagaggc agatgtgccg tggtgaaggg gttgatgctg tttcttgaca   14220
aaaggttaac tgagtctgga aacggaaggg aatattaagt agacacttct gataatgtta   14280
gttgtcgagt ccctccatga ctttcttttt tattaaagag ttaaggcgaa gtcacatctc   14340
ttagttccag agatcacgtt aagcacttgt ggctaatgac atggtgaatt gctgggggaag   14400 ttgtttcaga gttgcctgag gtagagaaga tgatcccatg aattggagga tgtgtatata   14460 tgttactttta attccttgac tctaagatgc catcaattgt gagacacacc atattgtttt   14520
atgtaccact aataaagaca cggaagtggc ccagcagggt ggtttatgcc tgtaatccca   14580
gcattttggg aagctgggtg gatcacctca ggtcaggagt tcaagaccag ccttaccaat   14640
gtggtgaaac cccgtctcta ctaaaaatgc aaaaattagc cgggtgtgtt ggtggacgcc   14700
tgtaatccca gttacttggg aggctgagac aggagaattt cctgaacccg ggaggcagag   14760
gttgcagtga gccgagattg tgccactgca ttccagacta ggtgacagag tgagactcca   14820
tctcaaaaaa aaaaaaaaaa agacagaggt gctgctagtt agtctagact gctttgcctt   14880
tgtatgatgc atcctcattt caaggacgtt aatgtgaggg aaaaaagcat gttttagaat   14940
tgataaaatg aggtaagccc tgtaatttgt atcataaaag gagttgaatt tcttttttaac   15000 tttatataag tagaactagg tataaatttct tgaaaccaag agtttcattt catttagaca   15060
aaagcaggaa ctatctttgt actgtaggta atacatcgat ggacttgaga agataatccc   15120
tgcagttata gctgaattag aaatgaattt aagaagagtt agatagacat ggggttattt   15180
tccatgatca gttatgaaag gaaggaaggg atgatcagag tatatttttt attatttaag   15240
aatagacaca aagttcttct attaaatagt tcagccaata ccaaattatt ttaattcagg   15300
atggaatttc ctgcatctta taaatgagat gttgttgaaa agtaattttt aagatgatgt   15360
tttattcttt tccccttctg tgcatttagg tatcttatgt tattcaggct gaaggaaaag   15420
agcatattat tcacttggaa aggaacaagt aagacattta atttattttg gcttttcagt   15480
aatgtttttc caatagtata ttggtttct ttctagtttg atatggttta gtggatcctg   15540
aaccctggga ttaagcagat ttagctcttc atattggtgc tgcacagtgg cagctggctg   15600
ggcaggcagt gacttctaaa caggaaagaa ggcagagact ggaaccaagt acctccagtt   15660
tattcttttc aaatgcatca ctaagggagc aaaggctaca catatgtggg ggagttgggg   15720
agaaggggag cctgcagtga ctgaataggg tccaattact ggaaagacta aggttccaca   15780
ggctacttct atgcctactc acatagactt taataaaggt aaaggatata atgcatcagg   15840
acaaagaaag tgcaggcagt catcaaggca tgacccccag agtcctttct cagttgcaca   15900
gatgtgcttt gcctccagat tatgaaccgc tgagatatgt gtgaggcatc atattttctg   15960
gggagcccag gcacaagttt actgaaggta tctttcctac tttgctgatc atgtagctaa   16020
agtcaggctg tgtacctaac taaatcggac aaaaaccttc catttattca tctctagtca   16080
atatagacag gctgtcaacc attgtggaag acagtatggc gattcctcaa ggatctagaa   16140
ctagaaatac catttgaccc agccatccca ttactgggta tatacccaat agattataaa   16200
tcatgctgct ataaagacac atgcacacat atgtttattg cggcactatt cacaatagca   16260
aagacttgga accaacccaa atgtccaaca atgacagact ggattaagaa aatgtggcac   16320
atagacacca tggaatacta tgcagccata aaaaaggatg agttcatgtc ctttgtaggg   16380
acatggatga agctggaaac catcattctc agcaaactat tgcaaggaca aaaaaccaaa   16440
caccacatgt tctcactcat aggtgggaat tgaacaatga gaacacttgg acacaggaag   16500
gggaacatca cacaccaggg cctgtcgtgg ggtagggggga gtggggaggg atagcattag   16560
```

-continued

```
gagatatacc taatgtaaat gatgagttaa tgggtgcagc acaccaactt ggcacatgta   16620
tacatatgta acaaacctgc acgttgtaca catgtaccct agaacttaaa ggataataat   16680
aataaaaaaa tatatagaca ggctggtccc gggtgcctcc aggggagttt tgaacttgaa   16740
agggcatatt tatgaatcac tagttagcac attacatctc tgacttgtcc ataaggcctg   16800
gaaataagca tacagctgct ccagtcctgc tgcaagagaa cgtgatcctc ataaacatgc   16860
ttgatgccac tgaacctcct taacatggag tgaagatttg gaaatcagga ataattgttt   16920
ctttcaacaa ttgagacaga aatttgcctc catacttagg aggttaattc ttatttatat   16980
agaactttaa gaaaagagtg taaaaaacca tttatttttc taatgtaaat atgatatact   17040
gtcaataacc cagtttttac ttttcctgtg agccatatct gaaaaattta gggacattat   17100
ttatgttgtc ttaaattttt tggaactagc attttaagac cattacaaaa tgtgtagctt   17160
aatattaaat attatttatg aataagtaat gtacactatt tcagagttgt ccgtttatga   17220
gctttttttt tttctccttt ttttttttttt aagagacaag gtcttactct gttatccagg   17280
gtggagtgca gaggcatgat catagctcac tgcagccttg aactcctggg cttaagcaat   17340
cctcccacct tagcttcctg agtagctggg actatatgtg tgtgccacta tgcccagcta   17400 atttttttatt ttttgtagtg acagggtctc accgtgttgc ttaggctggt ctcaaactcc   17460
tggcctcaag tgatcctcct acctcagcct tccaaaatgt tggggttaca agtgtgagcc   17520
actgcaccca gctgttatga gctttttaatt ttacaatagc acatttaaaa ataatttatc   17580
tggtgaaagt tcttatttac tcctgcttgt ctcctctagg aataatgcct tatgaatcgt   17640
gtccttagtt gtagatagat aacatatata taaacggtgt tttatttctc ttccagagac   17700
cttttgcctg aagattttgt ggtttatact tacaacaagg aagggacttt aatcactgac   17760
catcccaata tacaggtaat gtattttttct cttgatccca tagcaaattt taaaacaatt   17820
ataatttaaa aatgagttct gtataggcac tcaggactgt tacattgcac agccccacag   17880 ggtacctttta acattataac atatgggtta tcttgggaaa agtgggtgca tttctataga   17940
ctaagctgta ccttacagct ctccaggtac tcagtagtta aggttttttt tttaaagact   18000
aggaaaataa atcttctatt taatggtaat ccttactgat gagaaaattt gatatgtttt   18060
gaaaatagga gtttctgatt ttttttgttga aagttaatat ctctaaaagt gcacttatta   18120
aaacatttaa tttgtcagtg atatttagta aagaaaaaca ctcatttgat gttatgtgtt   18180
ctaatgttct aaattttttc tgaaaataat tgtttcctaa aagaggtgtg gtcctctctg   18240
catcagagaa cagagtactc ctggggacag agctggccag aatacccaaa ataattggca   18300
gatgtcaaat ttggctttct gtgtttatta ctagagcata aacatttcta gttttgtttg   18360 agtgtttttac agtccttttt ggcagttagg tattatacct tttttttcttt tgcaatggtt   18420 ttcatgagaa atctttattc ccattacatg tgtatgtttt attttttcttc tgaactttgt   18480 aatactttgc tatgttgaat tgtttctgtt ggtagcgcac ttttgcagca ttcttcaaat   18540
aggaggcaaa aaaatcttta gattaattat tagtacttac aaaaaccaag gaaatgctga   18600
cttaggccta tcttctggtc cactatctga tttctttatc ttagtgtgtt gttggtccat   18660
tgtttaatag aaaattagta gaggagtttg aatttacctt acagcataaa ccagatagaa   18720
aataacgcat tcatccagtc atgcatccaa tgattaccaa ggcagaaggc caaacaccac   18780
ataatttgtg tcacttgaca aaagcagtaa tgttaaaagg cattttttttc ctcatagagg   18840 tttcttggca tactttcttc agacatacac tgtttgggct tgagttttga ctcattattt   18900
```

-continued

```
gctgatgaag ctactttaat ctgtttgtgc cttggtatct tcgctttaaa atgtaataat   18960
agttaccact ttatggatat actgggaaac ttaactgagt taatacttac aagatgctta   19020
gaacagtctg acaattttta actcaacgaa tgttattatt tgttgctatt attgacagcg   19080
tatgttctta aaactgccaa aaattgattt aattatatag aaacttatgt aactattatc   19140
ttatataata cttaagtatc ataagtatga tagagttatg cttttctggg tgtttgaaaa   19200
atgtcaacta agacagatgg tgtctcactt atttcttggt tatttaatat tgttcagtta   19260
gatgaaagtg tgattgtaga tttgaaatac aaaataaaac ttggatactg tgattttttt   19320
aacatggcca gactgtcatg tattataatg acatatactt ttgtccataa aatgaaatta   19380
agtttcactg aaaaatttac atactttccc ctggggattc tattgcttca gattaaagtt   19440
tataaagtat cattagtgtc ttccacaggg tcattttaca caaacacagt tttagtgaga   19500
tgtcaactgg cttttgttgg ttgttggatt gactgtgatt taaaatgtta aagatgatat   19560
aatgcatctt gttctgcttc taggctgaaa ggtcactgag gcagagctgt ttgtaccttg   19620 tatccctgg aattttgcct aaacatttgt gtactcatag ggtggtagga gatagtccgc   19680
agatggtcta aagaatgcca tgtgatactg tgagatgcca ataatataaa taaaactttg   19740
ttattattaa acttgactgg cctaaagtaa ttttgttagc tctgcaattt ctgtgatgat   19800
tttcagcaat gtagcaatat ttgaagataa tacagtattt ttcatttaga atcattgtca   19860
ttatcggggc tatgtggagg gagttcataa ttcatccatt gctcttagcg actgttttgg   19920
actcaggtaa gcaatttcct ttatcttctt tttttttgtt tccctatgt cttaccctct   19980 ttcctgtttc tgtctccaaa ttaaatcatt ttgggcactt agcaaaattg gaatttactt   20040
tgatgttact gaacattttt acagctgtgt ttcagatatc cttggcatgt ttatttaaga   20100
aagtattata gttgatgagt tttaatatgt aaagaggaaa ttttttttga gaccactaaa   20160 tcattttgc tatttaaaat gaaatatact ttaaatttct gtagcacttt atatttataa   20220
aattttcact tgtattattt aagacttgta tttaagtctt attatgactg tgaataagag   20280
ctcattatct ctgtatttag gtgagcaaac tgaagttcag ataaattata ttacaattca   20340
aattaagtta ttatagtatt aacattacat tccttgaggt catggcaaca tggcactgtg   20400
ctggttggtt gactgcatga ttgcttgaac taaaacatat tagttctata taagatgaat   20460
atgattatat tcacttaggc actaacactt atttggtagt tactgtgtgc caggcaatat   20520
gttccgtgtg ttttctgctt attaagtaat tttgtttttca gaacaatcct gtgcagagtg   20580
caaaccaagg cagaggttaa atacctcgct gagagtcctg cagctagtag aagacatttg   20640
gaattcagac tcttgtcctc tggtccggat gccacattct tagccactat tttgtagtgc   20700
cttccatttc ccgtagatca ctcagggagg ttaagtgact tacaggcagt gacgctgcta   20760
agtagctatt tgagctttca atttaggtcc gtcccagccc tatctgtctg attctaaagc   20820
ctctattttc ttctctatgt aatgctatgc ctacttacac atttaagaat taggacttga   20880
acttaggttt tctgattcct tgtgtatttt ctttttctta aaatttgtat acgtgtaatg   20940
caacattcag aggattgctg catttagaga atgcgagtta tgggattgaa cccctgcaga   21000
acagctctca ttttgagcac atcatttatc gaatggatga tgtctacaaa gagcctctga   21060
aatgtggagt ttccaacaag gatatagaga aagaaactgc aaaggatgaa gaggaagagc   21120
ctcccagcat gactcagcta cttcgagtaa ggaaataaca taattcttca tggctcagac   21180
taccatttta gaaaaatcat gtatttattc atgaaatcaa tactatgagt agtgtttttt   21240
tttcttttct taattttgcc aaatatatgc cagacattgt gataggtact aggggatgaa   21300
```

-continued

```
aagatgagcg atatatagtt cctgctacca agttgagtac agtttagatc ctgtgggttt   21360
tggaaactag gacttaaatc tgcaacaatg ttcactgtgg ccttgacctc ttgagctcaa   21420
gcaatcctcc tgcctcagca tcccagtagc tactgctaca ggtctgtgcc acccaccgtg   21480
cctggctaat ttaaaacaac tttttgtaga gatgaggtct cattacatta cccaggctgg   21540
tcttgaaccc ctggtatcaa gcaatcctcc tgcctcagct tcccaaagtg ctgggattat   21600
aggcataagc cactgcaccc agtgcaatag agttttttatt taggtacctc ttagacaact   21660
caaatggtga ttcttgaacc ctagattgga aaaagagaga gatacggctt taggaactta   21720
atgacttcag atgtgtttca aggacactct gctaatgact ttaagtgatg ataaactatg   21780
tctgagtccc tctttggaga ctgctatagc acttcatgat ttactcttga catgggtgtc   21840
tcttagactg aaatggttct aggactagat caacttcagc tgcagggatt gtacctttct   21900
acatatgaga ttctgttgct gccttgaaag aggcatattt ttaattaagt tatactagtt   21960
tatggcatta tttttattgc ctctgctgct atccactctt ttgacttggg ctattctttt   22020
taactttaaa cattggaaaa cattaaaatt tttgcttatt ctacttcgca tgaatttctg   22080
taaaatgaca aaactagtca ttttttaaaa tggcaacctt attctaactt ctgctctggg   22140
atattagtgg atatgttttc tttatctctc agcatagtaa tgggcttttt cattaaaata   22200
tgtgtgtgtt tgcatgtgtg tgtgtgtgta gttttgattt tagaaaattg gtaattctgc   22260
tttgtaaact taaacccatt ttatctgtaa ctaacatttt tctcatatta gtgcagatag   22320
cagataacac ttcaaaaaca ttttttttccc ctcagacata gtttatcatc acttaaagtc   22380
attagcagaa ctggacaaag ttttcatcac taagaagcag ataacacttc aaaaaacata   22440
tttttcactt tcttgatata ggatatgtta agtaaaataa ttttatgatg ttcttagcag   22500
acatgaaata agtgatgaga gattaggatg tgatcatagc cttataactt ccttttgcct   22560
ttatgatgtt tgtgtttttg acagagaaga agagctgtct tgccacagac ccggtatgtg   22620
gagctgttca ttgtcgtaga caaggaaagg gtaagattgg tgacaatttt tcttctttc   22680 catgaaaagg atatgagaag tgagcattta atgaaggaaa tctaaactac acattgtttg   22740
tattgatttt acttaaataa tgattttaaa actaaaatgg ttttttttccc ttaaacttta   22800 taccaccaga ataccaacag aagctaaatg tagcaaatgt gactgccttt aactttatct   22860
tttattaatg atttttttttt cttttttcttg ctgatgactt gcttatgctg aatttttttga  22920 gtgaatctgt actgcctatc aggctcttga gaactttttca gattactttta atgggctgtg  22980 gctctaaaag gtttggcttt gttggctaat aaaattgctt tgctttctag aatttgagat   23040
aacctatatt gcactttgag agatggaaaa cctccaggtc ctggcatgct ttagaaggga   23100
atagtattaa tttccgtgta taggatcaca tgagggcatt ttccttattt atacttaaga   23160
aactgaacta agtgctttgc tttaactaag agaagtaatg tgtccctatt ttggcattta   23220
caggattatc agtttttagag ataatggctg tataatttat tttcatgttg cttttttttat  23280 tgatatataa tacttcacat gtttaggggg tacaggtgag tatttgttac aacagctgtg   23340
taatttaaaa aagagagtat ttttagtgtt ttgtttgact tttacttcca actttgttgt   23400
cagtgtgaaa aagttatttg tggaaactta ctatgattgg cagttccttt cttgtaagct   23460
gtagagacag ttttgaggtt tttttttggtt ttaaaaaaat tccttgttgt atgtaggttg   23520
gaaaataaca agccacccca aataactaat ttggagaaaa tattaagaga tagacttgga   23580
tttgtacatt ataggttcat tgccctcaag tggcagaagg aaaagcacat ggaatatgaa   23640
```

-continued

```
caagtgtgaa ctctgcccca aacagtgggc aaaaagcttc tgtagaagaa tgttttggac   23700
aagtcacaaa agtcaagatt caaaatgttt tccttggctg ggcgcagtgg ctcacgcctg   23760
taatcccagc actttgggag gccgaggcgg gcggatcacg agatcaggag attgatacca   23820
tcctggctaa cacggtgaaa tcccatctct cctaaaaata caaaaaatta gccgggcgtg   23880
gtggcgggcg cctgtgatcc cagaacccgg gaggcggagc ttgcagtgag ctgagatggc   23940
gccactgcac tgcagcctgg gtgacagagg gagacttcat ctcaaaaaaa caaaacaaaa   24000
caaaacacac acaaatgtt cttcttcatt gctgtctcca gatgtatttg ttatatacag   24060
atagaaaatg gttaaaaaaa aggttcaatt tcaatcaagc cctatcaaat atattaaatt   24120 aattttttt cttgtttagg aggatcatga ttagatccct aactgataaa atctgatata   24180
ttctgatact aatgctttta gcatagagca aaatcataaa tccttttaaa attttcttc   24240 tgctaaattg gttatataaa ttaatgttaa aaatagacat ttcagtttag ccaggtgtca   24300
aagaaaaatt agtcatattt atttggctta agatggttaa acttttatat attttcatct   24360
acatatgatt ttttaactag tgattattgg ttaatctctc atttttaatt cagcccagca   24420
tttagaaatg gtttattggt gctgatctgt aaccaatctg gctgtttctg tctcagttct   24480
attttctgta tgtcacttcg tttttctgtc cataaatctt cttccactat gtggctgcac   24540
agagtctctc tgaacctgtt ctggtttgga agccacacaa ttcttgaatc agtcattctt   24600
tgctcaacta aattctgtta aattaaaaaa aaaaaagtt tattgattac atcattagct   24660
taagaggtga aagggtcagg aagttcttta gattgtcttt tattctttta tctatgcatt   24720
ttgattgctt aaaactctac ctttgtgaaa tgcttgaaaa tattttttgca ttaaaataaa   24780 aggaacatta agaagataat tcgtttaaa gttctactaa tttggataaa atgaagtctt   24840
cagtgctctt tcattattat tcactttacc cttttacctg tttttctttt attcctgtca   24900
ctacaatgta accttaaat ttcttaattt gaaatgttga taaatgtcta aatgcctcaa   24960
ttttttgttc agaggaaata tttggattct tcatagtaac agacacattt ttattttatt   25020 tttattttt ttgagatgga gttttgctct ttctcccaga ctggagtgaa atggcgggat   25080
cttggctcac tgcaacttcc accccacgg gttcaagcga ttctcctgcc tcagtctcct   25140
gagtagctgg gattataggc acctgccacc acgcctggct aattttttgta ttttttagtag   25200 agagaaggtt tcgccatgtt ggctaggctg gtctcgaact cctgacctca ggtgatctac   25260
ccgcctgggc ctctcaaaat gctagaatta caggcatgag gtactgcacc cggccttaca   25320
tttctattct taaagtactt tggtgataat gattctcctt ctttgctttt ccagtatgac   25380
atgatgggaa gaaatcagac tgctgtgaga gaagagatga ttctcctggc aaactacttg   25440
gatagtgtaa gttgtatttt ctatcaacca ggatgattct gtcctattct ttcagtccca   25500
gaacagaact taaaaatgtc tcattttgag ttctgatttt cataggggcct caatgactta   25560 gtctttcaga ggtctgcttt ctggtttgtt ttgtaactct ttttaatgtt taaaggaaag   25620
taccagtgta gaaagactga gaagagcaag agatttcata ttagcatcta ctttatcttc   25680
agagttgcta ggcttaggtg ctttggcatt tatggaaaga tctttgaatt tttgtcgaat   25740
gcatcttatt ttgaataagg ctgccttcta ccctgaaaac atgatatgac aatatttgtg   25800
tgtgtgtgtg tgtgtgtgtg tgtgtgtgtg agagagagag agagagagag agaaagagag   25860
tgtttggttt gagattttgg agttcatccg gtgggagata ttaaagaatt agatatatgt   25920
tcttataatt ttatctacaa agctgatatg aacattaaac gtgatgatga cgatgatgat   25980
gatagcattc acttgagtac ttacagtgtg ctagacactg agctaagtgc tttacattta   26040
```

-continued

```
ttaacccatt tactccttac agtacccta tgaaattatg agttccacag tcctttatct  26100
gaaacctctg atgtacctgt gattaaaatt ttagataagt ttagaaaaac agtgtgatta  26160
actctgtatt atataacacc ttcgacagga tcttggggta gcacctcata atcagactca  26220
ttgatatttc tgcagtgaaa tataggaata tttacattaa ataggttaaa tgtggactat  26280
gaatgggctt gcattatatc agggcaaatt ttggagccag ttttaccaaa aacttaattt  26340
ccagagtttg tcagatttta gaatagaaga taataaggat ttcgaatctc tgttactatt  26400
attttatggt tgaggaaact gagactattg agaggttaaa gttttattgt atttttttt  26460 ttatgagatg agtctcgctc tgttgcccag gctggagtcc agtggcgcaa tctcggctca  26520
ctgcagactc tgcctcccag gttcaagcga ttctcctgcc tcagcctccc aagtagctgg  26580
gtttacaggt gtgcaccacc acgcccagct aattttttgta ttttagtaga gacgggattt  26640
caccatattg gccaggttgg tctccaactc ctgatctccg gtgatccaac tgcctcggcc  26700
tcccaaagtg ttaagattac aggcgtgagc cactgcgccc cgcccaaagt ctcattgtat  26760
taaaggaaag atagttttt ttaggcaggg gagtttaat ttaagtagcc gtgttacttc  26820
atgtggttaa aagattttc tcacgttctt tactatattt tatatacttt tatttctttc  26880
ttcccagatg tatattatgt taaatattcg aattgtgcta gttggactgg agatttggac  26940
caatggaaac ctgatcaaca tagttggggg tgctggtgat gtgctgggga acttcgtgca  27000
gtggcgggaa aagtttctta tcacacgtcg gagacatgac agtgcacagc tagttctgta  27060 agtattttt ttttaagtac tattaatgaa ataatcaaaa taataatttt tgcttatttt  27120
cttgtattag aattatattc tcttgaggtt ttggggtatt catttaaatg aggaaaactt  27180
agcttgatgt ggcattatca tgagacctct tctgtttttgg attcctgtga cctttctccc  27240
atatcctcct ttttttcttga gtttacatcc tcatttgggt atagtgtgct ttgtactagt  27300 ttttgtgaa cggatatata gaaagaaaac attttgacct cctgtgtgtc tgaaaatatg  27360
gtttcccagt ttcggaacag aattgaaaaa ttatctcaat ttgagttctg attactctag  27420
gcctaagtaa ctcagtattt cctaggcatg ctttgagttt cttttgcgtt tgttttttt  27480 ttttttttt tttttggaga cagagtctca ctctgttgcc cagaccagag tgcagtggca  27540
cgatcttggc tcactgcagc ctctgcctcc caggtcgaag caattctcct gcctcagcct  27600
cccgactagc tgggattaca ggtgcctgcc cccacacctg gctaattttt gtagtgtagc  27660
agagatgggg tctcaccatg ttggccaggc tggtctcgaa ctcctgacct caggtgatcc  27720
acctgttttg gcctcccaca gtgctgggat tataggcgtg acactgggta taaaattgta  27780
tccgtgaaat ccttttttctt cacgactttg aaggcgttgc tcttttgtct ttttttgtccc  27840 agcattacta ttgggaagtc tgaaacattc tgattcctga ccttttgtat gtggcctgtt  27900
tttccccgtc actggaaact tgtaggatct tctcttggtt cccaggcttc tgaattttcc  27960
tgatgatgtg ttttggtgtg ggtcttaatt tttagtaaaa tcgtacgctc acacatcctc  28020
gtaccagtga gaatgccatc tagttcacaa aataccataa ggagcaggtg tcaagcatac  28080
tcactatgcc ttgcccaacc acacccacca aactatctta accccctctc tttgtgtggt  28140
ctccatctgt cctgttagag acatttccca gatgcttgat gatttttagt tgtttgttta  28200
cagttgagaa tggggtcccg aaaacctttt tggaagcctt gagtccatga gtgcattttg  28260
gggcctatga gttccttata gggtggtttg gctggaatgt ccttgtcaat ctccttatgt  28320
cagtacctct ggtcatcttc tcctggctgg tcagatggcc cagagaagga tttatccatt  28380
```

-continued

```
catttaaaat atatttattg ggtgtatacc ccagacactg ggacatagca gtgaacaaaa   28440
ctggcaaaaa ttcctgctct catggagtcc atgttctggt ggaggagatt ggctatacat   28500
gtgataaata agtacatgta gtatgttaac caatgataag tggtaaggag aaaaataaaa   28560
cgggagggta gatataaaag cattggaggt tgtgattaaa attttagata aaagtttaga   28620
aaaacagtgt tattcactgt tgaattttga ggtgacatgg tctagccagg gagatgcctt   28680
ctgagtaaag acctgaagga ggtgagggaa tgagtctggg ttatattaat attagggaag   28740
agaggtccag gcggagggaa caggtgctga ggtacaggtg tgtggggtgt gactgggag   28800 gcacacaggg cccatcctga attctttttt ttttattttg gagacagagt ctcattctat   28860
cacccaggct ggagtgcagc ggtgcagtct tggctcactg tggcctccgc ctcccaggtt   28920
caaatgattc ttctgcctca gcctcccgag ttgctaggat tacagatgtg cgccaccatg   28980
gctggctaat tttcgtattt gttttttag tagagatggg gtttcatgat gttggccagg   29040
cttgtctcaa actcctgacc tcaggtgatc tgcccacctc ggcctcccaa agtactggga   29100
ttacaggcat gagccaccac gtctggccca tccttactcc tcatgttcac cctgctcact   29160
gccctgcagc tgcccgtgta aacatattca tttcattcgt tatctgtctc tcctcactaa   29220
aatgtgtatt ttaatatata gttaaatata ataagtgtat aaataaacct aatgtattt   29280 aggagaggtt tcacctagaa ggtaaaaaga aacaaacttg tctcggtatc cagaaagtgt   29340
cttcatttgt ctgaaaaaat taataagaag gagataaggc ataagtatat tctgatttta   29400 gaatttttttt ttttttgccat tttcctgcca tgttttgtag gttctcccaa tccagttgag   29460
attattcata aaataaaagc aatgtgttcc tttttttcccc aagaacattt tttaactttt   29520
acattttcat ttagaaagaa aggttttggt ggaactgcag gaatggcatt tgtgggaaca   29580
gtgtgttcaa ggagccacgc aggcgggatt aatgtggtac gttgttcttg atgtttaact   29640
ttggatgttt gcactgggac aatatcaagc atttattgac tgtatacttc ctcccctggt   29700
ccttaaaaca atattttggg tgttatgagg aacacagtag aagtcgcaga tgggttcttt   29760
ccccagagac tgggtcaagt tttaaaatat gtgctatgtg tttattagct ctttttctttt   29820 ttattcattt tattttactt taagttctgg gacacatgtg cagaatgtcc aggtttgtta   29880
cataggtata catgtgccat ggtggtttgc tgcacctatc aacccgtcat ctaggtttta   29940
agccccgcat atgttaggta tttgtcctaa tgctctccct cccccttgctc cccacctccc   30000 gacaggcccc ggtgtgtgat gttcccctcc ctgtgtccat gtgttctcat tgttcaactc   30060
ccacttatga gtgtagctct ttactttttta tgggtgagga aacatgtact ccattttaga   30120
gaattaaatt agaaccatta acttgttttc ctataaacta ccataagtaa tctgttggtg   30180
ctaaagtggt tgacctcttg cttgaaggat ccatgtccat cacgtgtgtg attcatgtta   30240 cttcttact agactgaaat gtataaagac tgttgttgga tgcttgattt atcacgtagg   30300
ctgtcaacag tgtagtgaat aaatttcctt ttgtgaaaaa ataatctgag cagcaaaaca   30360
ttttctttgc gttcagaaac ctaattacta ccttcctgtt ctgaacagtt tggacaaatc   30420
actgtggaga catttgcttc cattgttgct catgaattgg gtcataatct tggaatgaat   30480
cacgatgatg ggagagattg ttcctgtgga gcaaagagct gcatcatgaa ttcaggagca   30540
tcgtgagtac ctgggttctt cttctccttt atttggtatt gtagatccat gtttcttaca   30600
ctgtgaggga tattcatgtc tacattggga aaacaggaaa tgttatttcc ggtttgctga   30660
aattaattgc atgacatacc aatgagaagt ctttttttttt ttttttccag cctttttagat   30720 ttaggggggta catgtggagt ttgttacctg atgtattgct gaagtctatt ttttaattaa   30780
```

-continued

```
atgattccag agagctttaa gaaggcaata cttatgtagg cacaagtatg taactacact   30840
cttctgtaaa ccagttatag actgaaagta taagaacatg gcaaagttta ttatctgaat   30900
tagaaattaa gagggagttt ctgctaggtt cagtgtggat tggattacac tgaaggactg   30960
cataagaagt ttcttcacaa acctcttttt gagaaagtgc tgcattgtca ctgtaggtag   31020
aagagatcct gatatatttc tattaacaaa ccctgtttta tagagataaa ggtgggaggc   31080
aagacagaga agaggagaga gaatggttaa catttgttaa gctctttta tgtacaggca    31140 ctattgtagc catttaaaac gtatccactc acttactact catcagtgaa atgaggtgca   31200
catactttat ctccatttgc agatgaggaa actgaggtca cacatccaaa ttgctgactg   31260
ggattcaaag tcaggaagtc aaagcctgtg atctgagaac cctttcctgt cccagagcta   31320
aaaaataatt ataatagaag atcccatggt ggttgggcat cagaaatata gatttctaat   31380
gcagattcgt tgtaatgcca acgaggttcc ttcctaattt agaaggcagg agtcctaagc   31440
agagagctga atgtaactgt agttcgtacg tgtgtagatg ttgagcctga gtgaaaatta   31500
gatatgagag gtgatatctt taacaaatac aggacggacc tggtggctca tgcctataat   31560
ctcagcaatt agggaggatt gcttgagacc aggagttcaa gaccaacctg ggcaacacgg   31620
tgagaccctg tctctaaaaa aaaataaata aataaataaa aaataaaata ttaactgggt   31680
gtgttggtgc gtgcctgtag tcccagctac tcaggaggtt gaggcaggag gatcacttga   31740
gcccaggagt tcaaggctgc agtgagctat gattgtgcca ctgcactcca gcctgggcaa   31800
cagagcaaga ccctgtttca aaacaaacac agatgaagat ttcacatggg gaatatccgt   31860
ggccccaagt gttcatgcca cttcccacct ccctcaggct cctgaagcac tgacagagta   31920
ataaaaactt ctgtcaacca gcctttcagc tgaagttctg agtggacaag acaatttcaa   31980
tcacatgcta gtataaaggg aagcactcaa gcagaattta cagttttga acaaatacta    32040 ggctcaaaaa tagatatgga agagttaaaa tagtacttac aaaaagccat gcttcataaa   32100
aaaaaaatta ggtatgtaag gaacgtcata tgtttgtaaa agatttcctg taggagaggg   32160
aagtaaattt aggatttgct ttggccagca gtgaagttga gaaagacgtg agttcaggga   32220
aacaagaaat gtgtaatgag caatgagata agtcatagat taaaataaaa aagaagcatt   32280
cagaggtaag gagggaatgt tatgaaacag tgccatagtg gaatttaata tggtatagga   32340
agcaatgaag agtggaccca tactttattc accaacttgt caaacattta ttgagcactg   32400
accacctgcc agactttgtt ctcagcactt ggaatacctc agtgagttag atcgactcac   32460
ccttcaagga gtttacatct gggggggaaga caatctataa acataagaaa atcaataata   32520
tagagtgtta gaaggcgata agtgctatgg gaaataaaat agagcagaat gtggaggatt   32580
gggaggacgg agggtggtga aacaacagaa caggcttcag tatgacaaaa ctggatgtta   32640
ataacagaaa cctgagtgag ttggtattta aaaccactcc cctaaagtca accctgtgtc   32700
aagcagactt acagtatact taaaatattt tgaggagaat ggtattttg aatattatat    32760 ttaaaacagt gcatattgac gtttaaatat gaagataaca tgatttcaaa tttaaggtat   32820
ccatcatttt cccaagggaa gagccaaaaa agtgttgttg ttgtttttt tttttttgg     32880 ttgacttgaa tgtgtataaa cttgctaggg atacagtaga tagaaaggga gtgaactgtt   32940
cattactgga tcttggagag tctctgtagc cacaggggag actgacccca taggagttga   33000
ggtagaggga cactgataac atgaggatac tgataacatg aggtagaggg acactgataa   33060
cactgataac atgaggtaga gggacactga taacactgat aatagagagg gttccaggtg   33120
```

-continued

```
aattattcag ccttattctc ccagtgactt cttatctctt gaatagaagt ggccaaagtg   33180
agtacctatg tcttgtccag cttagtggga aagcttttga ttttttcactg tggagtatga   33240 tgttgtctgt gggcttttca tatatggcct ttattatatt gaagtgattt ccctcttcct   33300
agtttgttga gatcttttgt tgtgaaagaa tgttgaattt tatcaaatgc ctttttggca   33360
cctgttgaga tgattatgtg actttgatcc ttgattctgt taacgtggtg ttaatacatt   33420
tttgtgtgtt gaaccgtcct tgtgtcccag gtacaaatct catttggtcg gagggcctga   33480
tgtttctggt gtgttgttga gttctgtttg ctagtatttg ttttgaggat ttttacattt   33540
atgttgctag ggatattgac ttacaatttt ctttttctggt tgtcccttgt ctgactttga   33600
tattagggtg atgctgggct cataaaatga gtttggaagt gttccttcct cttcaatatt   33660
ttgagaagac ttttttttct tttaagcagt tttaggttca cagaataatc aagaggaaag   33720
tagaaagact cctcccatat actttctgtc cccacacttg catagtctct ccatttcaat   33780
atccctcaac agagtggtat ggttgttaaa actgacaaac ctatattgac acatcatgat   33840
ttctcaaagt ccatacttta tggttcagtc ttggtgttgt gcattctatg ggtatgaaca   33900
agtgtatgat gacaagtatc cctcattatg gtatcatgca gagtatttcc attgccttaa   33960
aaaatcctct gtgctccacc tagtcatctc tccccacccc tccaacccctt ggcaaccact   34020 aatcttttta ctgtctccat agtttcgtgt tttccagaat atcatatatt tagaatcatg   34080
cagtatgttg ccttttcata ttggcttctt tcacttagca atatgcattt aaggctcctc   34140
atgtcttttc atgtcttgat agctcattta tttgtagtgc tgaataataa cccattgttt   34200
ggatgtacca cagtttaacc atttacctac tgaaggacat attggttgct tctaagcttt   34260
ggcaattatg aaaaaagctg ccataagtgt ccgtgtgcag ggttttgtgt gatcatgttt   34320
tcagctcctt tgggtgaata ccaagggatg cgattgctgg atcatatgtt aagagagtat   34380
gtttagtttt gtaagaaact gccaaattgt cttccaaagt agctatacca ttttgtattc   34440
ccaccaacag tgaatgagaa ttgctgttgc tctacatctt tgtcagaatt tggtgttgtc   34500
agtgttctgg attttggcca ttcctatagg catgtagtgg tatctcattg tttcaattta   34560
catttccctg atgacatagg atgtagatga tctttttcct tctttatgtc ttctttgtgg   34620
catctgtgaa ggtctttggc ccattgttta atcagattgt ttcttttctt atttttttagt   34680 tttaagagtt gcttgcatac tttggataag agtcttttat caaatatgtc ttttgcaaat   34740
attttctact agtctgcagc ttatcttctc attctttttaa tattgtcttt cacagagcat   34800
acatttaata ttttaattct ttcatggacg atgccttttg tgttgtatct aaaaaataat   34860
tgccatatcc aagatgatct aggttttctc ccatgttatc tcccaggagt tttagagttt   34920
tgaattttac acttagacct ttgatccaca tggagttaat tgtggaggat gtaagatctg   34980
tgtctagatt tatttatttta tttttttgcat atgaatatct aattgtagca gcaccatttg   35040
ttgaaaagat tatcttttat tgtattgcct ttgctcctttt gtcagagatc agttagctgt   35100
atttatgtag gactcttttt gggctctcta tcttgttctc tttatctatc tgtcacctttt   35160 tgctaataac acagtcttga agcttgtgca tgcgtcacat agttctcgtg ccatggtttt   35220
cagctccatc aggccattta aggtccttttc taccctgttt attctagtta gccatttgtc   35280
taatcttttt tcaaagtttt tagcttcctt gcgatgggtt cgaatatcct cctttagctt   35340
ggagaagttt gttattacca accttctaaa gcctatttct gtcagcctgt caaagtcatt   35400
ctctgtccag ctttgttccg ttgctggcga ggagctgtga tccttttggag gagaaggggc   35460 gctctgattt ttagaatttt cagcttttct gctctggttt ctccccatct ttgtggtttt   35520
```

```
atctacctttt ggtctttgat gctgatgacc tacagatggg gttttggtgt ggatgtcctt   35580
tttgttgatg ttgatgctat tcctttctgt ttgttggttt tccttctgac agtcaggtcc   35640
ctcagctgca gatctgttgg agtttgctgg aggtccactc cagacccttt ttgcctgggt   35700
attaccagtg gaggctgcag aacagcaaat attgcagaac agcaaatatt gctgcctgat   35760
ccttcctctg gaagcctcat cccagagggg cacccgcctg tgtgaggtgt cattggcccc   35820
tactgggaag tgtctcccag ttaggctaca tgggtgtcag ggacccactt gaggaggcag   35880
tctgtctgtt ctcagagctc aaacactgtg ctaggagaac cactgctctc ttcagagctg   35940
tcagacaggg acgtttaaat ctgcagaaga ttctcttgcc ttttgtttag ctatgccctg   36000
ccccaagagg tgggatctac agaggcagca ggccttgcag agctgtggtg ggctccgccc   36060
agttgagctt ccctggctgc tttgtttacc tactcaagcc tcagcaatgg cagacgcccc   36120 tcccccctgcc aggctgctgc ctcacaggtc aatctgcctg ctgccctagc agtgagcaaa   36180
gctctgtggg cgtaggaccc gccgagccag gcgtgggatg taatctcctg gtgtgctgtt   36240
tgctaagacc attggaaaag cacagtattt gggtggggtt gtcccaattt tccaggtaca   36300
gtctgtcacg gcttcccttg gctaggagag ggaaatcccc tgacctcttg tgcttcctgg   36360
gtgaggcgat gccccgccct gctttggctc accctctgtg gactacaccc actgtccaac   36420
cagtcccaat gagatgaacc aggtacctca gttggaaatg cagaaatcac catcttctgc   36480
gtctgttaca ctgggagctg cagaccggag ctgttcctat tcggccatct tggaatggcc   36540
acacggtctt gattactgca gctttagagt aagtcttgaa gtcaggtagc accagtcctc   36600
caactttgtt cttcttcttt actattatat tggctattct gggtcttttg ccaccccatg   36660
taaacttaaa aatcagtttt atctatatcc acaaactaat ttgctgggat tttgattagg   36720
atcgcattga atgtatagat caagttgggg aactgacatc ttaatattga gtctgcctgt   36780
atgtgagcat gaaatatctc tccatttatt tagttctttg attctttcat cagatagtgt   36840
tatagtttcc ccatagagat cttatacata ttttgttaga tttataccta actctcattt   36900 ttggggggtcc taatgtacat gatattatgt ttttaatttc aaattctact tgttcattgc   36960
tggcatatag gaaagtaatt gacttttgta tattaacccct gtatcctata accttactgt   37020
aattgctttt tagttccagg agtcttttttc aattctttttt gattttctac atagatgatc   37080
atattatctc tgtacaaaga cagttttttct ttctttccag tcagtatacc ttttactttg   37140 ttttctttttc tcactgcagt agctaggact accaatctga tattgcttta ccttcctcac   37200
attttttttt tagcattgac agtgtgtttt ttttttattttt taatagttat gcttctaaaa   37260
catatttaaa ttttatttttt aatccaaatt gaaaatatat gtcttataat tatatcactt   37320
aatatattta tatttactgt aattactgat ccatttaatc aaatctaaat gccattgatt   37380
ataagataca ccacttttttc cataccactg agaaagaaat atggtgtcaa tgaaattaat   37440
acgtcaattg taatctgaaa tgaatctcag tttcaaagtt atttaaatat ggaaagaatg   37500
tgttttagaa tcaattaaat acagcatttg ggtttaaatc taccatctta tatctccttt   37560
atttgtcttc ttttatggtt tttttcttaa aagttttcgg tcttaaatat ttaagttgat   37620
ggatgttcca attccctgaa tttggtcttt acacattgta tgaatggatc aagtgatcac   37680
atgtatcctg agaatatata catctattgt gtatcagtta aaaatgggac gacaacaaca   37740
acaacaaaat cttctgtgtt atttcttttg ggttggtaga gtgttttttat atttattttc   37800 actttgtaga aatgggttct tgttatgttg cccaggctgg ttttgaactc ctaggcctaa   37860
```

-continued

```
gcaatcctcc caccttagcc tcctgatgtg ctgggattac aggtgtgagc cactgtgcac   37920
tgccagatag agtgtttta gtagatactg tttttcttct agacatattt ctagaatgga    37980
aattatgcag tctttattt tttttaaagt taccctagaa attattacac atgttcttat     38040
ttatcatgtc tactattaaa tcttatcctt ccccacacag ttcaaaggct atatcgtgcc    38100
ttaactccat tcatcacttt cttgactcat atagctgtgt gccaggaaga tattagtgat    38160
tgtttatcat tattcattta gattttgacc actgcccttg ctctttggtc ctcttgcatc    38220
tctgaccttc catttggtat ccatttttca gtctgatcaa agaaccagtt ttgactttcc    38280
tttaatgtgt ttttagtagt agtgtatctc ttagttttg tttttgtttt tctcctgagg      38340
gtgtctttgt ttctgttttt tgaggatatt tttgttgaat atagaatcgt agatcatcag    38400
ttatttttca tcatattggg attttttccat tgtcttttgc tttccatgtt gttgttgaga    38460
tgtcaaggtg tcagaccatt attccattga aatgaatctg tctatttacc tatggctgtt    38520
ttcacaattt tgtctttaaa cttttttttt tgacgtttca ttatcatgtt cctgttgtag    38580
aaagaaaaaa atatacaaca tgcatacata cgtatgttat gtatatataa cacatttaca    38640
catatatgtc ttcatatcct gcttagaaat tttttagtgt tttaaagttt gtggcttgat    38700 attttttcatc agtcggaaaa ttctcagtca tgtctttaca tattgcctgt gtacacaggg    38760
tgtctgcaca tttgctgtct ctcttacgcc tctgtgattc tagtgaactg tgtgttagac     38820
ctcactatgt ctcctttgtc tcttagtttt ttaaatatgt ttcctatctt tttgtgtttt    38880
tttcttctgt gtaatttctt ctgatatctt tcagctcact gattctgtct tcatatgtat    38940
tttgtctgtt gttaaactta tccattgaat tattaatttt gcttatttca tttgtcaaat    39000
ttatgtctgg ttcttttttca aatctgatat attagttttg tagattttag tttcctgccc    39060
aaattttcat gcttgtcact tttgtctctg atcatagtaa gcataaatgt cttatggcta    39120
tcatttgata atcctagaac tagtattagg agtctttatt ggactttatc tgctcgtttt    39180
tttctttctt gtagtgtatt gtggcttcat gtggtatttt atattgtgta gctgttatat     39240
ttaaaatttt ttttaagaat aatttctaga ccgggtgcgg tggctcacgc ctgtaatcct     39300
agcactttgg gaggctgagg caggtggatc acgaggtcag gagatcgaga ccatcctggc     39360
taatacgtga aaccccgtct ctgctaaaaa tacaaaacat tagccgggca tggtggcggg      39420
cgcctgtagt cccagctact gaggaggctg aggcaggcga atggcatgaa cccgggaggc     39480
agagcttgca gtgagctgag atcgtgccac tgcattccag cctgggtgac agagcgagac    39540
tctgtctcaa aacaaacaa aacaaaacaa aacaaaaaaa agaataattt ctgaactagg     39600
atgaggttat cctaggtaat acatattttt ttctcttatt tttcctcaga ttccttttta    39660
ctaccaagct gatattaaac tttctttttt tgagggcata tttcctaccc tctacttcat    39720
aggctgttta ataaatgtta attttctatc attttgtttg gctttttttt ttagatgcta    39780
gtgatgtaca tgtttcattt tttcccccctc agataactca gtcattggga gccagttcca    39840
tttaataaaa tggataatct accctcgtaa taagattttt ttgttattgt ttatgatatt    39900 ttggggggcac agtggtattc ttatgcattg ctgttagatt ctggaaagtg tgagttgctc    39960
ttcctgggag gtgcctttct agaaaaatgg ctttcttaac tctgcccctc aatgtcagca    40020
agcttccatc agcaagcttc cataatcagg tgtttttttc ttaatctaat tcagtaccag    40080
cacttagaat cttctcttaa gacttcctaa tcctaggctg tgggaatcag catagtaatg    40140
gtgaaaattg tgttctggga attttcagag gactcaaata aatatgtttt gaatgatagt    40200
tgaaattttt ttttttgtca tttccatgta aaacattttc attattgtcg atctcctttt    40260
```

```
gaagccattt tgggaaaatc acctagatgt gagaaaagag aggaggagag gctataaatc   40320
attaatattg tagagtctag aggtgataga gagtagaaat acttgagttg ctcttcaagc   40380
cccgtatcag gagaaagatc attcttttg ttgccatagg tgccagccag tgatggctag    40440
tggaagggta ttttcactgt agcctctaaa gcattttaaa gtctcactga aggccaacac   40500
aggggatgtt gttactatct cccatctgtt aaaaagcacc acaagtgtct atgattttgt   40560 tatgctttt agttctatag tcaattcatg tgggtgaatt ttttttttt tttggtagat     40620 tgctgaagga tcaagcattt gaaacattgt ttataagaaa atatccttca actaccagat   40680
aatgagctta tttaaaaaat aacttgttta gaggtggtag actttatgta ggttgaaatt   40740
agggactaaa atataggact atacatatgc ctgcgcaagt tcttttttt tttttttt      40800 tttttgaga cggagtctcg ctctgtcacc caggctggag tgcagtggcg cagtctcggc    40860
tcactgcaag ctctgcctcc cgggttcacg ccattctcct gcctcagcct ctctgagtag   40920
ctgggactac aggcgcccgc cactgcgccc ggctaatttt tttttttat ttttagtaga    40980 gacggggttt caccgtggtc tcgatctcct gacctcgtga tccacccgcc tcggcctccc   41040
aaagtgctgg gattacaagc gtaagccacc acgcccggcc tgcctgcgca agttctatgg   41100
ccattgtcta attaaatata tgtaatttat aaatatatat ttatgtagta tatatattta   41160
aatatatatt taagtgtgtg tgtgtgtgtg tttttttttt tttttttggag acagggtctc   41220 tggagagcag tggcttgatc atagctcact gcagccttaa actcctccca ccccagcctc   41280
ctgagtagct gggactacag gtgtgcacca ccatgcccag cttatttttt gtagagacag   41340
ggtctcatta tgttgcccag gtggccttga attcctgggc tcaagtgatc ctcttgcctt   41400
agcttcccaa agcattggga ttacattatt aaatatattc ctacagaaaa cattattgca   41460
tgtataccat gtagcaggcg ctgtgcttac cacataaaga tcaacagtac aaaataaaaa   41520
acaattacaa gcctctgttt aaactgcagt cttctttgtt tatcaaataa ttattttata   41580
ctgctttgac attttttactt gatgtctaat aggctcaaac tcctgtgatc cctcctaaag   41640
ttgtcctaaa atgtgatcta cccatagtct tccccatgtg aattaatggt aactccttcc   41700
ttctagtatc ccaggacaac aacctgggag tcattcttga tttctctttt ttctcactct   41760
tcatcttaat ggctgttcct ttaaaacaaa agcaatccaa ccacttctta cagctcccac   41820
tgtttcattt tggtccatca tcatctgttt ggtggatttc tctaagagcc ttctttgtag   41880
tcttcctctt aatagaacaa gtatggtgat cctattaaaa cattagtcaa atcacattac   41940
tcctgcactt ttcatggtct tccccttcca acttccccat tccacttaga gtagaaagcc   42000
acattcctac aatggcctat tcctgtcttt gctgactgta tctctcatga ctcatttcct   42060
cactgactca gtctgccagg aaagcttcta ccccagagtt tttgcatttg ctattccttc   42120
tttctatagt gttttcctcc cagatacaca gttttgattg aactgtcaca tatttgaggt   42180
gcctgtcctg actgccctttt taaaatcaca agcatccctt cctctgcaga gctcatcaca   42240
cccacacccc gtcgcctttt ttccccatag cacttattac cttataatat gctatctaat   42300
ttattatata agtaaatcac tgaatcataa tcataacctt tacatgggca gggatttttg   42360
tctgctatgt tcacagtttc atcccttgca ccaagaagaa tgccttgtac ataatagata   42420
ttcagtaaat atttgttgag tgagtggttg attgatattg cacaaaagga ctcctcccca   42480
caatattctt agtagcaaga aaaagaataa ggaagacaag tctttctgtt attgacaaaa   42540
gccttgtgct aaatgttttc tttccgtgag tcagaatttt gtctttgcct attcttttgt   42600
```

-continued

```
ctcaaaccat tgatagttta tgttctttct tttttctttc tctgccagtc tttttaaaatc   42660 cttccacgtc ctacatctag atacttttttt tgttttttttt ggtcaaacag cagttaacag   42720
taccaaaatg ttctaggcag actgcattcc aatccaagag gcaggagtca gtactatcaa   42780
cttttctaga gaccagttag caaagaagag tttaacatga ctactcaggg caaaaaatat   42840
gtttcttaga gttccttgga tatacaaaag accaagctat agatagggct gcttcttcat   42900
taactagaat gcaacatagc tttcactcct gctgctactt ctggtaccat tgctcaaact   42960
gatgaaaaga gattcagggt accaaattcc cttgaaaaaa tacaaatata tgtaagatat   43020
aaattttatt gtatttaaga tgtacaacat gttttgatgt aaatataggt ggtgaaatgg   43080
ttagtcaagc agattaacac atccatcatt ccacattgtt gcccattttt tgtgtgtgtg   43140
gcaaagagca cctataatct cttttagcaa aaatcttgaa tgtaatacaa tattattatc   43200
tatagtcctc atgctgtacc tgagatctct agacttgttt gtcttacata tctgctactt   43260
tgtatcagac ctacatgtcc catttcctcc acctccacca taatcagtgt tttatttttct   43320 gtctctggat tttccacttc ttttttttaga ttccaaaata agtgagatca tgcaacattt   43380
ttctttttct gtctggcttg cttcacgcag cataacatcc tccaggttcc tccatgttgt   43440
ggtaaatgtc aggatctcct tttataagga tgaataatta ccagtcttat atgtgccaca   43500
gttttgtcca ttcaactgtt gacactttgt ttgtttccat atcttggcta atgctgcact   43560
gaaaatggga taatacagac gtctttatga ggtggtgttt tcattttctt tgggtgtata   43620
cccaaaagtg agattgctgg gtcatatgat agttctgttt ttaatttctt tagggaactc   43680
ctattgtttt ccacagtggc tgcaccaatc tacattccca ccaacagtgc tcaagattcc   43740
tttttttcta tactctcact agcacttgtc atctctttta tttatttatt tatttattttg   43800 agacagagtc tctctctgtt gcccaagctg gagtgcagtg gtgcaatctc ggctcactac   43860
aacctctgcc tcccaggttc aagcgattct cctacctcag cctcccaagt agctgagatt   43920
acagacgtgc accaccacac ctggctaatt tttgtatttt agtagagacg gggtttttacc   43980 atgttggcca ggctggtctg gaactcctga cctcaagcga tccgcccgcc tcagcctccc   44040
aaagtgctgg gattacagcg gtgagccacc atacctggcc gttatctctt tttgatggta   44100
gtcatcctaa caagggtgag gtggtatttc attgtggttt tgatttgcac ttccttgatg   44160
attaatgata ttgagcatct tttcatgcac ctgttggcca ttttttatgtc atctttggag   44220 aaatgtctat ttaagtcttt tgttcatttt aaaaatcgag ttatttgttt ttctactatg   44280
gagttgtgtg agttttaaaa aatatatttt ggatataaga tacatggtta taagatacac   44340
cttataagat atgtggtttg cagatatttt ctcccaatct gcagactttt cattttgttg   44400
gttgttatct ttgctgtgca gagctttta gtttgatagc tatagtaatc aaaacagcat   44460
ggtagtggta taaaaacaga cacgtagacc gatggaacgg aatagagagc ccagaaacaa   44520
atccaaacat gtgtagtcaa ttaatttttg acaagggcac caggaggata caatgggaa   44580 aggatagttc tcttcaataa atggttctgg ggtaactgga tttctacatg caaaagaatg   44640
aaattggacc cttatcatac accatacaca aaaatcaact caaaatggat aaaataccta   44700
aatgtcagac ttgaaactgt aaaactttct aagaagaaaa cgttgaggaa aagctccttg   44760
acattggcct taacaatgat ttttggatat cacaccaaaa actcagtcta caaaagcaaa   44820
aataaaatag aatttttaatg tgacatggat tcctcaaaga tataggtgat gtataggtgt   44880
aatttccact agtttttcaaa ggtaaaaata gccagtggga ctacctgaaa gtattttata   44940
gttattgagt aaagtagtag ctaaaaaaaa aatcccaggt agaacatatc aaaattgcat   45000
```

-continued

```
ttatataaat ctcacatagc tcaagttgga catttcttaa aggccaacta actttcaaag   45060
tactaaccac ggttcccagg aattatcata aaatttatta tatgtaaagc tcaagttgaa   45120
aacttgtcat ataggagtag ctgaaattct acactgtgca gtctgccttt tgatggctag   45180
tgtgcatctg aactggagtt gcccatttgc attatttttg cagagctcct aataagtggt   45240
aatgggcatg ggtgaacata aaaatgttat ccttcagagt agaaaaaaga ttggagacaa   45300
cgtacagcta ccttccaata tttgaagaac ctttactgtg ttagataaat aaaactttat   45360
tctcatagga ctaaataatt tttaaagtct cttctgatgc tgagaattat cattttgtat   45420
ttcaatgtaa gtgatatgtt ttaaagatat tttattggaa gtacaatata ttgtaagaaa   45480
agtgaattat tatatagtag ctgaagtaat gttcaatatt tatcacaagt agatatgaat   45540
tctcatttct gtccactttt attagcttct tttctgtcat ttaaaatatt cacattttgt   45600
gggttaaagt catgacttaa cattttcaaa gtgagtaatc actgtgacat agatcttttt   45660
cttaatgttt attataggggg ttccagaaac tttagcagtt gcagtgcaga ggactttgag   45720
aagttaactt taaataaagg aggaaactgc cttcttaata ttccaaagcc tgatgaagcc   45780
tatagtgctc cctcctgtgg taataagttg gtggacgctg gggaagagtg tgactgtggt   45840
actccaaagg tcagtttaat ttttgacttt tgccttgtaa aattgccatg atatttgcaa   45900
gaaataaaat ggcttgcttt gggcaactct gacataggag ctaaagtaaa atttagtggc   45960
acagtgagga ttgttatttt gtttgtatgg ctgtgttcca gggattggtc atctccttct   46020
tctcagagta tgactaacgg tgccatctgt tttgaagtca gggaatgtgc catgtttatt   46080 ctctacttttt ttaatgctat tttctatgat ttatggttat tagcttatttt gctttaaaga   46140 atgaatttca cctggctctt tatttgtaag cttttcaccat tctggcactg ccattgcagg   46200
aatatttatt tagctggact cattttaaaa atgaattgga gctggcctgt cctccagcgt   46260
ccttcagtat tcaaagttct tgctactcaa agtagcactc taaaaaaaaaa aaaattcaag   46320 tagtaagtaa aagcaacctt acacacgttt atttccccca taaatctttt acttccttttt   46380 tttatgtttg atgtttttct ttttagacta ttctgttcat ttatatacag tatacagtag   46440
gtacatttat aaatattggg cttgtttttag gatttatttt tactttaatg tggtaagaat   46500
acttagcatg aaattgatcc ttctaagaga tttttaaatg tccagtacag tattgttaac   46560
tctgggtact gtgttgtaca gcacatctct agaacttttt cactgtgtgt aactgaaact   46620
ttgtatctgt tgatcggcag ctccccattt tccattccac aagcccctga ccaccactat   46680
tctgttcact gcttttatga acttgactat tttagatacc taatataagt ggaatcaaat   46740
ggtattatgt cctttgtggc tgccttatttt ctcttagcat ggtattgtat actcaagttt   46800
catctacgtt attgcaatga caagatttcc ttctttttttg ggaaatagta ttccattgta   46860
tgtgtgtata tgtatgtatg tatgtacatt ttctttatcc attcaactgt tgacagacat   46920
ttaggtggtt tctacatctt ggctactgtg aataatgctg cagtgaacat aggaatgcta   46980
atatctcttc aagatcttga tttttatttta gataagtacc cagaagtggg attgctagat   47040
cacatggtag ttatattttt aattttaaa agaaccttcg tactattttc catagtggct   47100
gcaccatttt gcattcttcc caacagtgca caagggttcc agtttctcca cattcttgcc   47160
gacacttgtt gtctttttgtt tttttccgtg atagcaatcc taacaggtat gaaattatat   47220
ttcattgtga ttttgatttg catttccatg atgatgagtg acattgagca tctttttcata   47280 tacctgttgg ctatttgtgt gtcttcatgg agcaatgtct attaagtctc aggcctgttt   47340
```

-continued

```
taattatttt tttgtttctt ttaacatttt tatatattta ggggatgtaa atgcagattt    47400
cttgcatgta tatattgcat attggtaaag tgagggcttt tcatgtacct gtcattcaaa    47460
tagtgaacat tgtacccaaa aggtaatttt tcagccctca cacccctccc atgctcccac    47520
tttttggggt ctccagtgtc tgttattcca ctctgtacat ccatgaatac tgattgctta    47580
gctcccactt ataagtgaga acatgcagta tttgactttc tgcttctgag ttacttcaat    47640
taggaaaatt aacccatttt aaatcaggtt attagttttt cattttttgc tattgagctg    47700
tagctcttcc tgtatatttt gaaagtttac cccttatggt ttgcagatat ttcccctat    47760 tccataactt ggcttttcac tctgttgatt gcttcctatg ctgtgtagaa ggttttagt    47820 ttgatatagc cccacttgtc tattttggc ttctgttgcc tgtaattttg gcatcatatc    47880
catgaaatca ttgccaagac caatgtcatg aagctttcc tctatgtttt cttctaagag    47940
ttttactgtt tcaggcctta tgtttaagtc tttaatccat tttaagttga tttttgtgta    48000
tggcgtaaga taaggttcca atttcattct tttgcatgtt gatatccagt tttccacggg    48060
ggaagggact accttttcac cattcttttt cttagcatcc ttgttgaaga tcaggtgatc    48120
tcatatgtgt gggttttat ttctgcattc tttattctgt tccattggtc tatatgtctg    48180
aattttattt tattttagat tcagggggta catatgtatg tttgttacat gggtatattg    48240
tatcctggtg gggattgggc ttctggtgta cccattaccc aaacaatgaa cattgtacct    48300
tataaataat ttgtcagccc tcactctcct cctaccctct ccagccctca ctctcctcct    48360
accctctcct cttttggagt tacccagtgt ccatcacctc catctttatg tccatgtgcg    48420
cgcattgttt agcccatgct tataagtgag aatatgcagt gtttgatttt gtgtttctga    48480
gttagttcac ttaggataat ggcctccagc tccatccatg ttgctgcaga ggacatgatt    48540
tcattctttt ttatggctac atatagtatt ccgtgggggtg tgtgtatgtg tgtgtgtgta    48600
tacatacata tatatgtata tatatgtgtg tgcacacata catatgtatg tatatatgtg    48660
tgtgcacaca tacctatgta tgtgtatatg tgtgtgcaca catacctatg tatgtgtata    48720
tgtgtgtgca cacataccta tgtatgtgta tgtgtgtgtg catacataca tatgtatgtg    48780
tatgtgtgtg tgcatacata catatgtgtg tgtgcataca tacatatgtg tgtgtgcata    48840
catacatatg tgtgtgtgca tacatacata tatgtgtata tatgtgtata catacatata    48900
tgtgtatata tgtgtataca tacatatatg tgtatatatg tgtatacata catatatgtg    48960
tatatatgtg tatacataca tatgtgtta tatatgtgta tacatacata tgtatatgtg    49020
tgtgtacacc tatacatgtg tgtgtacacc tatacatgtg tgtgtacacc tatacatgtg    49080
tgtacataca tataggtgtg tgtacataca cctataggtg tgtgtacaca cacctatatg    49140
tgcgcgtgtg tacacacacc tatatgtgcg cgtgtgtaca cacacctata tgtgcgtgtg    49200
tgtacacaca cctatatgtg cgtgtgtata catatgtgtg tgtacataca tatatatgtg    49260
catatgtgtg tatatatgtg tgtgtgtata tgtgtgtgtg tgtatatata tatatatata    49320 aaagatttt ctcatccagt cgactgttga tggacactta cattagtttc atgactttgg    49380
tattgtgaat agtgctgcaa tgagcatatg agtgcagata ccttttttac ataacgattt    49440
attttcctct gggtagatac ccagtagtgg aattgctggg tcaaatggta gttctagttt    49500
tagttctttg aaaaatcttt atactgtttt ccatagaggt tgaactaatt tacattctca    49560
ccaacaatgt ataagcattc cctttttct gcatctgcac caagatcagc ctttttttt    49620 ttgacttttt aatgatagcc attctgacta ttgtaagatg atatctcatt gtggtttaa    49680 tatgcattct ctgattttca atgatgttga gcatttttc ctgtgtttgg cagctgcttg    49740
```

-continued

```
tatttcttct tctgaggaat ggattttatt gaatctgcag atcactttgg gtaatatgga    49800
caatttacca attttaatta ttccaatcca tgaacatagg atgtctttcc atttatttgt    49860
atcatctttt atttctttta gcaatgtttt gtaagttttt agtgtgtgat cttttttcctc   49920 acttgttaag cttattcaca aatgttttgt tttcaatgct attgtaaata gctttgtttc    49980
cttaatttcc tttttgtagt tcattgttag tatgtgaaaa tgaccttatt tttgtgtgtc    50040
agttttgttt cctgcaactt tactgaattt atttattagt tataacaagt tttttgatgg    50100
actctttggg attttctata tgtatgatca tgtcatctta aaagagggac agtttttgctt   50160 catttccgat ttagatgcct tttagttttt cttgctaatt gttctggcta ggacttccaa    50220
tactaagttg aatagaagtg gcgagattgg gcatccttgc ttcatttctg atctcagagg    50280
aaaagctttt tgttttttcac aactaggtat gattttagct atgggaattt catatatggc    50340
ctaattatgt tgaagttatt ttcctttatt tctagtttgt tgagagcttt ttgcatgaaa    50400
gggtgtagaa ttttatcaag tgcttttttct gtatctattg agatgatcat gctatttta    50460 tccttcattt tgttaatgtg gtatatctca ttatttaatt aattaaattt ttttttttttt   50520 gagacagggt cttactgttg cccaggctgg actgcagtgc tgtgaacaca gctcactgca    50580
gctttgacct aatgggccca agtgatcctc gtgcctcagc ctcttgagta gtcgggacta    50640
caggcatatg ccaccatgcc tcacacattt ttgtatgttt tgtagagaag gggtttttgct   50700 acattgccta gactggtctc gaactcctgg actcaagcag tctgcctgcg taagacgccc    50760
agagtgctgg gattacaggt gtgcaccact gcacctgatc tcattaattg atttttgtat    50820
attgagcctt aattgatttt tgtatattga gccatcccaa tttataccca aggataaatt    50880
ctactaggtc atgttgtatt ttactttaa tgtgctgctg aatttggttt gctagtattt     50940
tgttgaggat tttgcatctg tatttgtttg gcacattggc ctgtagtttt ctatatttgg    51000
catattggcc ttggtgatac agtctgcatc aggataatgc tggcctcata aaatgagtgg    51060
aattttctcc tcctcctcta tttttttgggt gaattttttag aatgattggc attagttctt   51120
taaatgtttg gtagatttca ccagtaaagc cattggtcct gtgctttttct ttgctaggag   51180 gtttttgatt actgattcat atccttacta cttataggtc tgttcagact tatttcttta    51240
tgattcagtc ttggtgggat gtgtgtttct aggaatttat ccgtttctttt taggtgatcc   51300 agtttgttga tgtgtaaatg tttatagtag tcttttataa ttcttttttat ttatggcatc    51360 agttgaaatg tctcctttct catttctgat tttgagtctt ctctttctttt ttcttagtgt   51420 agctaagatt ggttaatatt gcttatcttt tgaaaaatac taactcttgg ttttgctgat    51480
ttttcaattc ttttttctagt ctcaattttg tttatttctg atctgaagtt cattatttcc    51540
cttatgataa ttttgggttt aaattttctg ttgcttttca gatttcttgg gttgtaaagt     51600
taggttgttt atttgagttt tttttttttaa tataggttat cacagcaagc tttccttgta   51660
tttttttttt ttgacagagt ctcactgtgt tgtccaggct ggagtgtagt ggggcaatct    51720
tggctcattg caacctccac ctcctggttt ctagtgattc ttgtgcctca gcctcctcag   51780
tagctaggat tacaggcgcg caccaccatg cctagctaat ttttgtattt ttagtagaga    51840
tggggtttcg ccatgttggc caggctggtc tcgatctcct gatctcaggt gatctacccg    51900
ccttggtctg ggattacagg cgtgagccac cacatctgtc ctcctttttag tattattttt   51960 gttttatttc ataagttttt acatattgtg ttttttgttt gtccaaaagt atttttttaat   52020 cttgtgtttg atttcctttt tgacccaatg gttgttccac agtgtgttgt ttaatttcca    52080
```

-continued

```
catattggtg aattttccat tttcctttct gcttttattg ttgtcttttt ctattctaat   52140
tgctagtttc atccattttg gtcagaaaat atatttggta tgatttcagt cttcttaaat   52200
ttctgaagac ctgttttgtg acctaaaatg tgagcctgga gagagttcca tgtgtgcctg   52260
agaatagtat gtattctgcc actgttgggt agaatgttct gtatatgtct attagtttga   52320
tttggtctgt agtgttgttc aagtcctgtg tttccgtatt gatcttctat ctagatgttt   52380
tatccataat taaaatgcag tcttgaagtt tcttactatt attgtgttgc tgtctctttc   52440
tttcttcagt tttgtcagtg cttgcattac atatttaggt gctctaatgc tgggtgcata   52500
tatatttatt attgttatat cttcctagtg aattgttact tttatcatta taaaatgttt   52560
ttctttgtgt tttgtgacaa ttctgacata gagtctcttt tctttgatac aaatataggt   52620
acccctgctc tctgtggtta ccatttgcat ggaatatctt tatccattct tcactttcag   52680
cctatatatg tccttagaac tatagtgagt ctcttgtaga tagcatatag tttttttttt   52740
ttttttttta tccattcagt atgctatgtg tttttgttgg ggagtttaac atatttacat   52800
ttaaagtaat tcttgatagg gaaggattta ctgtgattgt tttaaatgtt ttttgtttgt   52860
cttgtagctc ttttgcctgc cctttcttgc tgtttttcctt tgtaattttt tgattttgtg   52920
tgtgtgttga taattctttt atccctattc ctttttcttt tgtgtaactt ccttctatag   52980
gtatttgttt atggttacct tagagcgtgc ataaaatatc ttgtagtaat aacagtattt   53040
ttaagctgat aacaacttaa cctcaattac atacaaaaac tcttcacttt aagttctccc   53100
attacacagt ttatgttgtt gttacagttt acaatctatt aatattgtgt atcttccaac   53160 atattttta tagtttttt tttttttttt gagatggagt tttgttcttg ttgtccaggc   53220
tggagtgcag tggtgcgatg gctcactgta tcctccgcct cctgggttca agtgattctc   53280
ctgcctcagc ctcccaagta gctgggacta caggtgcctg ccaccacgct tggctaattt   53340 ttgtatttt agtggagatg gggtttttacc atgttgtcca ggctggtctc gaactcctga   53400
cctcaagtga tctgcctgcc tcggcctccc aaagtgctgg gattacaggc gtgagccact   53460
gcgcccggcc tatagttaca ttttatactt tttcttctaa atttacacta gaagtgaaag   53520
tgatttaccc agtaccatta acagcaacac agtattttgc atttgtctat atatttattc   53580
ttactaatta attttatact ttcttatgct cctgtgttgc tgtctagcag tctttcattt   53640
caaggtgcag aactccattt cacatttctt agaagaaagg tctaatcatg atgaacttcc   53700
ctgcttttgt ttttctagaa aagtcttaat gtcttcttca tttttaaagg atagtttttgc   53760 cagatatagg attctttctt ggcagttttt ttctttcatt actttaatat gtcacctcat   53820
taaccttctg gcctgcaaga tttctgctga aaaatccact aatggcctga tgggggttcc   53880
cttgtatgtg atgaattgct ttctttctta ctgctttcaa aattctcttt gtcttttgat   53940
aatttgattg taatgtttct tggtgttgat ttctttagat tcttcttact taaggttctt   54000
tgggcttcct gcatctggac gtccatttcc ttccccagat ttgggaaaat ttcaaccact   54060
acctctttga aataagcttt ttggtacttt ttcttagtct gctccttgtg ggattgccac   54120
agtgtgtata ttagtctctt gatggtgtct cataagtccc ttaagctttc ttcacttata   54180
tttctttttt tttttttgct cctctgactt gataaggtaa cccgactttg agttgttga   54240 atctttattc tgtttgctct gatctgctgt tgaactcctc tgttgcattt ttccattaag   54300
ttggtgtatt cttcagcccc gaaattagtg agaagacctt cactagttaa cctggccaga   54360
gctttttggg gcctctcaaa ctttcatgtt tgttatactg cctttctat tgttgttagc   54420 gctcagtgtc tacaatatgc tggagcctat cagtgttctg agagggggaga aagaagtgaa   54480
```

-continued

```
tttgttgggc aatccctaga aaagttggaa catgtgacat gtggtccaac agtttctctt   54540
tccagggaaa agcttggaag tgtttttttt tttttttttt ttttttttaat cactatgtta   54600 aactgggtag aggaactgtg gcgagtgtct gagtgatagt ttgaacaacc accttcattc   54660
tttgtagcct tcaggggtct agcacatacc agctccatct gtgctctgag agaggagagg   54720
gaaaagccaa tttcttgggt agctcctaga aaaattgtag cgttggatgt gtggtcctcc   54780
tttgggagaa gctaggagct gtggcaagtg cccacatgct agtttaacct actacctttg   54840
ttctctgaaa accccaggga tctaatatat tccaggtcct atatgttgtc agaggcagat   54900
gagatagaag gtagtccctc aggaagcact ctaaaaaact gtaatattgg atgtgtggcc   54960
caactctttc tctcctcagg gagatgctga gagctgtttc ctcctgatct tatatgacgc   55020
gtcatgagtt gggattgcgg cgagaaagga tctccagttt tcctactggt ttcagtgtgg   55080
ctggttttac aattgcctgg gatgtagtag cctctcaact agtttctgga tttctcacaa   55140
agggaattga ttagtgtgtt actgttgaat tgctgacttt ttataggaga tttgttagcc   55200
tccaataaaa gttaaaatgt acatgctttt agatctagta attctacctt tatgtaacta   55260
tcttagagaa atatttgtgt atatacacat ggggagtgta cagggatgtt tattgcagca   55320
ctgcctgttg gaggaaggag aatccagagc tttctattct cccattttgg tgatgccact   55380 ctggcttta tttttgtgca taaataaaat cagacttaat attgtttaaa attgacttaa   55440
aatctcttgt gtgcagattt ttttctatta cgatatcctg gacattttc tgtatcattt   55500 tattatgtag acatagccct ttaatttgct gaatagtatt ccaatacaag gatttactat   55560
gatttattta accatactct cattaattac tgtaattagt gtttctatt gtaaacagtg   55620 ctgccgtata catccttgta cacacctcat gtgtatatat acaaacatac acacctcatg   55680
tgtatatata cagatataca cacgtcgtgt atatatacaa atatttttct atgatagtta   55740
ttgtacataa aggtagaatt attgtatcta aaagcatgta cattttaact tatatcagaa   55800
gctaatgaat ttcctataaa tagtgtgggt cagtttgcat ttctgacaac agtatattat   55860
gccattgtgt acccatagtc ttaccagcac aggataatat gttttcttaa ttttggcaag   55920
ctgatgggta aaaaataaga agatactgtt ttagtttaca gtttttcatg tgattgtaga   55980
ttataggcat cattttcttc tatgaattat tattttatgt attccttatc agttctgttg   56040
gttcattaaa tcttctttta aattgatttt tagacctctt tctataagat ggacataact   56100
cctttgttat atatgttcta atattcttta tttatagctt atttaacttt tcataggtta   56160
cattttatgt tgaaatttaa aatttaaatg aaggcaaact tactaatttt tttcctgtaa   56220
tggtttcaga aatttgtatc ttgacctggt ttttagtatt cctatatata gatcatcatc   56280
atagcccctc tacaaattat tttagttttt tttaaattta aaatttttat gttaactctt   56340
ttaattgagg aggggggcatg tggagtaagc ttggaaatta aacttatcca ctaatgatca   56400
gttgttgtgg aaccatttaa aatggttctt ttacgataac ctaagttcct atatacatta   56460
tctatttcct gattccctat tctttcatga agccaactgt cctgcagtgt ttttgaactg   56520
gccagcattc accttcaaat ctttatgtga acttatgttt ttaatactgt tgggtaaatg   56580
tcccggagta gaatgacttg gttagatggt agaggtattt aacttttcaa gaaactctca   56640
aactgttttc taaagtgatt gttccatttt tcatttccat ccttagtgta tgggagttct   56700
aattgtttca tatcctgacc aatacttcgt gtggtcagtg tttttaattt tagccattct   56760
attgagtgtg aggtggtgcc tcattgaggt tttaatttgc atttccttag taactaatga   56820
```

-continued

```
tgcattgagc atgtttttcat gtgctttttt gccatcaggc tatcttatgg tgatatgact    56880
gttcaactct tttccctcat ttaaaaattt tgattactta ttgttgagtt ttgagaatac    56940
tttgtgtatt ctgtatacaa gttctctatc agattgtcaa tattttttcc aagttgtagc    57000
ttgcctttaa ttaacttagc agtatatttt gaagagcaga acttttttcat gttgatgaag    57060 tttatttttat aaacttgtaa ttttatcggt tgttcttttg gtgtcctatc taaggacttc    57120
ttgcctgctc cacagttgca aaggtttttct cctagaagtt ttatagtttt aggttttaca    57180
tttagttcca tgatgcattt tgacttttttt tgggtatatt tcaagatgta cattaaagtt    57240
catttatttt aaaatgttta ttatgaaata attataatct gaaaagaagt tgcaaaataa    57300
tatagagtcc tgtgtacttt tcacccagtt ttccttagtg gtgacatctt ataaagctgt    57360
accacagaat acaaaacaga acattgacat tgctatttta acagagaaga tgtctctgtg    57420
ggtgggagtt tggggggtaag aaggagccat ggtggcccag agtatagtga gagaagccaa    57480
gcaaggtaaa aaagagtgtt cagctagggt gaagagccat ccaacagaga agttagaccc    57540
tgagcatgaa gataaatgcc tttatggaca ctgacctctc tgtgatcatc aaacatactg    57600
ttatgaactg aatgtttgtg cttccccaaa actcatgtgt tggagccagc caccagcatg    57660
gctacatttg gagatggggc ctttaaggaa gtaattaagg ttaaacgagg tcataaggat    57720
ggggccctga tccactagga tcagtgtcct tgtaagaaga gacaccaaac atctcacttg    57780
ccgtctctct gcacacatgc actgaggaag ggctatgtca gcacacagca agaaggcagc    57840
cctctgcaag ccaggaagag aatcctcact agaaactgaa ctagtaggaa ccttgatctt    57900
ggatttctag cctcaagaac tgtgagaaaa taaatttctg cagtttaaac ctgtggtatt    57960
ttgttatggc attctgagca gactaagtaa ggcacatact atatgatttc tgtcctttga    58020
aatatgttga gacttatact tgcagctgaa gagacattgt taaatccaga aacagtaagc    58080
aactgtttct ggagggtaac tgctacaatc atgttagaat gaagtagatt ttaggtgtaa    58140
gatgagaatt ttattaatga gtattcatgt caattactaa tttctttatt gacagtcatt    58200
ttatgttcac aggaatgtga attggaccct tgctgcgaag gaagtacctg taagcttaaa    58260
tcatttgctg agtgtgcata tggtgactgt tgtaaagact gtcgggtaag gaattcctcc    58320
cttttggaaa caggaaaaaa aaaaaaaaaa aaaagaaaac ctgtgtatat caaaatttgt    58380
tttttgagat ttctgagtca gcactatttt tattttatgg tcatgggaaa aattttatgc    58440
cacttgtgta taattttaaa gcacactctt ttacgttaag tggtctgttg atattgtttt    58500
ctaagtagaa acattttttt tctgatttttt agagtaacat atgcctgtta gaaataatta    58560
aataacatga aaccatagaa agtagagaat gaaagatcct ctattatttt atactcttca    58620
ggtaaccact gttgataatt tgttaatata atcacgtttt ttctatacaa atgtgagtgt    58680
atgtgtgtat gtgtgttttt aagtgggtaa gcacagatac atatattttt actacctgct    58740
tttttcaata tgacaccatg gactttttttc ccattcatgt agttctataa tacatggtta    58800
tttaagtaat attacttgta tagttgtacc ataatttctt tagtcaacta atgatggaca    58860
ttttgattac ttccagttac tgcttataag agaaatcact ggtgcagaat attcatacta    58920
agtttttgat atacatttta tatatctttc acacatatgc caatctatac ttctaccaac    58980
agtattatca aatacttgtt tccttatgcc aatattgggt actagcaggc actatactcc    59040
tagttaattc aataggtgta aagggttctt gtatttttat ttagtttgca tttcttttgg    59100
ttacaaatga ggtcatgttt ctttactttc catagttagg acttacatga attacctgtt    59160
gttagccatt gttcattttt ctgttgggtt atttaatctt ttgctattgt tagaatgctt    59220
```

-continued

```
tatagatgta aatgctgtgg tttcacattt gattaatttg tggacattat cctgatattt   59280
ctgtttaatt tgaattctat ttcactagtt ccttccagga ggtactttat gccgaggaaa   59340
aaccagtgag tgtgatgttc cagagtactg caatggttct tctcagttct gtcagccaga   59400
tgtttttatt cagaatggat atccttgcca gaataacaaa gcctattgct acaacggcat   59460
gtgccagtat tatgatgctc aatgtcaagt catctttggc tcaagtaaga tatcatcatt   59520
tataattgat tgcttcgata ttatttattt ttgatttaga tattttaaaa aaggtaatga   59580
aacattattg ataaagttga ggctctcttg tttctcatcg tatttccttt cttctttgga   59640
ggcagtcatg atcatgaatt taatatgcac agattcagtt gatgtttct tatttttact   59700 gtctatatct tttttatattt tgtgtatcac gcacacacac agatacatat atagtatcta   59760
gttttaataa tgttgaattg tgcacaagga tctgctattt gcattgttca ctcagaattt   59820
tcttgaaatt catctatatt gatatattta tattatagta cattaaagta ttccattaga   59880
tgaatggatc atgatttagt tattctctta ctgatagata tttgggattt ttaaaaaatt   59940
tatgtatttt ttcttttaaa agttcttatt tttatcaagg gcatacatat aaagagccaa   60000
attattgtgt aatgcatagt atgaacaaat aaggactgtt cccacccact attcccatca   60060
cttgaggcag ttttacccttt tttggctaag attttttgtta acttgtgcta ggttttttaga   60120 taatctcttg gcaatgcgac gtttttgattt ttttgttcta ggcattagtt attaatttct   60180
cactatagaa gatgagttag ttttctttcc ttctcttcct tcaaccctta acaactccca   60240
tcatacctat gctgatttct cattcttcat cctcccaata gttagggcag tgatgactgt   60300
gtattgtata atggccacat taatgctctt cacaactaaa ctgtatagta agttataatt   60360
acttgcctga tttctctaga gttactaatt ctgtctttct gtttctctct ctctcttttg   60420
gtttggttaa tttcctatgt actttccatt aattgacctg tatattgtta accattggcc   60480
tgattgtgcc ttgagttgat tagtggcatc aagtattcta tttatttcaa tttgttcaaa   60540
taagtctgaa cagaaggcct ctgttcctct tcagtcttga ctggtttccc tctgtatagt   60600
tagttagggt tctctagaga aatggaacca ttgtgttgtg cgtttatgta tacagtcata   60660
taccgcataa caacattttg gtcagtgaga gattgcatat acaacagtgg tctcataaaa   60720
ttataatgct gtatttttac tgtaactttt ctatgtttag atatgtttag atacctttc   60780 tatgtttaga tacgtttaga tgccattgtg ttaccattgc ctacagtatt tagtacagtg   60840
acatggtgta cagatttgta gcttaggagc aataggctgt accacatagc ctagatgtgt   60900
agtaggctat accacctagg tttgtttaag tgcactctgt gatgtttgca caatgacaaa   60960
atcacctaac aactcatttc tcagatcata tccctgttgt taagtgacac attactgtag   61020
atattactgt atatataatc tggaggaatt attacgtgaa tctaatattt atatataata   61080
tataatttac atataatata ttaaatatat aatatcttat atatgtatta catgaaaatc   61140
aaatatattc tcctggagga atctgatata ttagattcat gtaataaatc ctgcgtaata   61200
gcatgagccc atatatgaat tggcttgtgt gattgtggaa gctgctaagt gtcagatctg   61260
cagggagagt cagcaatctg gagaccctgt agagctgatg gtatagttcc agttagaagt   61320
ctggcaggct catgaccatg gaagagctag tgtttcagtt caattccaaa ggcaggaaaa   61380
aagctgatgt ctcattccaa aggccttcag gaagactttt ctcttacttg agggaggact   61440
ggccttttcg ttcaagttta aaattgattg gatggggccc acctccaata gggagggcag   61500
tctgctttac tcatcctact gatttcaatg ttaatctcat ccaaaatcac ccttacagag   61560
```

-continued

```
acatccgtaa ttatgtttga ttaaatatct ggggattctg tggctcagtc aaattaactc    61620
tactaaaaag ggtaaaatta accctcatca aaaatccact ccttgtcagc ttgaaaccca    61680
tagacacctt aaaccatacc aaatctccaa atgtggacct tgttaagggc ataattccac    61740
ctagcatgat ataataacac tatcctgcat gcaactaaaa cctcactaac ctcttttcca    61800
gaaaaggagg taaagtgatg tttattcttc ttcttgatat cccataactt aaatactggg    61860
atataaaatt aacaatactt aaatgctata atatcaagtc aatatgtctt atgctgcatg    61920
ataaaggtat aaggaatgag aacatatttg ctcagtacgt gtgtgtgaat gcacacacac    61980
atacacacat gcagctattc ttaatgaaac agtcttcgtt tctgcaactg gtcatgtggt    62040
tgtagctggt atttataact aacttccacc cattctgtat tccctttgcc ttcagcaagc    62100
acgttagctg tttgtggttc tttacctgtt agggtgaccc aaactgtcgt tcttgaaggg    62160
tctgggccat ttgtagtcct tcctagattg ggttgttaaa gttttccatt gaacttaaac    62220
ttaatcatga agcatggtaa tactaagaga tgccctaagg gatctccggc attctagaca    62280
tactcttcct tgcctccatt ttggagtagt aggccagttt ccctttggtg gttcggatca    62340
gtaattctac ctggcataga aactgccttc tttgcctgtt gacttggagg tatgaggagc    62400
caatgtggct gggcctctgg cttaatttct agttcagtag aatcattatt gtggctcctg    62460
gtggcagcat tcctcctttt ggaactaagg cctctagtcc agtagagcat aaggtcgtgg    62520
gaacaggaaa caaaattttg ctagtgggtc actatggata atggtgagtg gtgtttctcc    62580
catttccacc ccttgatacc tggacacgtg aatcctggtt atgggaaaat cagcattgga    62640
tgttggctgc tgattgagag catatacagc ctttttggaga accttgcccc agcactgtaa    62700
ggtattgcta cctagtggca ctgtaactga gtctccaaaa ggcatttcca ccatgctgtc    62760
agccagctgc ttcaggatgg tggggaagga acatggtaag gccagtgaat tccatgtgca    62820
tgggcccatt gcctcatttc atttgctatc aagtgaattc tttggtttga agcagtgctg    62880
tgtagaatat tatgatggtg ggggaggaat tctgtatgtc cacagaaggt agttttggta    62940
gttcacagga gtgttgctac agagatggca aatctatatc aagagtacgt gtgtctgtcc    63000
cagtaagaac aaagcactgc ttctttcatc atggaaaggg aaaaatgtaa tcaacctgcc    63060
accaggcagc tgactgacta acctagggaa tggtgtcata ctggggactc aggattggac    63120
tttgctactg gagaatttgg gcacttagca gcaacaatgc caggtcagtt gttgagagga    63180
agtccatgat gctgagccca cgcatcgcct ccaaccctgc cactgtgagt acgtggttcc    63240
tgagcccatg gatgagaata gttggctggg gaaagaatga gtcatcctat ctacttgatt    63300
attaaaattc tcctctactg aggccaccct ttggtgaaca ttcacatggg acacaaatat    63360
ctttgcccta caacccagtc atgggccata gcccataaat tggtgtataa tcacgtctgg    63420
ctgtttcttc tcccaaggaa agtgaacaac caggtgcact tcagggatgt cccagaaagg    63480
ggctgcagtg ctacagtcat ccacttttgg ttcttcatat catatcatgt gtagaaccat    63540
ctgcaaacca ggtctccgtc ttcttttcta ctgtcacctg atgggtagga agttccccgt    63600
gaggtcatag ttgctggcta ggagagaaaa tgtagtgtag caggagtggg gagcaggggc    63660 atgtgggca cttctttatg taacttgtgc cttccaggcc ttggtttggc tcaattacat    63720
acgtagcact tccatttcat gatggggtgc tgctgcatat gcccagcttt atagcttggt    63780
gagtcagatg acatccagtt tatcatgggc aactcaggtt gaatggtaac ttggtgggtg    63840
gcccatggtt aaatgttcaa tttctacttt aaggcccagt agcaggccaa tagttttttc    63900
tcaaaaggag agtagttatt cgcagaggat cacaaggctt tgctccaaaa tcctaaatgc    63960
```

-continued

```
ctgcactgca cctgacctat agggaactgt cggaggcgct aaacagcatt tctgtctgta   64020
actgctgctt caagcactgt ttgatctgct tgatcaagtg ggctaagcag cagagcatct   64080
tgcctgacag cctggaccta ttgcagagtt tctctttgtt ctgggcccag ctcaaaacta   64140
gcagctcttt gggtcagtgg gtaaatgggc cagagttatg caaccaaatg aggaatattt   64200
tgccttcaga aatccaaatg gacctctaaa cattgtgcca ttctgttggt tgtgggagtg   64260
gccagatgca acttcttctt ccccttagaa aggatatctt gacatgtccc acaccactgg   64320
acatgtagaa atttcactga ggtagaaggc acctgaattt ttgtcagatt tattttctac   64380
tttttgtcgt gcaaatatct tgccagtgac aagaatagtt gctgtttctt gctcactagg   64440
tctaatgagc ataatgtttt caatgactag tgtgatattt tgtggaagga aaaggtaatc   64500
aagatcccca aaactaaatt atgacatggg gctccagagt tgatattctt cctaagtagg   64560
acagtgaagg tgtattgctg gccttgccag ctgaaagcag ctgcttctgg taggctgtgt   64620
ggatgggtat aggtaaaggt ttttttcagat cacagctgca taccatgtat tagggatgt    64680 gttaatttgc tcaaacaatg aaatacattt ggtatagcag cttcagttgg agtcaccact   64740
tagctaagct tataataatc cactatcatt ctccaagatc tgtctgtctt ctgcacaggg   64800
caaataggtg aattgaatgg agatgtgatg agagtccctg cccctgcatc tttcaagtcc   64860
ttgatgttga cacgaatctc tgcaatccct ccagagatgt ggtattgctt ttggcttact   64920
attttcctag gtagaggcag ttctagtggg ttccacctgg cctttcttac cataataacc   64980
atcactccac aggtcaggga accagtgtgg caattctgcc agctgttgag tgtgtctgtt   65040
tcaattatgc attctggaat tgtgggaaaa aacccacaag gtgggttcag ggacccacta   65100
ggcctgctgt gagatggacc tgaggtaaaa cttcatctat cacctgacct tcataagccc   65160
ctactctgac ttcttgacca cagtgacatt ttgggtttgc tcaattattt cagatatagg   65220
gttctgtgtt cctgaaaggt cgaatttttt tctcagtgca cagtgtctta gtctgatcaa   65280
ttctgtctca gtctattttg tgctattata acaaaatgcc acagaccggg taattaatag   65340
tgaacagaaa tttattggct tctggaggct gggaagtcca agataaaggt gctgccatct   65400
gatgagggtc gttttgctga gccatcacat gacggaaggt ggatgggcaa gagacgaagt   65460
ggggccaaac gcaccctttt ataacaatat taatcttatc ccagagggca gagccatcat   65520
ggactaatca cctcttaaag gtcccacctc ttaatgctgt cacaatggta attaaatttc   65580
aacatgaatt ttagaggggga cagacattta aaccatatct ggctgctcta acaagatata   65640
ctgtagactg tgtggcttaa atggcagaca cttatttctc agagttctgg aggctgggag   65700
tctaagatca aagtgccagt caatttggtt cttggtgagg gatctctctt ttcttcttat   65760
aagatcgcca atcccatcat aagggtccca tcctcatgat cccacctaac tctgattacc   65820
tcccaaatgg cccatctcca aataccatca ctttggggtt agggcttcaa cagatgaatt   65880
atgggataca caaacattga aggggtacac aaacgttcag tatataacca ttgccctggt   65940
aaaagccata ggtcccttgg aaatgtctgg gataatgatt aatagtataa attttttggca   66000 ttgtatggga gggttcttcc ttaaagaaac ttaccctgcc tttagttgag agtttctgtt   66060
tctgtaaact ggctcaactc aaggaattga ttaagaggct gtgactttct gtttttatga   66120
ttcaaattag acttttgttt acttggccta gagttttctt atttggtaca ggtcaagtaa   66180
gactatggga agctgcctat cttgcttcta cttagacaga aacagtgtga tcaactagcc   66240
aatgccgtaa gttttacat gggtcaggtt attctgattg ctgctttgac tctgctctcc    66300
```

-continued

```
attatggtaa ccttggctct ccattatgcc aaccttggct ctccattatg cccaccttgc   66360
ctttggtggt tgaatgttga cactttccta tcacctagaa tctgatactt tcattgcatt   66420
taagtttccc aactcagtgg ccatagctcc tactataagg tctgcccttt agataagagt   66480
gatcacagag cttttcaagg atgctaggcc tccccttaca aatttatttc ttacagtctt   66540
ggtgaaaggt gtgtttctg gattcttcca gggtgggtaa atacatctta agtgacaaat   66600
cgactcaaac attttagtct ccctcagact ttgaatccct ttctctgcat taaactgaga   66660
taggccctgc attcctgact tgctcactgt gagctgcctt ttgattcaca tttcagccaa   66720
ccaaccgaac aaactgttag agacctttct aactccctga atggcaacat tcaatgcaga   66780
ctgtctgctt cgtgagtcct caccaatgaa ttcatcccaa tccaacttta tgttcctccc   66840
accattatct cacgcccctta atatccattc ccacacatgt tccctggatt tctgtctgtg   66900
taaattagaa aactcaagta gtcttggagt gtggtgaacc tcctcatggg ttgtatttag   66960
tatttcacct ttaggggcat tttctatgac ttgagtctag ttataggttt agaaccaatg   67020
agatattttg gaggtggatc ctgagggaaa ttggcattat cttgcatggc agctgcctcc   67080
agggaggcta ttacagtttc ctcaggcaat gcagggttag tcccctcaga tgttggagac   67140
gctgtttcca ctggcaaaga cgactcatca gaatttagag gctcagccag gcgcctgtaa   67200
tcccagcact ttgggaggtg aggcaggcag atcacttgag gtcaggagtt tgagaccagc   67260
ctggccaaca tggcgaaacc ctgtctccat taaaaacaca aaaattagcc aggcatagtg   67320
gtgcactcct gtagtcccag ctacttggga ggctgaggca ggagaatcgc ttgaacttgg   67380
gaggtggagg ttgcagttag ctgagattgt gccactgcac tccagcctgg gcaacagagc   67440
aagactctgt ctcaaaacaa acaaacaaga aagaaagag tttagagctc agtgtaccca   67500
gctttatcaa agtctcccca catgtcctca tttcaacttt caagatccag ttccttattg   67560
atcaataacc tcaatttaac agtagatacc ctacaaggct aggagttcaa tttgctttca   67620
gccagtcaca ggataagatt ctaggtttga ttttcaacaa tctcagctct gcaactaccg   67680
gcgatatggc tgtcctttag ggcacacaca gaaaatttca ggtcacttat atggtgcttg   67740
aactaggaat ccctgcgctt atcatcttct ttccctactt tgtccagtaa aataaggagc   67800
aaccaggcaa tctcatactg ttagtatgag aaaaatgttt gaaggcatca tatacatagt   67860
tacccagatc cttgcttctt gtaaatgtct gattaggagt ctctagtgtt gatatgtttt   67920
tggactgcaa ttaccatatc atgccgtgaa ctatcagtgc tacgttaact tttggaaata   67980
gagtcataag tgtctttaaa aatctaatca gattagatag cccattctag aaaccttgga   68040
atcaattcag aaaactcatt ctcaaagttc tgttcctctg gaaccactgt tggtccaaaa   68100
tctgaattag ttagactgca gagaaacaat atcaattgga tatatacata ttatatatat   68160
gtttattcat ttattataag caattggctc atgcgattat ggtaagcaac tgaaaatccc   68220
agatttgtag gatgatttgg caagatggag acacaggaga gatgatggtt tagttccagt   68280
ccagatttga aggcctgaga accaggattg ccaatagtgt aatcagtatt tatcctgaga   68340
tctttcacca taatctgaag gcgaatcatt ggctctctcc cttttgaatc tcctgtttgc   68400
atttcccata ttaccttctt tctttgttta tttcctcctt tcatggagct ttcctttcgg   68460
tagtttcctt agataaggtg aattagaggt aaattttttg agatcctgca agtgtgaaaa   68520 tggtttatt tggactaaat acttgattga tggggatgga aatcattttc tgtcacagtt   68580
ttgaaggcat tgctttattg tcttccagtt tacagagttc ctgttggaaa gtctgaagcc   68640
attctgattt ttatacctag cttttccctc accccctctg aaaaagcttg gagaatgacc   68700
```

```
tcttcaaggt gatatgcctt gatgtggggtt tgttttttatt caccgtgcta tgtaattggt  68760
gggtacattc aatctgggaa ctcattttttt ttagttctgg aaatttcttc cctttcattt  68820
ttttggtgtg atttctttttc ctggatcaca tattatttgg atattggatt tactagattt  68880 ccttggatttt tggatttcct ggatttttctt atctttcctg tctttttatc tgtgttttttt  68940 tttgtttttt ttttttgacc tactttctga gcaacttctt caactttatc ttctaactct  69000
tttattgcgg ttttcatttc aggcactatg atttttagttt tcagaaactc ttttatattc  69060
tctgagtttt tttcccactt atttttaaga aataatctat tcttggccag gcgcggtggc  69120
tcacgcctgt aatcccagct ctttgggagg ctgaggtggg cggatcacaa ggtcaggaga  69180
ttgagaccat cctggctaac gtggtaaaac cctgtctcta ctaaaaatac caaataaaaa  69240
aattagcctg gtgtggtggc aggcgcctgt attcccagct actcgggagg ctgaggcagg  69300
agaatggcgt gaacccggga ggcggagctt gcagtgagcc gagatcgcac cattgcactc  69360
gagtctgggc gacagtgcga ggctacatct caaaaaaaaa aaaaaaaaa aaaaggacat  69420 aatctgttct tatttcatgc acgaaacatc tctcatgttt gtcagtatgt taatgataat  69480
ttttttcttt tttttaaata tattttaagt tctagggtac atgtgcacaa cgtgcaggtt  69540
tgtcacatat gtatacatgt gccatgttga tatgctgcag ccattaactc gtcatttaca  69600
ttaggtgtat atcctaatgc tatcccttcc cactcccccc accccatgac aggcccggt  69660 gtgtgatgtt cccttttcctg tgtccaagtg ttctcattct tcaattccaa cctatgagtg  69720
agaacatgcg gtgtttggtt ttttgtcctt gggatagttt gctgagaatg acggtttcca  69780
gcttcatcca tgtccctacg aaggacatga actcatcctt tttcatggct gcataatatt  69840
ccatggtgtc tatgtgccac gttttcttaa tccagtctat cattgatgga catttgggtt  69900
ggttccaagt ctttgctgtt gtgaatagtg ctgcaataaa catacgtgtg catatgtctt  69960
tatagcagca tgatttataa tcctttgggt atatacccag taatgggatg gctgggtcaa  70020
atggtatttc tagttctaga tccttgagga atcgccacac tgtcttccac aatggttgaa  70080
ctagtttaca gtccaaccaa cagtgtaaaa gtgttcctat ttctccacat cctctccagc  70140
acctgttgtt tcctgacttt ttaatgatcg ccattctaaa tggcgtgaga tggtatctca  70200
ttgtggtttt gatttgcgtt tgtctgatgg ccagtgatga tgagcatttt ttcatgtgtc  70260
tgttggcttc ataaatgtct tcttttgaga aatgtctgtt catctccttt gcccacttttt  70320 tgatgggggtt gtttgatttt tgttgtaaat ttgtttgagt tctttgtaga ttctggatat  70380
tagccctttg ttagatgagt agattgcaaa aattttctct catttttgtag gttgcctgtt  70440 cactctgatg gtagtttctt ttgctgtgca gaagctcttt agtttaatta gatcctattt  70500
gtcaattttg gctttttgttg ccattgcttt tggtgtttta gacatgaagt ccttgcccat  70560
gcctatgtcc tgaatggtat tgcctaggtt ttcttctagg gtttgtatga ttttgggtct  70620
aacatttcag tctttaatcc atcttgaatt aattttttgta taaggtgtaa ggaagggatc  70680
cagtttcagt tttctacata tggctagcca gttttcccag cactatttat taaataggga  70740
atcctttccc catttcttgt ttttgtcagg ttttttcaaag atcagatggt tgtagatgtg  70800
tggtattatt tctgagggct ctgttctgtt ccattggtct atatctctgt tttggtacca  70860
gtaccatgct attttggtta ctgtggcctt gtagtatagt ttgaagtcag gtagtgtgat  70920
gcctccagct ttgttcttttt ggcttaggat tgacttggca atgtgggctc ttttttggtt  70980
ccatatgaac tttaaagtat ttttttccaa ttctgtgaag aaagtcattg gtagcttgat  71040
```

```
ggggatggca ttgaatgtat aaattacctt gggcagtatg gccattttca cgatattgat   71100
tattcctatc catgagcatg gaatgttctt ccatttgttt gtgtcctctt ttatttcatt   71160
gagcagtggt ttgtagttct ccttgaagag gtccttcaca tcccttgtaa gttggattcc   71220
taggtatttt attctctttt tagcaattgt gaatgggagt tcacttatga tttggctctc   71280
tgttattggt gtataagaat gcttgtgatt tttgcacatt gattttgtat cctcagactt   71340
tgctgaagtt gcttatcagc ttaaggagat tttgggctga gacggtgggg ttttctagat   71400
gtacaatcat gtcatctgca aacagggaca atttgacttc ctctttttcct aattgaatac   71460 cctttatttc tttctcctgc ctgattgccc tggccagaac ttccaacagt atgttgaata   71520
ggagtggtga gagagggcat ccctgtcttg tgccagtttt cagaggggat gcttccagtt   71580
tttgcccatt cagtatgata ttggctgtgg gtttgtcata aatggctctt attattttga   71640
gatatgtccc atcaatacct aatgtattga gagttttttag catgaagggc tgttgaattt   71700
tgtcaaaggc ctttttctgca tctgttgaga taaccatgtg gtttttgtct ttggttccgt   71760
ttatatgctg gattatgttt attgatttgc atatgttgtt taaaaagttt tctttcttct   71820
gcgtaacctc tgtttcatat tacctttttt cttttgtttga gtttccatct ttcacattag   71880
ccatgttcct cagctctccc atagtccctg gtccaaagga ggggaataag aagcagagag   71940
gtcactctag gctcatgggg gaggcttgtt aactgaaagc tttcctatag gatgatacag   72000
ctgaactttt taattaggga aatggaaaat ccacatcttt aggttttttt cctcttgggc   72060
ttgttaagat tcccttgtga agaccttatc tatctgcatc ctggagggcc aagtcctagc   72120
tgtcagtcgg gcacggtggc tcacacctct aatcctagca ctttgggagg ccgaggcatg   72180
tggattgcct gaggtcagga gttcgagacc agcctggcca acatggtgaa gccctgtctc   72240
tactaaaaat acaaaaatta gcttggcatg atggcgggca cctgtaatcc cagctactca   72300
ggaggctgag gcaggagaat cgcttgaacc agggaggtgg aggttgcatt gagccgagat   72360
catgccattg cactccagcc cgagtgacaa gagtgaaact tctcctcaaa aaaaaaaaa   72420 aaaaaaaaa aaaaaaaaa aaaaaagacc tgactgtcag cattctggga gggaaacagg   72480
aggtgaggga aaataaggct gggacctcag tatgaggtag gtaaatgctc agttcatccc   72540
cttgttttta gaagagtttc tgtgcctgtt actgtgcctg gtatctcttg agtcctggaa   72600
ccttgtgttc tactctctcc agaaaataaa cctccagtgt tttgccaggg tagagaagag   72660
acagtcactt ggcttcacaa agatggtagg tgacttgtgg gccaaactgc ttcttaagca   72720
gatttaaaat ttttcctctt tattcctgcc acctgccct cctattctc tatagccaga   72780 ggtacctatt actaccagtt tcttatctcc gaggaattct acggtgtaaa aagggttgat   72840
ctcagttttt tctgttgcca ctttaagatt cagtttctg agatacattg agtcatttat   72900
tacttcacca atttcttttc ggcttctaag ttttgtgcag tctcctttcc cagttccatt   72960
gtctgtgggt ttatgaatta aaaaaaaaa actactttct gtgggatttt aggagggagg   73020
gaaaatacgt gcatgtattc agacttctta cctgaagttt gttgatggct tctgatttta   73080
aagataagtc aattctggtg ttataggtct agttttcatt cctttgaaca tttgaacatg   73140
tggagaataa ggatttaaaa gtccttcact agctcatgca ttctcaaatt ccttatattt   73200
ttagtaaaca ccaaataaat atttatcaaa taagtgaaga acttgagagc taacataaga   73260
gaaggtattg acgcttacta tcaaatttgg cccttaaaaa accttatgag gaaggcaggg   73320
ctcagagagc taaatggttt gcctgaggtc acacaacaga aagcagcaaa accatgatct   73380
catccaccgt gagcatggtg agctgatgaa gacttactgc tagaatttat caaagacatt   73440
```

-continued

```
gttaaaggaa aataacttac attggtttac ttcttaaatg gaaataggac atattgaaat  73500
attgaatata caaataagca aaaggtagaa aataaatatt tcctctactg tcaatattct  73560
ggataagtaa ctgttgaaaa tttcatgaat atctttcact tattttttgt gcatatgagt  73620
gtataatata caaaaatggt atcatattga catactgctt taaaacctgc tgcctttcag  73680
cctgggctgc atagcaagac cttgtctcac taaaaaaaaa aaaaaaaaaa aaaaattagt  73740
caagtgtggt ggtgcatgcc tgcatttcca tctacttagg aggctaaggc aggaggatca  73800
ctttagcctg tgaggtaaag gctgcagtga gctatgacct tgccactgca ttctagcctg  73860
ggcaacagaa tgagactctg tctcaaaaaa aaaaaaaaaa aaaaagctaa aatgtaactg  73920
cccgttttca atactaacaa taaattgtga atacttttcc atgttaacca tttttctaca  73980
acattgtgtt aatgatatac tataatttat ttaaacagtc aacagtgtta gcagtaaaca  74040
tctgtatggt ttagttgtgg cctccattta tccttctgga taaatttcca gaagcaggat  74100
tcctgtatta aaggcttcta agacatttcc acataatctc cagaaatata taccactttt  74160
taccttcatt tgctatacgt gactgttcat tccttcatat gtttccaaca tcaagtattt  74220
ccatttttaa aactttgcca attgaatagc cacaaaacat attttttatta tttaaaaata  74280 tgcattttgc aacataggca acatagcaag accccatctc tacaaaaata aaaacaaaaa  74340
ttagccaagc atggtggcgt gtacctgtag ttctagctgt ttgggaggct gaggtgggag  74400
gattgcttga gaccaagagt tcaaggttac agtaagctat gaacgtgcca ctgcactcca  74460
gcctgggtga cagagtgaga tcctgtctct taaaaaaaaa aaaaaagggg aaagcaagaa  74520
tagattgtta ctttgtcatc tgtcgtcagt gtttgtcaat gtatttaatt agtagggaca  74580
tctaaaccaa gcatccatat atgataaatg aaaaaaacaa aagtattagc tggcagtgtt  74640
ttctccaacc cttcctagct gatctaacca gtggtgcagt tggtttatat gtgagagcaa  74700
tgagaatgaa tatgctgcaa atggtactat actgtgcatg gttttttaatt tacttataat  74760 ctattattta atagtgtttc ttttagggct tgagtttgaa ttcaggctaa cttttaagta  74820
caacttaaga tttatttta cattttgtca ttacatatga aatgtggaac aaaaatgtat  74880
catgtgtgag gcaggaaagg ttttccacgg tgttgagggg tattgaggct gttcatccag  74940
gtgtttagac tgttgtaggg aatactttta tttcaaaagc taaattgcca taacttttt  75000 tttctttttt taaatgttta atgttacaga agccaaggct gcccccaaag attgtttcat  75060
tgaagtgaat tctaaaggtg acagatttgg caattgtggt ttctctggca atgaatacaa  75120
gaagtgtgcc actgggtaag tggaggtgcg gtcataatgg aatatgaaag attataagat  75180
ccgtcatctc tagtatcttt ttttttttt tttttttgag acggagtctt gctctgttgc  75240
caggctggag tgcagtggcg cgatctcggc tcgctgcacc ctccgcctcc caggttcaag  75300
tgattcccct gcctcagcct cctgagtagc tgggactaca ggcatgtgcc accacgccca  75360
gctaattttt tgtatttttag tagagatggg gtttcaccat gttggccagg atggtcttga  75420
tctcctgact tcgtgatccg ctcgcctcag cctcccaaag tgctgggatt agaggcgtga  75480
gccactgtgc ccggccgtct ctagtatctt ttacaactgc tctctgtgac cgctgatttt  75540
ctccccctta aatacctaac tttttcaaaca ttttacaatg caaagcttca gagagactct  75600
ggtgttagga aaagaactgg taacataatt tgtcccttta gacatcaact acaatctagt  75660
ggtttttaga ctcttatttt gtttatcctt gattatataat aagaacccca actaaacacc  75720
attttcattt tcctttccat aaaagattat gttactaagt ccctagataa aggtacctgc  75780
```

-continued

```
agaagaaact ctgaacttca ttattttctt ctagctttgt ataatttcaa gatgatgaat   75840
ttaaaatatt ttatatttct acaattaaca tttgcttttt gtaaaacatt aataatgaaa   75900
cattacaaag gaggaaaaag tcatgtataa tctcaatcca tatatgttca ctaatatcag   75960
tgaaattatt ttcttcttca cactaacatt ttacatagtt ggaattattc tgtaatatta   76020
tcattgcttc tacccattct acctcctatg ctatcagtta agctaagcaa ctacagtaaa   76080
acagtgcttg ctaagaagaa atagcaacaa agaccccat gtcactcaat ctgacagtcg    76140
tttttaggtc ttcatacaat agtacttgac ctgtcagtag cattcaatta tgctggccat    76200
tttctccttc ttgaagaaac ctcttttttt ttggtgattg tgtagggtgt tcttcttctc    76260
ccctgacccc atgtgatttc gtttacttcc gtggcttcat ttgcctcctc tctgagaagc    76320
tccagccctg ctggcctgca tgtggcctgc ggccacaggg ctctgcacct gctgttccct    76380
ctgttcagca tgctgtcttt ccccctctca gcctgctcag ttcttcgtcc tccagatctc    76440
aggtgaagtg tggtttcctt acagaagact tcttccactt cctcaacagg accagctctc    76500
cctctgacag gtgttcttga tgctgtttgc ttctttttca tagaatttga tatgtttttca    76560 ttattttta gttcatagta ttttctaatt tacactgatt ttttttccttt gactcgtgtt     76620 attgaaagcc tattgcttaa ttcccgagta gttgggaata tactggttat ctgtttggtt     76680
ttgatgtcta gttcaattcc attgagaaca cattctatat gatttcactt ttttggaatt     76740
tgagatgtgc attattcagt tacacttgga acattcatcc atacagacta atatgtgggc     76800
cagcctctta ataccagacc aatatatggt ctgtatgggt aaatgttcca tgtataattg     76860
aaagaaaaag tatattctgc agttgttaga gatgttattc tataaatgtc aagttaatag     76920
tcttattcaa atatttcata tctatggtgt acgtgtgtta tatctgttcc ttcaatttct      76980
gagagaggtg tgttgaagtc tccagttatg attgtggatt tgtctatttta tcttttttagg     77040 tatgtaaatt tttgctgtgt atgtttttaaa tttgttacta ggtgcataca caattaggat     77100
tgttatgccc tcctgatgac ttggagggca ttagcaaatt tatcattagc aaattctttt     77160
catttctgga atattctttt gaagtatttg tcagtttcat taattatgta gctcttttgt      77220
tatcgctgtt cctcactaaa ctgtaaggtt cagtgacaca ttttatcttg catttagcat     77280
aatgcttgga ggaaacataa taaatgacta ttaaacattg aatgaatgaa ggtacagatg     77340
atatggatga agaatgaatg ggtggagaat taatataacc gattgaatga actgatttaa     77400
aatctaggga taagtggatt aatgcagact tggaaagaat ttgctggaca tataccatat     77460
tcttgtcttt agccttgtct tgtttcatat ttttatgaat atcttattga aaatagcaac    77520
tatacttatc aaactttaaa attactgagt catttaggaa gcattttatg taatagtagt    77580
atacaaacaa tatagtcatt aagaatatac atttgaagtt agactctttg gatttgaatc     77640
cttgttcaat cacttaacat ctctgagtct ttggacaaat tacttcacat acatacctca     77700
tttttctgtt ctgtaaaatg gggataataa tggcacctgt ttccaagtgt tgtttttgaac    77760 tgaatgagtt aatgggtgtt agtactaaga ggaatatctg gttcattgtc acattcatca     77820
tcatcatcac tattttttgtt gtcatcctcc ttggagaatg tgtaaaatct ggaaaagtct      77880
tttctaccca ttgaaactac caaaaacatc tagaaacatt taaagaaagg attcacatat     77940
ggtcctacca tccagagata tttccttaag tttttgttgt atttcttttt tatgtgtata     78000
tacatttata aacataagcc aaatgtttcc tttcactaaa agggttatct tttagtacat     78060
agacaatgtc atttttttcaa gcattataaa aaagaaattc caaatataca gaggagtaga     78120
aagaatagtg tgatgaacac caatatatcc cagaccaaga cattattaat gccttatcat     78180
```

-continued

```
tatttgcttc atcaagattt tgctgaacca ttttaagtaa attatagaca tgatactttta   78240 ctcctaaatt cctcagcatc cgtcttcaac aaataaggcc attcacatga tcacatcaca   78300
cctaacaaaa tgaatgattt cctaatatca tctagtatct gatcaatatt agtatttcca   78360
taagtgtcct caaactgtct tttatagccg gcattttcca acatccggac tcaatcaagg   78420
atcacacatt gcatttagtt gttatgtcac ttaagtcact tttaatccag aatacctttt   78480
agactgattt ttttttctttt cagtgacatt gatttatgga aatggctggg ccagtgggct   78540
catgttctgg atttgtttta gtttcctttt ggtgttgctt aacttatgtc tctatcatcc   78600
gaattttatt taaatcagaa gttaagccca aaatcttttt tttttttttt ttttttttgag   78660 tagagcctca ctctctcgct caggctggag tgcagtggca tgatctcagc tcactgcaac   78720
ctccacctcc cagattcaag tgattcttgt gcctcagcct ctggagtagc taggactaca   78780
ggtgtgcacc atcatgcctg gctaagtttt gtatttttag tagagatggg gtttccctat   78840
gttggccagg ctggtctcaa attcctgacc tcaaatgatc cgcttacctt agcctcccaa   78900
agtgctggga ttacaggcgt gagccaccgc gcctggccct aagcccaaaa tcttaattga   78960
attcaggtta aatatttttg gcgagaatgt tcataagcaa tgcattatat caaggagtca   79020
cttagtgctg ggtagtctta ttaatattag tgatactaag tggcaatgac cagatcttgc   79080
tattgtggag ttatgctttt taaaattgca gctgtcaggt aatatgtgga gtgatgagtt   79140
tgtgccatat gaatatccag ttcctgacca gtgtttcact ttatggatga tccttgcctg   79200
aagcaattat tttactgagg gttgtaactg aattttgttt ctgttagtat tattcaacag   79260
tgaatgagca tctcagtttt gttggctgtt tacatttctt attttatgag ctgcctgttt   79320
acatctttgc taattttttct gttgaagtga tttttctttgt cttaatgatt tgtaacagct   79380
ttttatattc taagagtatt ttcctttact ttttaatgta tcaccaagcc tatgtatgaa   79440
atactgagta tatcatagca atgtgaattt tggtaggccc caacagatct taactgaggt   79500
ctactttatg ctacactttg ttttttgaggt tttcatatct aatttcagct aattatgtga   79560
gataggcatc atttatctca tttttttttcag ctgaagaaac tgaagctcag aaaatgtaag   79620
cacttctctc aggtcagcta gcaaataaat ggtgacataa gaataaatgt aaagttggga   79680
caaaattatt aactcttaaa tgcaggatga agggaagatg aagacttaat agcagcacaa   79740
caaaaattag gagtttttagt gatatattca aggacatcaa taatataatg tagttataaa   79800
agctattgta atcttgaact taatagaagt acagtatcta gaataaacaa gagctccatt   79860
tttttctttg ctcaccaggc tgtcactgaa atttcatgct ccattctgag cactatgctt   79920
caagaggcag tgaggcaaac tggaacatat ttaggaggga gcgtccttgt tgcatgaaaa   79980
gtgattgtag gatagtgacc tggtgaagta agtatttagg agctgcataa taattgtcct   80040
aaaatagctg ctgtgtgaaa gaaggaaaag atatctgtgt agtctcatgg ggaagatctg   80100
ggaccaatga ggataaatgc tttacagatg tagattttta cctaataagc agaaagaaga   80160
acgtgatggg agctagaatg ggcagtttca ggagggtgta aattagagat attgggaaaa   80220
tatatcctat gatgactggg cagtgatatc atagagaaga ttcagatata gagtaggtgc   80280
ttggatcaga tgacaatcag ttaaacagga aatctcagta cagcatcata agagttattg   80340
ttggaaatac ctagagtgtt atgaaaggat ataggaaggg catttaattc acacagcctt   80400
ggcaataaga attatggtca gggaagcctt catagagttc tgatatttaa ttaatgaatt   80460
aacgagttaa tgaattgatt ctttaaataa gtaaccaaga gttagccagg aaaagagggg   80520
```

-continued

```
tggaatcctt tcttagttat tttgcattat agaatctaat ttcttcttta tcataactct    80580
gtaagaagac ataattgaat tttgatattg ctatattatt ttctgtataa tagaatttat    80640
aaaattatac ttagaaacaa ctttattagt taggctgttg agctctagac agacagtgaa    80700
gaagattaag tgtggtaaaa gaagaagcat cagcaccagc tggtgcccta atttgcatct    80760
tagcatccac ttaactcttt tttcgccttt tctgccgtat ttaaagagag ctactttgac    80820
ctctcttgct ctcatacact ttctctgttg agattccctc catagcagca aactctgtcc    80880
atatgcaaat atataaattt tttctttgt tatgtatact ggatgcattt tatgttgcat    80940
tatttctctc tctttatagg aatgctttgt gtggaaagct tcagtgtgag aatgtacaag    81000
agatacctgt atttggaatt gtgcctgcta ttattcaaac gcctagtcga ggcaccaaat    81060
gttggggtgt ggatttccag ctaggatcag atgttccaga tcctgggatg gttaacgaag    81120
gcacaaaatg tggtgctgga aaggtaatca aaatattttt tatttacaaa gtaaaatgaa    81180
aaaaattaaa aaaattatta tacatagtaa gtggttgctc ttttctgatt gtaaaagtaa    81240
tctaaattca ttatagaaat tttagaaaat acaaagccac caaaagaaaa ttaagaacta    81300
taattctgtt atccacattt ccttactggg gtcagataac cagtgttttc cactttgcaa    81360
tatactgtgc atggttccct cccctactga tatgctacaa tttattagcc agtttgctat    81420
tactgggaca ctttggcgat gtcctgaatt tcagggtgtg tgtctgtgta ctagaaatgt    81480
catggagctt gtcctgccca tgttcctgac cacctgagct ctgctgtttg gattagatag    81540
aaggccagag tcagtcagcc catgacttat tactagtggt ttcatatgag aagatgccct    81600
gggccaaatt cctttttttg gagaatataa aattaaggag ggtaattaag agtgcgggca    81660
gaaactgtaa gaattcgttg ggagatgctg tgaagtagga gctggggtag aagggatgtg    81720
gcagccttaa gccatataca agagatatga gggagcagga ttgttgagta agttgaagaa    81780
accaactcag aggagagaga gaaggagaat atatgattga ctgattagcc catgaaaaag    81840
acaggtgggt gggccttcaa gttacttcac tttctcccaa gttttcagtt ccaattctgt    81900
ttctcacttc tctttacaag aagatccata tattttggt cctgtccttg caactaaata    81960
aacttgatcg ttgcagctgt tataaacaat gataagagat atatacattt aagttttga    82020 tagtgcaatt tcccttttcaa taaggtggta acaatctata tcccagccta ggcagcagag    82080
gaagactctg tctcaaaaaa aaaaaaaaaa attgtgctga aaggctcatg acaaaaacaa    82140
ctctctgaca tgctcttatc taatctgcca gtctagacgc ctagaagcaa ctgtggttac    82200
ttctgttaat tacctcccta tttttaaatta gggctgggca cggtggctca tgcctgtaat    82260
cccagcactt tgggaggctg aggtgggcgg atcacttgaa gtcaggagtt cgagactagc    82320
ctgaccaaca tggtgaaacc tcgtctctac agaaaataca aaaactagcc agtgtggtgg    82380
tgcatgcctg tagtcctaac tactcaggag gctgagacag gagaatcgct tgaacctggg    82440
aggcacaggt tgcagtgagc cgagattatg ccactgtact ccagcctggg caacaaagtg    82500
agactcccat ctaaaaataa agtaaaataa aataaaataa aatagtatgc tatttctaga    82560
tttatctatt ttagacatta tccactagtt ttattttga tagataagaa ttcaattttc    82620
ttatgcaaat cccagtttcc ctgctgtacc tttttcaaaat aagtgcttaa tatttacata    82680
attaatattg gggtgttatt gaatgagtcc acaacatctc actgttcact gggcatattc    82740
cagacgaggt gagagaaaac aggggaggct aaacaattgg agatcaaagg atcattttta    82800
ttaggaagaa agcatgtaac atgacttaag tagatagcaa aaatgggctt cctaatgctg    82860
ccctacacag ttaaacttac ctgtccagcc ttacctgcga agtttaactg catggttgaa    82920
```

-continued

```
agggcagacc agaatgcacc ctttctgcca cctcagctta ctactagctg gcaccacagg  82980
tgtaaccagc atgcctggct aattttttt aatttttctg tagagacagg atcttgctat  83040
gttgcctagg ctggtcttca gctcctgggc tcaagcgatt ctccctcctc agcctcccaa  83100
agtgctggga ttacaggtgt gagccactgc acctagctgg gcatctttcc atgtctttat  83160
tagatccatg tattttttc tgagaagttc atattgatat ctcttttct attagcttgc  83220 cattttttga ggcttctcat atgagaagaa tattaactgt cagtcagtta tatctatgta  83280
aatatgatca acaatttgac ataagcctat tttaaaatat catgaatttt tttttttt  83340 ttttggagcc tcactctgtc acccaggctg gagtgcagtg gtgcaatctc agtgcaacct  83400
ccgcctccca ggctcaagtg attcttgtgc ctcagcctcc ccagtagctg ggattacagg  83460
catctgccac catgtctggc taatttgtgt gtttttagta gagacggggt ttcgccatat  83520
tggccagact ggtctcgaat tcctaacctc aagtgatctg cctgccttgg cctccaaaag  83580
tgttgggatt acaggcgtga gccatggcat ccggccttaa aatatcatga aattatatca  83640
gtcttatctg ttttgtcttg gtttcatgtc atgtttagaa aagcttttg tatctcagta  83700 taatatgaat atctggcttt tattggcaca atttattaac atttcatcct atttctctga  83760
tcttattgct gctgttaaat attttcttga tattttctac tttatcttcc tcttgcagta  83820
ttacacaaat tatttatttg tgtgtggggt gtgtgtgtgt gtgcacatac actttggtag  83880
ttgtatgtct ttctattctg cttgtttact taataacaaa aaaatgaata tattttctc  83940 aaagttgtcg tgattaaaaa tagtatctac tgattgttgc agtgtaagct ataccactat  84000
tacttccaaa cccccatgtc ccagttttta cttggtagga aaaatattgg ctttagattc  84060
caggttgtta ttaacatata tcaatgtatt tttaagacct tttgtctttc tggattttat  84120
tgctaactgc atagttttct agctatgaca ataatattta tgtacaagaa aggatagcaa  84180
gtggttggtg tgtgtacctg gactgataca ccttgaccca aactgacatg ccgttgagac  84240
catataccac acgttctgta cagctgtaac tttgtaactg ttggtttaat ctatgagtct  84300
aacacccaag ttttcacacg gcagatagga tcctgtccct tctggtatgt accaaagcct  84360
agactggaca gtttgagcag actgacaact tggtacttct tcagatctgt attctttata  84420
tatttattca acatttattt ccaggacaag ctaaacgtgg ggtaggggga aaagtggaaa  84480
ataagaactc ctcaccttca ttttttattgt cccaggtagt tcaattttgc tccccacttg  84540
catcctgaaa tcagtaaacc agaagtccta tagtcaagtt tgctctactt gctgcgtggt  84600
ggttgttggt ggtggccatg ggtggtaggg ggagtggtag tagtatgtga gaggatggtc  84660
ttaccttccc actgtgagag tttttttttt tttttttttt gaggcagggt ctcgctcttt  84720
gacccaggct ggagtgcagt agagtgcaga tcttggctca ctgcagcctc tgcctcctgg  84780
gttcaaacga ttctgctgcc tcccaggtag ctggaattac aggcttgcac caccatgccc  84840
ggctaatttt tgtgatttta gtggagatgg gggtttcacc atgttggcca ggctggtctt  84900
gaactcctgg cctcaagtga ttcacccacc tcggcctccc aaagtgctgg gattacaggc  84960
gtgagccact gcacccggtc cccactgtga gagttttgg gtgtattcct ttcagtttga  85020
tttttcccat tccacaaggt aaacactgcc aatcagaaca ccctttctct ggaggacttg  85080
gaattttcct gccccttaaa gtaaatctgc cagttattaa cacatttcat cttatttaac  85140
acttcaggtg tccgctatga atcaattatt gacaggaaaa tcttctttta actggtaggg  85200
aaactcttgg taaatatctc ctctaaagac ttgcggatgt aagaaaaaag tattttgaaa  85260
```

-continued

```
tctttattca ggagtagtgc atggctagag gacacatgag gagtgactta ctgtagaatc   85320
ttctgtaatt ttggaatttt aaatcatata tgtcctattt aaaaattaat ggaaaattgg   85380
aggaaacagt gtttggagat cttttgactt taaaagtaca attctgttta aacctgtgta   85440 tttttagag tggtaaggct atcgatattt cgttgtaggt ttgttctcta attgttcttt    85500
atttcatttg agcatttaaa tattctgatc ttgtacacaa gatcagttgg ttagttacct   85560
aataaaattt taaaatagca ctcaacagtc ttttaaaacg ttagtcttct ttttttcctc   85620
taacatcaca acagagcagt tttcacaaag atgtcaacta aaaaatttct aaaatgtgtt   85680
gagctgattt ctttagatct taggtttaat attttttttct gaggtaatgg tttttatctc   85740
tcagtagcta ggattcattt ctgtttcata tctcatcata tgaactagaa tttcttgaac   85800
catgtaagat tataacttat tttcaacagt gcttttaata gaaatatcta atcatggtac   85860
tagaaaacag attttatctt gtcaacaaag tacccttta tttttgaaag aattttaaaa    85920
attaaaatga gttttaaata ttatcctttt gatatctgtc atagtaacaa cactttatga   85980
gaggtgtaat agaaatagac cttctatcct tgaaactttc ttgtagtcct ggggttaact   86040
ctatctagtt acttttgatt tgaaaaagtc tatttgtgaa tatttatttt aggatcttca   86100
catcaatatt cacatggaag gatagataat agttttatct ttgtttttgg tctttatgtc   86160
atctttgtgt tttttgataa ttaattttgt atcaattaat taatgccact tattttttctg   86220 cattttaaa aatataatat gggaattaat ggttccttga aagtttgaaa gaattctgca   86280
atgaaataat ctgtacccag gtctttttttc tgggtacttt ttaatgactg tgctcaatct   86340
ttctttactt agttcatttt ttttttttttc agatctgtag aaacttccag tgtgtagatg   86400
cttctgttct gaattatgac tgtgatgttc agaaaaagtg tcatggacat ggggtaggta   86460 atgtttttctt ttggcttgtt cctgaaagta gtgctaaata atgagaaatc tcaggactag   86520
atgagagttc ccaggatttt cagatgttgg ggaatttaga ttcctgataa aatttttcatt   86580 cttaaacagt gtcagtaagc ttgtatgaat ttagtccttt ctcttggttt ccattcttga   86640
gttgatgata tagagcaaca ttcacaatta acaaaagtgg tatttttgatt gtttttgaagg   86700 tatgtaatag caataagaat tgtcactgtg aaaatggctg ggctccccca aattgtgaga   86760
ctaaaggata cggaggaagt gtggacagtg gacctacata caatggcaag taatatagaa   86820
gaaaattagt gtgatctccc agtggcccaa ggcataaatt gggcatcctc gtacctctcc   86880
ctcacttccc acatcagtta tacatttaat tatgttgatt cagcctccta aattccttgt   86940
gactgtttcc attttttctca tccccattta ttactttcaa tttcttgcct ggacatacat   87000
catagcctct tatgtaggct ccctattttt catcttgctt cctataatcc atgtttcact   87060
ctacattaca gtttcagtgt tttcctacaa gaattcagtt ttgattttgt cagcgtcttg   87120
ctttaattca gtgcgtctgc attgctatta gaatgaagtc cacaactcct taacatgggt   87180
taaatgccct gcatgacttg cccctagctt gcctttcaag cctcatttca ctatgttgaa   87240
gacatattgt aacttctttg atttcctgta ctaggctact atcttttacc tgtgggcttt   87300
cataccgtat tattttcaca ttgttggccc ttggctaatt gctatttagg tttcagatta   87360
tacctcattt tctaaagaaa gtttcccctg gctgcttaaa tctaaattat catttccttc   87420
tattgctttt ctagtactgt tagcactatc tgttagcact aattgctata ctaattactg   87480
atttgctttt taaaattccc tgatagacca tgagctccca gtttatcggt atctttctag   87540
tgacatcata tgcttttttt ctcttgggta actaccagct agaatgacta gtcatatagt   87600
aggtgtatgt taagctttta aagaaactgc caaactgttt cccaacgtgg ctataccagt   87660
```

```
ttacatcctt actagctgta tatgagagaa ttcccccaat ttccccacat cctctctaac   87720
agttgctatt gtcagtcttt ttaattttta gccattccag taggtatgta gtggtatttc   87780
agtgtggttt taatttgcat ttctctaatt actaatgatg ttgagcatct tttcttgtac   87840
ttatttgcca tctacatatc ttctttggtt atgtgtctgt ttaaatcttt tttccagttt   87900
ttaatggatt gtcttaatga gttttgaaag ttctttgcat gtcactgatt caagtattca   87960
agttctttat gaaatatgtg ccttgtatat attttctctt agtctgctta ctttgggttt   88020
catttgttct ttttctagtt tcttaaggtg gaggatgagg tcatcttttt tttttttttct   88080 gatacagaca ttttattgct atcagttttc ctttaattca gaaattttga catgttatac   88140
ctccatgttc attcagttct gaataccttc taatatgctt ttttttttctt tgacttacag   88200 gttatttaga tatgtgctat ttcttttgaa atacctgtgg attttttagt tatcttaatg   88260
ttactaattt aaattttact gtagcaagag aacatattgt gtatgacttg aatccttttt   88320 ttttttttaaa cttgtcttgt agcccagaat gtggtttatc ttagtaaaag ttctgtgtac   88380
acttgaaaag aatgcgtatt ctactattct taggtggaat attctgtaag ttattagttc   88440
atgtcagtta ataggtagtc ggatctttca tatccttact gattttctgg tctacttact   88500
ctgtcagtta ttgagaggaa tattgagttc tttggctata actgccaatt tgcctatttc   88560
tcttaatagt tctatcaatt tttgctttat ttattatgat gttctgttat taggtacata   88620
aacacttaga attattctat cctctttgta aattgactct ttatccttat gaaatagcct   88680 tcttttttccc tagtaatatt ctctgccctg caatgagata ttgttaatat agctactcca   88740
gattcctatt aattagtcag catggaaaat cttttcccat cctttttactt ttaatttctt   88800 tatatcatgc tatagtaatt agtacatata gttggatctt gcttttttatc taatctgcca   88860 ttctctgtct ttcaattaag ttgtttcgat aatttatatt taacttgact attgatgtgt   88920
ttatgtttaa atttactgtc ttgatatttt ccatcagtct ccttgtagtg atattgtaac   88980
acttcagtat atttccattt ctctcatttt gtgccattgt tgtcacatgt tttacttcta   89040
ctaatgttat aaatcccaca attcattgtt actcattttg ctttgaacag ttgattatct   89100
ttcagagact taatggtaga aaaagtcttt atatttaccc atataattac catttctggt   89160
gtttttcatt tatgtaaatt tgcatttcaa tctgatttaa tttctgcttg aaggatttcc   89220
ttttacattt cttataatac cagtgtgcta gtgacaaata ttttttagctt ttgtatgtct   89280 gaaaaagtct ttaatttgcc ttgctgcttg aataataatt taactgggca aggattttgg   89340
gtgatagttt tcctcccgtt ttacttctaa ggatattcct tgtcttctga cttgcattgt   89400
ttttcctgaa aaatctgcta tcatcctttt ctttgtatat aatgtcttcc gtatatgtct   89460
ttttctaatc tctggtcact tgtaatgttt tgctctttat ctctggtttt tatattgtgc   89520
cttggtgtag ttgggatttt ttgagctttt tggatctgtg cttttatagt tttcttcaaa   89580 tttgaaaat ttttggccat cgtttcttcg aatatttttt tctgtcttcc tctttctcct   89640
catccaggtc ctccaatttt atgtatattt ggctgcttgg tgttatttca catgtcactg   89700
attggctgtt gattttttat ttttgttttt ttttcttaaa ttttaattta actttacttt   89760
ttttgagaca gagtcttgct ctatcaccca ggctggagtg cagtggtatg atcttggctc   89820
atggcaatct ctgcctccgg ggttcaagca attcttatgc ctcagcctcc tgagtagctg   89880
ggactacagg cgtgtgccac cacgcctggc taacttttgt attttttagta gagacagggt   89940 tttacgctgt tggccaggct ggtctcaaag tcctggcctc aaatgattca cccacctcag   90000
```

```
cctcccaaag ttctgggatt ataagtgtga gccagcatgc ctggctggct gttgattttt   90060
aaaaattatt ccttattctc catgtttaat tttgagtaac ttctgttact cttcaagttt   90120
acatttcttg tgtgaagtct aatttgccat taacttgatc tagtgtgttt ttcattttag   90180
acattgtagt ttttatttct ggaagttcca tttgtttctt ttatatatct ttcatgactc   90240
tacataagat gctcaatctt tacttttttg aacaaataga atacagttgt aataactgct   90300
aatgtccttg tctactaatt ctgtcatatg ggtaatttct cagttttgat attttttccct   90360 ctttttatttt ctgtatttttt gtaggcctta tacatttttta ttagatgcca gaagtttttaa   90420 atcctacttt gtgggttatt ggatatttttt ggatttctat tgatgaggtt tgtactagta   90480
tgtttgagtt acgtcgacat agtttgatcc ttctgggtct tgcttttaag cttttaaggc   90540
aggacctgaa tagcatttag tctagggctg attctgcttc attactgagg caaaaccact   90600
tctgtttatc ctgcttagta ccacgttaat tatgagattt cccactgaat tataggagca   90660
agtgctcttc ctagtcctgt gtgagctgtg gggcttattt ccaccaatct tttcacatgg   90720
ttctttctcc agcttcatgt ggtctcctta catgcatata tccatcagca ccgatgcaga   90780
tctttcagct ttttctctgt agctctcttc cctttggtac tttgcctagg aactgtagct   90840
gccttgccct cttcagaata ccagctccat ctctttaact gagggagacc actgggtttt   90900
gctttggtgc ccacacccga gtgtctgtta actttctttta ggcactaacc ttggacaatt   90960
ctaaggctca catttttttt ttctgcctct cagggatcat tgctctttgt tgcctgatgt   91020
ccagtgtctt gaaaactgtt gtttcatata ttatgtctgg ttttctggtt attttagctg   91080
gcagagtaaa tctggtccct gttattccac cttggctata actggaagtc agaactatgg   91140
attttaatgg ctgtgtatca tttcatccag tggatgtgct ataacttcac ttagctgttt   91200
tctaattatt tgacatttag attgtttcta aggttttgat aactcactgt taacattgta   91260
gtgtacatgt taatgtgtat gcattttttcc aattgaagaa tcaattgcca gtaatgagat   91320
tagtttgaag agaataatcc ttttttatggt tcttttagga gtaaaaattc ctaataaatg   91380
atacatttgt gtaatgccac taacagtgcg aaggtatcag tttcaaaata atcttgccag   91440
tgttgaatgc tttaatttaa attttgtgta ctcattagta agtataaaat gatatatgaa   91500 gcttgctttta attttttata cagttgaccg ttgaacaatg caaaggttag gggctccaac   91560
tccctgcata gttgaaaacc catgtgtaac ttttggcttc cccaaaactt aactacgaat   91620
agtctgctgt tgactggaag acttaccaat aacataaaca gttgattacc atagattttg   91680
tctgttatat gtattatata ctgtattatt ataataaagc aagctagaga aaagcaaatt   91740
tattaagaaa atcataagag aaaatatata tactattcat taagtggaag tagattatca   91800
taaagacctt catcctcatc atcttcctgt agagtaggct gaggaggagg aggaagagga   91860
gaggttggtc tcaggggtgg cagaaacaca agatagcctg catataagtg gacctgcaca   91920
gttcaaaccc acattgttcc agggccaact gtattttgat tttcagttgg gataaatatt   91980
gtttcatata gttttataca actttttttt tttttgagat ggagtctcgc tctgttgccc   92040
acgctggagt gcagtggtgc aatctcggct ccgcctcccg ggttcatgcc attctcctgc   92100
ctcagcctcc cgagtggctg ggactacagg cgcctgccac cacgcccagc taattttttt   92160
ttgtattttt agtagagacg gggcttcacc atgttagcca ggatggtctc gatctcctga   92220
ccttgtgatc cgcctgcctc ggcctcccaa agcgctggga ttacaggtgt gagccactgc   92280
gcccggccag tttttatacaa cttttttacag aaatttctgg ttcttttaca aacttaaaat   92340
tatgaatcag tttaccactc ccgtttatat ctactatatt gtttctcaaa agaacacaga   92400
```

-continued

```
acagataaaa tacttaaaga atttgtaaaa gttctaatga aacttaaaat ctagaaggcg   92460
taaaaataag attgataaat tcaactatac aaaaataata aacttttccg tggagaaaag   92520
catagtgcca taggttaaaa tggggaaaat atttccaact tgtatcatgg acaaagctaa   92580
tctctctaat atataaagaa cttttagaaa ttaagaagaa aaaagcaaga gtccagtaga   92640
aaaacagtca aaggactgag cagaaaaaaa taaataatgt ttccttaaga aaaaagtgag   92700
gccaggcacg gtggctcacg cctgtaatcc cagcacttag ggaggccgag gcgggcagat   92760
catgaggtca ggagttggag accatcctgg ccaacatggt gaaaccgtc tctactaata   92820 atacaaaaaa attagctggg cgtggtggcg catacctgta atcccagcta ctcgggaggt   92880
ggaggcagca gaatcgcttg aacccaggag gcagaggttg cagtgagtgg agatcgtgcc   92940
attgcactag cctgggcaac agggtgagac tccatctcgg gaaaagaaaa gaaaaaaaaa   93000
ttatcaactc atagtataaa aaaatgtaaa ttaaaattct ataagagaaa atttttcacc   93060
tgcctggttg gcaaaaatcc ggaaatttgg ctctgtgggt gaggctatgg ggaattctta   93120
tatattgctt gtaatattct tataaattgt aaccattact attgaaagac aatttgacaa   93180
tacctaaaag aaatgatgaa tgcacttatt tattgataca gcatttctgc tttagggaaa   93240
ttattctgta gttattatac ctgcactaat atgatacaac atatgtgcaa ggttattcat   93300
tatagcagtt tttttggtag tagcaaaaga ttggaaaaat ataagtgttt atcagtaggg   93360
tacaagttaa ataaactcta gaacatcttc acaatggagt ttcatatagc tgtatggaaa   93420
acgaggaggt ccactatgta cagataagtg gaaaaaaact gatgcaccaa atggtatata   93480
aatagtatgc taccttttgt gtaagaaagt gttgacagta gaaacgtatt ttgttcttga   93540
ttgtttgctc gaagaaatac tgtaaggtta cagaagaaac taataaaagt ggttattttt   93600
gtgaaggcag aagtaaagcg gacaggaatg aactttgtgg aagacttctc aatatattca   93660
attaatatca gtttgatttt tgagtaatgt gaaaattaat gtaaagtgtt tataatcatc   93720
tagtattttc tgcctagtat gagtttggtg actgttgatg taaaattctt ctctctagaa   93780
atgaatactg cattgaggga cggacttctg gtcttcttct tcctaattgt tcccttatt   93840 gtctgtgcta tttttatctt catcaagagg gatcaactgt ggagaagcta cttcagaaag   93900
aagagatcac aaacatatga gtacttagat tttttctttt taattcctat attaaatata   93960
tacatacatt ttctgagaca gaatctcgac ttccctgggc tcaggtgatt cccctgcct   94020 cagccttcca agtagttggg attacaggca caccaccaca cccagttaat ttttatattt   94080
ttttgtagag atggggtttc gccatgttgc ccgggctggt cttgaacttt ttgaagccat   94140
ccatctgcct cagcctgcca aagtgcaggg attactggag tgagcctcca cgctcagcct   94200
atattaaata atttataaag tattaatgct gatagtcata tcaccagaga ttggtaatcc   94260
tctaaaatag ggttctaagt tatttctctg accttttgac atgattagca tgggttgaaa   94320
ggtggtggtg accaagccac ctcttttaat ggggaggaga aaggcttatg ttggtcagcc   94380
tttaggctgc tgaaagtgac cctcagggtt cattttgctt aacaccaatt tctgatagag   94440
gactaagtag atacttcgta tcatacttcc aactgaccag tctatgcaaa taactccccc   94500
atctgcattt ttgaagtttg agttccataa ctacagctat cttttcataca tctccactgc   94560 actgatttgc tgtcacttca gcatgtctaa aacttaccta ttaccttttcc agccaatcca   94620 ttcactaccc ttggatttcc taattttaa aatgactact tggcaacctg agaatatgct   94680
tttactcttc tctgatttta ggaagacttg agaaaagtta gggaacattg gcctaattga   94740
```

-continued

```
ccaaatttca caatttctta aaatttcagt ttaattataa aatgtggtta gtaatgcttt    94800
ctaataccat aaggattaaa aatacgtgaa agctgttaaa atgccctaaa aatttaaacc    94860
gtatcatgat tatcatcccc accactacca acatcattat tctgtatttg ggaaaatgca    94920
aaatgtgtgt aatatttcat gtagaaatgt ttttatctta atttagatca aaagtaattg    94980
tatctttcag gtcagatggc aaaaatcaag caaacccttc tagacagccg gggagtgttc    95040
ctcgacatgt ttctccagtg acacctccca gagaagttgt aagtataaaa tgaaaaatta    95100
tttttcttta ctgtattaaa ggatcaaatg cttaaggatt aaaaacacag ttatatagct    95160
atagctagaa acatagatac cttcttaaga attcaagagt attgtaggtg gtccctgagt    95220
tttttgtttt tgttttcgag acagagcctt gctctgttgc ccgggggtgga gtactgtggc    95280 acaattgcgt ctcattgcaa cctctgcctc ccagtttcaa atgatttcgt gcctcagcct    95340
cccgagtagc tgggattaca ggtgtgtacc accacgcctg gctaattttt gtatttttca    95400
tagagacggg gtctcaccgc attggccagg ctggtcttga actcctgacc tcaagtgatc    95460
cacccgcctt ggcctcccaa agtgctggga ttacaggtat gagccactgt gcctgcccc     95520 ctgagttctt taaaggaaaa ccagcggagt ccttggctca gaggacacag aaaaagacag    95580
ctggacatta ggaatgcctt gcctagcaac caggattggg aaatgacatg ggacgtatgc    95640
tatcactgct ttttctgtg tctgctcttt tcctattttc aatacctgtc tccatctccc    95700
tatgggatgt taccaaagac ctggtgctga gctcttggat cggcctaatt gtctaagctg    95760
taggactgat agtcactgtt ctgcaagtgt attagggagt gtttagatca tgatatactt    95820
ttattgagtg tttagatcat gatatacttt tattgatctg catgtatccc taagcaatat    95880
gtaatttttt aatgtttaa aacttttaag aacgttttat ttgataattt gcacatatat    95940
ctgcaacctg tttttcccct taatgtcact ttgtgattta tctctatcga tagatatagc    96000
tgtgattcat tcattttcac tgttgaaaat gattagaaat ccttcatttt ttaatatatt    96060
tatacacaca cacacacaca cacacacaat ctccctattc cacccccttt atctttataa    96120
aaaggagaca aaaatcgtta ggcccttct cctcttaacc atgtatcttg gagatttttc    96180
catgttgtta tgtatacagg atggccacaa aggccatatg catgctagtt caaaattatc    96240
tgtatactct tcttcatcat tgccatatat gtatatattt cttatttggt tttggcaaaa    96300
tatatataaa atttgccatt ttaaccattg ttttcaagat tttttttgtaa atttaacagt    96360 agtggtaaaa aaaaaaccca ctaatatta ccatcttaac aatttttaca tgtacagtgc    96420
agtactccta agaatattta cctatgtttt ctttttagtag ttttatagtt tcaggtctta    96480
tgtttaaatc tttaatccag tttgagttga ttttttgtata tggtatgaaa taccagttca    96540
ttttcatttt tcttcatgtg gatatgaagt gtcccaaca ctattaattg aagtgactgt    96600
cccttcttca ttgtgtattc ttggcacctt cgttgaagat tagctgacca taaagttgtg    96660
gatttggggt tctctattct gttccatttg tctttatgtc tgttttatgc cagtagtatg    96720
ccattttaat tagtatagct ttgcagtata ttttgaaatt tggtaatgtg atgcttctag    96780
ctttgttctt tttgctcaag attggtttag tgattctggg tcttttgtgg ttccatatga    96840
attttagtat tttttctatt gttacaaaaa ttgtcattgg aatattaata gatattgcat    96900
tgaatctgta gtttgctgtg gttattttaa tattaactct tccagtcagt gagcatggga    96960
tatctttcca tttatttatg tcttcaattc ctttcatcaa tgtttcatag atttccttgt    97020
acagatactt attttttgtg gttaaattta ttcctatatt atttatgtat gtattttga    97080 tgtcattcta aatggaattt tttttctgga tttctttttc agatagcttg ttgtagtgta    97140
```

-continued

```
tagaaatact agtgattttc atatgttgat tttgtattat gcaactttag tgaattcatt   97200
agttctaaca gttttttggt tgactcttta gggtttccta tataaaagac catgtcatct   97260
gcaaacaagg acagtttac ttcttccttt ccaatttgga tgtcttttat ttcttttct    97320 tgcctaactg ctctggttag aacttctagt actatattga gtagaagtgg taggagtgga   97380
catccttgtc ttattcctga tcttagagga aaagctttca gtttttcatt gttcagtatg   97440
aagttagctg tgggcgtgtg atgtacagcc tttattgttc tgaggttcat tatttctttc   97500 tttcttttc tttgtttttg agatagagtc tcgctctgtc acccaggctg cagtgcagtg   97560
gcacgatctc ggcttactgc aacctctttc tcacaggttc aagtgattct cctgcctcag   97620
cctcctgagt agctgggatt acaggcatgt gccaccctgc ccagctaatt tttatatttt   97680
tagtagagag acagggtttt gccatattgg ccaggctggt cttgaactcc ggacctcagg   97740
tgatccacct gcctcggcct cccaaagtgc tgggattaca ggcgtgagcc accatgcctg   97800
gcccagtttg ttctttctat acaaatttgt tgagagtttt tatcatgaaa gaatgttgaa   97860
atttgtcaaa tgcttttccc tcatttctta aaatgatcac atggttttg ttagtctatg    97920 ttcttcattt ctgtttttg tttgttaatg ttgttattta ttgatttgaa tatgttaaac    97980
catcctcgca tccccagaat aaatcccact tggtcattgg gaaatatcct tttatgtgct   98040
gctgaattca gtttgctagt attttgttga agatttttgc atctgtgttc ataaaggata   98100
ttggcctgta attttctttt cttgtggtgt ccttgtctgg ctttggtttc agggtaatgc   98160
tggccttgta aaatgagttt ggaaatattc cttcctcttc aagtgttggg aagagtttga   98220
gaaggattgc attagttctt ctttaaatgt ttggtagaat tcatctgtga ctttatcagg   98280
tcctgagttt ctttaatggg agactttta aagttactaa ttcaatctcc ttacttatta    98340
ttgatctttt cagattttt attttgtctt gattcagtct ggataggttg tatgtttcta    98400
ggaatttatt ttttctagg ttcaatttgt tggtgtatga ttgttcatag cagtctctta    98460
taaaactttc tatttctgtg gtatcagctg taatgtcttc tctttcattt ctgattttga   98520
ttcctctttc tttttttctt agtctactta atggtgtgtt aattttattt atctttttcaa  98580 aaaaccaact cttagtttta ttgattctat taatactatt tttccagtat ttcattcatt   98640
tttgctctga acttcactat tcccttttctt ctactaactt taggctcaga ttgttcctct   98700
ttttctaggt cttgaggtgt aacattaggt tatttgagat tttttaaaaa atgtaggcac   98760
ttattggtat agacttgcta taaacttccc ccttagaatt gcttttttctg tgttgcatac  98820 attttgttat gttgtgtttc tattttttgtt gtctcaagat atagttgttt cttggtacac  98880
attggggatt ggttccagga cccctacata tagcccaatc tgcctatact caattaattc   98940
tgttggccct gtagaaccca catataggaa aagttggccc tctgtatatg tgggtcatga   99000
atactgtatt ttcaatctgt gtttggttga aaaatatctg catatagatg tacctgtgca   99060
gttcaaaccc gtgttgctta agtgtcagct atattttaaa atatttcttt ttatctgtca   99120
ttgaccaagt gattgtttag gagcatgttg tttaattttc atgtatttgt gactttccta   99180
aatttcttca gttattgatt ttgagtccta atattgtagt tggaaaacat acttgatgtc   99240 agtctttaa aatttgttaa ggcttgtttt gcagtttaac atattatttg tcctggagaa    99300
tgttctgtgt gcgtttgaga agaatgtgta ttctgctttt gttggatgga atgtgtctat   99360
tagatctgtt ttgtttaaag tctagtttga gccaaatgtt ttcttactga tttgttgtct   99420
ggatgaccta tctgttgttg aaagtgaagt attgaagttt cctagtagta ttgggttgct   99480
```

-continued

```
atttagctct ctctccagat taattaatat tcgctttata tatttaggtg ctctaaattg    99540
gctgcatatg tatttacagt tgttatatcc ttgtgatgaa tcgacacctt taccattaat    99600
gcactttttc atctctgttt ttattgtttt tgatgttaca tcattttgtc tgatgtaagt    99660
attgctatcc ttgttctctt ggtttccatt tgcacagaat acttactcat atttaaaaga    99720
attactgata gatggggact tactattgct attttgtttt tgacccttcc ttcttccctt    99780
gctgcattct tttgtatttc tttttaatta aaaaaatcaa ttatggatac ataatagttg    99840
tacatatcac atggggtaca tgtgatattt tgaaacaagc atatagtgtg taatgatcaa    99900
atcagggtaa ttgggatagt catcacctca aggatttatc atttctatgt taggaacatt    99960
ccaactctac tcttttagct attttgaaat atacaataaa ttaatcattt tctttgtttt   100020
tttgtagtaa tattttgatt ctcattttcc tttgtgcata ttctatagca catatattgt   100080
gatatctttg caattacata aaatatttta taaatttata gcaatctatt ttaaactgat   100140
tacttcaatc acaaaaactc taccccttta tatttcttct tcttccactt tatgtaactg   100200
atgacacaaa attacctctt tttatattgc ttatcattaa cacagattca ttactttta   100260 tgctatgctt ttaacattct aacaagattt aaaagtgatt ttcacactca cattacagta   100320
ctacaggatt ctctgtctat acacttacca ttattatcga gttttatatt ttcatatggt   100380
tttgtgttgc tatttatttt cctttctctt cacctttttt gctcctctgc cactttgatt   100440
ttgaatatac tagtctttga gtccactgat gctttcttct gcctcatcat gtttgttgtt   100500
gaatcctttt agtgaatctt tcaatttagc attacagtag ttttcagctc cagaattgct   100560
gtttggttct tctttatagt tcctgtctct ttgttgatat tctcattttg ttcatacatc   100620
attttcctga tttcttttag ttgtccatct gcattctctt ttaattttt gaacatcatt   100680 atgatggtaa tttttgaatt ctttggtaat ttatatatat ctgtttcctt agggtcagtt   100740
tctggagatt gagtttgttt ctttaaatgt gccatgtttc tatttctttg tattatttgt   100800
catttattat tgggattttg gcatttgaag aattagctgc ctttctcaga ttttgcagcc   100860 ttgtttttgta caaggaggac ttacgctact cagcctggct agagattctg gtagcctctc    100920 aaatctttt tggggatgtg tcctctgtga ggttttttc tgcagtctcc taattgtgga   100980
ggtttgctag tttctactca agagcacccc caggtgtctg tgatactgtg gtctctctga   101040
cttttttttt tttttgaga cagagtcttt ctcggttgcc caggctggag tgcagtggtg   101100
ccatctcggc tcattgcaac ctccgcctcc caggttcaag caattctcct gcctcagcct   101160
cctgagtagc tgggaataca ggcatgcgcc actactccca gctaatttt gtattttta   101220 gtagagatgg ggtttcacca tattggccag gctggtctcg aactcctgac ctcgtgatcc   101280
gcccgccctg gcctcccaaa gtgctgggat tacaacttga gccactgagc ttggcctgtt   101340
gtctagtatt ttaagtctttttttttaaaaa aattctacaa tatagatatg actattgaat   101400
tatgaaatgt ttgtttaggt ttgtgaggcc atacaccaat taaattaatt aagaggatgg   101460
actgtgagcc aaactgccca gtttgagtac tgcctttgtc actttataag ctgtgacttt   101520
aggcaagatt ctcaaactct ttctgtactt gtttcctcat ctgtaaaata ataatagtac   101580
taatcacaaa tgacttttgt gaaaatcaga gggattcgta tgtgtggagc actgagaagt   101640
gcttgtggca catgtgaagt gctctgtgag ctttagctat tttcccatgt gttgattgtc   101700
tgctttcaac cttattgaat ctcagcttat ttttctgata tatctacttc aactgggtat   101760
cttttagaag ttcccttagc gaaggtattt tggtagtaaa ttctgtcagt ttttgtcttt   101820
tccggatgtt tttggctgac agctttttt tttcctaaga actttaaata gactatattt   101880
```

-continued

```
taacatcctt tgttgcaatt taaacattgt ctgttactct aattgatgct gtagatgata 101940
tcttttccat gtggcttttt cttctgtatc tttagactat ttggtgtaga tgtggactta 102000
aaaaaactcc tttgccagta aatagacttc cggagttgat ttacattttt cagttctagc 102060
aaattcttag caattatttc tttattgcct ctgtctcatt atctaattaa ctctttcatg 102120
catttcttgc atgttagact ttttactatc tctgtttctt aacctctctt tggtatttcc 102180
aatattcttg tgtattccat tctgattata ttggatctac cttctattca ctaagtctct 102240
actaaactat gccaaatcta cttaaccaac tcattgaata tctcatttca ctagttttat 102300
agtacattta attcctgtag ttctacttag ttctatttcg aatctgcctg gttatttgtg 102360
attgtttgtt atagttttat tatctgtttt aaagctttta tttcttaaag catattcaaa 102420
cacctaattt ttgtgctgta tctgatcatt ttaatatgta tgcccttggt gggttctcag 102480
gtttgttatt tctgctgact ctcgtgatgg ctcatttctt agtgcccttg tgatgttgat 102540
tgtaaactca ccttctttgg aactttatat tggaaataaa tatatttgaa tcctgaatta 102600
tagtgggttc ctaccgagag tattttttctt tgccagatgc ttgggggcat ggtcaatctt 102660
tgatgtcttt aaactgaaat ttttgttgat atatatatat ttttttgcca cacaaatgtt 102720
aggaactctg gtccccaaac tcttatgagg atgggtgtgt ggtaagaatt tctccatgga 102780
gactattttt ttagttcccc atctatcagc accaaggcag tatcaccacg ggccttcctt 102840
gaggcaggtt tttgtttttc tagttaaccc atggggatac cacccttcat atgtctaggc 102900
tttgtatagg gccttgtatt caccattcca tccagctcag gccccagctt ttgcctcctt 102960
tatctatggg tcactgaaaa cgcatactgc cacctgccaa ggataggaag atttccacag 103020
gacaaaggca actccgtagt ttggactctt tcatacgttc ttggtttttt tttggcctgt 103080
aagatgtttc ttacttccca ccaacccagc caagtgtttc aaaatacctt ttaaatattt 103140
taggcagcat tttaggtgta ctgtactggg aagtttcctc tggacatttg gtccactatt 103200
tgcaagaagt gaacatgtac ttcattgttt ttaataaccg catgctgttc cctcttataa 103260
atttaccaga aatttaaaaa caggttgttt ccagtcttat accataaaaa aatgtggcac 103320
caagcatcct tgtaaataga tctttgcata catttaaaag tatatgtcag ataaatgcca 103380
aaaaagatta aaatttttt aaattaattt tagttttaat tggcaaatca tagttgtata 103440
catttatggg gtacagcatg atgtttatg taaacaatgt ggaagtgatt aaatcaagct 103500
aattaacata tccagcacct tgcttgcttg taatctttag cttgttttca ttaatttata 103560
tttaattgac aaataataat tgtgtatatt ttggggtatc gtgtttgttt tttttttttt 103620 ttttttttg agatggagtc tcgctgtgtt gcacaggctg gagtgcagtg gcatgatctc 103680
ggctcattgc aaccactgcc tctcgggttc aagcaattct tctgccttag cctcctgagt 103740
agctggaatt acaggcgtgc gccatcatgc ccgggtgatt tttttgtaga dacggggttt 103800
tgccatgttg gccaggctgg tcttgaactc ctgacctcat gtgatccacc tgcctcagcc 103860
ttccaaagtg ttgtgattac aggcgcctgg ccacaatgtg atgttttggt ctatgtatac 103920
cttgttgtaa gattcagtcg gctgggcgcg gtggctcata cttgtaatcc caacactttg 103980
ggaggctgag gtgggcggat catgaggtca ggagatggag accatcctgg ctaacatggt 104040
gaaaccccgt ctctactaaa aatacgaaaa aaaaattagc caggcgtggt ggtgggtgcc 104100
tgtagtccca gctactcggg aggctgaggc aggagaatgg tgtgaacctg ggaggcggag 104160
cttgcagtga gctgagatcg cgccactgca ctccagccag ggcgacagag ccagactccg 104220
```

-continued

```
tctcaaaaaa aaaaaaaaaa gattcagtga agctaattcc catacccatc acctcaccac 104280
attgtcattc caaaagtgga cttgatccct ttagagtgct gttcctatgg cttgtggaaa 104340
gggatggaga cattttgttg cattttttcac ccattttcac agtacatata aatcattctg 104400
tggggaaaaa aattgcagat gatagaccac ctgttctatg gtagaagcca gagggtgctc 104460
aaggtcttca ccaccactgt gcattctctg ccagtcatag aactttagga gttaacagta 104520
gatagtaaag aacatcttgg tcaaggtcac ttcatcattg atttagtaat tccatctgat 104580
cattcctaac gtcttatagt gtaatgtgat atgtgaaaaa tattactttt actttcttat 104640
ttgaggctaa gttatacagt ttcactttgt tgtaaacttc aactacttca tcaaggaagg 104700
atataatgaa ttccaaaacc gaggattcta gctgagtggt ttttatagta ttagttagat 104760
actgtatagg tttggcaata cattttggaa gattttattt aaaatacatt gacataggaa 104820
atatgttacc ttctaactaa tacagttggt ttgaaccaag atcttagtac tttggtatta 104880
ctgaatttaa aaaaatacct taaaagaatt aagtattcca cattcagtgg taaagatatg 104940
tcaaataagc aaaatatttt tgactgtcag cattataaat aaatacaggt tgagcacccc 105000
taatctgaaa atccaaagtg ctccaaaacc caaaactttc tgagcaccaa catgatgcca 105060
caggtggaaa tttccacacc tgccctcatg tgatgagttg cagtcagaat gcactgttta 105120
gtacttatat gtgaataaat ctaagaaaat gattgcttac cagtagtata taaattcaga 105180
gtcaggagtg atggtgagcc aaacaaccac agattgtcca catgaggggc tgagagagta 105240
acacctttgc tttctgatgg ttcagcatac acagacatta ttttatgcac aaaattattt 105300
aaaatattgt ataaaattac cctgaggtta tatgtatgag gcctatatga aacatcaatg 105360
acttttctgt ttagacttgg gtcccgtccc caaaatatct gattatgtac gtgcaaatat 105420
tccaaaattg gaaaaaaaat ctgaaatttg aaactcttct ggttctaagc atttctgata 105480
aggaatattc aactgtagtc tgtttattga ttttaaatat gtagatttct tctatttaga 105540
aatcatattt atgagcacat agtggtaata accttatttt ttttttcttt ttagcctata 105600
tatgcaaaca gatttgcagt accaacctat gcagccaagc aacctcagca gttcccatca 105660
aggtcagaag aaaatttgct tagatttttt ggccagaata aaacctaggg gttaatgtct 105720
aataatttcc cctgtatttt aatgtaattt agtgaaaggt atttattgtc aacagtttac 105780
aagaatatga tttgcagaaa ggttttaaaa taactttata taaattttat catattggta 105840
cagggtcaaa atgaaatatt aaataagctt gagcaagaca gattctgctg ccacagcttt 105900
catgtgcata cgatttagaa gcaagggcct ttgagataac cagcagtagg aaaccagatg 105960
ggttggaaca gccttcccgt caaaaacagc taaaaaagct ggacaatata agaaaatatg 106020
tgtttgaagg catagaagac taaagaagtg aggaattgtg ggggtaaggt caggagagga 106080
aggaaatcta gaaatgatcc cagctttggg ggccactttt ccttcctaga tgagtttacc 106140
tgttctgaca acagagaggc taggaagctg aggagagctt tctacaaact cacagggcag 106200
aggggacaaa atttagaatc ctgccaaaga ggaggcaccc tggcaaacat ctcagggtct 106260 gtgctggac ccagaagtaa gagtgaacta gaccttcaac tgatttctac aatttcttat 106320
gttttgctca tgatcaaaaa aagccaagtg taaaagaaaa gaaatatga ctaaaaccaa 106380 gaaacaatag accatagaaa cagactgaga tggtatccag ttaatagaca tggactttaa 106440
aataactatg atgtcatgga attaaaagtc aagattgaga atttcagcac agaactaaaa 106500
actaaaagaa tcaatgcaaa ttctagaact gaaaaacaca ggaactgaag tgactcaatg 106560
gatgggctta aaatcatcag gaaggaagat aatttattac ttcattttgt atcacataaa 106620
```

-continued

```
atgcaaatgc atgtgaccct cccatcccct agaagtcttt caaattacaa ttgcgttgca 106680
actctgagga ctatcttcat atgtaatctt tattatacag taagaataca ttgaaatccg 106740
actgaggatc agggaaagag tatataaatt gtgagggaaa cattcaccag gtagtgttct 106800
agtgttactg gagtagaggt gtactagaat tggatgatga ggttaggagc gggtgtccac 106860
aggtggaagt atgaggtttg agatggacag gtatagaagt cataacactt ttaattctca 106920
gagtgaatct catgttgagg gagctataaa cagctaggtt tacaccagca gtaatttgct 106980
gccctcaaat tctaacagca caggcaagtg cttgatcact tagtgtactc acttgtcttt 107040
tacagtttat ctttaccatt tcatgtgctt tttttttttt tgaaaaaaca tgtaaactag 107100
aaccttcata caacattgtt gattatggag taatattatt taaagtagtt attccatttt 107160
agactctaat tggagccttt tagccattga atatcaccct aatactgatc tcagaatgta 107220
cagtaccctt tcctgttgtc agagatgttg aggatggtgt tatgttgagc ttgtaatgaa 107280
tatggcatta tttcacccag tctaaacact ctattaacta tctctttttcc cctcgcaggc 107340 cacctccacc acaaccgaaa gtatcatctc agggaaactt aattcctgcc cgtcctgctc 107400
ctgcacctcc tttatatagt tccctcactt gattttttta accttctttt tgcaaatgtc 107460
ttcagggaac tgagctaata ctttttttttt ttcttgatgt tttcttgaaa agcctttctg 107520
ttgcaactat gaatgaaaac aaaacaccac aaaacagact tcactaacac agaaaaacag 107580
aaactgagtg tgagagttgt gaaatacaag gaaatgcagt aaagccaggg aatttacaat 107640
aacatttccg tttccatcat tgaataagtc ttattcagtc atcggtgagg ttaatgcact 107700
aatcatggat tttttgaaca tgttattgca gtgattctca aattaactgt attggtgtaa 107760
gagttttgtc attaagtgtt taagtgttat tctgaatttt ctaccttagt tatcattaat 107820
gtagttcctc attgaacatg tgataatcta atacctgtga aaactgacta atcagctgcc 107880
aataatatct aatatttttc atcatgcacg aattaataat catcatactc tagaatcttg 107940
tctgtcactc actacatgaa taagcaaata ttgtcttcaa aagaatgcac aagaaccaca 108000
attaagatgt catattattt tgaaagtaca aaatatacta aaagagtgtg tgtgtattca 108060
cgcagttact cgcttccatt tttatgacct ttcaactata ggtaataact cttagagaaa 108120
ttaatttaat attagaattt ctattatgaa tcatgtgaaa gcatgacatt cgttcacaat 108180
agcactattt taaataaatt ataagcttta aggtacgaag tatttaatag atctaatcaa 108240
atatgttgat tcatggctat aataaagcag gagcaattat aaaatcttca atcaattgaa 108300
cttttacaaa accacttgag aatttcatga gcactttaaa atctgaactt tcaaagcttg 108360
ctattaaatc atttagaatg tttacattta ctaaggtgtg ctgggtcatg taaaatatta 108420
gacactaata ttttcataga aattaggctg gagaaagaag gaagaaatgg tttttcttaaa 108480 tacctacaaa aaagttactg tggtatctat gagttatcat cttagctgtg ttaaaaatga 108540
atttttacta tggcagatat ggtatggatc gtaaaatttt aagcactaaa aatttttttca 108600 taacctttca taataaagtt taataatagg tttattaact gaatttcatt agttttttaa 108660
aagtgttttt ggtttgtgta tatatacata tacaaataca acatttacaa taaataaaat 108720
acttgaaatt ctcttttgtg tctcctagta gcttcctact caactattta taatctcatt 108780
aattaaaaag ttataatttt agataaaaat tctagtcaaa tttttacaga tattatctca 108840
ctaattttca gacttttgcc aaagtgtgca caatggcttt ttgttaataa agaacagatt 108900
agttttgaag aaggcaaaaa tttcagtttt ctgaagacag catgttattt taacaatcaa 108960
```

-continued

```
gtatacatat taaaaattgt gagcaatctc aaatgaaggt ccatcgtttc attttaaatc 109020
tctaaatgaa ttcatataag actcaaacgt ttgtgctgtt cactcatgta gcctcagttt 109080
ttgcaattgt gatgcatatc actgaaattt tacagttggt aatgtattaa ctatgtaact 109140
taacacttgg aattaaatag ttctttggat atttgactag ttaagttttt aaaaagacta 109200
ttggatctga acttctttta tatatttttt aatatgcttt atgttttta cttacttggt 109260 catggatgcc acttcaaaat ttgaaaatat taaaggacat cctttcttc ttcaaaaaga 109320 ataaataagg gtaaattata tgcaagtttg acatctctgt ttgactctgt atgtcaaact 109380
gaccttgttc agagtattgc attctcgctt tctcctgtgt ctgtaaccat agagttaagc 109440
acaatttggg ttttctaaac tcaaatcaga ttttat                          109476
```

<210> SEQ ID NO 105
<211> LENGTH: 23101
<212> TYPE: DNA
<213> ORGANISM: Homo sapiens

<400> SEQUENCE: 105

```
cctcctgcct ccggccctgg gtaatatgca tgaagtattt agccaactgg cacctttcga      60
ggtgcgtctg ctgctgctca gtgtctgggg ttttctccgg gagcatgggc ccttgcctca     120
gaagttcatc ttccaatcag agcggggtcg cttcattcgg gacttctcca gggagggtgg     180
aggtgagggt ggaccccatc tggctgtgct gcacagtgtc ctccaccgca acatcgaccg     240
cctaggtctt ttctctggcc gtttccaggc accttcaccg tccactctcc ttcgacaggg     300
gacgtagcct tttcttgctc tggaagccca gggaggttga gcagtgagag agggaaggga     360
ctaacgtgct ccggaagggt ggaggtttct cttctaagtc cttggtctaa agagcgctgt     420 cactttttc tctcccactt tttttttct aaataaaatt tgccaacttg agaaaaccag     480
tccagtgctt ctgtcatgct gagagcgtgc aaagtctgac agcgcctggc tctggacgtt     540
cccgcccctg gcctgaagcc ccgcccctg cgataatttg gagtgcgcac tctaccaatg     600
agacagctgc ccggcggcgc tcaggtcgaa ccaatcataa ggccggaagg ggcgggaact     660
aggatacgtg gctgagcgcg cgcgatgggg cgggaggttt ggggtcaagg agcaaactct     720
gcacaagatg gcggcggtag cggcagtggc ggcgcgtagg aggcggtgag gagcccggaa     780
tctgggggcg cgcccgggac gccccagat ccccaagtc ccattccact ccttcctgtg     840
tgtctcttga cactctgcca cccccggcct cgtgaggaac ctttgttcct ctggaggcgg     900
cctcagacgc ctccggtctc cccgtggtag atccgagcga cgctgggggc cttgcctgtg     960
gggctccggg ctcccgcccg gcggtttagt aaagccacag ctgtgcgtct ttcttggtct    1020
tggccgctct cagccgccgc cctccttttgg ctgcttgcgg cggtcaacgt cgccgccccc    1080
ttcctgcagt gcgcggggtc gtcggggcgg gggaaaagat gcggcctggc ctcggggaat    1140
gcagcctgcg gccccgcggc ccctcggctg agctggaagc accgggccag cagttaagcc    1200
tgtactaccc ttctggctct accctgtaga gctccgaatc ctcctctgcc cttgtcttca    1260
cgtgagcacc agctctggct tagttcagtg tccacggtcg ctgggcacgg cccagggtcc    1320
agtaagctca cggcgtggat ggtgttgctc aaacacaaca tgtaatcgaa tggcttggtc    1380
cacgctctcg ggtttatatt actggggaaa aaaaaagatt cgaaacatat caccagtgcc    1440
acaaatgttt actaggacct aacgatata ctggggtggg gtaggcgtgt actctccaaa    1500
gcgatgaaga aagcgtggat cataaactca gttccctcgg agcctgtgat ctgaaacaat    1560
aaatgcgtgc aacttgccct gcagcttatt cctgactttg gcctatgaac acctctcttg    1620
```

-continued

```
gggtggtcaa ggccgccgtg aattccttag ggccctccaa caggtcatat ctgaaagatg   1680
ctttaggaat cctatctcca ttggcatctt tccgaaccaa ttttacagac tgtgcaaata   1740
gggccccaga gggtatttaa ctcactgtac gtcttttttt tttttttttg agagacagag   1800
tctcgctctg ttgcccaggc tggagtgcag tggcgagatc tcggctcact gcaagctccg   1860
cctcctgggt tcacgccatt ctcctgcctc agcctcccga gtagctggga ctacaggcac   1920
ccgccaccac gcctggctat ttttttgtat ttttagtaga cacggggttt cactatgttg   1980
gtgaggatga tctcgatctc ttgacctcgt gatccacccg cctcggcctc ccaaagtgct   2040
gggattacag gcgtgagcca ccgcgcccgg cctcaactca ctgtacttct atttactgct   2100
gcttttggca ggtggacgtg ggtcagtggc caagagtgcc tgttgcagtc actcaggtca   2160
ctcactgcag gacctgtgcc gcatgccttg ctatggagtt ttgtggtagc atttattctg   2220
cttggcctat taaaccacag tgcctagtgt tttcttcatt tttctgtctg gcctgctgtg   2280
gaacagttgt ttcgtacatt cctctggagc tggaggagag tcctgtgatg agatcatagt   2340
acactctgtg atctcatttc tggtaatttt cttttagctt tcaagcagat gctgaagcta   2400
atgctagata actagataca atgtgtataa tagaccctgt ctttagttac cttattatag   2460
gttgtcaaat tttatttatt tatttatttg tttgtttact tattgaaaca gggtctcgct   2520
ctgttgccta ggatggagtg caggggtgca atctcggctt actccagctt ccacctcccg   2580
agttcaagcg attctcctgc ctcatcctcc cgagtcctgg gattacagac gtgtgccacc   2640
gtgcccagct aattttttgta tttttagtag acaccccatt gaccagtctt aattaattta   2700
cttttttgag acagagtctt gtgctgtggc ccaggctgga gagcagtggt gcaatcgtag   2760
ctcatgcagc ctcaaactct tgcgttcagg cagtcctccg gcttcagcct cctgattagc   2820
tgggactaca ggcacctgcc accatgcctt gctactcttt tttttttta agtagagacg   2880 aggtcttgct gtgttgccca atcttcccct tttgacctcc caaagtgcta ggattataga   2940
cgtgagccac tgtgcctggc tggttgtaaa actttattgc ttagaagaac cctcccaccc   3000
ccagtttgaa acactttctc agagtatgct cgtattctgc ccatatcagt gtcactggga   3060
gagcatgttt aaaatgtggt gtcagccggg cacgatggct cacacctgta atcccagcac   3120
tttgggaggc cgaggctggc gaatcacctg aggttgggag ttcgagacca gcctgaccaa   3180
cacagagaaa ccccgtctct actaaaaata caaaattagc cgagtgtggt ggcacgcgcc   3240
tgtaatccca gctacttggg aggcagaggc aggagaattg cttgaacccg cgaggcagag   3300
gttgcggtga gccaagatcg tgccattgca ctccagcatg ggcaacaaga gtgaaactca   3360
gtttcaaaaa aaattaaaaa taaaatgcgg tatccagggt gggtgcagtg gctcacgcct   3420
gtaattccag cattttggaa ggccaaggtg gaaagatggc tttagcctag aagttcaaga   3480
caagcctggg caacttttt ttcttgtttt tgagacagag tcacactttg tcacccaggc   3540
tagagtgcag tggtgcgatc tcagctcact gcaacctctg actcccaggc tcaaaccatt   3600
ctcgttcctc agcctcccca gtagctggga ttataggcat gtgccactac gcctggctaa   3660 ttttttgtata tatctatttt tttctaggtg gtgtttcgct gtgtcgccca ggctggaatg   3720
cagtggcaca accttggctc actgcaacct ctgcctcccg ggttcaagca attttcctgc   3780
ctcagcctcc tgagtagctg ggactgcagg cgtgtgccac catgccctgt taattttttt   3840
tttgtatttt tagtagagac ggggtttcat catgttggcc aggctggcct caaactcctg   3900
acctcaggtg atccacccgc ctcagcttca caaagagctg ggattacagg tgtgagccac   3960
```

```
cacgcccggc ctaatttttg tattttttagt agagatggag tttcgccatg ttggccaggc   4020
tggtctaact cctgatctcg tgatctgccc acctgggcct cccaaagtgc caagattata   4080
ggtgtgagct accatgcctg gctgattctt aacagacatt aaaatttgag aatctctgtt   4140
taggatttat tcagaatcct aaggatgaat cctggatgaa tatattcttc aaactaactt   4200
atttaaataa gcctattagt ctcttatctg tcatttcata gcacattggg aaattgacaa   4260
ttcgtgataa ccttgggatg atggtcctca atgagacagg cccatttcat cctgctagtg   4320
attagtgtgc tgtattgtgc atcatggtaa agcacatggg ccccagagtc aagcacaact   4380
gggttcagtt cgtttcatcc cttaccagct atttaatctt gggtgaacta ttcaacctttt   4440 tatgctttaa ttttcccatc tggaaataaa ccccaaccct atattcacca agaaacaat   4500 ggaagaaagg gaaagaaga tgcatgtaaa gaagtggttg tgaacccagg ttgctcatta   4560
gagttgttta gggaactttta aaaaaacttt agccagtggg gcgcgatgac acaacgcctg   4620
taatcccagc actgtgggag actgagacgg gcggatctag gtcaggagtt cgatacgagc   4680
ctggccaaca tgatgaaacc ccgtctctac taaaaataca aaaaattagc tgggcatggt   4740
ggtgggcacc tgtaatccca gctgctcggg aggctgaggc gggagaatcg cttgaaccca   4800
ggaggcagag gttgcagtga gctgagatca tgtcactgca ctccaacctg ggtgacagag   4860
caaggctcca tctcaaaaaa aaaaaaaaag tctgatgccc aggcttctct ctgattaagt   4920
taaaattttt agaagtgaga ccaggtcact gatattgtta aaaactgcag gcaggctggg   4980
cacagtggct gacactataa tcccaacact ttgggaggcc aagatgggag gactgcttga   5040
gcccaggagt ttaagaccag cctgggcaac aaagtgaggc cctgttgcta ccaaaaaaaa   5100 ttttttattta tttttttttga gtcagagtca cgctctgttg cccaggctgg agtgcaatgg   5160
catgatctgc tcagtgtaac ctccacctcc tggttcaagc agttctcctg cctcagcctc   5220
ctgaatagct gggattacag gcccctgctc ccatgcctgg ctaatttttg tattttttagt   5280 agagatgggg tttcaccata ttggccaggc tggtctcttt gccagcctgg tctcgaactc   5340
ctgaccttgt gatccgccca ccccggcctc ccaaagtgct gggtttacag gtgtgagcca   5400
ctgcgcctgg ccagaaaaaa aacaaaaacc acaacttttt aaaaattagc tgggtgctgt   5460
ggcgagcaac tgtagtccca gctacttggg agggtgaggc aggtggatca cctgaggtca   5520
ggaattcaag atcagcctgg ccaacatggt gaaactccgt ctctaccaaa aatacaaaaa   5580
ttagctgggc atggtggcgt gctcctgtaa ttcagttact taggaggttg aggcatggga   5640
attgcttgaa cctgggaggc ggaggttaca gtgagctgag atcatgccat ggcactctag   5700
ccagggtgat ggagtgagac tgtctcaaag caaaaaacaa aaactgcagg cagtattaaa   5760
aactagtaat ataaagtgat tacccaggcc cctaggggtg cattagggct cagaacattt   5820
tagctattgt tatttttttt cagctttggg tagtgatggt ggtgttttga agatacagga   5880
gtagaaatca gagaaacagg ctgcctaggg tgctagggat gttaggaccc taggaactgt   5940
aaccagcagg ctagctgagg gtacatcttt tttttttttt ttttctgag agttttgctc   6000 catcacctag gctggagtgc agtagcacaa tcttggctca ctgcaacctc tgcctcccgg   6060
gttcaagcga ttctcatgcc tcagcctccc gagtagctgt cactacagat gctcaacgcc   6120
atgcccagct aatttttgta ttttaagtag agatggggtt tcatcatgtt ggccaggctg   6180
gtcttgaact cctgacctca agtgatccac ccgcctcagc ctcccaaagt ggtgggatta   6240
cagacgtgac atgagccact cgcccgccc ttcatgttta gctctttaac tttgcatcca   6300
cccaatgcct tgccgataga aagatgtggc ttgctttgtt tctctgttcc acgcatatgg   6360
```

-continued

```
tactaccatt tcctctgaga ctggctgtta ctgctccttt cctctgagag gctgatgtca    6420
ccagagtcaa caccagggcc tctgaaggtg aaagatcctc tgtgtactct gccttttttt    6480
tttttttttt ttttgagagg gagtttttact ttgtcgccca ggctggagtg cagtggagtg    6540
atctcagctc actgcaagct ccacctccca ggttcacacc attctcctgc ctcagcctcc    6600
cgagtagctg ggactacagc tgcccaccac cacgcctgga taattttgtg tatttttaat    6660
agagacagag tttcaccgtg ttagccagga tggtctcaaa ctcctgacct cgtgatctgt    6720
cagccttggc ctccctaagt gctgggatta caggcatgag ccaccgcacc cggccctttt    6780
tttttttttt tttggagatg gagtctcact ctgtcaccca ggctggagtg cagtggtgcg    6840
atcttgactc actgcaagtt ctgcctcccg gattcatgcc attctccagc tccagcctcc    6900
caagtagctg ggactacaga cacctgccac cacgcccggc taattttttg tattttttagt    6960 agagacgggg tttcactgtg ttagccagga tggtctcgat ctcctgacct cgtgatccgc    7020
ccacttcagc ctcccagagt gctgggatta caggcgtgag ccaccgcgcc tggcttttt    7080 tttttttttt tttttttttgt ctagctctgt cgcccaggct ggagtgcagt ggcacgatct    7140
tggctcactg taagctccgc ctcctgggtt cacgccattc tcctgcctca gcctcccgag    7200
tagctgggac ttcaggtggc cgccaccacg cccagctaat tttttttgta tttttagtag    7260
agacagggtt tcaccgtgtt agccaggatg gtcttgatct cctgacctcg tgatccgccc    7320
gccgcagcct cccaaagtgc tgggattaca ggagtgagcc accacgccca gcctactctg    7380
cctttcaaag ggaaggtgtg agtgagccaa cttctcaggc ctgatcctta accctgtgtc    7440
cactctgcct tgtttttgtat ttgatgtgac tacatctttc tcccctcttt cctcaactat    7500
cttctagtgc tatgacagga agaagctttt ccttttgaag ggggccccctt ctgacctcca    7560 tgctgattgc tctgtctttg tccttttctc cttaggtctt gggcgtctttt ggtactggct    7620 tttttagggg tctgcctggg gattaccctt gctgtggata gaagcaactt taagacctgt    7680
gaagagagtt ctttctgcaa gtatgatatt tctgggggag agggatggaa tgtagggttg    7740
tagggtaatg tgggagatat ctgtggcaga tggagtgcct aaggacactg caggtgatag    7800
actgacttag ggacattgca ggtggccttt accttacttc ccaacccttc acttggcagg    7860
cgacagagaa gcatacggcc aggcctctct ccataccgag ccttgctgga ctctctacag    7920
cttggtcctg attccctcac ggtccatctg atccatgagg tcaccaaggt caggagagac    7980
aaggaagagt ctggtggggg tggggcaatg gctgtggggt aatttggaaa gggggaaatt    8040
gtggccaaca tcttgtccca gcctaatctt tggactttta ctttatgaag aaatgtgatc    8100
ttggccttta ggcaaagggc tcaaaggaag aaacccctta ggagagaatg ggttcaaaga    8160
gcattccatg gtgtatccca tttcctttct ccagatccaa acctctgtcc ccgcaggtgt    8220
tgctggtgct agagcttcag gggcttcaaa agaacatgac tcggttcagg attgatgagc    8280
tggagcctcg gcgaccccga taccgtgtac cagatgtttt ggtggctgat ccaccaatag    8340
cccggtaaat tttttcctgag aaacatccat ttctgtggcc cctttctcct tcctgatgaa    8400 ccttttttttg gttgctgata ttctttccca aaataaggta gtagttaact agcatagcac    8460
cttgccatac tcctcaacct ttccccacct cttcttctgt ttcacttttc tctttatccc    8520
tttatcctca ttcattcatt cagcaaacaa ttattgcttt ttcctccctg acaggcctgg    8580
gctggatgct ggttatataa gcagaaataa acaaggccct gtttatttac agatctcgtt    8640
ctccaggaat acaatgtcta cctgcttgct tgtttgcttg cttccttcct tccttccttc    8700
```

-continued

```
cttccttcct tccttccttc cttccttcct tccttccttc cttcctcctt tccttttcct       8760
tagatattca gaataggatt actcagattc ttgtgtcatg atactctgtc accagtgttc       8820
catgcatcca tccatgactt tctcttaaat acataattca gaaaataaca tagtggccgg       8880
gcatggtggc tcaacgcctg taatcccagc actttgggag gtcgaggtgg gcagatcacg       8940
aggtcaggag ttggagacca gcttggccaa catggtgaaa ccccatctct actaaaaata       9000
caaaaatcag ccaggtgtgg tggtgcggac ctgtaatccc agctactcag gaggccgagg       9060
caggacggtt acttgaaccc aggaggcaga ggttgcagtg agccgagatt gtgtcactgc       9120
actacagcct gggcgacaga gtgagactcc gtctcaaata ctccacccta taaactcttc       9180
actcagccca acccgcactg tcctgtaccc ttgacggctc cagacgtagg tagtcgttat       9240
tctgaagctt atccttcctt tgcctttttt ttgttcttac agttgtatta tgtgtgtata       9300
catatgcaca catatgtctg tgtgcctaag caataaatta tatatatttt ttgttttttga      9360 gctttacaga ggaagtgtct tagtgcatgt ggtcttctgg ggtttccgtt ttttcttttt       9420
ttttttttga gatggagtct cgctgtctcc caggctggag tacagtggcg tgatctgcgt       9480
tagccaggat ggtctcaatc tcctgacctc gtgatccgcc cgcctcagcc tcccaaagtg       9540
ctggaattac aggtgtgagc caccgcgccc ggctgggttt ccgttttttca cataacttta     9600 tttaattcca tttcatatag ctctagttca ttcattttta ctgctgcata ttattatgtt       9660
gtatgaatat accccaactg attaatccat ttttaggttg ataagccttg gggttgtttc       9720
cagtgttttg ctagccaaag tgttgctacg aaccttcttg tacatgtctc ctgttatcct       9780
tgcttgggag tttctctttg gtgtataact aggagaggaa ttgcaggatt gtagaatatg       9840
gagatgatca gcttcgcaag ataaagccaa agtggtttac caatttacac ttccaccagt       9900
gatttataag aagccctcat tgaagctggg caagccagga tggtctcgat ctcctgacat       9960
cgtgatctgc ccatctcagc ctcccaaagt gctaggatta caggcttgag ccaccacacc      10020
cggccagcct tccctattat taatatgact atggttcatt tgtgatacct agtgaattga      10080
tagtgataca ttagttacta aagttcatac ttgaggtttc tttagttttt gtgtatgttc      10140
tttttctgtt ccaggatttc atccaggata tgttattaca tttagttgtc atgtttcctt      10200
agggccctct agactgataa aatttcttag acttttcctt tttcttaatg atcctaaagg      10260
tacttttgat aaacagaaat tcctaatttt aatgtattta gatgtatcag tcttttacct      10320
tctgttgtta gccttttgtt tgttgtattt agtctttatc taccccaagg tcagaaaaaa      10380
atatatatat atatatttttt tgagacagag tcttgctctg ttgcttaggc tgagtgcagt     10440
agtgcgatct ggctcacca caacctccgc ctcctgtgtt gaagcgattc tttcttcagc       10500
atcagcctcc cgagtagctg ggactacagg cgtgcaccac tatgcctgag tagctgggac      10560
tacaggcgtg caccactatg cccgagtagc tgggactgca ggctcatgcc actatgccca      10620
agtagctggg actacaggcg tgcgtcacta tacccggcta ctttttgtat ttttagtaga      10680
gacagggttt cactatgttg accaggctgg tctcaaactc ctgacctcat gatccacctg      10740
cctcggcctc cgaaagtgct gagattacag gaatgagcca ccatgcctgg ccaaaaatat      10800 atttttttaat tttcttctaa cacttttgct ttcatttatt tacttatttt gagatcgggt      10860
tatgagactg gctaattttt gtatttttgg tagagatggg tttttgccat gttgcccagt      10920
ctggtcttga acaccagggc tcaagcgatc cacctgcctc ggcctcccaa agtgctggga      10980
ttacaatagt gggccaccga gcccatccta aagctttac ttttaaattt taagcaggct        11040
gggtgtgatg gctcatacct gtaatcccag cacttcgaga ggccaaggcg gacagatcac      11100
```

-continued

```
ttgaggtcag gagtacaaga ccagcctggt caacatggtg aaaccccgtc tctactgaaa   11160
atacaaaact tagccgggcg tggtggtggg cgcctgtaat tccagctact cgggtgcctg   11220
atgcacaaga atcacttgaa actgggaggc agaggttgca atgagccgag attgtgccac   11280
tgcactccag tctgggtgat agagtgagac tatcttaaga aaaaaaaatt ttttaagtca   11340
taatctttct gcagttgata cttgtatctg gtattagata gaaatatgat atcaaggggt   11400
tgggcgtggt agctcatgcc tgtaatccca gcactttggg aggccgaggc aagtggatca   11460
cttgaggtca ggagtttgag attagcctgg ccaacatggc gaaaaatcat atctcctaaa   11520
aatacaaaaa aaaattagcc gggtgtggtg gcacctgcct gtaatatcag ttactaggga   11580
ggctgagtca ggagaatcac ttgaacctgg aaggtggagg ttgcagtgag ccaaggttgt   11640
gccactgtgc tccagcctgg gcaacagagc gagactccat ctcaaaaaaa aaaaaaagaa   11700
gtacatcatt tttcttcata tttggaaaat cattttttt cctatatgga aaatgttttt    11760
tcagttccat ttttgaatag ttctcctttc ctctctcatc tgctatgcca cctcttagta   11820
tttagtacat ttaaaaaagt aataagtggc caggcacagt ggctcacgcc tgtaatccca   11880
gcactttgcg aggccgaggt gggtggatca cctgaggtca ggagtttgag accagcctca   11940
acatgaagaa accccatctc tactaaaaat acaaaattag ccaggtgtgg tggtgcatgc   12000
ctgtaatccc agctatttgg aggctgaggc aggagaattg cttgaacctg ggagacggag   12060
gttgcggtga gccgagattg cgccattgca ctccagcctg ggcaacaaga gtgaaactcc   12120
gtctcaaaaa aaaaaagaa aaagtaata aatatgcttg ggtctgtttc tgggcccttt     12180
ggttctgttt attaacttgt ctatccctgc tctgttacca cactgcctat ttctcttaac   12240
aggtagattt cccccggtct tctaaagtgt cattactcct cttggcccctt tgtacttcct   12300 tatatttctt ttgatatgtt tcccaggctt tctgtctctg gtcgtgatga gaacagtgtg   12360
gagttaacca tggctgaggg accctacaag atcatcttga cagcacgccc attccgcctt   12420
gacctactag aggaccgaag tcttttgctt agtgtcaatg cccgaggact cttggagttt   12480
gagcatcaga gggcccctag ggtctcgtga gtacaggggt tgggactgca gggaacctag   12540
tgtgaaagag catagggtg ttgtgaggtc tggcacgggg aggagacggt ggtgggacag    12600
ccaggtaggg cctgggggct gggagaagct ctctgtcagg gagggtagga accagacccg   12660
ggtgcggttt tttccattc ctgtacagac caggaggcag tcacttttgt ccctgagctg    12720
taccctgggc atctctggga ggcctgcctg ggtctgtgtc tccttcttcc ccttctcaca   12780
tcatcacatt tcccagattt attttcttcg tttttattta tttatttttt ttggtttctt   12840
tttcccccca tctctggaag tttgtcgact gaaactcact tttatgtttc tgtttttgtg   12900
ttggttttgt gcctcttttt ccccttccct acccatctcc tcctgcccca gtttctcgga   12960
taaggttaat ctcacgcttg gtagcatatg ggataagatc aagaaccttt tctctaggta   13020
aatccatggc caccggtact gtatctgttc ctctgcccctt acccattcct cactctagcc   13080 tttggggga ggtgccccag acccttccag cctttcactc accccacttt ccctgctgt     13140 gtgatgtctg gtcctgttac ctgttacccct ggctgggagc ccccagaaga aggaaggtga   13200
gatactgaaa gtcaggtcct tcgggaatgt agggagctta ttgctttgcc aggggatgga   13260
gagatgctgc ctattgctgg ggttcctgac tctcagctga ggggcacctg aggttctggg   13320
cagagctact tgcccttgaa agcattttt ggcagaatct cttgaagtcc ctatgtatgt     13380
ctgtagaggc ttggtatagt atgacccaca tgcctttgca aagccattgt gtcaggccag   13440
```

-continued

```
gaggctgagg cccagggaga gcacttgggg ccagaatctc tcagtagagg caacagagcc   13500
aggattggca ttcataaccc aggcccctga atcattctgc ctttctcttc tgggatgttg   13560
acagaggctg gtgttcaggc ctgtgcctcc tggtggcact tattcctcat tttcctttct   13620
catttctctc cccatccttt gcaaacttat ctgctcattg tgggttccct ctccaagctt   13680
taacatttag tcccttcctc caatgccttc gttcctttgg acccttggct ctctattccc   13740
caacccctcc ttccactagc ccctcgtccc tgcccctct ggattggagc agacagctct    13800
cctaccttcc aggcaaggat caaaagaccc agctgagggc gatggggccc agcctgagga   13860
aacacccagg gatggcgaca aggcaagttg gagcgggtgg gtggttggag gatagggctg   13920
gctgggaggg tggaggggag aggcccatga gaaacttgaa cttagtctcc ccatcaggga   13980
tgggatttag ttgatgggag cggggaaaga gagaactggt atgattggag agtggtcctc   14040
ttttcttctt aacagccaga ggagactcag gggaaggcag agaaagatga gccaggagcc   14100
tgggaggaga cattcaaaac tcactctgac agcaagccgt atggtgaggg gctcgggttc   14160
cttgggctgg ggtgcagggc tcctttccaa gcagaagctc tgaagcttgt ttgttttct    14220 tccaggcccc atgtctgtgg gtttggactt ctctctgcca ggcatggagc atgtctatgg   14280
gatccctgag catgcagaca acctgaggct gaaggtcact gagtgagtcc tatggtgaca   14340
tcaggaagat ggaggtgggc aggaaggagt caggccttta gggagatggg tgtgcatatt   14400
ggatactcta ggcaagcatg ggtcatttct tgtgtccaga atcacctttg gtgatagaaa   14460 atttttgag aaaggacaag aggagccttt gcttatctct cacctgtgtc tgtggagtgg    14520
tgttagcata taacgcagcc tggggccagt tagcagccca agtctgtctg tttgcctgca   14580
ggggtgggga gccatatcgc ctctacaatt tggatgtgtt ccagtatgag ctgtacaacc   14640
caatggcctt gtatgggtct gtgcctgtgc tcctggcaca caaccctcat cgcgacttgg   14700
gcatcttctg gctcaatgct gcagagacct gggttgatat atcttccaac actgccggga   14760
aggtgagagc acaggcacgg ggaaaaagga gggagtgaag cttccaggcc ttgaggcaaa   14820
taggtatact aggggcatta gctatttggg gactgggttt aagaaggggc tgtgggcctg   14880
gtgggcagca tttgagttcc ctaatcactc ccaggtgaca cgctcactca cattcttagg   14940
gaaggcattg cctattctgg gctgacggaa tgcacttatt atcagtgtgt tacgtgctag   15000
gtactcttct gggtgctggg gatatagtgt taactgaggt tgaaaaggtt ctgggctggg   15060
tgtggtggct catgcctgta atcccagcac tttgggaggc tgaggtgggc ggatcacctg   15120
aggtcagaag ttggagacca gcctggccaa catggcgaaa cctcatctct actagaaaaa   15180
caaaaattag cagggtgtgg cggcggactc ctgtaatccc agctattcgg gaggctaagg   15240
caggttaatt gcatgaatct ggttggtgga ggttgcagtg agcggagatt tcaccactgc   15300
actccagcct gggtgacaga gtgagactct gtttcagaaa aaaaaaaag aaaggttctg    15360 actcacaggg aggaagacac gttaaacaca taacaaagga ggcaagatgg ggccgggcat   15420
gatagctcat gtctgtaatc ccagcacttg gggaggctga ggcaagagga tcgcttgagg   15480
ccaggagttc gagaccagcc tgggcaacat ggcgagaccc catctctata aaaacgtttg   15540
aaaaataaaa ataataagca agatgatgcc gggtgcagtg gctcccacct ctaatcccag   15600
cactttggga gggcgaggtg gacagatcac aaggtcaaga gatcgagacc atcctggcca   15660
acattgtgaa accctgtttc tactgaaaat acaaaagtta gctgggtgtg gtggtgtgcg   15720
cctgtagtct tagctactcg ggaggctgag gcaggagaac tggttgaact ggggaggtgg   15780
agattgcagt gagctaagat cacaccattg cactccagcc tggcaaaaga gtgagactct   15840
```

-continued

```
gtctaaaaaa aaaaaaaaga atgcaagatg agtttggggt gattaagtgc taacaaagac    15900
atgaaagaga gtctttgtta gcacttaacc accccaaact ggtggggtag gggtgggggc    15960
tgtactgctt tagatagtgt ggtctaggaa agcctcactg aagaggcccc gtttagtctt    16020
accgaaagca gcttacatga gccagctctg tgtggactct gggagaaaat tgctactttt    16080
tgtcttgggg ttggaaaatg ggagggcagg aggtgtctga cccctttgtg gtcacctata    16140
cagaccctgt ttgggaagat gatggactac ctgcagggct ctggggagac cccacagaca    16200
gatgttcgct ggatgtcaga gactggcatc attgacgtct tcctgctgct ggggccctcc    16260
atctctgatg ttttccggca atatgctagt ctcacaggta catggttttc cctgcctcat    16320
tcttctgctc ttttcttgtc gggtgattct atgtgttttc agagatcctg tgccccagct    16380
tgttttctag gttatacccc ctcagcctgc ctctagttca caagcctccc tcagtttctg    16440
ggtgttgggc ctgatcctcg ttgtgaccc c catccctcat gaacctgcag gaacccaggc    16500
gttgccccca ctcttctccc tcggctacca ccagagccgt tggaactacc gggacgaggc    16560
tgatgtgctg gaagtggatc agggctttga tgatcacaac ctgccctgtg atgtcatctg    16620
gctagacatt gaacatgctg atggcaagcg gtatttcacc tgggacccca gtcgcttccc    16680
tcagccccgc accatgcttg agcgcttggc ttctaagagg cggaaggtaa ggggttgcag    16740
tcacgcttgg tcttctcagg gtagggctga agcatagttt agccttaaag agacctgaac    16800
acccctgttc cttgccccca gctggtggcc atcgtagacc cccacatcaa ggtggactcc    16860
ggctaccgag ttcacgagga gctgcggaac ctggggctgt atgttaaaac ccgggatggc    16920
tctgactatg agggctggtg ctggccaggt aagcagaccc agaattgagg gagagttgat    16980
tggccagcgg ggtagaatgg tggctctttt gccccttagg ggattgagag ccacccttaa    17040
cttctcccag gctcagctgg ttaccctgac ttcactaatc ccacgatgag ggcctggtgg    17100
gctaacatgt tcagctatga caattatgag gtagggaagg cctctcccca tgacctgcgt    17160
ctgtctgttc cacctgcctc cctgaatctc tctcggcttg ccaacccttc tatggttgat    17220
tgcctgcaac atatcagggg gccttgatga tccggggagg gccctgaaaa atgcatcttt    17280
ttagattcct aggagctctc ttctctgaca ctgtttgtct tcttcctccc ctctgtcctt    17340
ctgtccccat tttctgccca cgttcccagg gctcagctcc caacctcttt gtctggaatg    17400
acatgaacga accatctgtg ttcaatggtc ctgaggtcac catgctcaag gatgcccagc    17460
attatggggg ctgggagcac cgggatgtgc ataacatcta tggcctttat gtggtaaggg    17520
cctgagagag gagagttggt ggaaagaggg aaaacagccc agagactgag ggcctaggga    17580
acttgcacca gatgacagct ggcttttgct cctcactacc cgtctcttct ctcctcaccc    17640
agcacatggc gactgctgat gggctgagac agcgctctgg gggcatggaa cgcccctttg    17700
tcctggccag ggccttcttc gctggctccc agcgctttgg taaggtttag agaatggagc    17760
tgtggcagaa gggtgtgaag gccagatctc aggagccatg gacctggacc tgcctctctg    17820
aggaatggga gccacacact gcatctgttt cctctcagct atgcgctttg aaggaagtca    17880
gggtgtggga ggtccactcc ttgttcaaat gttcttgtga actgcatctt cagcagggtt    17940
ctggggaccc agagcggatg tgggaggtca gccatgtaaa aagctgaact cctttaccat    18000
gtgcaagctc cccacttctt gtcttcctca ggagccgtgt ggacagggga caacactgcc    18060
gagtgggacc atttgaagat ctctattcct atgtgtctca gcttggggct ggtgggactt    18120
tccttctgtg ggggtaagac agggaggaat ttggggtctt ggtttggtgg gaaaggggca    18180
```

-continued

```
aagtagaggg cacaggacca aggtgttgta agcaaagaga gttgagagtc caagttaggg   18240
ccttgggaag tttctcaagc agtatctctc cttcaccctc ttttccaacc tgcttcctct   18300
ctctcctcta ccagcggatg tgggtggctt cttcaaaaac ccagagccag agctgcttgt   18360
gcgctggtac cagatgggtg cttaccagcc attcttccgg gcacatgccc acttggacac   18420
tgggcgacga gagccatggc tgttaccatc tcagcacaat gatataatcc gagatgcctt   18480
gggccagcga tattctttgc tgcccttctg gtacaccctc ttatatcagg cccatcggga   18540
aggcattcct gtcatgaggt gaggcattca cttgggctgt gaagagtggg ctgaggtggc   18600
tgggggtatt agggactggg cttcatctct gggtctcttt cttcactcac tacagccttg   18660
taaaggatgg aaaatcatta aggtcaagag tgaaggggag cttaatggag atgaataata   18720
gtaaacattt aaagaaaatt gacagcagtc ataagctctt tcagaaaaat aaaacagggt   18780
aatgggatta ggtggtcata aaatcccttt ttgaggccgg gcacagtggc tcacacctgt   18840
aatcccagca ctttgggagg ccgaggtggg cagatcacct gaggtcagga gtttgagacc   18900
agcctggcca acatggcaaa accccatctc tactaaaaat acaaaaatta gctgggcatc   18960
atggcgcctg taatcccagc tactcgggag gctgaggcat gagaatcact tgaacccagg   19020
aggtagaggt tgcagtgagc cgagattgct ctgctgcatt ctagcctggg tgacagaggg   19080
agactccatc tcaaaaaaat gaaaaaaaaa aaaaaaaaa agttttgaga agaaggctgt   19140
gtgagatgag gcctgaatga gtgggacaga ccatgttatg taggaagaat cttccaagca   19200
gagggaattg caagtacaaa aattctaaag gagaaattag tttgttatgt actaggaata   19260
gaaaaaaaca gtatgtcttg ggtaaagaag cagaaggaga gctaggagat gagattaaga   19320
agaaagtgtg atctgctcct ggagggcctt gcaagccagg gttgcaaccc agggttgtaa   19380
gccagggcgg tgaaacatgc aaggaggcta ctggcaggct gctgtgcagc atggtttcag   19440
tagagggcag agaagaagca gggagatggc ttaggaagtt aaatgtctaa gactggattg   19500
tataactgag acctgaaccc caacccgact gtctgactgc aaactcctgg gtcttaaccc   19560
ctgtgctgtt cttttctttt cttttttttt ttgagacaaa gtctcactct cgtcccccag   19620
gctggagtgc gatggtgtga tcttggctca ctgaatgcac tccgcctccc gggttcaagt   19680
gattctccag cctcagcctc ctgagtagct gggatcacag gtgcctgcca ccatgcccgg   19740 ctaattttg tatttttagt agagacgggg tttcaccatg ttgttcaggc tgatctcgaa   19800
ctcctgacct caggtgatct tcccgcctcg gcctcccaaa gtgttgggat tacaggtgtg   19860
agccaccaca cccggcctat gctgttcttt tcttattgcc agttcctgga ggagcatttc   19920
tgacttgtgc caaaattgaa aagttttcct ttattgtctt tcttccttcc taggcccctg   19980
tgggtgcagt accctcagga tgtgactacc ttcaatatag atgatcagta cttgcttggt   20040
gagaaatgag gatagttggt ggtgggttgg ctttgggcca agcagcactg cggatgccca   20100
gggagggact agtgaagctg gtggtgcaga gggcaggcac tttggtgttc cctgttctgg   20160
gaactaatcc ccctattcag agttgattct ggcatatttt aggggatgcg ttgctggttc   20220
accctgtatc agactctgga gcccatggtg tccaggtcta tctgcctggc caaggggagg   20280
tgagttaagg aagggcatgg tggggaaaga tggtggaagc caaaggaggc aaacaggacg   20340
ggacccctgt gcactgagtg atccggtatc ttacctcttt tgtcactcac aggtgtggta   20400
tgacattcaa agctaccaga agcatcatgg tccccagacc ctgtacctgc ctgtaactct   20460
aagcagtgtg agtaagcctg gtctggctgc cggttccatc tccctgtaaa tttccagaag   20520
gggagggaat gtgtgcctta gggtccagta cctatgtggg catacatgag taagcaaaac   20580
```

-continued

```
atgctgtggg gcccaaggtt ggacaagggg gcaacttcat cctggcattg ctcttgccct  20640
agatccctgt gttccagcgt ggagggacaa tcgtgcctcg atggatgcga gtgcggcggt  20700
cttcagaatg tatgaaggat gaccccatca ctctctttgt tgcacttagc cctcaggtaa  20760
gtgcataggc agcgagtctc ctcagccatt tgcctgcctt cctaggactc agttctctgg  20820
ggttgtgccc ctcactccct cttgggctca ggcgctcacc tatcccactt cttgctcagg  20880
gtacagctca aggagagctc tttctggatg atgggcacac gttcaactat cagactcgcc  20940
aagagttcct gctgcgtcga ttctcattct ctggcaacac ccttgtctcc aggtaatggg  21000
tcacccactc ttccttggct gcctttgctg gggcctgatc cttgtggggg ctcccagttc  21060
actgtgctct tttctcacat tctgaccttg ctttgggtct cctccttcct tctgttctgt  21120
tatttttccc cctgatggac atctgctttt accatctcca gctcagcaga ccctgaagga  21180
cactttgaga caccaatctg gattgagcgg gtggtgataa tagggctgg aaagccagca  21240 gctgtggtac tccagacaaa aggtgagtga ccaatctggc ccctaggatg ggggaaggag  21300
gggaagccgg ggcaggttta gggatgccct tgcctgtagg aacgttgttg ttatgctata  21360
gcccattggt atgactatgg cactctttta ttcctcctcc aggatctcca gaaagccgcc  21420
tgtccttcca gcatgaccct gagacctctg tgttggtcct gcgcaagcct ggcatcaatg  21480
tggcatctga ttggagtatt cacctgcgat aacccaaggg atgttctggg ttaggggag  21540 ggaaggggag cattagtgct gagagatatt ctttcttctg ccttggagtt cggccctccc  21600
cagacttcac ttatgctagt ctaagaccca gattctgcca acatttgggc aggatgagag  21660
ggctgaccct gggctccaaa ttcctcttgt gatctcctca cctctcccac tccattgata  21720
ccaactcttt cccttcattc ccccaacatc ctgttgctct aactggagca cattcactta  21780
cgaacaccag gaaaccacag ggcccttgtc gccccttctc tttcccttat ttaggagccc  21840
tgaactcccc cagagtctat ccattcatgc ctcttgtatg ttgatgccac ttcttggaag  21900
aagatgaggg caatgagtta gggctccttt tcccctttccc tcccaccaga ttgctctccc  21960 accttcatt tcttcctcca ggctttactc ccctttttat gccccaccga tacactggga  22020
ccacccctta ccccggacag gatgaatgga tcaaaggagt gaggttgcta aagaacatcc  22080 ttttcctct cattctaccc ttttcctctc cccgattcct tgtagagctg ctgcaattct  22140
tagaggggca gttctacctc ctctgtccct cggcagaaag acgtttccac acctcttagg  22200
ggatgcgcat taaacttctt ttgccccctt cttgtcccct ttgaggggca cttaagatgg  22260
agaaatcagt tgtggtttca gtgaatcatg gtcacctgta tttattgcta ggagaagcct  22320
gagggtgggg ggagatgatc atgtgtgctc ggggttggct ggaagccctg ggtgggggt  22380 tgggggagga ctaatgggga gtcggggaat atttgtgggt attttttta cttcctcttg  22440 gttcccagct gtgacacgtt ttgatcaaag gagaaacaat aaagggataa accataaata  22500
actggtggta gtctggattc tagttctagc ctgagccaca gaccctagaa gcctagagac  22560
cttacatttg cttttcctttt ttttttcttttt ttgagactga gtctcactct gttgcccagg  22620
ctggaatgca atggcatgat ctgggctcat tgcaacctct gcctcccagg ttcaagcagt  22680
tctcgtgcct caacctcccg agtcgctggg actacaggca tgcgccacca tgcccagcta  22740 attttgtat ttttattaga gatggggttt caccatgttg gccaggctgg tctggaactc  22800
ctgacctcag gtgatccgcc tgcctcggcc tcccaaagtg ctggaattaa aggagtgagc  22860
cactgcgccc tgggtctttt tttttttttt tttttttttg agacagagtg tcgccaggct  22920
```

```
ggagtacagt gtgtgatcct ggctcgttgc aacctctgcc tcctgggttc aggcagttct    22980
cccacctcag cctccttaat agctgggatt acgggcacct gcgaccatgg ccagcttcat    23040
ttttgtattt ttagtagaga tggggtttcg ccatgttagc catgctgatc ttgaactcct    23100
g                                                                    23101
```

<210> SEQ ID NO 106
<211> LENGTH: 2587
<212> TYPE: DNA
<213> ORGANISM: Homo sapiens

<400> SEQUENCE: 106

```
tcagcttgtg cctggctttg agcagccaca ggcagaaaat tgctgcattg tcccgacatt      60
agggcaacta atgcggcgtt gcgggtataa ccagagcatg aagtgcataa agaggcgtcg     120
ccttggcatc ttcatcagtc ccgagggagc ccagagccct gtcatagtca gtgaggcagc     180
ctgtggccag ctggcccatg tacctcccca gtaggtgacc cctggaatgc ttgcactcca     240
gggtatcaag gacttggcaa gtgggactgg agaacttacg gggattggga caggatgggc     300
atggaggggg tgggcatggc aggggtcctc agactgggga agtggtggag gccagagaga     360
taaggaaaag acagataaag gggagggggg ggtccctcgg gagacagggg gggtcctgaa     420
ggtgagagga agcctaggct atgggagggg gctgagggaa ggaggtgggg agcttcccag     480
tgcgtcctcc ctcggtcccc tcctcctcaa ggtttctaga gtccagaggg cctcattgac     540
atgtaaacga gggtccctat aaaggcggcg ctgcctcgca ctggtgcatg gactgcaaca     600
tgggcacgga gcctgctgcc cggggcagcc tccccggcaa cttccgaaag gtctggggtc     660
ttgagggact aggggcaggc acccttcccc gggaggtgtg ggggggtgcc gagggcagga     720
gggtggcagt cctgcactct aaaggctgtt catctgcaga tttccaagcc gctgatggag     780
aaaaagcgcc gggcacgcat caatgtgtca ctggagcagc tcaagtcgct gctggagaaa     840
cactactcgc accaggtgag actcaggcgg ggtggggggtg ggtgggtgat acgatcccaa     900
cctccctctc tccacctcgg gaggccggtc taatagacct ttccatggtc gggtagatcc     960
ggaagcgcaa attggagaag gccgacatcc tggagttgag cgtgaagtac atgagaagcc    1020
ttcagaactc cttgcaaggt ataggggagg gctggaggga ggaggggag gcttgtggga     1080 tcagagccag ggatgcacaa ggccaaataa agagggatac ctcaaggacc gcttgacccc    1140 gggctttga gaccagcctg ggcaacatgg caagacagca aatataaaga ggacaactcg    1200
gaggcaggtg cagttggtga ggagggggcc ccagctcgct aggggcgag ggaggagcag     1260 taaagcccgg gctggctgtg cgattgcaat ctgggtggta ggtctggacc ccgggggaga    1320
cgttcgggtc gtctgacctc cgccctcctc ttcccttcct caacacgctt cctccctcct    1380 ttccctcca cctccactcc cctctcctcc ctcccttcct ccctccccct ccctccccct    1440 tccctcctc tccctccccc tccccttccc cttccctctc ttccctcccc tgtttctcgc    1500
gtccgctctt ccccacaggg ctctggcctg tgcccagggg agccgagcaa ccgtcgggct    1560
tccgcagctg cctgcccggc gtgagccagc tccttcggcg cggagatgag gtcggcagcg    1620
gcctgcgctg ccccctggtg cccgagagcg ccgccggcag caccatggac agcgccgggt    1680
tgggccagga ggcgcccgcg ctgttccgcc cttgcacccc tgccgtctgg gctcctgctc    1740
cggccgccgc cggcccgcgg tccccaccac ccctgctcct cctccccgaa agtctccctg    1800
gctcgtccgc cagcgtcccc ccgccgcagc cagcgtcgag tcgctgcgcc gagagtcccg    1860
ggctgggcct gcgcgtgtgg cggccctggg gaagcccgg ggatgacctg aactgaaggc    1920
```

-continued

```
gctccctatt tggtctcgcg acacagggac tattttcagc acgcccacag tgactgccag    1980 gacccccag tcgtccgttc tggtcgtggg gcgggggtgg cttggagagg gccgcgcacc     2040
ccgcaagcgc agggaaatac ccccagccct gccggactgg gtctgcgcgt ctgggcataa    2100 tccacccca ctctagctcc acctacacac gccggaccgc tcgctctccg cccatcctcc      2160
ggaggggctg ggagggggtg tcctgggctg cgcccctttc ccagggaccc ctggcgggca    2220
acccgcccgc ccccacccc gcccggttgc cgcgcagcgg tgggaatgtc gcagttggca      2280
acagcgcaga gctgacccct cgcagcgagg agaatcgctg ccccgccccg gaccattcag    2340
cggaccgcgg gcgcccggtt cccaccggca caaagcgcgc ctggccccgc cccgccggca    2400
aggggccccc agcctccccc aacccgggat cctcttgact tccaaggacc tccttcgcaa    2460
gcggtgctgc ccaccgggct ggcgcattcc ccgaggccca cccttctcag aagccccgcc    2520
cctaagatgc accgccccaa ccggacgccc cgcccacgcg gttcctggaa gggacccatt    2580
gcttggt                                                              2587
```